(12) United States Patent
Reddy

(10) Patent No.: US 11,260,083 B2
(45) Date of Patent: Mar. 1, 2022

(54) COMPOSITIONS AND METHODS FOR TREATING AND PREVENTING GRAFT VERSUS HOST DISEASE

(71) Applicant: The Regents of the University of Michigan, Ann Arbor, MI (US)

(72) Inventor: Pavan Reddy, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 89 days.

(21) Appl. No.: 16/085,090

(22) PCT Filed: Mar. 15, 2017

(86) PCT No.: PCT/US2017/022456
§ 371 (c)(1),
(2) Date: Sep. 14, 2018

(87) PCT Pub. No.: WO2017/160944
PCT Pub. Date: Sep. 21, 2017

(65) Prior Publication Data
US 2019/0381116 A1    Dec. 19, 2019

Related U.S. Application Data

(60) Provisional application No. 62/308,603, filed on Mar. 15, 2016.

(51) Int. Cl.
| | | |
|---|---|---|
| *A61P 37/06* | (2006.01) | |
| *A61K 35/742* | (2015.01) | |
| *A61K 9/00* | (2006.01) | |
| *A61K 9/19* | (2006.01) | |
| *A61K 9/48* | (2006.01) | |
| *A61K 35/00* | (2006.01) | |

(52) U.S. Cl.
CPC .......... *A61K 35/742* (2013.01); *A61K 9/0053* (2013.01); *A61K 9/19* (2013.01); *A61K 9/48* (2013.01); *A61P 37/06* (2018.01); *A61K 2035/115* (2013.01)

(58) Field of Classification Search
None
See application file for complete search history.

(56) References Cited

U.S. PATENT DOCUMENTS

| | | |
|---|---|---|
| 9,415,079 B2 | 8/2016 | Honda et al. |
| 9,421,230 B2 | 8/2016 | Honda et al. |
| 9,433,652 B2 | 9/2016 | Honda et al. |
| 9,642,881 B2 | 5/2017 | Honda et al. |
| 9,642,882 B2 | 5/2017 | Honda et al. |
| 9,649,345 B2 | 5/2017 | Honda et al. |
| 9,662,381 B2 | 5/2017 | Honda et al. |
| 9,801,933 B2 | 10/2017 | Honda et al. |
| 9,808,519 B2 | 11/2017 | Honda et al. |
| 9,827,276 B2 | 11/2017 | Honda et al. |
| 9,833,483 B2 | 12/2017 | Honda et al. |
| 10,052,353 B2 | 8/2018 | Honda et al. |
| 10,058,578 B2 | 8/2018 | Honda et al. |
| 10,092,603 B2 | 10/2018 | Honda et al. |
| 10,183,045 B2 | 1/2019 | Honda et al. |
| 10,238,694 B2 | 3/2019 | Honda et al. |
| 10,322,150 B2 | 6/2019 | Honda et al. |
| 10,328,108 B2 | 6/2019 | Honda et al. |
| 10,342,832 B2 | 7/2019 | Honda et al. |
| 10,555,978 B2 | 2/2020 | Honda et al. |
| 10,588,925 B2 | 3/2020 | Honda et al. |
| 10,624,933 B2 | 4/2020 | Honda et al. |
| 10,835,559 B2 | 11/2020 | Honda et al. |
| 2013/0149339 A1 | 6/2013 | Honda et al. |
| 2015/0190435 A1 | 7/2015 | Henn et al. |
| 2017/0143775 A1* | 5/2017 | Mulder ..................... A61P 9/00 |
| 2020/0246399 A1 | 8/2020 | Honda et al. |

FOREIGN PATENT DOCUMENTS

| | | |
|---|---|---|
| WO | WO2015/156419 | 10/2015 |
| WO | WO2015/179437 | 11/2015 |
| WO | WO2017/160944 | 9/2017 |

OTHER PUBLICATIONS

Drancourt et al. 2000 (16S Ribosomal DNA Sequence Analysis of a Large Collection of Environmental and Clinical Unidentifiable Bacterial Isolates; Journal of Clinical Microbiology, 38(10): p. 3623-3630) (Year: 2000).*
Fredricks 2019 (The gut microbiota and graft-versus-host-disease; The Journal of Clinical Investigation; 129(5):1808-1817) (Year: 2019).*
Mathewson et al. 2015 (The Microbiome and Graft Versus Host Disease; Curr Stem Cell Rep 1:39-47) (Year: 2015).*
Atarashi K et al. 2013 (Treg induction by a rationally selected mixture of Clostridia strains from the human microbiota; Nature 500: 232-236). (Year: 2013).*
Arpaia et al., "Metabolites Produced by Commensal Bacteria Promote Peripheral Regulatory T-cell Generation" Nature. Dec. 9, 2013;504(7480):451-5.
Atarashi et al., "Treg Induction by a Rationally Selected Mixture of Clostridia Strains From the Human Microbiota" Nature. Aug. 8, 2013;500(7461):232-6.
Chang et al., "The Microbial Metabolite Butyrate Regulates Intestinal Macrophage Function via Histone Deacetylase Inhibition" Proc Natl Acad Sci U S A. Feb. 11, 2014;111(6):2247-52.
Charney et al., "Nonionic Diffusion of Short-Chain Fatty Acids Across Rat Colon" Am J Physiol. Mar. 1998;274(3):G518-24.
Chen et al.,"The Role of Intestinal Microbiota in Acute Graft-versus-Host Disease" J Immunol Res. 2015;2015:145859. 10 pages.
Choi et al., "Graft-versus-host Disease" Panminerva Med. Jun. 2010;52(2):111-24.

(Continued)

*Primary Examiner* — Mary Maille Lyons
(74) *Attorney, Agent, or Firm* — Casimir Jones, S.C.; Tanya A. Arenson

(57) ABSTRACT

Provided herein are compositions and methods for administering bacterial strains to reduce GvHD and improve survival after allogeneic BMT.

17 Claims, 28 Drawing Sheets
Specification includes a Sequence Listing.

(56) References Cited

OTHER PUBLICATIONS

Choi et al., "Vorinostat Plus Tacrolimus and Mycophenolate to Prevent Graft-Versus-Host Disease After Related-Donor Reduced-Intensity Conditioning Allogeneic Haemopoietic Stem-Cell Transplantation: A Phase 1/2 Trial" Lancet Oncol. Jan. 2014;15(1):87-95.

Cook et al., "Review Article: Short Chain Fatty Acids in Health and Disease" Aliment Pharmacol Ther. Jun. 1998;12(6):499-507.

Cresci et al., "Colonic Gene Expression in Conventional and Germ-Free Mice With a Focus on the Butyrate Receptor GPR109A and the Butyrate Transporter SLC5A8" J Gastrointest Surg. Mar. 2010;14(3):449-61.

David et al., "Diet Rapidly and Reproducibly Alters the Human Gut Microbiome" Nature. Jan. 23, 2014;505(7484):559-63.

Desantis et al., "Greengenes, a Chimera-Checked 16S rRNA Gene Database and Workbench Compatible With ARB" Appl Environ Microbiol. Jul. 2006;72(7):5069-72.

Drancourt et al., "16S ribosomal DNA sequence analysis of a large collection of environmental and clinical unidentifiable bacterial isolates" J Clin Microbiol. Oct. 2000;38(10):3623-30.

Eriguchi et al., "Graft-versus-host Disease Disrupts Intestinal Microbial Ecology by Inhibiting Paneth Cell Production of α-Defensins" Blood. Jul. 5, 2012;120(1):223-31.

Ferrara et al., "Graft-versus-host Disease" Lancet. May 2, 2009;373(9674):1550-61.

Fleming et al., "Digestion and Absorption of Fiber Carbohydrate in the Colon" Am J Gastroenterol. Jul. 1986;81(7):507-11.

Fredricks et al., "The gut microbiota and graft-versus-host disease" J Clin Invest. May 1, 2019;129(5):1808-1817.

Furusawa et al., "Commensal Microbe-Derived Butyrate Induces the Differentiation of Colonic Regulatory T Cells" Nature. Dec. 19, 2013;504(7480):446-50.

Ganapathy et al., "Transporters and Receptors for Short-Chain Fatty Acids as the Molecular Link Between Colonic Bacteria and the Host" Curr Opin Pharmacol. Dec. 2013;13(6):869-74.

Gao et al., "Histone Deacetylases Inhibitor Sodium Butyrate Inhibits JAK2/STAT Signaling Through Upregulation of SOCS1 and SOCS3 Mediated by HDAC8 Inhibition in Myeloproliferative Neoplasms" Exp Hematol. Mar. 2013;41(3):261-70.e4.

Hanash et al., "Interleukin-22 Protects Intestinal Stem Cells From Immune-Mediated Tissue Damage and Regulates Sensitivity to Graft Versus Host Disease" Immunity. Aug. 24, 2012;37(2):339-50.

Hill et al., "The Primacy of the Gastrointestinal Tract as a Target Organ of Acute Graft-Versus-Host Disease: Rationale for the Use of Cytokine Shields in Allogeneic Bone Marrow Transplantation" Blood. May 1, 2000;95(9):2754-9.

Jenq et al. "Regulation of Intestinal Inflammation by Microbiota Following Allogeneic Bone Marrow Transplantation" J Exp Med. May 7, 2012;209(5):903-11.

Jenq et al., "Allogeneic Haematopoietic Stem Cell Transplantation: Individualized Stem Cell and Immune Therapy of Cancer" Nat Rev Cancer. Mar. 2010; 10(3):213-21.

Jumpstart Consortium Human Microbiome Project Data Generation Working Group, "Evaluation of 16S rDNA-based Community Profiling for Human Microbiome Research" PLoS One. 2012;7(6):e39315. 14 pages.

Lahl et al., "In Vivo Depletion of FoxP3+ Tregs Using the DEREG Mouse Model" Methods Mol Biol. 2011;707:157-72.

Lahl et al., "Selective Depletion of Foxp3+ Regulatory T Cells Induces a Scurfy-Like Disease" J Exp Med. Jan. 22, 2007;204(1):57-63.

Mathewson et al., "The microbiome and graft versus host disease." Current Stem Cell Reports 1.1 (2015): 39-47.

Narushima et al., "Characterization of the 17 Strains of Regulatory T Cell-Inducing Human-Derived Clostridia" Gut Microbes. May-Jun. 2014;5(3):333-9.

Noth et al., "Increased Intestinal Permeability and Tight Junction Disruption by Altered Expression and Localization of Occludin in a Murine Graft Versus Host Disease Model" BMC Gastroenterol. Oct. 6, 2011;11:109.

Rajilic-Stojanovic et al., "The First 1000 Cultured Species of the Human Gastrointestinal Microbiota" FEMS Microbiol Rev. Sep. 2014;38(5):996-1047.

Reddy et al., "Histone Deacetylase Inhibition Modulates Indoleamine 2,3-dioxygenase-dependent DC Functions and Regulates Experimental Graft-Versus-Host Disease in Mice" J Clin Invest. Jul. 2008;118(7):2562-73.

Reddy et al., "Histone Deacetylase Inhibitor Suberoylanilide Hydroxamic Acid Reduces Acute Graft-Versus-Host Disease and Preserves Graft-Versus-Leukemia Effect" Proc Natl Acad Sci U S A. Mar. 16, 2004;101(11):3921-6.

Schloss et al., "Introducing Mothur: Open-Source, Platform-Independent, Community-Supported Software for Describing and Comparing Microbial Communities" Appl Environ Microbiol. Dec. 2009;75(23):7537-41.

Schloss et al., "Reducing the Effects of PCR Amplification and Sequencing Artifacts on 16S rRNA-based Studies" PLoS One. 2011;6(12):e27310.

Sealy et al., "The Effect of Sodium Butyrate on Histone Modification" Cell. May 1978;14(1):115-21.

Soler et al., "Increased Tight Junctional Permeability is Associated With the Development of Colon Cancer" Carcinogenesis. Aug. 1999;20(8):1425-31.

Sun et al., "Cutting Edge: Negative Regulation of Dendritic Cells Through Acetylation of the Nonhistone Protein STAT-3" J Immunol. May 15, 2009;182(10):5899-903.

Suzuki "Regulation of Intestinal Epithelial Permeability by Tight Junctions" Cell Mol Life Sci. Feb. 2013;70(4):631-59.

Topham et al., "Mitosis and Apoptosis: How is the Balance Set?" Curr Opin Cell Biol. Dec. 2013;25(6):780-5.

Turnbaugh et al., "A Core Gut Microbiome in Obese and Lean Twins" Nature. Jan. 22, 2009;457(7228):480-4.

International Search Report of related PCTUS2017022456, dated Aug. 22, 2017, 20 pages.

* cited by examiner

Figure 2
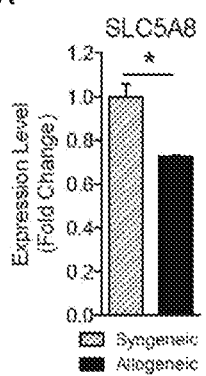
Fig. 2A
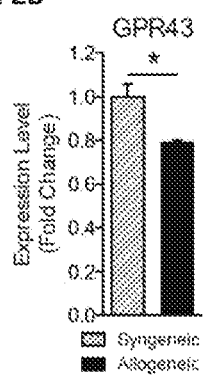
Fig. 2B
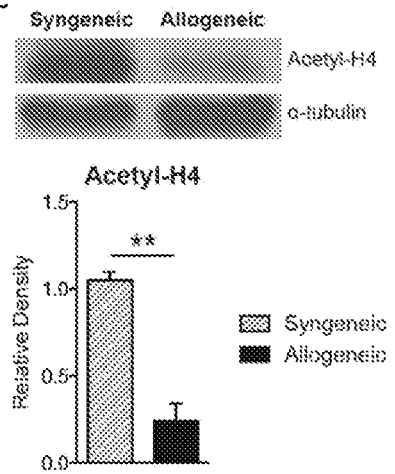
Fig. 2C
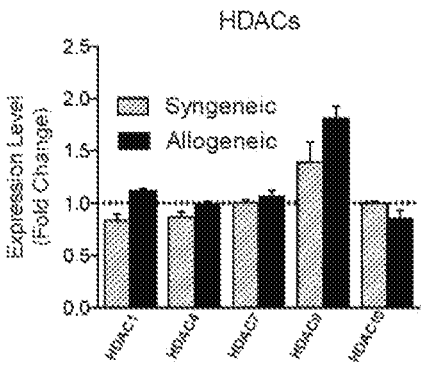
Fig. 2D
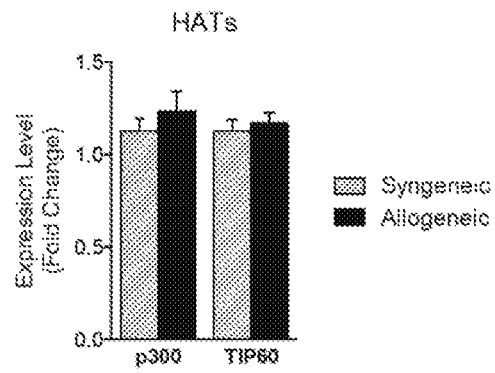
Fig. 2E Figure 3
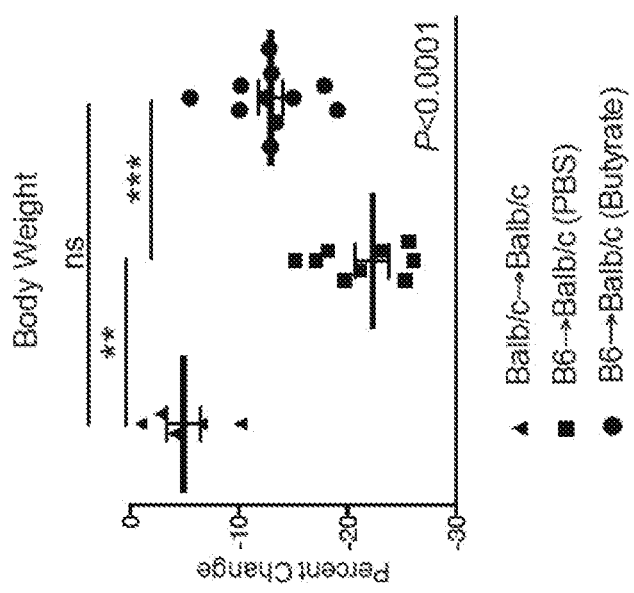
Fig. 3B
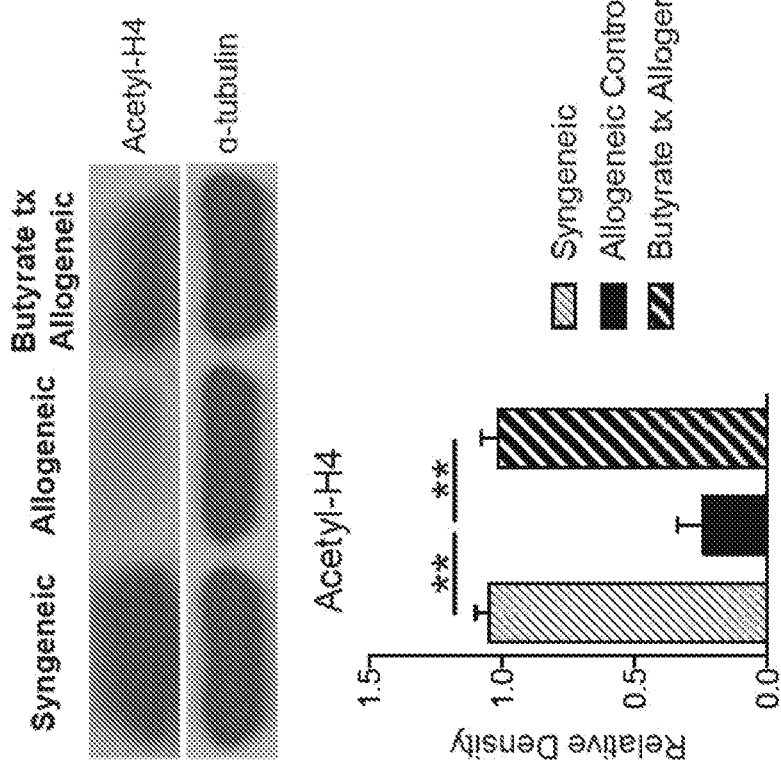
Fig. 3A Figure 3 (cont.)
Fig. 3C
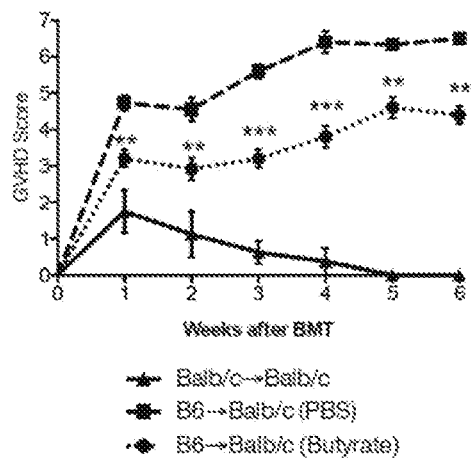
Fig. 3D
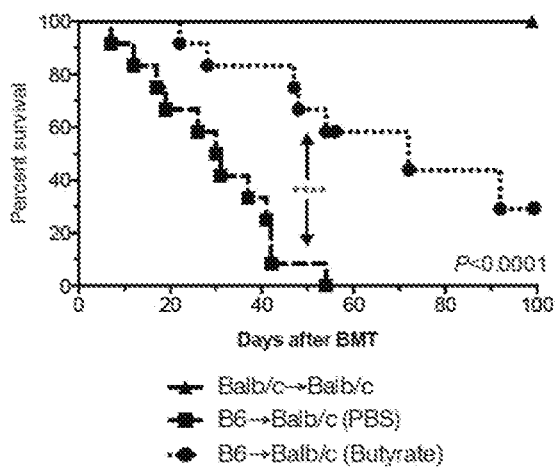
Fig. 3E
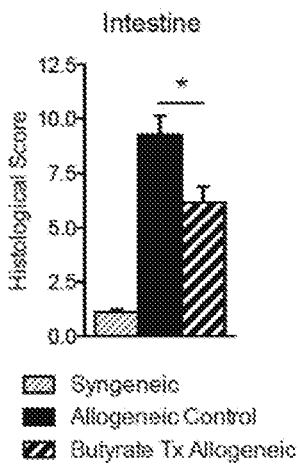

Figure 4 (cont.)
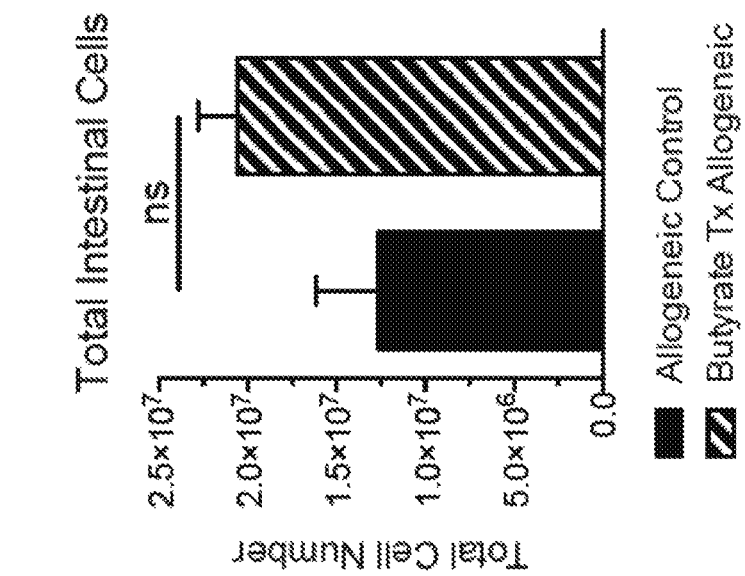
Fig. 4C
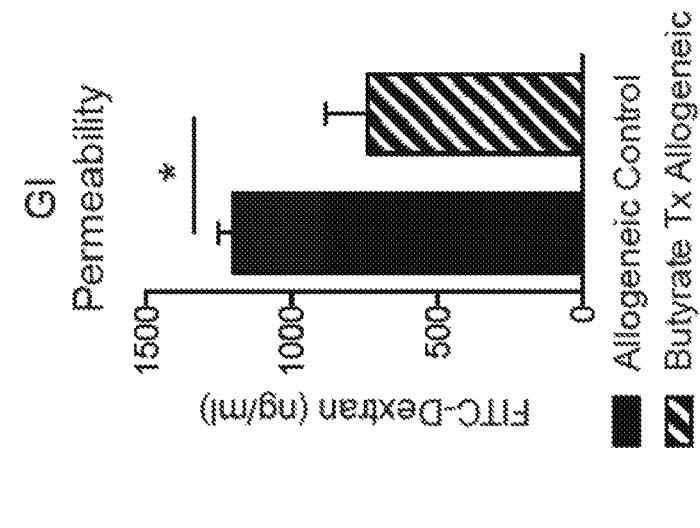
Fig. 4B

Figure 5
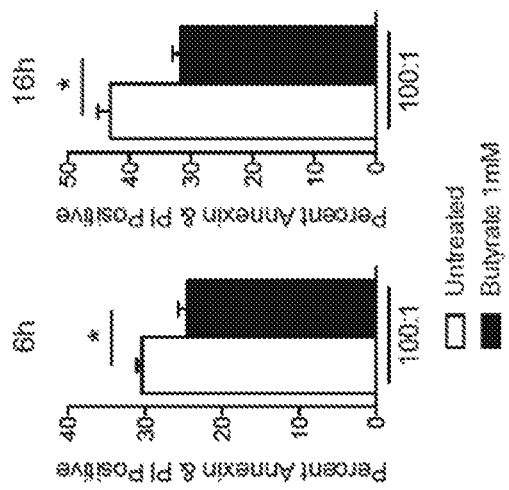
Fig. 5A
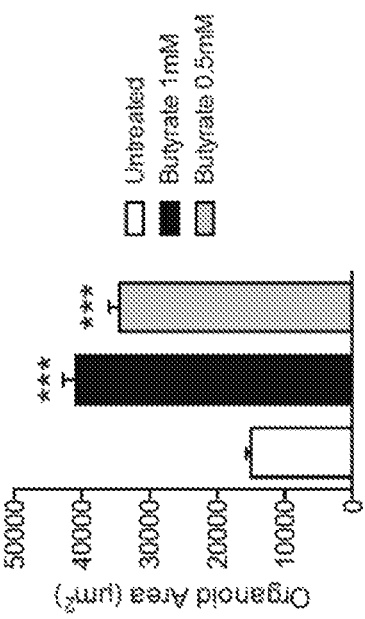
Fig. 5B
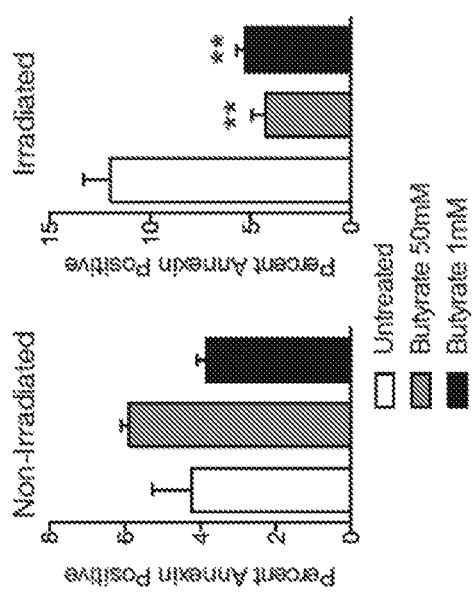
Fig. 5C
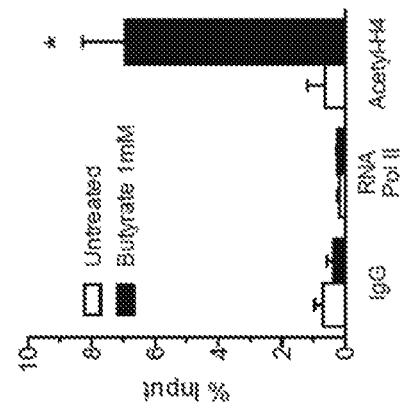
Fig. 5D Figure 5 (cont.)
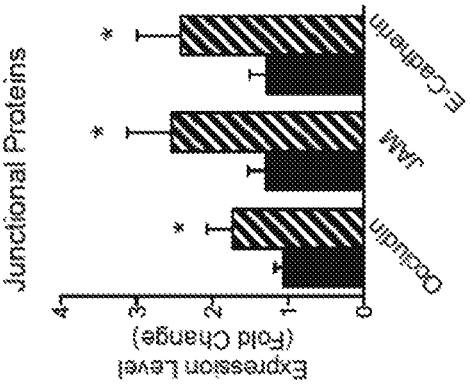
Fig. 5H
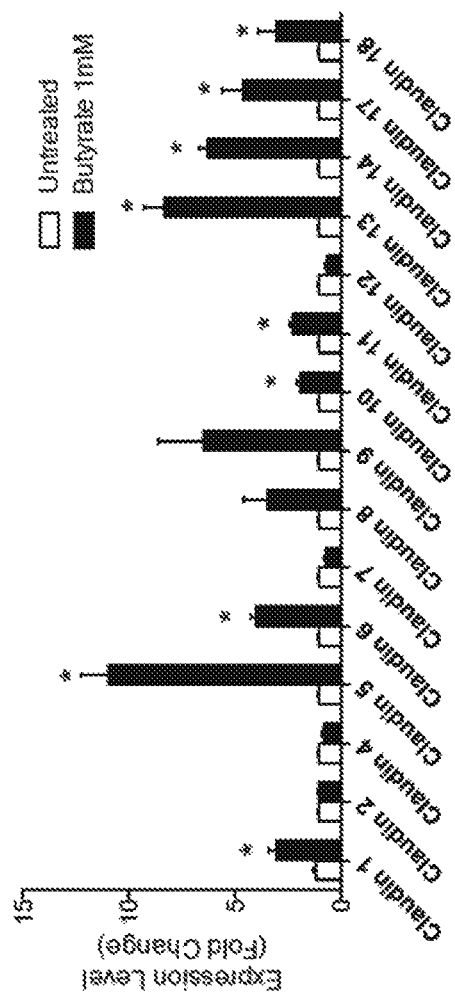
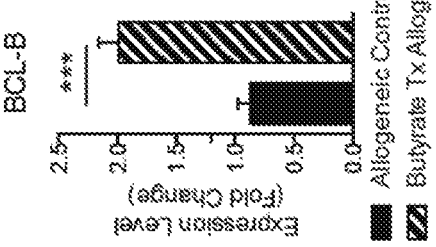
Fig. 5G
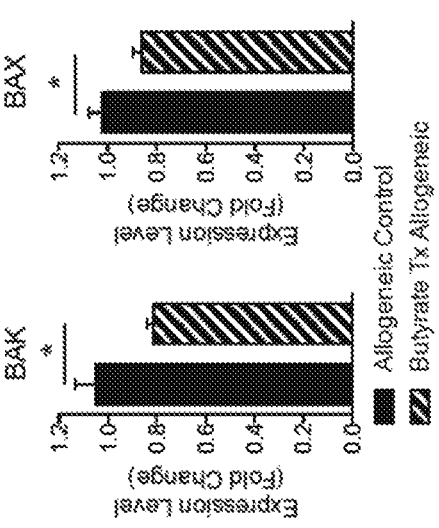
Fig. 5E
Fig. 5F Figure 6 (cont.)
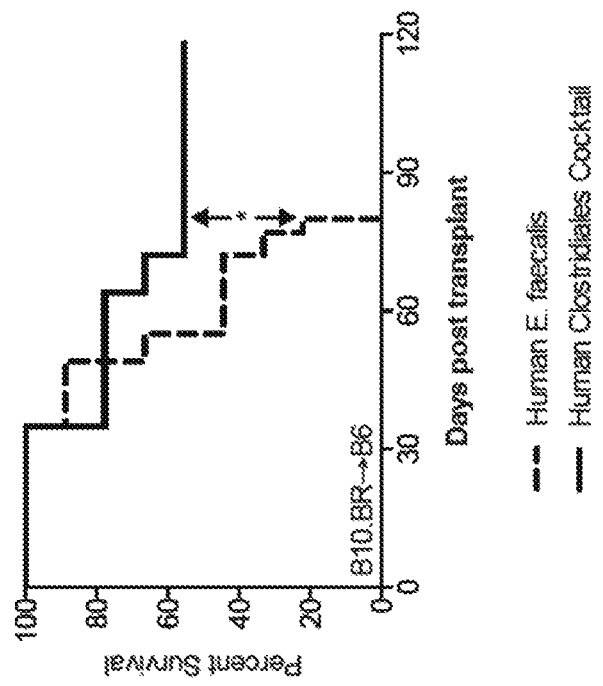
Fig. 6E
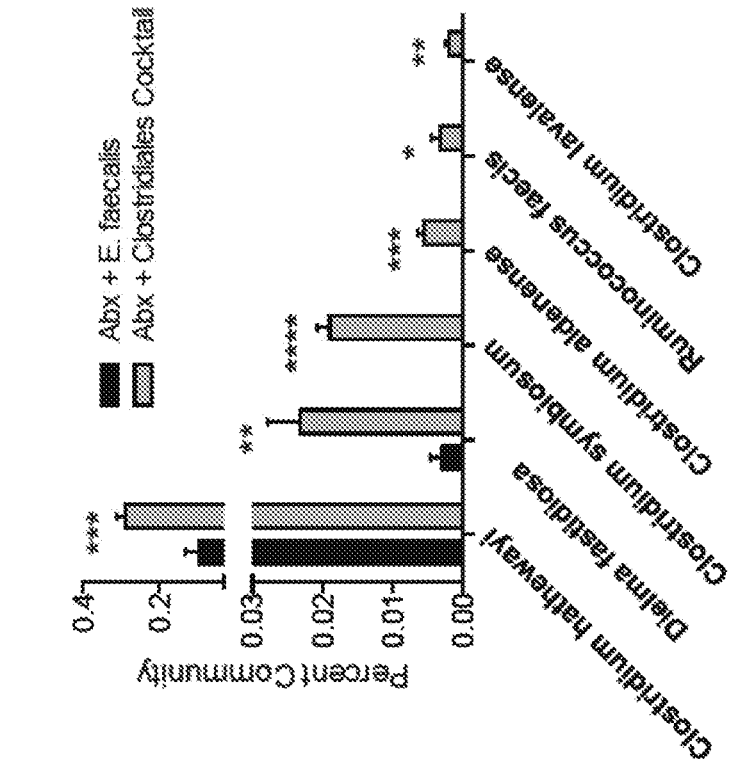
Fig. 6D

Figure 7

SEQ ID NO:1-VE202-01_16S_prokka_VE202-01_00052 16S ribosomal RNA
ATGGAGAGTTTGATCCTGGCTCAGGATGAACGCTGGCGGCGTGCCTAATACATGC
AAGTCGAACGCGGGCAGCAATGCCCGAGTGGCGAACGGGTGAGTAATACATAAG
TAACCTGCCCTTTACAGGGGGATAACTATTGGAAACGATAGCTAAGACCGCATA
GGTAAAGATACCGCATGGTAAGTTTATTAAAAGTGCCAAGGCACTGGTAGAGGA
TGGACTTATGGCGCATTAGCTAGTTGGTGAGGTAACGGCTCACCAAGGCGACGA
TGCGTAGCCGACCTGAGAGGGTGACCGGCCACACTGGGACTGAGACACGGCCCA
GACTCCTACGGGAGGCAGCAGTAGGGAATTTTCGGCAATGGGGGGAACCCTGAC
CGAGCAACGCCGCGTGAAGGAGGAAGGTCTTCGGACTGTAAACTTCTGTTATAA
AGGAAGAAAGGCGGATACAGGGAATGGTATCCGAGTGACGGTACTTTATGAGGA
AGCCACGGCTAACTACGTGCCAGCAGCCGCGGTAATACGTAGGTGGCAAGCGTT
ATCCGGAATTATTGGGCGTAAAGAGGGAGCAGGCGGCAGCAAGGGTCTGTGGTG
AAAGACTGAAGCTTAACTTCAGTAAGCCATAGAAACCGGGCAGCTAGAGTGCAG
GAGAGGATCGTGGAATTCCATGTGTAGCGGTGAAATGCGTAGATATATGGAGGA
ACACCAGTGGCGAAGGCGACGATCTGGCCTGCAACTGACGCTCAGTCCCGAAAG
CGTGGGGAGCAAATAGGATTAGATACCCTAGTAGTCCACGCCGTAAACGATGAG
TACTAAGTGTTGGGAGTCAAATCTCAGTGCTGCAGTTAACGCAGTAAGTACTCCG
CCTGAGTAGTACGTTCGCAAGAATGAAACTCAAAGGAATTGACGGGGGCCCGCA
CAAGCGGTGGAGCATGTGGTTTAATTCGAAGCAACGCGAAGAACCTTACCAGGT
CTTGACATACTCATAAAGGCTCCAGAGATGGAGAGATAGATATATGGGATACAG
GTGGTGCATGGTTGTCGTCAGCTCGTGTCGTGAGATGTTGGGTTAAGTCCCGCAA
CGAGCGCAACCCTTATCGTTAGTTACCATCATTAAGTTGGGGACTCTAGCGAGAC
TGCCAGTGACAAGCTGGAGGAAGGCGGGGATGACGTCAAATCATCATGCCCCTT
ATGACCTGGGCTACACACGTGCTACAATGGATGGAGCAGAGGGAAGCGAAGCCG
CGAGGTGGAGCGAAACCCAGAAAACCATTCTCAGTTCGGATTGTAGTCTGCAAC
TCGACTACATGAAGTTGGAATCGCTAGTAATCGCGAATCAGCATGTCGCGGTGA
ATACGTTCTCGGGCCTTGTACACACCGCCCGTCACACCATGAGAGTTGATAACAC
CCGAAGCCGGTGGCCTAACCGCAAGGAGGGAGCTGTCTAAGGTGGGATTGATGA
TTGGGGTGAAGTCGTAACAAGGTATCCCTACGGGAACGTGGGGATGGATCACCT
CCTTT

Figure 7 (cont.)

>SEQ ID NO:2-VE202-03_16S_prokka_VE202-03_00359 16S ribosomal RNA
TATTGAGAGTTTGATCCTGGCTCAGGATGAACGCTGGCGGCGTGCTTAACACATG
CAAGTCGAACGGGGTGCTCATGACGGAGGATTCGTCCAACGGATTGAGTTACCT
AGTGGCGGACGGGTGAGTAACGCGTGAGGAACCTGCCTTGGAGAGGGGAATAAC
ACTCCGAAAGGAGTGCTAATACCGCATGATGCAGTTGGGTCGCATGGCTCTGACT
GCCAAAGATTTATCGCTCTGAGATGGCCTCGCGTCTGATTAGCTAGTAGGCGGGG
TAACGGCCCACCTAGGCGACGATCAGTAGCCGGACTGAGAGGTTGACCGGCCAC
ATTGGGACTGAGACACGGCCCAGACTCCTACGGGAGGCAGCAGTGGGGAATATT
GGGCAATGGGCGCAAGCCTGACCCAGCAACGCCGCGTGAAGGAAGAAGGCTTTC
GGGTTGTAAACTTCTTTTGTCGGGGACGAAACAAATGACGGTACCCGACGAATA
AGCCACGGCTAACTACGTGCCAGCAGCCGCGGTAATACGTAGGTGGCAAGCGTT
ATCCGGATTTACTGGGTGTAAAGGGCGTGTAGGCGGGATTGCAAGTCAGATGTG
AAAACTGGGGGCTCAACCTCCAGCCTGCATTTGAAACTGTAGTTCTTGAGTGCTG
GAGAGGCAATCGGAATTCCGTGTGTAGCGGTGAAATGCGTAGATATACGGAGGA
ACACCAGTGGCGAAGGCGGATTGCTGGACAGTAACTGACGCTGAGGCGCGAAAG
CGTGGGGAGCAAACAGGATTAGATACCCTGGTAGTCCACGCCGTAAACGATGGA
TACTAGGTGTGGGGGGTCTGACCCCCTCCGTGCCGCAGTTAACACAATAAGTATC
CCACCTGGGGAGTACGATCGCAAGGTTGAAACTCAAAGGAATTGACGGGGGCCC
GCACAAGCGGTGGAGTATGTGGTTTAATTCGAAGCAACGCGAAGAACCTTACCA
GGGCTTGACATCCCACTAACGAAGCAGAGATGCATTAGGTGCCCTTCGGGGAAA
GTGGAGACAGGTGGTGCATGGTTGTCGTCAGCTCGTGTCGTGAGATGTTGGGTTA
AGTCCCGCAACGAGCGCAACCCTTATTGTTAGTTGCTACGCAAGAGCACTCTAGC
GAGACTGCCGTTGACAAAACGGAGGAAGGTGGGGACGACGTCAAATCATCATGC
CCCTTATGTCCTGGGCCACACACGTACTACAATGGTGGTTAACAGAGGGAGGCA
ATACCGCGAGGTGGAGCAAATCCCTAAAAGCCATCCCAGTTCGGATTGCAGGCT
GAAACCCGCCTGTATGAAGTTGGAATCGCTAGTAATCGCGGATCAGCATGCCGC
GGTGAATACGTTCCCGGGCCTTGTACACACCGCCCGTCACACCATGAGAGTCGG
GAACACCCGAAGTCCGTAGCCTAACCGCAAGGAGGGCGCGGCCGAAGGTGGGTT
CGATAATTGGGGTGAAGTCGTAACAAGGTAGCCGTATCGGAAGGTGCGGCTGGA
TCACCTCCTTT

Figure 7 (cont.)

>SEQ ID NO:3-VE202-04_00856 16S ribosomal RNA (partial)
ACGGCCCAAACTCCTACGGGAGGCAGCAGTGGGGAATATTGGACAATGGGCGAA
AGCCTGATCCAGCGACGCCGCGTGAGTGAAGAAGTATTTCGGTATGTAAAGCTCT
ATCAGCAGGGAAGAAAATGACGGTACCTGACTAAGAAGCCCCGGCTAACTACGT
GCCAGCAGCCGCGGTAATACGTAGGGGGCAAGCGTTATCCGGATTTACTGGGTG
TAAAGGGAGCGTAGACGGTTAAGCAAGTCTGAAGTGAAAGCCCGGGGCTCAACC
CCGGTACTGCTTTGGAAACTGTTTGACTTGAGTGCAGGAGAGGTAAGTGGAATTC
CTAGTGTAGCGGTGAAATGCGTAGATATTAGGAGGAACACCAGTGGCGAAGGCG
GCTTACTGGACTGTAACTGACGTTGAGGCTCGAAAGCGTGGGGAGCAAACAGGA
TTAGATACCCTGGTAGTCCACGCCGTAAACGATGAATACTAGGTGTCGGGGGAC
AACGTCCTTCGGTGCCGCCGCTAACGCAATAAGTATTCCACCTGGGGAGTACGTT
CGCAAGAATGAAACTCAAAGGAATTGACGGGGACCCGCACAAGCGGTGGAGCA
TGTGGTTTAATTCGAAGCAACGCGAAGAACCTTACCAAGTCTTGACATCCCATTG
AAAATCACTTTAACCGTGTCCCTCTTCGGAGCAATGGAGACAGGTGGTGCATGGT
TGTCGTCAGCTCGTGTCGTGAGATGTTGGGTTAAGTCCCGCAACGAGCGCAACCC
TTATCCTTAGTAGCCAGCACATGATGGTGGGCACTCTGGGGAGACTGCCAGGGAT
AACCTGGAGGAAGGTGGGGATGACGTCAAATCATCATGCCCCTTATGATTTGGG
CTACACACGTGCTACAATGGCGTAAACAAAGGGAAGCAAAGGAGCGATCTGGAG
CAAACCCCAAAAATAACGTCTCAGTTCGGATTGCAGGCTGCAACTCGCCTGCATG
AAGCTGGAATCGCTAGTAATCGCGAATCAGAATGTCGCGGTGAATACGTTCCCG
GGTCTTGTACACACCGCCCGTCACACCATGGGAGTTGGTAACGCCCGAAGTCAGT
GACCCAACCGTAAGGAGGGAGCTGCCGAAGGCGGGACTGATAACTGGGGTGAA
GTCGTAACAAGGTAGCCGTATCGGAAGGTGCGGCTGGATCACCTCCTTT >SEQ ID NO:4-VE202-06_16S_prokka_VE202-06_00032 16S ribosomal RNA
CCGCATGGTCTGGTGTGAAAAACTCCGGTGGTATGAGATGGACCCGCGTCTGATT
AGCTAGTTGGAGGGGTAACGGCCCACCAAGGCGACGATCAGTAGCCGGCCTGAG
AGGGTGAACGGCCACATTGGGACTGAGACACGGCCCAGACTCCTACGGGAGGCA
GCAGTGGGGAATATTGCACAATGGGGGAAACCCTGATGCAGCGACGCCGCGTGA
AGGAAGAAGTATCTCGGTATGTAAACTTCTATCAGCAGGGAAGAAAATGACGGT
ACCTGACTAAGAAGCCCCGGCTAACTACGTGCCAGCAGCCGCGGTAATACGTAG
GGGGCAAGCGTTATCCGGATTTACTGGGTGTAAAGGGAGCGTAGACGGAAGAGC

Figure 7 (cont.)

AAGTCTGATGTGAAAGGCTGGGGCTTAACCCCAGGACTGCATTGGAAACTGTTGT
TCTAGAGTGCCGGAGAGGTAAGCGGAATTCCTAGTGTAGCGGTGAAATGCGTAG
ATATTAGGAGGAACACCAGTGGCGAAGGCGGCTTACTGGACGGTAACTGACGTT
GAGGCTCGAAAGCGTGGGGAGCAAACAGGATTAGATACCCTGGTAGTCCACGCC
GTAAACGATGAATACTAGGTGTCGGGTGGCAAAGCCATTCGGTGCCGCAGCAAA
CGCAATAAGTATTCCACCTGGGGAGTACGTTCGCAAGAATGAAACTCAAAGGAA
TTGACGGGGACCCGCACAAGCGGTGGAGCATGTGGTTTAATTCGAAGCAACGCG
AAGAACCTTACCAAGTCTTGACATCCCTCTGACCGTCCCGTAATGGGGGCTTCCC
TTCGGGGCAGAGGAGACAGGTGGTGCATGGTTGTCGTCAGCTCGTGTCGTGAGA
TGTTGGGTTAAGTCCCGCAACGAGCGCAACCCTTATCCTTAGTAGCCAGCACATG
ATGGTGGGCACTCTAGGGAGACTGCCGGGGATAACCCGGAGGAAGGCGGGGAC
GACGTCAAATCATCATGCCCCTTATGATTTGGGCTACACACGTGCTACAATGGCG
TAAACAAAGGGAAGCGAGACAGCGATGTTGAGCGAATCCCAAAAATAACGTCCC
AGTTCGGACTGCAGTCTGCAACTCGACTGCACGAAGCTGGAATCGCTAGTAATCG
CGGATCAGAATGCCGCGGTGAATACGTTCCCGGGTCTTGTACACACCGCCCGTCA
CACCATGGGAGTCAGTAACGCCCGAAGTCAGTGACCTAACCGAAAGGAAGGAGC
TGCCGAAGGCGGGACCGATAACTGGGGTGAAGTCGTAACAAGGTAGCCGTATCG
GAAGGTGCGGCTGGATCACCTCCTTT

>SEQ ID NO:5-VE202-07_16S_prokka_VE202-07_00002 16S ribosomal RNA
ATGAGAGTTTGATCCTGGCTCAGGATGAACGCTGGCGGCGTGCCTAACACATGC
AAGTCGAACGAAGCAATTAAAATGAAGTTTTCGGATGGATTTTTGATTGACTGAG
TGGCGGACGGGTGAGTAACGCGTGGATAACCTGCCTCACACTGGGGGATAACAG
TTAGAAATGACTGCTAATACCGCATAAGCGCACAGTACCGCATGGTACGGTGTG
AAAAACTCCGGTGGTGTGAGATGGATCCGCGTCTGATTAGCCAGTTGGCGGGGT
AACGGCCCACCAAAGCGACGATCAGTAGCCGACCTGAGAGGGTGACCGGCCACA
TTGGGACTGAGACACGGCCCAAACTCCTACGGGAGGCAGCAGTGGGGAATATTG
CACAATGGGCGAAAGCCTGATGCAGCGACGCCGCGTGAGTGAAGAAGTATTTCG
GTATGTAAAGCTCTATCAGCAGGGAAGAAAATGACGGTACCTGACTAAGAAGCC
CCGGCTAACTACGTGCCAGCAGCCGCGGTAATACGTAGGGGGCAAGCGTTATCC
GGATTTACTGGGTGTAAAGGGAGCGTAGACGGCGAAGCAAGTCTGAAGTGAAAA
CCCAGGGCTCAACCCTGGGACTGCTTTGGAAACTGTTTTGCTAGAGTGTCGGAGA

Figure 7 (cont.)

GGTAAGTGGAATTCCTAGTGTAGCGGTGAAATGCGTAGATATTAGGAGGAACAC
CAGTGGCGAAGGCGGCTTACTGGACGATAACTGACGTTGAGGCTCGAAAGCGTG
GGGAGCAAACAGGATTAGATACCCTGGTAGTCCACGCCGTAAACGATGAATGCT
AGGTGTTGGGGGGCAAAGCCCTTCGGTGCCGTCGCAAACGCAGTAAGCATTCCA
CCTGGGGAGTACGTTCGCAAGAATGAAACTCAAAGGAATTGACGGGGACCCGCA
CAAGCGGTGGAGCATGTGGTTTAATTCGAAGCAACGCGAAGAACCTTACCAAGT
CTTGACATCCTCTTGACCGGCGTGTAACGGCGCCTTCCCTTCGGGGCAAGAGAGA
CAGGTGGTGCATGGTTGTCGTCAGCTCGTGTCGTGAGATGTTGGGTTAAGTCCCG
CAACGAGCGCAACCCTTATCCTTAGTAGCCAGCAGGTAAAGCTGGGCACTCTAG
GGAGACTGCCAGGGATAACCTGGAGGAAGGTGGGGATGACGTCAAATCATCATG
CCCCTTATGATTTGGGCTACACACGTGCTACAATGGCGTAAACAAAGGGAAGCA
AGACAGTGATGTGGAGCAAATCCCAAAAATAACGTCCCAGTTCGGACTGTAGTC
TGCAACCCGACTACACGAAGCTGGAATCGCTAGTAATCGCGAATCAGAATGTCG
CGGTGAATACGTTCCCGGGTCTTGTACACACCGCCCGTCACACCATGGGAGTCAG
CAACGCCCGAAGTCAGTGACCCAACTCGCAAGAGAGGGAGCTGCCGAAGGCGG
GGCAGGTAACTGGGGTGAAGTCGTAACAAGGTAGCCGTATCGGAAGGTGCGGCT
GGATCACCTCCTTT

>SEQ ID NO:6-VE202-08_00015 16S ribosomal RNA (partial)
CGGCCACATTGGGACTGAGACACGGCCCAAACTCCTACGGGAGGCAGCAGTAGG
GAATTTTCGGCAATGGGGGAAACCCTGACCGAGCAATGCCGCGTGAGTGAAGAC
GGCCTTCGGGTTGTAAAGCTCTGTTGTAAGGGAAGAACGGCATAGAGAGGGAAT
GCTCTATGAGTGACGGTACCTTACCAGAAAGCCACGGCTAACTACGTGCCAGCA
GCCGCGGTAATACGTAGGTGGCAAGCGTTATCCGGAATTATTGGGCGTAAAGGG
TGCGTAGGCGGCTGGATAAGTCTGAGGTAAAAGCCCGTGGCTCAACCACGGTAA
GCCTTGGAAACTGTCTGGCTGGAGTGCAGGAGAGGACAATGGAATTCCATGTGT
AGCGGTAAAATGCGTAGATATATGGAGGAACACCAGTGGCGAAGGCGGTTGTCT
GGCCTGTAACTGACGCTGAAGCACGAAAGCGTGGGGAGCAAATAGGATTAGATA
CCCTAGTAGTCCACGCCGTAAACGATGAGAACTAAGTGTTGGGGAAACTCAGTG
CTGCAGTTAACGCAATAAGTTCTCCGCCTGGGGAGTATGCACGCAAGTGTGAAA
CTCAAAGGAATTGACGGGGCCCGCACAAGCGGTGGAGTATGTGGTTTAATTCG
ACGCAACGCGAAGAACCTTACCAGGCCTTGACATGGTATCAAAGGCCCTAGAGA
TAGGGAGATAGTTATGATACACAGGTGGTGCATGGTTGTCGTCAGCTCGTGTC

Figure 7 (cont.)

GTGAGATGTTGGGTTAAGTCCCGCAACGAGCGCAACCCTTGTTTCTAGTTACCAA
CAGTAAGATGGGGACTCTAGAGAGACTGCCGGTGACAAACCGGAGGAAGGTGG
GGATGACGTCAAATCATCATGCCCCTTATGGCCTGGGCTACACACGTACTACAAT
GGCGTCTACAAAGAGCAGCGAGCAGGTGACTGTAAGCGAATCTCATAAAGGACG
TCTCAGTTCGGATTGAAGTCTGCAACTCGACTTCATGAAGTCGGAATCGCTAGTA
ATCGCGGATCAGCATGCCGCGGTGAATACGTTCTCGGGCCTTGTACACACCGCCC
GTCAAACCATGGGAGTTGATAATACCCGAAGCCGGTGGCCTAACCGAAAGGAGG
GAGCCGTCGAAGGTAGGATCGATGACTGGGGTTAAGTCGTAACAAGGTATCCCT
ACGGGAACGTGGGGATGGATCACCTCCTTT

>SEQ ID NO:7-VE202-09_16S_prokka_VE202-09_00011 16S ribosomal RNA
ATGAGAGTTTGATCCTGGCTCAGGATGAACGCTGGCGGCGTGCTTAACACATGCA
AGTCGAACGAAGCATTTTGGAAGGAAGTTTTCGGATGGAATTCCTTAATGACTGA
GTGGCGGACGGGTGAGTAACGCGTGGGGAACCTGCCCTATACAGGGGGATAACA
GCTGGAAACGGCTGCTAATACCGCATAAGCGCACAGAATCGCATGATTCGGTGT
GAAAAGCTCCGGCAGTATAGGATGGTCCCGCGTCTGATTAGCTGGTTGGCGGGG
TAACGGCCCACCAAGGCGACGATCAGTAGCCGGCTTGAGAGAGTGGACGGCCAC
ATTGGGACTGAGACACGGCCCAAACTCCTACGGGAGGCAGCAGTGGGGAATATT
GCACAATGGGGGAAACCCTGATGCAGCGACGCCGCGTGAGTGAAGAAGTATTTC
GGTATGTAAAGCTCTATCAGCAGGGAAGAAAAAGACGGTACCTGACTAAGAAG
CCCCGGCTAACTACGTGCCAGCAGCCGCGGTAATACGTAGGGGGCAAGCGTTAT
CCGGAATTACTGGGTGTAAAGGGTGCGTAGGTGGCATGGTAAGTCAGAAGTGAA
AGCCCGGGGCTTAACCCCGGGACTGCTTTTGAAACTGTCATGCTGGAGTGCAGGA
GAGGTAAGCGGAATTCCTAGTGTAGCGGTGAAATGCGTAGATATTAGGAGGAAC
ACCAGTGGCGAAGGCGGCTTACTGGACTGTCACTGACACTGATGCACGAAAGCG
TGGGGAGCAAACAGGATTAGATACCCTGGTAGTCCACGCCGTAAACGATGAATA
CTAGGTGTCGGGGCCGTAGAGGCTTCGGTGCCGCAGCAAACGCAGTAAGTATTC
CACCTGGGGAGTACGTTCGCAAGAATGAAACTCAAAGGAATTGACGGGGACCCG
CACAAGCGGTGGAGCATGTGGTTTAATTCGAAGCAACGCGAAGAACCTTACCTG
GTCTTGACATCTAACTGACCGGTTCGTAATGGGACCTTTCCTTCGGGACAGTTAA
GACAGGTGGTGCATGGTTGTCGTCAGCTCGTGTCGTGAGATGTTGGGTTAAGTCC
CGCAACGAGCGCAACCCCTATCTTTAGTAGCCAGCATATAAGGTGGGCACTCTAG
AGAGACTGCCAGGGATAACCTGGAGGAAGGTGGGGACGACGTCAAATCATCATG

Figure 7 (cont.)

CCCCTTATGGCCAGGGCTACACACGTGCTACAATGGCGTAAACAAAGGGAAGCG
AAGTCGTGAGGCGAAGCAAATCCCAGAAATAACGTCTCAGTTCGGATTGTAGTC
TGCAACTCGACTACATGAAGCTGGAATCGCTAGTAATCGTGAATCAGAATGTCAC
GGTGAATACGTTCCCGGGTCTTGTACACACCGCCCGTCACACCATGGGAGTCAGT
AACGCCCGAAGTCAGTGACCCAACCTTATAGGAGGGAGCTGCCGAAGGTGGGAC
CGATAACTGGGGTGAAGTCGTAACAAGGTAGCCGTATCGGAAGGTGCGGCTGGA
TCACCTCCTTT

>SEQ ID NO:8-VE202-13_16S_prokka_VE202-13_00016 16S ribosomal RNA
AAAGAGTTTGATCCTGGCTCAGGACGAACGCTGGCGGCGCGCCTAACACATGCA
AGTCGAACGGAGCTTACGTTTTGAAGTTTTCGGATGGATGAATGTAAGCTTAGTG
GCGGACGGGTGAGTAACACGTGAGCAACCTGCCTTTCAGAGGGGGATAACAGCC
GGAAACGGCTGCTAATACCGCATGATGTTGCGGGGGCACATGCCCCTGCAACCA
AAGGAGCAATCCGCTGAAAGATGGGCTCGCGTCCGATTAGCCAGTTGGCGGGGT
AACGGCCCACCAAAGCGACGATCGGTAGCCGGACTGAGAGGTTGAACGGCCACA
TTGGGACTGAGACACGGCCCAGACTCCTACGGGAGGCAGCAGTGGGGGATATTG
CACAATGGGCGAAAGCCTGATGCAGCGACGCCGCGTGAGGGAAGACGGTCTTCG
GATTGTAAACCTCTGTCTTTGGGGAAGAAAATGACGGTACCCAAAGAGGAAGCT
CCGGCTAACTACGTGCCAGCAGCCGCGGTAATACGTAGGGAGCAAGCGTTGTCC
GGAATTACTGGGTGTAAAGGGAGCGTAGGCGGGATGGCAAGTAGAATGTTAAAT
CCATCGGCTCAACCGGTGGCTGCGTTCTAAACTGCCGTTCTTGAGTGAAGTAGAG
GCAGGCGGAATTCCTAGTGTAGCGGTGAAATGCGTAGATATTAGGAGGAACACC
AGTGGCGAAGGCGGCCTGCTGGGCTTTAACTGACGCTGAGGCTCGAAAGCGTGG
GGAGCAAACAGGATTAGATACCCTGGTAGTCCACGCCGTAAACGATGATTACTA
GGTGTGGGGGGACTGACCCCTTCCGTGCCGCAGTTAACACAATAAGTAATCCACC
TGGGGAGTACGGCCGCAAGGTTGAAACTCAAAGGAATTGACGGGGGCCCGCACA
AGCAGTGGAGTATGTGGTTTAATTCGAAGCAACGCGAAGAACCTTACCAGGTCTT
GACATCGGATGCATAGCCTAGAGATAGGTGAAGCCCTTCGGGGCATCCAGACAG
GTGGTGCATGGTTGTCGTCAGCTCGTGTCGTGAGATGTTGGGTTAAGTCCCGCAA
CGAGCGCAACCCTTATTATTAGTTGCTACGCAAGAGCACTCTAATGAGACTGCCG
TTGACAAAACGGAGGAAGGTGGGGATGACGTCAAATCATCATGCCCCTTATGAC
CTGGGCTACACACGTACTACAATGGCACTAAAACAGAGGGCGGCGACACCGCGA
GGTGAAGCGAATCCCGAAAAAGTGTCTCAGTTCAGATTGCAGGCTGCAACCCGC

Figure 7 (cont.)

CTGCATGAAGTCGGAATTGCTAGTAATCGCGGATCAGCATGCCGCGGTGAATAC
GTTCCCGGGCCTTGTACACACCGCCCGTCACACCATGGGAGTCGGTAACACCCGA
AGCCAGTAGCCTAACCGCAAGGGGGGCGCTGTCGAAGGTGGGATTGATGACTGG
GGTGAAGTCGTAACAAGGTAGCCGTATCGGAAGGTGCGGCTGGATCACCTCCTTT

>SEQ ID NO:9-VE202-14_16S_prokka_VE202-14_00005 16S ribosomal RNA
TACGAGAGTTTGATCCTGGCTCAGGATGAACGCTGGCGGCGTGCCTAACACATGC
AAGTCGAGCGAAGCGCTGTTTTCAGAATCTTCGGAGGAAGAGGACAGTGACTGA
GCGGCGGACGGGTGAGTAACGCGTGGGCAACCTGCCTCATACAGGGGGATAACA
GTTAGAAATGACTGCTAATACCGCATAAGCGCACAGGACCGCATGGTGTAGTGT
GAAAAACTCCGGTGGTATGAGATGGACCCGCGTCTGATTAGGTAGTTGGTGGGG
TAAAGGCCTACCAAGCCGACGATCAGTAGCCGACCTGAGAGGGTGACCGGCCAC
ATTGGGACTGAGACACGGCCCAAACTCCTACGGGAGGCAGCAGTGGGGAATATT
GCACAATGGGGGAAACCCTGATGCAGCGACGCCGCGTGAAGGAAGAAGTATTTC
GGTATGTAAACTTCTATCAGCAGGGAAGAAGATGACGGTACCTGAGTAAGAAGC
ACCGGCTAAATACGTGCCAGCAGCCGCGGTAATACGTATGGTGCAAGCGTTATC
CGGATTTACTGGGTGTAAAGGGAGCGTAGACGGATAGGCAAGTCTGGAGTGAAA
ACCCAGGGCTCAACCCTGGGACTGCTTTGGAAACTGCAGATCTGGAGTGCCGGA
GAGGTAAGCGGAATTCCTAGTGTAGCGGTGAAATGCGTAGATATTAGGAGGAAC
ACCAGTGGCGAAGGCGGCTTACTGGACGGTGACTGACGTTGAGGCTCGAAAGCG
TGGGGAGCAAACAGGATTAGATACCCTGGTAGTCCACGCCGTAAACGATGACTA
CTAGGTGTCGGTGTGCAAAGCACATCGGTGCCGCAGCAAACGCAATAAGTAGTC
CACCTGGGGAGTACGTTCGCAAGAATGAAACTCAAAGGAATTGACGGGGACCCG
CACAAGCGGTGGAGCATGTGGTTTAATTCGAAGCAACGCGAAGAACCTTACCTG
GTCTTGACATCCGGATGACGGGCGAGTAATGTCGCCGTCCCTTCGGGGCATCCGA
GACAGGTGGTGCATGGTTGTCGTCAGCTCGTGTCGTGAGATGTTGGGTTAAGTCC
CGCAACGAGCGCAACCCTTATCTTCAGTAGCCAGCATATAAGGTGGGCACTCTGG
AGAGACTGCCAGGGAGAACCTGGAGGAAGGTGGGGATGACGTCAAATCATCATG
CCCCTTATGGCCAGGGCTACACACGTGCTACAATGGCGTAAACAAAGGGAAGCG
AGAGGGTGACCTGGAGCGAATCCCAAAAATAACGTCTCAGTTCGGATTGTAGTC
TGCAACTCGACTACATGAAGCTGGAATCGCTAGTAATCGCGGATCAGCATGCCG
CGGTGAATACGTTCCCGGGTCTTGTACACACCGCCCGTCACACCATGGGAGTCAG
TAACGCCCGAAGCCAGTGACCCAACCTTAGAGGAGGGAGCTGTCGAAGGCGGGA

Figure 7 (cont.)

CGGATAACTGGGGTGAAGTCGTAACAAGGTAGCCGTATCGGAAGGTGCGGCTGG
ATCACCTCCTTT

>SEQ ID NO:10-VE202-15_16S_prokka_VE202-15_00018 16S ribosomal RNA
ATTTGAGAGTTTGATCCTGGCTCAGGATGAACGCTGGCGGCGTGCCTAACACATG
CAAGTCGAACGAAGCATTTTAGATGAAGTTTTCGGATGGATTCTGAGATGACTGA
GTGGCGGACGGGTGAGTAACACGTGGATAACCTGCCTCACACTGGGGGACAACA
GTTAGAAATGACTGCTAATACCGCATAAGCGCACAGTACCGCATGGTACGGTGT
GAAAAACTCCGGTGGTGTGAGATGGATCCGCGTCTGATTAGCCAGTTGGCGGGG
TAACGGCCCACCAAAGCGACGATCAGTAGCCGACCTGAGAGGGTGACCGGCCAC
ATTGGGACTGAGACACGGCCCAAACTCCTACGGGAGGCAGCAGTGGGGAATATT
GCACAATGGGCGAAAGCCTGATGCAGCGACGCCGCGTGAGTGAAGAAGTATTTC
GGTATGTAAAGCTCTATCAGCAGGGAAGATAATGACGGTACCTGACTAAGAAGC
CCCGGCTAACTACGTGCCAGCAGCCGCGGTAATACGTAGGGGGCAAGCGTTATC
CGGATTTACTGGGTGTAAAGGGAGCGTAGACGGCATGGCAAGTCTGAAGTGAAA
ACCCAGGGCTCAACCCTGGGACTGCTTTGGAAACTGTCAAGCTAGAGTGCAGGA
GAGGTAAGTGGAATTCCTAGTGTAGCGGTGAAATGCGTAGATATTAGGAGGAAC
ACCAGTGGCGAAGGCGGCTTACTGGACTGTAACTGACGTTGAGGCTCGAAAGCG
TGGGGAGCAAACAGGATTAGATACCCTGGTAGTCCACGCCGTAAACGATGAGTG
CTAGGTGTTGGGGGGCAAAGCCCTTCGGTGCCGTCGCAAACGCAATAAGCACTC
CACCTGGGGAGTACGTTCGCAAGAATGAAACTCAAAGGAATTGACGGGGACCCG
CACAAGCGGTGGAGCATGTGGTTTAATTCGAAGCAACGCGAAGAACCTTACCAA
GTCTTGACATCCTCTTGACCGGCGTGTAACGGCGCCTTTCCTTCGGGACAAGAGA
GACAGGTGGTGCATGGTTGTCGTCAGCTCGTGTCGTGAGATGTTGGGTTAAGTCC
CGCAACGAGCGCAACCCTTATCCTTAGTAGCCAGCATTAAGATGGGCACTCTAGG
GAGACTGCCAGGGACAACCTGGAGGAAGGTGGGGATGACGTCAAATCATCATGC
CCCTTATGATTTGGGCTACACACGTGCTACAATGGCGTAAACAAGGGAAGCGA
CCCTGCGAAGGTGAGCAAATCTCAAAAATAACGTCCCAGTTCGGACTGTAGTCTG
CAACCCGACTACACGAAGCTGGAATCGCTAGTAATCGCGAATCAGAATGTCGCG
GTGAATACGTTCCCGGGTCTTGTACACACCGCCCGTCACACCATGGGAGTCAGCA
ACGCCCGAAGTCAGTGACCCAACCGAAGGAGGGAGCTGCCGAAGGCGGGGCA
GGTAACTGGGGTGAAGTCGTAACAAGGTAGCCGTATCGGAAGGTGCGGCTGGAT
CACCTCCTTT

Figure 7 (cont.)

>SEQ ID NO:11-VE202-16_16S_prokka_VE202-16_00043 16S ribosomal RNA
ATGAGAGTTTGATCCTGGCTCAGGATGAACGCTGGCGGCGTGCCTAACACATGC
AAGTCGAACGAAGCGATTTAACGGAAGTTTTCGGATGGAAGTTGAATTGACTGA
GTGGCGGACGGGTGAGTAACGCGTGGGTAACCTGCCTTGTACTGGGGGACAACA
GTTAGAAATGACTGCTAATACCGCATAAGCGCACAGTATCGCATGATACAGTGT
GAAAAACTCCGGTGGTACAAGATGGACCCGCGTCTGATTAGCTAGTTGGTAAGG
TAACGGCTTACCAAGGCGACGATCAGTAGCCGACCTGAGAGGGTGACCGGCCAC
ATTGGGACTGAGACACGGCCCAAACTCCTACGGGAGGCAGCAGTGGGGAATATT
GCACAATGGGCGAAAGCCTGATGCAGCGACGCCGCGTGAGTGAAGAAGTATTTC
GGTATGTAAAGCTCTATCAGCAGGGAAGAAAATGACGGTACCTGACTAAGAAGC
CCCGGCTAACTACGTGCCAGCAGCCGCGGTAATACGTAGGGGGCAAGCGTTATC
CGGATTTACTGGGTGTAAAGGGAGCGTAGACGGTAAAGCAAGTCTGAAGTGAAA
GCCCGCGGCTCAACTGCGGGACTGCTTTGGAAACTGTTTAACTGGAGTGTCGGAG
AGGTAAGTGGAATTCCTAGTGTAGCGGTGAAATGCGTAGATATTAGGAGGAACA
CCAGTGGCGAAGGCGACTTACTGGACGATAACTGACGTTGAGGCTCGAAAGCGT
GGGGAGCAAACAGGATTAGATACCCTGGTAGTCCACGCCGTAAACGATGAATAC
TAGGTGTTGGGGAGCAAAGCTCTTCGGTGCCGTCGCAAACGCAGTAAGTATTCCA
CCTGGGGAGTACGTTCGCAAGAATGAAACTCAAAGGAATTGACGGGGACCCGCA
CAAGCGGTGGAGCATGTGGTTTAATTCGAAGCAACGCGAAGAACCTTACCAGGT
CTTGACATCGATCCGACGGGGGAGTAACGTCCCCTTCCCTTCGGGGCGGAGAAG
ACAGGTGGTGCATGGTTGTCGTCAGCTCGTGTCGTGAGATGTTGGGTTAAGTCCC
GCAACGAGCGCAACCCTTATTCTAAGTAGCCAGCGGTTCGGCCGGGAACTCTTGG
GAGACTGCCAGGGATAACCTGGAGGAAGGTGGGGATGACGTCAAATCATCATGC
CCCTTATGATCTGGGCTACACACGTGCTACAATGGCGTAAACAAAGAGAAGCAA
GACCGCGAGGTGGAGCAAATCTCAAAAATAACGTCTCAGTTCGGACTGCAGGCT
GCAACTCGCCTGCACGAAGCTGGAATCGCTAGTAATCGCGAATCAGAATGTCGC
GGTGAATACGTTCCCGGGTCTTGTACACACCGCCCGTCACACCATGGGAGTCAGT
AACGCCCGAAGTCAGTGACCCAACCGCAAGGAGGGAGCTGCCGAAGGCGGGAC
CGATAACTGGGGTGAAGTCGTAACAAGGTAGCCGTATCGGAAGGTGCGGCTGGA
TCACCTCCTTT

Figure 7 (cont.)

>SEQ ID NO:12-VE202-18_16S_prokka_VE202-18_00016 16S ribosomal RNA
ATGGAGAGTTTGATCCTGGCTCAGGATGAACGCTGGCGGCGTGCCTAATACATGC
AAGTCGAACGCGAGCACTTGTGCTCGAGTGGCGAACGGGTGAGTAATACATAAG
TAACCTGCCCTAGACAGGGGGATAACTATTGGAAACGATAGCTAAGACCGCATA
GGTACGGACACTGCATGGTGACCGTATTAAAAGTGCCTCAAAGCACTGGTAGAG
GATGGACTTATGGCGCATTAGCTGGTTGGCGGGGTAACGGCCCACCAAGGCGAC
GATGCGTAGCCGACCTGAGAGGGTGACCGGCCACACTGGGACTGAGACACGGCC
CAGACTCCTACGGGAGGCAGCAGTAGGGAATTTTCGGCAATGGGGGAAACCCTG
ACCGAGCAACGCCGCGTGAAGGAAGAAGGTTTTCGGATTGTAAACTTCTGTTATA
AGGAAGAACGGCGGCTACAGGAAATGGTAGCCGAGTGACGGTACTTTATTAGA
AGCCACGGCTAACTACGTGCCAGCAGCCGCGGTAATACGTAGGTGGCAAGCGT
TATCCGGAATTATTGGGCGTAAAGAGGGAGCAGGCGGCAGCAAGGGTCTGTGGT
GAAAGCCTGAAGCTTAACTTCAGTAAGCCATAGAAACCAGGCAGCTAGAGTGCA
GGAGAGGATCGTGGAATTCCATGTGTAGCGGTGAAATGCGTAGATATATGGAGG
AACACCAGTGGCGAAGGCGACGATCTGGCCTGCAACTGACGCTCAGTCCCGAAA
GCGTGGGGAGCAAATAGGATTAGATACCCTAGTAGTCCACGCCGTAAACGATGA
GTACTAAGTGTTGGATGTCAAAGTTCAGTGCTGCAGTTAACGCAATAAGTACTCC
GCCTGAGTAGTACGTTCGCAAGAATGAAACTCAAAGGAATTGACGGGGGCCCGC
ACAAGCGGTGGAGCATGTGGTTTAATTCGAAGCAACGCGAAGAACCTTACCAGG
TCTTGACATACTCATAAAGGCTCCAGAGATGGAGAGATAGCTATATGAGATACA
GGTGGTGCATGGTTGTCGTCAGCTCGTGTCGTGAGATGTTGGGTTAAGTCCCGCA
ACGAGCGCAACCCTTATCGTTAGTTACCATCATTAAGTTGGGGACTCTAGCGAGA
CTGCCAGTGACAAGCTGGAGGAAGGCGGGGATGACGTCAAATCATCATGCCCCT
TATGACCTGGGCTACACACGTGCTACAATGGATGGTGCAGAGGGAAGCGAAGCC
GCGAGGTGAAGCAAAACCCATAAACCATTCTCAGTTCGGATTGTAGTCTGCAA
CTCGACTACATGAAGTTGGAATCGCTAGTAATCGCGAATCAGCATGTCGCGGTGA
ATACGTTCTCGGGCCTTGTACACACCGCCCGTCACCACGAGAGTTGATAACAC
CCGAAGCCGGTGGCCTAACCGCAAGGAAGGAGCTGT >SEQ ID NO:13-VE202-21_16S_prokka_VE202-21_00009 16S ribosomal RNA
AACGAGAGTTTGATCCTGGCTCAGGATGAACGCTGGCGGCGTGCTTAACACATG
CAAGTCGAGCGAAGCGCTTTACTTAGATTTCTTCGGATTGAAAAGTTTTGCGACT

Figure 7 (cont.)

GAGCGGCGGACGGGTGAGTAACGCGTGGGTAACCTGCCTCATACAGGGGATAA
CAGTTAGAAATGACTGCTAATACCGCATAAGACCACAGTACCGCATGGTACAGT
GGGAAAAACTCCGGTGGTATGAGATGGACCCGCGTCTGATTAGCTAGTTGGTAA
GGTAACGGCTTACCAAGGCGACGATCAGTAGCCGACCTGAGAGGGTGACCGGCC
ACATTGGGACTGAGACACGGCCCAAACTCCTACGGGAGGCAGCAGTGGGGAATA
TTGCACAATGGGGGAAACCCTGATGCAGCGACGCCGCGTGAAGGATGAAGTATT
TCGGTATGTAAACTTCTATCAGCAGGGAAGAAAATGACGGTACCTGACTAAGAA
GCCCCGGCTAACTACGTGCCAGCAGCCGCGGTAATACGTAGGGGGCAAGCGTTA
TCCGGATTTACTGGGTGTAAAGGGAGCGTAGACGGTTATGTAAGTCTGATGTGAA
AACCCGGGGCTCAACCCCGGGACTGCATTGGAAACTATGTAACTAGAGTGTCGG
AGAGGTAAGTGGAATTCCTAGTGTAGCGGTGAAATGCGTAGATATTAGGAGGAA
CACCAGTGGCGAAGGCGGCTTACTGGACGATGACTGACGTTGAGGCTCGAAAGC
GTGGGGAGCAAACAGGATTAGATACCCTGGTAGTCCACGCCGTAAACGATGCAT
ACTAGGTGTCGGGTGGCAAAGCCATTCGGTGCCGCAGCAAACGCAATAAGTATG
CCACCTGGGGAGTACGTTCGCAAGAATGAAACTCAAAGGAATTGACGGGGACCC
GCACAAGCGGTGGAGCATGTGGTTTAATTCGAAGCAACGCGAAGAACCTTACCT
GCTCTTGACATCCCCCTGACCGGCGCGTAATGGTGCCTTTCCTTCGGGACAGGGG
AGACAGGTGGTGCATGGTTGTCGTCAGCTCGTGTCGTGAGATGTTGGGTTAAGTC
CCGCAACGAGCGCAACCCTTATCTTTAGTAGCCAGCGGTTTGGCCGGGCACTCTA
GAGAGACTGCCAGGGATAACCTGGAGGAAGGTGGGGATGACGTCAAATCATCAT
GCCCCTTATGAGCAGGGCTACACACGTGCTACAATGGCGTAAACAAAGGGAGGC
GAAGCCGCGAGGTGGAGCAAATCCCAAAAATAACGTCTCAGTTCGGATTGTAGT
CTGCAACTCGACTACATGAAGCTGGAATCGCTAGTAATCGCGAATCAGAATGTC
GCGGTGAATACGTTCCCGGGTCTTGTACACACCGCCCGTCACACCATGGGAGTTG
GTAACGCCCGAAGTCAGTGACCCAACC

>SEQ ID NO:14-VE202-26_16S_prokka_VE202-26_00001 16S ribosomal RNA
TGAGTGGCGGACGGGTGAGTAACGCGTGGGCAACCTGCCTTGCACTGGGGGATA
ACAGCCAGAAATGGCTGCTAATACCGCATAAGACCGAAGCGCCGCATGGCGCAG
CGGCCAAAGCCCCGGCGGTGCAAGATGGGCCCGCGTCTGATTAGGTAGTTGGCG
GGGTAACGGCCCACCAAGCCGACGATCAGTAGCCGACCTGAGAGGGTGACCGGC
CACATTGGGACTGAGACACGGCCCAGACTCCTACGGGAGGCAGCAGTGGGGAAT
ATTGCACAATGGGGGAAACCCTGATGCAGCGACGCCGCGTGAAGGATGAAGTAT

Figure 7 (cont.)

TTCGGTATGTAAACTTCTATCAGCAGGGAAGAAGATGACGGTACCTGACTAAGA
AGCCCCGGCTAACTACGTGCCAGCAGCCGCGGTAATACGTAGGGGGCAAGCGTT
ATCCGGATTTACTGGGTGTAAAGGGAGCGTAGACGGCGATGCAAGCCAGATGTG
AAAGCCCGGGGCTCAACCCCGGGACTGCATTTGGAACTGCGTGGCTGGAGTGTC
GGAGAGGCAGGCGGAATTCCTAGTGTAGCGGTGAAATGCGTAGATATTAGGAGG
AACACCAGTGGCGAAGGCGGCCTGCTGGACGATGACTGACGTTGAGGCTCGAAA
GCGTGGGGAGCAAACAGGATTAGATACCCTGGTAGTCCACGCCGTAAACGATGA
CTACTAGGTGTCGGGTGGCAAGGCCATTCGGTGCCGCAGCAAACGCAATAAGTA
GTCCACCTGGGGAGTACGTTCGCAAGAATGAAACTCAAAGGAATTGACGGGGAC
CCGCACAAGCGGTGGAGCATGTGGTTTAATTCGAAGCAACGCGAAGAACCTTAC
CTGATCTTGACATCCCGATGCCAAAGCGCGTAACGCGCTCTTTCTTCGGAACATC
GGTGACAGGTGGTGCATGGTTGTCGTCAGCTCGTGTCGTGAGATGTTGGGTTAAG
TCCCGCAACGAGCGCAACCCCTATCTTCAGTAGCCAGCATTCCGGATGGGCACTC
TGGAGAGACTGCCAGGGACAACCTGGAGGAAGGTGGGGATGACGTCAAATCATC
ATGCCCCTTATGACCAGGGCTACACACGTGCTACAATGGCGTAAACAAAGGGAG
GCGAACCCGCGAGGGTGGGCAAATCCCAAAAATAACGTCTCAGTTCGGATTGTA
GTCTGCAACTCGACTACATGAAGCTGGAATCGCTAGTAATCGCGAATCAGAATGT
CGCGGTGAATACGTTCCCGGGTCTTGTACACACCGCCCGTCACACCATGGGAGTC
AGTAACGCCCGAAGCCGGTGACCCAACCCGTATGGGAGGGAGCCGTCGAAGGTG
GGACCGATAACTGGGGTGAAGTCGTAACAAGGTAGCCGTATCGGAAGGTGCGGC
TGGATCACCTCCTTT

>SEQ ID NO:15-VE202-27_16S_prokka_VE202-27_00024 16S ribosomal RNA
AGAGAGTTTGATCCTGGCTCAGGATGAACGCTGGCGGCGTGCCTAACACATGCA
AGTCGAACGGAGTTATGCAGAGGAAGTTTTCGGATGGAATCGGCGTAACTTAGT
GGCGGACGGGTGAGTAACGCGTGGGAAACCTGCCTGTACCGGGGATAACACTT
AGAAATAGGTGCTAATACCGCATAAGCGCACAGCTTCACATGAGGCAGTGTGAA
AAACTCCGGTGGTACAGGATGGTCCCGCGTCTGATTAGCCAGTTGGCAGGGTAA
CGGCCTACCAAAGCGACGATCAGTAGCCGGCCTGAGAGGGTGAACGGCCACATT
GGGACTGAGACACGGCCCAAACTCCTACGGGAGGCAGCAGTGGGGAATATTGCA
CAATGGGGGAAACCCTGATGCAGCGACGCCGCGTGAGTGAAGAAGTATTTCGGT
ATGTAAAGCTCTATCAGCAGGGAAGAAAATGACGGTACCTGACTAAGAAGCCCC
GGCTAACTACGTGCCAGCAGCCGCGGTAATACGTAGGGGGCAAGCGTTATCCGG

Figure 7 (cont.)

ATTTACTGGGTGTAAAGGGAGCGTAGACGGCATGACAAGCCAGATGTGAAAACC
CAGGGCTCAACCCTGGGACTGCATTTGGAACTGCCAGGCTGGAGTGCAGGAGAG
GTAAGCGGAATTCCTAGTGTAGCGGTGAAATGCGTAGATATTAGGAGGAACACC
AGTGGCGAAGGCGGCTTACTGGACTGTAACTGACGTTGAGGCTCGAAAGCGTGG
GGAGCAAACAGGATTAGATACCCTGGTAGTCCACGCGGTAAACGATGATTGCTA
GGTGTAGGTGGGTATGGACCCATCGGTGCCGCAGCTAACGCAATAAGCAATCCA
CCTGGGGAGTACGTTCGCAAGAATGAAACTCAAAGGAATTGACGGGGACCCGCA
CAAGCGGTGGAGCATGTGGTTTAATTCGAAGCAACGCGAAGAACCTTACCAAGT
CTTGACATCCCAATGACGTGTCCGTAACGGGGCATTCTCTTCGGAGCATTGGAGA
CAGGTGGTGCATGGTTGTCGTCAGCTCGTGTCGTGAGATGTTGGGTTAAGTCCCG
CAACGAGCGCAACCCTTATCCTTAGTAGCCAGCAGGTAAAGCTGGGCACTCTAG
GGAGACTGCCGGGGATAACCCGGAGGAAGGCGGGGATGACGTCAAATCATCATG
CCCCTTATGATTTGGGCTACACACGTGCTACAATGGCGTAAACAAAGGGAAGCG
AGACAGTGATGTTGAGCAAATCCCAGAAATAACGTCTCAGTTCGGATTGTAGTCT
GCAACTCGACTACATGAAGCTGGAATCGCTAGTAATCGCGAATCAGCATGTCGC
GGTGAATACGTTCCCGGGTCTTGTACACACCGCCCGTCACACCATGGGAGTTGGA
AATGCCCGAAGCCTGTGACCTAACC

>SEQ ID NO:16-VE202-28_16S
AATTTGAGAGTTTGATCCTGGCTCAGGATGAACGCTGGCGGCGTGCCTAACACAT
GCAAGTCGAACGAAGCATCttATAGGAAGTTTTCGGATGGAATATGGGATGACTG
AGTGGCGGACGGGTGAGTAACGCGTGGATAACCTGCCTCACACTGGGGGATAAC
AGTTAGAAATGGCTGCTAATACCGCATAAGCGCACAGTACCGCATGGTACGGTG
TGAAAACCCAGGTGGTGTGAGATGGATCCGCGTCTGATTAGCCAGTTGGCGGG
GTAACGGCCCACCAAAGCGACGATCAGTAGCCGACCTGAGAGGGTGACCGGCCA
CATTGGGACTGAGACACGGCCCAAACTCCTACGGGAGGCAGCAGTGGGGAATAT
TGCACAATGGGCGAAAGCCTGATGCAGCGACGCCGCGTGAGTGAAGAAGTATCT
CGGTATGTAAAGCTCTATCAGCAGGGAAGAAAATGACGGTACCTGACTAAGAAG
CCCCGGCTAACTACGTGCCAGCAGCCGCGGTAATACGTAGGGGGCAAGCGTTAT
CCGGATTTACTGGGTGTAAAGGGAGCGTAGACGGCGATGCAAGTCTGAAGTGAA
AGCCCGGGGCTCAACCCCGGGACTGCTTTGGAAACTGTGTGGCTGGAGTGCAGG
AGAGGTAAGTGGAATTCCTAGTGTAGCGGTGAAATGCGTAGATATTAGGAGGAA
CACCAGTGGCGAAGGCGGCTTACTGGACTGTAACTGACGTTGAGGCTCGAAAGC

Figure 7 (cont.)

GTGGGGAGCAAACAGGATTAGATACCCTGGTAGTCCACGCCGTAAACGATGAAT
GCTAGGTGTCGGGGGGCAAAGCCCCTCGGTGCCGCCGCTAACGCAATAAGCATT
CCACCTGGGGAGTACGTTCGCAAGAATGAAACTCAAAGGAATTGACGGGGACCC
GCACAAGCGGTGGAGCATGTGGTTTAATTCGAAGCAACGCGAAGAACCTTACCA
AGTCTTGACATCCCCCTGACCGGACAGTAACGTGTCCCTTCCTTCGGGACAGGGG
AGACAGGTGGTGCATGGTTGTCGTCAGCTCGTGTCGTGAGATGTTGGGTTAAGTC
CCGCAACGAGCGCAACCCTTATCCTTAGTAGCCAGCAccTCGGGTGGGCACTCTA
GGGAGACTGCCAGGGATAACCTGGAGGAAGGTGGGGATGACGTCAAATCATCAT
GCCCCTTATGATTTGGGCTACACACGTGCTACAATGGCGTAAACAAAGGGAaGcg
GCCCTGCGAAGGTGAGCAAATCCCAAAAATAACGTCCCAGTTCGGACTGTAGTC
TGCAACCCGACTACACGAAGCTGGAATCGCTAGTAATCGCGGATCAGAATGCCG
CGGTGAATACGTTCCCGGGTCTTGTACACACCGCCCGTCACACCATGGGAGTCAG
CAACGCCCGAAGTCAGTGACCCAACCGAAGGAGGGAGCTGCCGAAGGCGGGG
CAGGTAACTGGGGTGAAGTCGTAACAAGGTAGCCGTATCGGAAGGTGCGGCTGG
ATCACCTCCTTTCTAAGGAAGAAGAAGTAgGGGTTTT

>SEQ ID NO:17-VE202-29_16S
gAaTtGAcAAaCAGTTACGCCTTATGtAtAATAACaTTtgCGctaCCGAATGGGaACgCGCA
cTTCaTATTGGTAGAGgATAGTtCAGTTTtGTGGaGAAAtACtCAaGAGGCTGAAgAGG
CGCCCCTGCTAAGGgtGTAGGtCGTTTATAgcGGCGCGAGGGTTCAAATCCCtcTTtCT
CCGTtCCCTTtACCGATatAAAGGGGAGCTTGaTTAtaGCTTcGCGGGAAAaGAATcTtA
AGaGATTGAGaTttctTTTTTTtCGCACTTTtGCCGgATGAAAAGAACGAGTAAAaCTTA
TGGAAAatATAGGTTAAAAAaGTTGTTGACATTTGACAAatATGGTGCTATAAtGA
AAGTCCACCGCGAATGGCGATGGAaCAGAGATTTAAAaGAAATAAAAAAAGTTA
AAAAaGTGCTTGACTGGCAGAACAACATGTGATAAGATATCAACTGTTGCGGCTG
AGAAAGCAGCACACAGAACCTTGACAAATAAACAGTAATGCAACCcTGAAAATT
CTAAAAAaGAAAATTCAGAGAACAAGTTTTAAAGCTTCGAGAGAAGACCTTtAAG
ACACCCAAAAACAGTAAGAAATGTTTGGAAACAAACAAACGGTTAAAcATTAGC
TAGAGTtAATCTtAaCCGgATTAAaCACTtAAaCAAGAGAGTTtGATCCTGGCTCAGG
ATGAACGCTGGCGGCGTGCCTAACACATGCAAGTCGAACGAAGTTAgACaGAGG
AAGTTTTCGGATGGAATCGGTATAACTTAGTGGCGGACGGGTGAGTAACGCGTG
GGAAACCTGCCCTGTACCGGGGGATAACACTTAGAAATAGGTGCTAATACCGCA
TAAGCGCACGGAACCGCATGGTTCtGTGTGAAAAACTCCGGTGGTACAGGATGGT

Figure 7 (cont.)

CCCGCGTCTGATTAGCCAGTTGGCAGGGTAACGGCCTACCAAAGCGACGATCAG
TAGCCGGCCTGAGAGGGTGAACGGCCACATTGGGACTGAGACACGGCCCAAACT
CCTACGGGAGGCAGCAGTGGGGAATATTGCACAATGGGGGAAACCCTGATGCAG
CGACGCCGCGTGAGTGAAGAAGTATTTCGGTATGTAAAGCTCTATCAGCAGGGA
AGAAAATGACGGTACCTGACTAAGAAGCCCCGGCTAACTACGTGCCAGCAGCCG
CGGTAATACGTAGGGGGCAAGCGTTATCCGGATTTACTGGGTGTAAAGGGAGCG
TAGACGGCATGGCAAGCCAGATGTGAAAACCCAGGGCTCAACCTTGGGATTGCA
TTTGGAACTGCCAGGCTGGAGTGCAGGAGAGGTAAGCGGAATTCCTAGTGTAGC
GGTGAAATGCGTAGATATTAGGAGGAACACCAGTGGCGAAGGCGGCTTACTGGA
CTGTAACTGACGTTGAGGCTCGAAAGCGTGGGGAGCAAACAGGATTAGATACCC
TGGTAGTCCACGCGGTAAACGATGATTGCTAGGTGTAGGTGGGTATGGACCCATC
GGTGCCGCAGCTAACGCAATAAGCAATCCACCTGGGGAGTACGTTCGCAAGAAT
GAAACTCAAAGGAATTGACGGGGACCCGCACAAGCGGTGGAGCATGTGGTTTAA
TTCGAAGCAACGCGAAGAACCTTACCAAGTCTTGACATCCCAATGACGCACCTGT
AAAGAGGTGTTCCCTTCGGGGCATTGGAGACAGGTGGTGCATGGTTGTCGTCAGC
TCGTGTCGTGAGATGTTGGGTTAAGTCCCGCAACGAGCGCAACCCTTATTCTTAG
TAGCCAGCAGGTAAAGCTGGGCACTCTAAGGAGACTGCCGGGGATAACCCGGAG
GAAGGCGGGGATGACGTCAAATCATCATGCCCCTTATGATTTGGGCTACACACGT
GCTACAATGGCGTAAACAAAGGGAAGCGAGACAGTGATGTGGAGCAAATCCCA
GAAATAACGTCTCAGTTCGGATTGTAGTCTGCAACTCGACTACATGAAGCTGGAA
TCGCTAGTAATCGCGAATCAGCATGTCGCGGTGAATACGTTCCCGGGTCTTGTAC
ACACCGCCCGTCACACCATGGGAGTTGGAAATGCCCGAAGTCTGTGACCTAACC
GAAAGGGAGGAGCAGCCGAAGGCAGGTCTGATAACTGGGGTGAAGTCGTAACA
AGGTAGCCGTATCGGAAGGTGCGGCTGGATCACCTCCTTTCTAAGGCGAAGAAG
TAGGGGTTGTATTACTGTTTAGATGTT

SEQUENCE LISTING

<160> NUMBER OF SEQ ID NOS: 57

<210> SEQ ID NO 1
<211> LENGTH: 2313
<212> TYPE: DNA
<213> ORGANISM: Clostridiales bacterium VE202-01

<400> SEQUENCE: 1

```
caggattcct cgtgtcccgc cgtactcagg tgctgtctca agcttcctca ctatttcgac      60
tacggggctc tcaccctgtt tcgccggact tcccattccg ttcgtctata atgtcttctt     120
gctctttctc gacagtcctt caacccgat ccttggatcg gtttgggctc ctcccctttc     180
gctcgccact acttagggaa tcatttcttt attttctctt ccttcaggta cttagatgtt     240
tcagttccct gagtctcacc tctctgaagc tattttttca cttcaggata cccggtctct     300
actccgggtg ggttccccca ttcggatatc gacggctctt cgcatgctta ctgcttaccg     360
tcgcatttcg ctgtttgctg cgtccttctt cgcctctctg tgcctaggca tccgccatac     420
gctctttctt actttaccta ttggtgttct tgatcacttt actatttact ttcgtctctt     480
cagtgattct tttcttagtt ttcgacttct ctagaaagac ctcaataatc ttcttatctc     540
gatctcttct tttctatcgc aaatttcttc tattatccag ttttcaatga tctctttta     600 gcaatactcc tcctgagcat cactcaaaac taaacagtat taatgaaact tcacttctct     660
tctttctcct tagaaaggag gtgatccatc cccacgttcc cgtagggata ccttgttacg     720
acttcacccc aatcatcaat cccaccttag acagctccct ccttgcggtt aggccaccgg     780
cttcgggtgt tatcaactct catggtgtga cgggcggtgt gtacaaggcc cgagaacgta     840
ttcaccgcga catgctgatt cgcgattact agcgattcca acttcatgta gtcgagttgc     900
agactacaat ccgaactgag aatggttttc tgggtttcgc tccacctcgc ggcttcgctt     960
ccctctgctc catccattgt agcacgtgtg tagcccaggt cataagggc atgatgattt    1020 gacgtcatcc ccgccttcct ccagcttgtc actggcagtc tcgctagagt ccccaactta    1080
atgatggtaa ctaacgataa gggttgcgct cgttgcggga cttaacccaa catctcacga    1140
cacgagctga cgacaaccat gcaccacctg tatcccatat atctatctct ccatctctgg    1200
agcctttatg agtatgtcaa gacctggtaa ggttcttcgc gttgcttcga attaaaccac    1260
atgctccacc gcttgtgcgg gccccgtca attcctttga gtttcattct tgcgaacgta    1320
ctactcaggc ggagtactta ctgcgttaac tgcagcactg agatttgact cccaacactt    1380
agtactcatc gtttacggcg tggactacta gggtatctaa tcctatttgc tccccacgct    1440
```

```
ttcgggactg agcgtcagtt gcaggccaga tcgtcgcctt cgccactggt gttcctccat    1500
atatctacgc atttcaccgc tacacatgga attccacgat cctctcctgc actctagctg    1560
cccggtttct atggcttact gaagttaagc ttcagtcttt caccacagac ccttgctgcc    1620
gcctgctccc tctttacgcc caataattcc ggataacgct tgccacctac gtattaccgc    1680
ggctgctggc acgtagttag ccgtggcttc ctcataaagt accgtcactc ggataccatt    1740
ccctgtatcc gcctttcttc ctttataaca gaagtttaca gtccgaagac cttcctcctt    1800
cacgcggcgt tgctcggtca gggttccccc cattgccgaa aattccctac tgctgcctcc    1860
cgtaggagtc tgggccgtgt ctcagtccca gtgtggccgg tcaccctctc aggtcggcta    1920
cgcatcgtcg ccttggtgag ccgttacctc accaactagc taatgcgcca taagtccatc    1980
ctctaccagt gccttggcac tttaataaa cttaccatgc ggtatcttta cctatgcggt    2040
cttagctatc gtttccaata gttatccccc tgtaaagggc aggttactta tgtattactc    2100
acccgttcgc cactcgggca ttgctgcccg cgttcgactt gcatgtatta ggcacgccgc    2160
cagcgttcat cctgagccag atcaaactc tccattgtct ctttatcttt acaatctttc    2220
gtttgtttag ctcttctttt tctcttctat ccgtttccgg atccttcttt gacgtgtgtt    2280
tcttaattct gtttagtttt caatgatctc tcc                                 2313
```

<210> SEQ ID NO 2
<211> LENGTH: 5698
<212> TYPE: DNA
<213> ORGANISM: Clostridiales bacterium VE202-03

<400> SEQUENCE: 2

```
ttttgtgtcg gcgttaccta tcttcccggt ccgtctccag acaagtattt tcggcgcagg      60
tgagcttaac ttccgtgttc gggatgggaa cgggtggacc ctcaccgcaa tcaacaccaa     120
cttactttcc ttcgaaaaga aaagtaagca aagaaactc taacaacttt cttctcctta     180
ccgttcttct caacgataag tcattatatt cattttcttc ctctttgtca agagaaaaat    240
gatggtgacc cgtgcgggaa tcgaacccac gtttgcggcg tgagaggccg ccgtcttagc    300
cgcttgacca acgggccatt ggtgcgcctt cacggattcg aaccggggac ccactgatta    360
agagtcagtt gctctaccag ctgagctaaa ggcgcttgtc gccaccatcc agggtgctgc    420
accctcaaaa ccgaacaatg taaatcttcc gcacttcgca agcgcctgca atcatccatg    480
ttaaggtcaa gccctcggct tattagtacc ggtcagctgc acacgttacc gtgcttccac    540
ctccggccta tcaacgacat agtctacgtc gtgccttact tctttcgaat gagagatcta    600
atcttagggg gagtttcacg cttagatgcc ttcagcgttt atctcgtccg tacatagcta    660
cccagctatg cccttggcag acaactggt gcaccagagg tacgtccatc ccggtcctct    720
cgtactaagg acagctccct tcaaatctct tacgcccgca acagataggg accgaactgt    780
ctcacgacgt tctgaaccca gctcgcgtgc cactttaatc ggcgaacagc gaacccttg    840
ggaccgaata cagccccagg atgtgacgag ccgacatcga ggtgccaaac ctccccgtcg    900
ctgtggacgc ttgggggaga tcagcctgtt atccccaggg tagctttat ccgttgagcg    960
acggcacttc cacttgcata ccgccggatc actaactcca actttcgtta ctgctcgacc   1020
cgtcggtctc gcagttaggc tcgtttatgc gtttacactc actgcacggt ttccgtccgt   1080
gctgaacgaa cctttgagcg cctccgttac cttttaggag gcgaccgccc cagtcaaact   1140
gcccacctaa cagtgtcccc cgaccggatt cacggccgca ggttagaaaa ccagcaaatc   1200
```

```
aagggtggta tcccaagggt gactccacca aagctgacgc cctggcttcc aagtctccca    1260
cctatcctgt acatgattta ccgatttcca gtattaagct acagtaaagc tccatggggt    1320
ctttccgtct agttgcgggt aactggcttc ttcaccagta caacaatttc gccgggtggg    1380
ctgttgagac agcgcccaag tcgttacgcc attcgtgcgg gtcagaactt acctgacaag    1440
gaatttcgct accttaggac cgttatagtt acggccgccg tttactgggg cttcgattca    1500
atgcttcgcc ttgcggctaa catctcctct taaccttcca gcaccgggca ggcgtcagcc    1560
cctatacgtc atctttcgat ttagcagaga cctgtgtttt tggtaaacag tcgcttgggc    1620
ctattcgctg cggcctcccg taggaggctc cccttatccc gaagttacgg ggtcattttg    1680
ccgagttcct taacaaccct ctcccgttg gccttaggat tctctcctca tctacctgtg    1740
tcggtttgcg gtacgggcac cttagcatac catacacctt ttctcgccac agagcatcgc    1800
ggacttccct actaaagttc ggtcccttac gcccgggtca accaacgccc gggtcccgct    1860
atctccatgt gtcagtgtac ttaaggttcg gtggctacgg aatttcaacc gtatgtgcat    1920
cgactacgcc ttccggcctc gccttagctc ccggcttacc ctgggcggac gaaccttccc    1980
caggaaacct tagattttcg gccattatga ttcccacata attctcgcta ctcattccgg    2040
cattctcact cgaatacagt ccaccgctgc ttccgctgcg acttcacccc atattcgacg    2100
ctcccctacc ccgcacattg ctgtgcagcc caagcttcgg tgttacgctt agccccgtta    2160
tattttccgc gcagagtcac tcgaccagtg agctattacg cactcttta atgagtggct    2220 gcttctaagc caacatcctg gttgttttcg caactccaca tcgtttttcca cttagcgtat    2280 ctttgggacc ttagctgtgg gtctgggctg tttcccttt gtccacgaga cttatctcac    2340
gtagactgac tgctggccat caattatccg gcattcagag tttgataggg ttcagtaacc    2400
ttatcggccc ctagcccatt cagtgcttta cctccggtaa tctaagccaa cgctagccct    2460
aaagctattt cggggagaac cagctatctc cgagttcgat tggaatttca ccgctatcca    2520
caggtcatcg ccgaccattg caacgggcgt gcgttcggtc ctccatgggg ttttaccccc    2580
acttcaacct gcccatggat aggtcacccg gtttcgggtc tattgccact gacttcatac    2640
gccctattca gactcggtct ccctgcgcct ccggcactga atgccttaag cttgccagta    2700
acaataactc gccggaccat tctacaaaag gtacctcatc acccttaac gggctttgag    2760 tgcttgtaag cacaaggttt caggttctct ttcactcccc tcccggggtc cttttcacct    2820
ttccctcacg gtactgctcc tctatcggtc atcaggtagt atttagggtt ggagggtggt    2880 cccccccagct tcccaccggg tttcacgtgt ccggcggtac tctggatcca gtcgcacaac    2940
cttccctttc ggatacgggg ctatcacccg ctatggccgg ccttcccata ccgttctcct    3000
agttccagtt gctaaaaaac tgtccacaac cccggaggat aaatcctccg gtttgccctc    3060
ttccgcgttc gctcgccact actagcggaa tctcggttga tttctcttcc tcgccctact    3120
tagatgtttc agttcaggcg gttccccgcg tacgcctatt tgattcaacg cacgctgaca    3180
gagtattgct ctgccgggtt tccccattcg gaaatctgcg ggtcaaagct tatgtgcagc    3240
tcaccgcagc ttatcgcagc ttgtcacgtc cttcgtcggc tcctgatgcc aaggcattcc    3300
ccttgcgctc tttctagctt gaccttgtag aacagtctca tctctgagct gttctcaaaa    3360
tcatgaatta tgcaggcatc acagaagttt tgcaattagc tccattgttt ttacccttac    3420
tagaacggct ttcgccattc tatcttagtt ccacaacatt gctgttttgc cctctgttgc    3480
ttgctcttgt actttcgatt tacattgttc agttttcaag gtgccgcctt ccagccttta    3540
aggccagatt ttaacactca atcccttgag tgttaaaatc cattcttaaa ttggtggagg    3600
```

```
ttaccggact cgaaccggtg accccctgct tgcaaagcag gtgttctacc agctgaacta    3660
aaccccagg gttttggtgg tgggcccaag tggactcgaa ccaccgacct cacgattatc    3720
agtcgtgcgc tctagccagc tgagctatgg gcccgtcgtc gtcgacgcaa agtccgctcc    3780
gttcgtgacg tcctcacggc catccctcac tgcgctctct tgcgtctcct ctcccgaaca    3840
gacccgcttc gccgggctct gttcgggtac ccgagagtgt accctctaaa ttaaacaacg    3900
tgaaagccat tcgctccaga aagctgacct taggacgtta caacagaaaa ctacttccgt    3960
tgaagtctcc ttagaaagga ggtgatccag ccgcaccttc cgatacggct accttgttac    4020
gacttcaccc caattatcga acccaccttc ggccgcgccc tccttgcggt taggctacgg    4080
acttcgggtg ttcccgactc tcatggtgtg acgggcggtg tgtacaaggc ccgggaacgt    4140
attcaccgcg gcatgctgat ccgcgattac tagcgattcc aacttcatac aggcgggttt    4200
cagcctgcaa tccgaactgg gatggctttt agggatttgc tccacctcgc ggtattgcct    4260
ccctctgtta accaccattg tagtacgtgt gtggcccagg acataagggg catgatgatt    4320
tgacgtcgtc cccaccttcc tccgttttgt caacggcagt ctcgctagag tgctcttgcg    4380
tagcaactaa caataagggt tgcgctcgtt gcgggactta acccaacatc tcacgacacg    4440
agctgacgac aaccatgcac cacctgtctc cactttcccc gaagggcacc taatgcatct    4500
ctgcttcgtt agtgggatgt caagccctgg taaggttctt cgcgttgctt cgaattaaac    4560
cacatactcc accgcttgtg cgggcccccg tcaattcctt tgagtttcaa ccttgcgatc    4620
gtactcccca ggtgggatac ttattgtgtt aactgcggca cggagggggt cagaccccc    4680
acacctagta tccatcgttt acggcgtgga ctaccagggt atctaatcct gtttgctccc    4740
cacgctttcg cgcctcagcg tcagttactg tccagcaatc cgccttcgcc actggtgttc    4800
ctccgtatat ctacgcattt caccgctaca cacggaattc cgattgcctc tccagcactc    4860
aagaactaca gtttcaaatg caggctggag gttgagcccc cagttttcac atctgacttg    4920
caatcccgcc tacacgccct ttacacccag taaatccgga taacgcttgc cacctacgta    4980
ttaccgcggc tgctggcacg tagttagccg tggcttattc gtcgggtacc gtcatttgtt    5040
tcgtcccga caaaagaagt ttacaacccg aaagccttct tccttcacgc ggcgttgctg    5100
ggtcaggctt gcgcccattg cccaatattc cccactgctg cctccgtag gagtctgggc    5160
cgtgtctcag tcccaatgtg gccggtcaac ctctcagtcc ggctactgat cgtcgcctag    5220
gtgggccgtt accccgccta ctagctaatc agacgcgagg ccatctcaga gcgataaatc    5280
tttggcagtc agagccatgc gacccaactg catcatgcgg tattagcact cctttcggag    5340
tgttattccc ctctccaagg caggttcctc acgcgttact cacccgtccg ccactaggta    5400
actcaatccg ttgacgaat cctccgtcat gagcaccccg ttcgacttgc atgtgttaag    5460
cacgccgcca gcgttcatcc tgagccagga tcaaactctc aataaaatgg tatctaaaga    5520
acgtctccgt tcctcaaatc atcttatcga agcttaattc atagcttcaa agaaatctat    5580
tcaagagcct tcttcatcaa gcttgcgctt gctcagaagg acttctcgtc ctttctggtg    5640
cttcgtgttt ctctcacgtt gtttaattta caaggtacac gcccctgtca gcttttcc      5698
```

<210> SEQ ID NO 3
<211> LENGTH: 1232
<212> TYPE: DNA
<213> ORGANISM: Hungatella hathewayi VE202-04

<400> SEQUENCE: 3

```
aagactcaac agtatataaa acccttactt cttcttcctt agaaaggagg tgatccagcc        60
gcaccttccg atacggctac cttgttacga cttcacccca gttatcagtc ccgccttcgg       120
cagctccctc cttacggttg ggtcactgac ttcgggcgtt accaactccc atggtgtgac       180
gggcggtgtg tacaagaccc gggaacgtat tcaccgcgac attctgattc gcgattacta       240
gcgattccag cttcatgcag gcgagttgca gcctgcaatc cgaactgaga cgttattttt       300
ggggtttgct ccagatcgct cctttgcttc cctttgttta cgccattgta gcacgtgtgt       360
agcccaaatc ataaggggca tgatgatttg acgtcatccc caccttcctc caggttatcc       420
ctggcagtct ccccagagtg cccaccatca tgtgctggct actaaggata agggttgcgc       480
tcgttgcggg acttaaccca acatctcacg acacgagctg acgacaacca tgcaccacct       540
gtctccattg ctccgaagag ggacacggtt aaagtgattt tcaatgggat gtcaagactt       600
ggtaaggttc ttcgcgttgc ttcgaattaa accacatgct ccaccgcttg tgcgggtccc       660
cgtcaattcc tttgagtttc attcttgcga acgtactccc caggtggaat acttattgcg       720
ttagcggcgg caccgaagga cgttgtcccc cgacacctag tattcatcgt ttacggcgtg       780
gactaccagg gtatctaatc ctgtttgctc cccacgcttt cgagcctcaa cgtcagttac       840
agtccagtaa gccgccttcg ccactggtgt tcctcctaat atctacgcat tcaccgcta        900 cactaggaat tccacttacc tctcctgcac tcaagtcaaa cagtttccaa agcagtaccg       960
gggttgagcc ccgggctttc acttcagact tgcttaaccg tctacgctcc ctttacaccc      1020
agtaaatccg ataacgcttg ccccctacg tattaccgcg gctgctggca cgtagttagc       1080
cggggcttct tagtcaggta ccgtcatttt cttccctgct gatagagctt acataccga       1140 aatacttctt cactcacgcg gcgtcgctgg atcaggcttt cgcccattgt ccaatattcc      1200
ccactgctgc ctcccgtagg agtttgggcc gt                                     1232
```

<210> SEQ ID NO 4
<211> LENGTH: 1385
<212> TYPE: DNA
<213> ORGANISM: Clostridiales bacterium VE202-06

<400> SEQUENCE: 4

```
cgcacaggac cgcatggtct ggtgtgaaaa actccggtgg tatgagatgg acccgcgtct        60
gattagctag ttggaggggt aacggcccac caaggcgacg atcagtagcc ggcctgagag       120
ggtgaacggc cacattggga ctgagacacg gcccagactc ctacgggagg cagcagtggg       180
gaatattgca caatggggga aaccctgatg cagcgacgcc gcgtgaagga agaagtatct       240
cggtatgtaa acttctatca gcagggaaga aaatgacggt acctgactaa gaagcccgg       300 ctaactacgt gccagcagcc gcggtaatac gtaggggca agcgttatcc ggatttactg       360
ggtgtaaagg gagcgtagac ggaagagcaa gtctgatgtg aaaggctggg gcttaacccc       420
aggactgcat tggaaactgt tgttctagag tgccggagag gtaagcggaa ttcctagtgt       480
agcggtgaaa tgcgtagata ttaggaggaa caccagtggc gaaggcggct tactggacgg       540
taactgacgt tgaggctcga aagcgtgggg agcaaacagg attagatacc ctggtagtcc       600
acgccgtaaa cgatgaatac taggtgtcgg gtggcaaagc cattcggtgc cgcagcaaac       660
gcaataagta ttccacctgg ggagtacgtt cgcaagaatg aaactcaaag gaattgacgg       720
ggacccgcac aagcggtgga gcatgtggtt taattcgaag caacgcgaag aaccttacca       780
agtcttgaca tccctctgac cgtccgtaa tgggggcttc ccttcgggc agaggagaca       840 ggtggtgcat ggttgtcgtc agctcgtgtc gtgagatgtt gggttaagtc ccgcaacgag       900
```

```
cgcaacccct tatccttagta gccagcacat gatggtgggc actctaggga gactgccggg    960
gataacccgg aggaaggcgg ggacgacgtc aaatcatcat gccccttatg atttgggcta   1020
cacacgtgct acaatggcgt aaacaaaggg aagcgagaca gcgatgttga gcgaatccca   1080
aaaataacgt cccagttcgg actgcagtct gcaactcgac tgcacgaagc tggaatcgct   1140
agtaatcgcg gatcagaatg ccgcggtgaa tacgttcccg ggtcttgtac acaccgcccg   1200
tcacaccatg ggagtcagta acgcccgaag tcagtgacct aaccgaaagg aaggagctgc   1260
cgaaggcggg accgataact ggggtgaagt cgtaacaagg tagccgtatc ggaaggtgcg   1320
gctggatcac ctcctttcta aggaagaaga agtagagaaa agtgtttcac tgttgagtta   1380
ccaag                                                               1385
```

<210> SEQ ID NO 5
<211> LENGTH: 1684
<212> TYPE: DNA
<213> ORGANISM: Clostridiales bacterium VE202-07

<400> SEQUENCE: 5

```
acttcttctt ccttagaaag gaggtgatcc agccgcacct tccgatacgg ctaccttgtt     60
acgacttcac cccagttacc tgccccgcct tcggcagctc cctctcttgc gagttgggtc    120
actgacttcg ggcgttgctg actcccatgg tgtgacgggc ggtgtgtaca agacccggga    180
acgtattcac cgcgacattc tgattcgcga ttactagcga ttccagcttc gtgtagtcgg    240
gttgcagact acagtccgaa ctgggacgtt atttttggga tttgctccac atcactgtct    300
tgcttccctt tgtttacgcc attgtagcac gtgtgtagcc caaatcataa ggggcatgat    360
gatttgacgt catccccacc ttcctccagg ttatccctgg cagtctccct agagtgccca    420
gctttacctg ctggctacta aggataaggg ttgcgctcgt tgcgggactt aacccaacat    480
ctcacgacac gagctgacga caaccatgca ccacctgtct ctcttgcccc gaagggaagg    540
cgccgttaca cgccggtcaa gaggatgtca agacttggta aggttcttcg cgttgcttcg    600
aattaaacca catgctccac cgcttgtgcg ggtccccgtc aattcctttg agtttcattc    660
ttgcgaacgt actccccagg tggaatgctt actgcgtttg cgacggcacc gaagggcttt    720
gcccccccaac acctagcatt catcgtttac ggcgtggact accagggtat ctaatcctgt    780
ttgctcccca cgctttcgag cctcaacgtc agttatcgtc cagtaagccg ccttcgccac    840
tggtgttcct cctaatatct acgcatttca ccgctacact aggaattcca cttacctctc    900
cgacactcta gcaaaacagt tcccaaagca gtcccagggt tgagccctgg gtttcactt    960
cagacttgct tcgccgtcta cgctcccttt acacccagta aatccggata acgcttgccc   1020
cctacgtatt accgcggctg ctggcacgta gttagccggg gcttcttagt caggtaccgt   1080
cattttcttc cctgctgata gagctttaca taccgaaata cttcttcact cacgcggcgt   1140
cgctgcatca ggctttcgcc cattgtgcaa tattccccac tgctgcctcc gtaggagtt   1200
tgggccgtgt ctcagtccca atgtggccgg tcaccctctc aggtcggcta ctgatcgtcg   1260
ctttggtggg ccgttacccc gccaactggc taatcagacg cggatccatc tcacaccacc   1320
ggagtttttc acaccgtacc atgcggtact gtgcgcttat gcgtattag cagtcatttc   1380
taactgttat cccccagtgt gaggcaggtt atccacgcgt tactcacccg tccgccactc   1440
agtcaatcaa aaatccatcc gaaaacttca ttttaattgc ttcgttcgac ttgcatgtgt   1500
taggcacgcc gccagcgttc atcctgagcc aggatcaaac tctcatgttt aaaagttgat   1560
```

```
tccaggtttc agactactta gcttggctag ttatctttaa ccttcattac ttggttttgt    1620
tctgaatttt ctcaaatcca aaggcctaaa ccagacctt tgtttttaga attttcaggg    1680
tttt                                                                1684

<210> SEQ ID NO 6
<211> LENGTH: 4583
<212> TYPE: DNA
<213> ORGANISM: Clostridiales bacterium VE202-08

<400> SEQUENCE: 6
cggccacatt gggactgaga cacggcccaa actcctacgg gaggcagcag tagggaattt      60
tcggcaatgg gggaaaccct gaccgagcaa tgccgcgtga gtgaagacgg ccttcgggtt    120
gtaaagctct gttgtaaggg aagaacggca tagagaggga atgctctatg agtgacggta    180
ccttaccaga aagccacggc taactacgtg ccagcagccg cggtaatacg taggtggcaa    240
gcgttatccg gaattattgg gcgtaaaggg tgcgtaggcg gctggataag tctgaggtaa    300
aagcccgtgg ctcaaccacg gtaagccttg gaaactgtct ggctggagtg caggagagga    360
caatggaatt ccatgtgtag cggtaaaatg cgtagatata tggaggaaca ccagtggcga    420
aggcggttgt ctggcctgta actgacgctg aagcacgaaa gcgtggggag caaataggat    480
tagataccct agtagtccac gccgtaaacg atgagaacta agtgttgggg aaactcagtg    540
ctgcagttaa cgcaataagt tctccgcctg ggagtatgc acgcaagtgt gaaactcaaa      600
ggaattgacg ggggcccgca caagcggtgg agtatgtggt ttaattcgac gcaacgcgaa    660
gaaccttacc aggccttgac atggtatcaa aggcctaga gataggagaa tagttatgat    720
acacacaggt ggtgcatggt tgtcgtcagc tcgtgtcgtg agatgttggg ttaagtcccg    780
caacgagcgc aacccttgtt tctagttacc aacagtaaga tggggactct agagagactg    840
ccggtgacaa accggaggaa ggtggggatg acgtcaaatc atcatgcccc ttatggcctg    900
ggctacacac gtactacaat ggcgtctaca agagcagcg agcaggtgac tgtaagcgaa    960
tctcataaag gacgtctcag ttcggattga agtctgcaac tcgacttcat gaagtcggaa    1020
tcgctagtaa tcgcggatca gcatgccgcg gtgaatacgt tctcgggcct tgtacacacc    1080
gcccgtcaaa ccatgggagt tgataatacc cgaagccggt ggcctaaccg aaaggaggga    1140
gccgtcgaag gtaggatcga tgactggggt taagtcgtaa caaggtatcc ctacgggaac    1200
gtggggatgg atcacctcct ttctaaggag aaagtaagaa aaagatattt cctgttcagt    1260 tttgaaggt gcgagaagca cagtccgaaa gcagttcgtt cttttgaaaac caaataacag    1320 aagacataag agataaaaac atgatctttc tgaatagaaa agcaaaagat aaatcgagaa    1380
aaaatgttaa acaaacagta actcagaaaa ataagatcca agcaattgga cgcgaaaaac    1440
acaacgatga gagaacaacg taaaaaacac aatacttaaa gtgattaagt agagaagggc    1500
gtacggtgaa tgcctagcca catacagctg aagaaggacg catcaaacgg cgaaacgcca    1560
cggggagcgg taagaacgca aggatccgtg ggtatccgaa tggagaaatc cgataacggt    1620
aatgcgttat catccatgag taaatcaata gctcatgaga gagaaaccca gggaattgaa    1680
acatcttagt acctggagga aaagaaaaca aaagtgattc cgtcagtagc ggcgagcgaa    1740
cgcggaagag gccaaaccag aacatgttct ggggttgtag gacctcgagg tgagactttg    1800
acgattagaa gaacggcatt gaaaggccgg ccgaagaagg tgcaagccct gtaaacgaaa    1860
atcgaagaag ctctagaggg atcctgagta cggcggggca cgaaaaccc agtcggaagc    1920 agccgggacc atccggcaag cctaaatacg agtatgtgag cgatagtgaa ccagtaccgt    1980
```

```
gagggaaagg tgaaaagaac cccgggaggg gagtgaaata gaacctgaaa ccgtatgcct    2040
acaagaagtc agagcccgtt aaagggtgat ggcgtgcctt ttgtagaatg aaccggcgag    2100
ttaccatatc gtgcgaggtt aagtagaaga tacggagccg aagcgaaagc gagtctgaaa    2160
agggcgagag tacgatgcgg tagacccgaa accaggtgat ctagccatga tcaggttgaa    2220
gtcaaggtga tacttgatgg aggaccgaac cgaccccgt tgaaaagttg gcggatgaat     2280
tgtggctagg ggagaaattc caatcgaacc tggatatagc tggttctccc cgaaatagct    2340
ttagggctag cgtcggagga aaccatgtgg aggtagagca ctgaatgcat gatggcccca    2400
tccaggggta ctgaatgcaa tcaaactccg aatgccatgt ggaactatcc ggcagtcaga    2460
ctgtgggtga taaggtccat ggtcaaaagg gaaacagccc agaccgccag ttaaggtccc    2520
aaaatgtatg ctaagtggaa aaggatgtgg agatgcacag acaactagga ggttggctca    2580
gaagcagcca tccttgaaag agtgcgtaac agctcactag tcgagtgact ctgcgccgaa    2640
aatgtaccgg ggctaagcat actaccgaag ctgcggattt gcaagcaatt gcaagtggta    2700
ggggagcgtt ccatgaacgt agaagccgta tcggaagaag cggtggagag catggaagtg    2760
agaatgccgg tgtgagtagc gagatgcagg tgagaatcct gcacaccgat agcccaagga    2820
ttccagggga aggttcgtcc gccctgggta agtcgggacc taaggcgagg ccgaaaggcg    2880
tagtcgatgg aaaacaggca gatattcctg tacccgcgtg agaatgaagg agtgacggag    2940
aaggttagtg gatccactta atggattgtg gtccaaacgc aggagcagat acataggcaa    3000
atccgtgtat caatgcaaag gcgtgatggg gagtgaaagc tacggcaagt agcgaagtcc    3060
atgataccag cttccaagaa aagcttctag tgctaatctc atcgcggccc gtaccaaaac    3120
cgacacaggt gggcaaggcg agaagcctga ggtgagcgag agaactgttg ccaaggaact    3180
cggcaaaatg accccgtacg ttcgcaagaa ggggtgctcg aaagagccgc agtgaagagg    3240
cccaagcgac tgtttaacta aaacacagct ctctgcaaag tcgcaagacg aagtatagg    3300 ggtgactcct gcccggtgct ggaaggttaa gaggatgtgt catcccgcaa gggagaagca    3360
ttgaattgaa gccccagtga acggcggccg taactataac ggtcctaagg tagcgaaatt    3420
ccttgtcagg taagttctga cccgcacgaa aggagtaacg atttgggcgc tgtctcggca    3480
gcagactcgg tgaaatctta gtcccggtga agatgccggg tacccgcaac tagacgaaa    3540 gaccccatgg agctttactg tagcctgata ttgaattttg atcaaacatg tacaggatag    3600
gtgggagacg aagagacctg cacgccagtg taggaggagt cgacgttggg ataccaccct    3660
tgtttgattg aagttctaac ctgcttccat gaactgggag agggagagtg tcaggtgggc    3720
agtttgactg gggcggtcgc ctcctaaaga gtaacggagg cgccaaaagg taccctcaga    3780
ttggttggaa atcaatcgac gagtgcaaat gcagaagggt gcttgactgc gagaccaaca    3840
agtcgagcag ggacgaaagt cgggattagt gatccggcgg tgccgaatgg aagggccgtc    3900
gctcaacgga taaaagctac cctgggata acaggctgat ctcgcccaag agttcacatc     3960
gacggcgagg tttggcacct cgatgtcggc tcatcgcatc ctggagctga attcggttcc    4020
aagggttggg ctgtccgccc attaaagcgg tacgcgagct gggttcagaa cgtcgtgaga    4080
cagttcggtc cctatctgtt gtgggcgtag gaaatttgag gagatctgtc cttagtacga    4140
gaggaccggg atggacctac cgctggtgca ccagttgtat cgccagatgc atagctgggt    4200
agctaagtag ggaacggata agcgctgaag gcatctaagc acgaaaccga ctccaagatg    4260
agatttccca tacgcaagta gtaagccccc ttgaagacga caaggtagat aggtcagaga    4320
```

```
tggaagtgta gaaatacatg agttgactg atactaatgg gtcgaggact taatcacaca    4380
actaggaaga aagagaatgg aagtcaactg ttatttggtt ttgagggaat gacctcagaa    4440
gatctggtgg cgatggcaaa gtggagacac ctgtacccat cccgaacaca aagttaagc    4500 actttaacgg tgacaatagc tggacctgct cccgtgaaga taactagctg ccaggtgatc    4560
gacccttcat tgggtctttt ttt                                           4583

<210> SEQ ID NO 7
<211> LENGTH: 1699
<212> TYPE: DNA
<213> ORGANISM: Clostridiales bacterium VE202-09

<400> SEQUENCE: 7
aaacaataag acaaccccta cttcttcttc cttagaaagg aggtgatcca gccgcacctt      60
ccgatacggc taccttgtta cgacttcacc ccagttatcg gtcccacctt cggcagctcc     120
ctcctataag gttgggtcac tgacttcggg cgttactgac tcccatggtg tgacgggcgg     180
tgtgtacaag acccgggaac gtattcaccg tgacattctg attcacgatt actagcgatt     240
ccagcttcat gtagtcgagt tgcagactac aatccgaact gagacgttat ttctgggatt     300
tgcttcgcct cacgacttcg cttccctttg tttacgccat tgtagcacgt gtgtagccct     360
ggccataagg ggcatgatga tttgacgtcg tccccacctt cctccaggtt atccctggca     420
gtctctctag agtgcccacc ttatatgctg gctactaaag ataggggttg cgctcgttgc     480
gggacttaac ccaacatctc acgacacgag ctgacgacaa ccatgcacca cctgtcttaa     540
ctgtcccgaa ggaaaggtcc cattacgaac cggtcagtta gatgtcaaga ccaggtaagg     600
ttcttcgcgt tgcttcgaat taaaccacat gctccaccgc ttgtgcgggt ccccgtcaat     660
tcctttgagt ttcattcttg cgaacgtact ccccaggtgg aatacttact gcgtttgctg     720
cggcaccgaa gcctctacgg ccccgacacc tagtattcat cgtttacggc gtggactacc     780
agggtatcta atcctgtttg ctccccacgc tttcgtgcat cagtgtcagt gacagtccag     840
taagccgcct tcgccactgg tgttcctcct aatatctacg catttcaccg ctacactagg     900
aattccgctt acctctcctg cactccagca tgacagtttc aaaagcagtc ccggggttaa     960
gccccgggct ttcacttctg acttaccatg ccacctacgc accctttaca cccagtaatt    1020
ccggataacg cttgccccct acgtattacc gcggctgctg gcacgtagtt agccggggct    1080
tcttagtcag gtaccgtctt ttttcttccc tgctgataga gctttacata ccgaaatact    1140
tcttcactca cgcggcgtcg ctgcatcagg gtttcccccca ttgtgcaata ttccccactg    1200
ctgcctcccg taggagtttg ggccgtgtct cagtcccaat gtggccgtcc actctctcaa    1260
gccggctact gatcgtcgcc ttggtgggcc gttaccccgc caaccagcta atcagacgcg    1320
ggaccatcct atactgccgg agcttttcac accgaatcat gcgattctgt gcgcttatgc    1380
ggtattagca gccgtttcca gctgttatcc ccctgtatag ggcaggttcc ccacgcgtta    1440
ctcacccgtc cgccactcag tcattaagga attccatccg aaaacttcct tccaaaatgc    1500
ttcgttcgac ttgcatgtgt taagcacgcc gccagcgttc atcctgagcc aggatcaaac    1560
tctcatgttc aatcttggat ctaaaaagcg ctagcttttt tatccttgtt ttactgtgtc    1620
cttttataaa gaacgttcgt gtatctttttt tcaaaagata ctgaaaatct cttagaattt    1680
tcaaggttgt cttattgtt                                                1699

<210> SEQ ID NO 8
<211> LENGTH: 1571
```

<212> TYPE: DNA
<213> ORGANISM: Clostridiales bacterium VE202-13

<400> SEQUENCE: 8

```
atcaaagagt tgatcctgg ctcaggacga acgctggcgg cgcgcctaac acatgcaagt    60
cgaacggagc ttacgttttg aagttttcgg atggatgaat gtaagcttag tggcggacgg   120
gtgagtaaca cgtgagcaac ctgcctttca gaggggata acagccggaa acggctgcta    180
ataccgcatg atgttgcggg ggcacatgcc cctgcaacca aaggagcaat ccgctgaaag   240
atgggctcgc gtccgattag ccagttggcg gggtaacggc ccaccaaagc gacgatcggt   300
agccggactg agaggttgaa cggccacatt gggactgaga cacggcccag actcctacgg   360
gaggcagcag tggggatat gcacaatgg gcgaaagcct gatgcagcga cgccgcgtga    420
gggaagacgt cttcggatt gtaaacctct gtctttgggg aagaaatga cggtacccaa    480
agaggaagct ccggctaact acgtgccagc agccgcggta atacgtaggg agcaagcgtt   540
gtccggaatt actgggtgta aagggagcgt aggcggatg gcaagtagaa tgttaaatcc    600
atcggctcaa ccggtggctg cgttctaaac tgccgttctt gagtgaagta gaggcaggcg   660
gaattcctag tgtagcggtg aaatgcgtag atattaggag gaacaccagt ggcgaaggcg   720
gcctgctggg ctttaactga cgctgaggct cgaaagcgtg gggagcaaac aggattagat   780
accctggtag tccacgccgt aaacgatgat tactaggtgt gggggactg accccttccg    840
tgccgcagtt aacacaataa gtaatccacc tggggagtac ggccgcaagg ttgaaactca   900
aaggaattga cggggcccg cacaagcagt ggagtatgtg gtttaattcg aagcaacgcg    960
aagaaccta ccaggtcttg acatcggatg catagcctag agataggtga agcccttcgg   1020
ggcatccaga caggtggtgc atggttgtcg tcagctcgtg tcgtgagatg ttgggttaag   1080
tcccgcaacg agcgcaaccc ttattattag ttgctacgca agagcactct aatgagactg   1140
ccgttgacaa aacggaggaa ggtgggatg acgtcaaatc atcatgcccc ttatgacctg   1200
ggctacacac gtactacaat ggcactaaaa cagagggcgg cgacaccgcg aggtgaagcg   1260
aatcccgaaa agtgtctca gttcagattg caggctgcaa cccgcctgca tgaagtcgga   1320
attgctagta atcgcggatc agcatgccgc ggtgaatacg ttcccgggcc ttgtacacac   1380
cgcccgtcac accatgggag tcggtaacac ccgaagccag tagcctaacc gcaagggggg   1440
cgctgtcgaa ggtgggattg atgactgggg tgaagtcgta acaaggtagc cgtatcggaa   1500
ggtgcggctg gatcacctcc tttctaagga gcgaagccgg cggagagccg gcggactctg   1560
gtcagacagg g                                                        1571
```

<210> SEQ ID NO 9
<211> LENGTH: 1732
<212> TYPE: DNA
<213> ORGANISM: Clostridiales bacterium VE202-14

<400> SEQUENCE: 9

```
aagttcttat tacgagagtt tgatcctggc tcaggatgaa cgctggcggc gtgcctaaca    60
catgcaagtc gagcgaagcg ctgttttcag aatcttcgga ggaagaggac agtgactgag   120
cggcggacgg gtgagtaacg cgtgggcaac ctgcctcata caggggata acagttagaa    180
atgactgcta ataccgcata agcgcacagg accgcatggt gtagtgtgaa aaactccggt    240
ggtatgagat ggacccgcgt ctgattaggt agttggtggg gtaaaggcct accaagccga    300
cgatcagtag ccgacctgag agggtgaccg gccacattgg gactgagaca cggcccaaac    360
```

| | |
|---|---|
| tcctacggga ggcagcagtg gggaatattg cacaatgggg gaaaccctga tgcagcgacg | 420 |
| ccgcgtgaag gaagaagtat ttcggtatgt aaacttctat cagcagggaa gaagatgacg | 480 |
| gtacctgagt aagaagcacc ggctaaatac gtgccagcag ccgcggtaat acgtatggtg | 540 |
| caagcgttat ccggatttac tgggtgtaaa gggagcgtag acggataggc aagtctggag | 600 |
| tgaaaaccca gggctcaacc ctgggactgc tttggaaact gcagatctgg agtgccggag | 660 |
| aggtaagcgg aattcctagt gtagcggtga atgcgtaga tattaggagg aacaccagtg | 720 |
| gcgaaggcgg cttactggac ggtgactgac gttgaggctc gaaagcgtgg ggagcaaaca | 780 |
| ggattagata ccctggtagt ccacgccgta acgatgact actaggtgtc ggtgtgcaaa | 840 |
| gcacatcggt gccgcagcaa acgcaataag tagtccacct ggggagtacg ttcgcaagaa | 900 |
| tgaaactcaa aggaattgac ggggacccgc acaagcggtg gagcatgtgg tttaattcga | 960 |
| agcaacgcga agaaccttac ctggtcttga catccggatg acgggcgagt aatgtcgccg | 1020 |
| tcccttcggg gcatccgaga caggtggtgc atggttgtcg tcagctcgtg tcgtgagatg | 1080 |
| ttgggttaag tcccgcaacg agcgcaaccc ttatcttcag tagccagcat ataaggtggg | 1140 |
| cactctggag agactgccag ggagaacctg gaggaaggtg gggatgacgt caaatcatca | 1200 |
| tgccccttat ggccagggct acacacgtgc tacaatggcg taaacaaagg gaagcgagag | 1260 |
| ggtgacctgg agcgaatccc aaaaataacg tctcagttcg gattgtagtc tgcaactcga | 1320 |
| ctacatgaag ctggaatcgc tagtaatcgc ggatcagcat gccgcggtga atacgttccc | 1380 |
| gggtcttgta cacaccgccc gtcacaccat gggagtcagt aacgcccgaa gccagtgacc | 1440 |
| caaccttaga ggagggagct gtcgaaggcg ggacggataa ctggggtgaa gtcgtaacaa | 1500 |
| ggtagccgta tcggaaggtg cggctggatc acctcctttc taagggaaga agtaagggac | 1560 |
| gttgtctatt gttgagcgat cgaagagggg agacccgaag aggagctcag aagcagttgg | 1620 |
| tggtgatgcg ttttggggaa acacccgtac ccatcccgaa cacgacggtt aagcccaaga | 1680 |
| cggccgagag tactgcactg gagacggtgt gggagggtag gtggccgcca ac | 1732 |

<210> SEQ ID NO 10
<211> LENGTH: 1744
<212> TYPE: DNA
<213> ORGANISM: Clostridiales bacterium VE202-15

<400> SEQUENCE: 10

| | |
|---|---|
| aaatccaaga ttcaacagta tataaaaccc ttacttcttc ttccttagaa aggaggtgat | 60 |
| ccagccgcac cttccgatac ggctaccttg ttacgacttc accccagtta cctgccccgc | 120 |
| cttcggcagc tccctccttt cggttgggtc actgacttcg ggcgttgctg actcccatgg | 180 |
| tgtgacgggc ggtgtgtaca agacccggga acgtattcac cgcgacattc tgattcgcga | 240 |
| ttactagcga ttccagcttc gtgtagtcgg gttgcagact acagtccgaa ctgggacgtt | 300 |
| atttttgaga tttgctcacc ttcgcagggt cgcttccctt tgtttacgcc attgtagcac | 360 |
| gtgtgtagcc caaatcataa ggggcatgat gatttgacgt catccccacc ttcctccagg | 420 |
| ttgtccctgg cagtctccct agagtgccca tcttaatgct ggctactaag gataagggtt | 480 |
| gcgctcgttg cgggacttaa cccaacatct cacgacacga gctgacgaca accatgcacc | 540 |
| acctgtctct cttgtcccga aggaaggcg ccgttacacg ccggtcaaga ggatgtcaag | 600 |
| acttggtaag gttcttcgcg ttgcttcgaa ttaaaccaca tgctccaccg cttgtgcggg | 660 |
| tccccgtcaa ttcctttgag tttcattctt gcgaacgtac tccccaggtg gagtgcttat | 720 |
| tgcgtttgcg acggcaccga agggctttgc cccccaacac ctagcactca tcgtttacgg | 780 |

```
cgtggactac cagggtatct aatcctgttt gctccccacg ctttcgagcc tcaacgtcag    840
ttacagtcca gtaagccgcc ttcgccactg gtgttcctcc taatatctac gcatttcacc    900
gctacactag gaattccact tacctctcct gcactctagc ttgacagttt ccaaagcagt    960
cccagggttg agccctgggt tttcacttca gacttgccat gccgtctacg ctccctttac   1020
acccagtaaa tccggataac gcttgccccc tacgtattac cgcggctgct ggcacgtagt   1080
tagccggggc ttcttagtca ggtaccgtca ttatcttccc tgctgataga gctttacata   1140
ccgaaatact tcttcactca cgcggcgtcg ctgcatcagg ctttcgccca ttgtgcaata   1200
ttccccactg ctgcctcccg taggagtttg ggccgtgtct cagtcccaat gtggccggtc   1260
accctctcag gtcggctact gatcgtcgct ttggtgggcc gttaccccgc caactggcta   1320
atcagacgcg gatccatctc acaccaccgg agttttcac accgtaccat gcggtactgt    1380
gcgcttatgc ggtattagca gtcatttcta actgttgtcc cccagtgtga ggcaggttat   1440
ccacgtgtta ctcacccgtc cgccactcag tcatctcaga atccatccga aaacttcatc   1500
taaaatgctt cgttcgactt gcatgtgtta ggcacgccgc cagcgttcat cctgagccag   1560
gatcaaactc tcaaattaaa agttgattct tggtcttaga ctactagct tggctagtta    1620 tctttaacct tcattacttg gttttgttct gaattttctc aaatccaaag gtctaaacca   1680
gacctttatt tttagaatt ttcagggttt tacatactgt tcaatctttg attttcaagg    1740
ttct                                                                 1744

<210> SEQ ID NO 11
<211> LENGTH: 1640
<212> TYPE: DNA
<213> ORGANISM: Clostridiales bacterium VE202-16

<400> SEQUENCE: 11
aagttcgaga gaacattcag aacaaaaaaa ccaaacaaca gtaatacggt ttaaaaatta     60
gccaagcgaa ttttgaacg gaatcaaaac ttaaacatga gagtttgatc ctggctcagg    120
atgaacgctg gcggcgtgcc taacacatgc aagtcgaacg aagcgattta acggaagttt    180
tcggatggaa gttgaattga ctgagtggcg gacgggtgag taacgcgtgg gtaacctgcc    240
ttgtactggg ggacaacagt tagaaatgac tgctaatacc gcataagcgc acagtatcgc    300
atgatacagt gtgaaaaact ccggtggtac aagatggacc cgcgtctgat tagctagttg    360
gtaaggtaac ggcttaccaa ggcgacgatc agtagccgac ctgagagggt gaccggccac    420
attgggactg agacacggcc caaactccta cgggaggcag cagtggggaa tattgcacaa    480
tgggcgaaag cctgatgcag cgacgccgcg tgagtgaaga agtatttcgg tatgtaaagc    540
tctatcagca gggaagaaaa tgacggtacc tgactaagaa gccccggcta actacgtgcc    600
agcagccgcg gtaatacgta gggggcaagc gttatccgga tttactgggt gtaaagggag    660
cgtagacggt aaagcaagtc tgaagtgaaa gcccgcggct caactgcggg actgctttgg    720
aaactgttta actggagtgt cggagaggta agtggaattc ctagtgtagc ggtgaaatgc    780
gtagatatta ggaggaacac cagtggcgaa ggcgacttac tggacgataa ctgacgttga    840
ggctcgaaag cgtggggagc aaacaggatt agataccctg gtagtccacg ccgtaaacga    900
tgaatactag gtgttgggga gcaaagctct tcggtgccgt cgcaaacgca gtaagtattc    960
cacctgggga gtacgttcgc aagaatgaaa ctcaaaggaa ttgacgggga cccgcacaag   1020
cggtggagca tgtggtttaa ttcgaagcaa cgcgaagaac cttaccaggt cttgacatcg   1080
```

```
atccgacggg ggagtaacgt cccccttccct tcggggcgga aagacaggt ggtgcatggt      1140 tgtcgtcagc tcgtgtcgtg agatgttggg ttaagtcccg caacgagcgc aaccccttatt     1200 ctaagtagcc agcggttcgg ccgggaactc ttgggagact gccagggata acctggagga     1260
aggtggggat gacgtcaaat catcatgccc cttatgatct gggctacaca cgtgctacaa     1320
tggcgtaaac aaagagaagc aagaccgcga ggtggagcaa atctcaaaaa taacgtctca     1380
gttcggactg caggctgcaa ctcgcctgca cgaagctgga atcgctagta atcgcgaatc     1440
agaatgtcgc ggtgaatacg ttcccgggtc ttgtacacac cgcccgtcac accatgggag     1500
tcagtaacgc ccgaagtcag tgacccaacc gcaaggaggg agctgccgaa ggcgggaccg     1560
ataactgggg tgaagtcgta acaaggtagc cgtatcggaa ggtgcggctg gatcacctcc     1620
tttctaagga agaagaagta                                                 1640
```

<210> SEQ ID NO 12
<211> LENGTH: 1543
<212> TYPE: DNA
<213> ORGANISM: Clostridiales bacterium VE202-18

<400> SEQUENCE: 12

```
gacagctcct tccttgcggt taggccaccg gcttcgggtg ttatcaactc tcgtggtgtg       60
acgggcggtg tgtacaaggc ccgagaacgt attcaccgcg acatgctgat tcgcgattac      120
tagcgattcc aacttcatgt agtcgagttg cagactacaa tccgaactga gaatggtttt     180
atgggttttg cttcacctcg cggcttcgct tccctctgca ccatccattg tagcacgtgt     240
gtagcccagg tcataagggg catgatgatt tgacgtcatc cccgccttcc tccagcttgt     300
cactggcagt ctcgctagag tccccaactt aatgatggta actaacgata agggttgcgc     360
tcgttgcggg acttaaccca acatctcacg acacgagctg acgacaacca tgcaccacct     420
gtatctcata tagctatctc tccatctctg gagcctttat gagtatgtca agacctggta     480
aggttcttcg cgttgcttcg aattaaacca catgctccac cgcttgtgcg ggccccgtc      540 aattcctttg agtttcattc ttgcgaacgt actactcagg cggagtactt attgcgttaa     600
ctgcagcact gaactttgac atccaacact tagtactcat cgtttacggc gtggactact     660
agggtatcta atcctatttg ctccccacgc tttcgggact gagcgtcagt tgcaggccag     720
atcgtcgcct tcgccactgg tgttcctcca tatatctacg catttcaccg ctacacatgg     780
aattccacga tcctctcctg cactctagct gcctggttc tatggcttac tgaagttaag     840
cttcaggctt tcaccacaga cccttgctgc cgcctgctcc ctcttttacgc ccaataattc     900 cggataacgc ttgccaccta cgtattaccg cggctgctgg cacgtagtta gccgtggctt     960
tctaataaag taccgtcact cggctaccat ttcctgtagc cgccgttctt cctttataac    1020
agaagtttac aatccgaaaa ccttcttcct tcacgcggcg ttgctcggtc agggtttccc    1080
ccattgccga aaattcccta ctgctgcctc ccgtaggagt ctgggccgtg tctcagtccc    1140
agtgtggccg gtcaccctct caggtcggct acgcatcgtc gccttggtgg gccgttaccc    1200
cgccaaccag ctaatgcgcc ataagtccat cctctaccag tgctttgagg cacttttaat    1260
acggtcacca tgcagtgtcc gtacctatgc ggtcttagct atcgtttcca atagttatcc    1320
ccctgtctag ggcaggttac ttatgtatta ctcacccgtt cgccactcga gcacaagtgc    1380
tcgcgttcga cttgcatgta ttaggcacgc cgccagcgtt catcctgagc caggatcaaa    1440
ctctccattg tttatttaaa caactcttcg tttgtttagc tcttttttct ttttttatcct   1500 tctggatatt gacgtgtgtt tcttaattct gtttagtttt caa                      1543
```

<210> SEQ ID NO 13
<211> LENGTH: 1620
<212> TYPE: DNA
<213> ORGANISM: Clostridiales bacterium VE202-21

<400> SEQUENCE: 13

```
caacaaagca ccttgataat taaacaatag acaacaaacc cttgaaaatt tcttatagag      60
aaaaattttt aagaacagca tcataatgat gcacccatca ctgagattaa tctcggtggt     120
aagaacagta aaagggata gaattagcta gtagttaatt ctgacccgga tacaaacact     180
tttaacgaga gtttgatcct ggctcaggat gaacgctggc ggcgtgctta acacatgcaa     240
gtcgagcgaa gcgctttact tagatttctt cggattgaaa agttttgcga ctgagcggcg     300
gacgggtgag taacgcgtgg gtaacctgcc tcatacaggg ggataacagt tagaaatgac     360
tgctaatacc gcataagacc acagtaccgc atggtacagt gggaaaaact ccggtggtat     420
gagatggacc cgcgtctgat tagctagttg gtaaggtaac ggcttaccaa ggcgacgatc     480
agtagccgac ctgagagggt gaccggccac attgggactg agacacggcc caaactccta     540
cgggaggcag cagtggggaa tattgcacaa tgggggaaac cctgatgcag cgacgccgcg     600
tgaaggatga agtatttcgg tatgtaaact tctatcagca gggaagaaaa tgacggtacc     660
tgactaagaa gccccggcta actacgtgcc agcagccgcg gtaatacgta ggggcaagc     720
gttatccgga tttactgggt gtaaagggag cgtagacggt tatgtaagtc tgatgtgaaa     780
acccggggct caaccccggg actgcattgg aaactatgta actagagtgt cggagaggta     840
agtggaattc ctagtgtagc ggtgaaatgc gtagatatta ggaggaacac cagtggcgaa     900
ggcggcttac tggacgatga ctgacgttga ggctcgaaag cgtggggagc aaacaggatt     960
agatacccctg gtagtccacg ccgtaaacga tgcatactag gtgtcgggtg caaagccat   1020
tcggtgccgc agcaaacgca ataagtatgc cacctgggga gtacgttcgc aagaatgaaa    1080
ctcaaaggaa ttgacgggga cccgcacaag cggtggagca tgtggtttaa ttcgaagcaa    1140
cgcgaagaac cttacctgct cttgacatcc cctgaccgg cgcgtaatgg tgcctttcct    1200
tcgggacagg ggagacaggt ggtgcatggt tgtcgtcagc tcgtgtcgtg agatgttggg    1260
ttaagtcccg caacgagcgc aacccttatc tttagtagcc agcggtttgg ccgggcactc    1320
tagagagact gccagggata acctggagga aggtggggat gacgtcaaat catcatgccc    1380
cttatgagca gggctacaca cgtgctacaa tggcgtaaac aaagggaggc gaagccgcga    1440
ggtggagcaa atcccaaaaa taacgtctca gttcggattg tagtctgcaa ctcgactaca    1500
tgaagctgga atcgctagta atcgcgaatc agaatgtcgc ggtgaatacg ttcccgggtc    1560
ttgtacacac cgcccgtcac accatgggag ttggtaacgc ccgaagtcag tgacccaacc    1620
```

<210> SEQ ID NO 14
<211> LENGTH: 1483
<212> TYPE: DNA
<213> ORGANISM: Clostridiales bacterium VE202-26

<400> SEQUENCE: 14

```
gcgactgagt ggcggacggg tgagtaacgc gtgggcaacc tgccttgcac tgggggataa      60
cagccagaaa tggctgctaa taccgcataa gaccgaagcg ccgcatggcg cagcggccaa     120
agccccggcg gtgcaagatg ggcccgcgtc tgattaggta gttggcgggg taacggccca     180
ccaagccgac gatcagtagc cgacctgaga gggtgaccgg ccacattggg actgagacac     240
```

-continued

```
ggcccagact cctacgggag gcagcagtgg ggaatattgc acaatggggg aaaccctgat      300
gcagcgacgc cgcgtgaagg atgaagtatt tcggtatgta aacttctatc agcagggaag      360
aagatgacgg tacctgacta agaagccccg gctaactacg tgccagcagc cgcggtaata      420
cgtaggggga agcgttatc cggatttact gggtgtaaag ggagcgtaga cggcgatgca       480
agccagatgt gaaagcccgg ggctcaaccc cgggactgca tttggaactg cgtggctgga      540
gtgtcggaga ggcaggcgga attcctagtg tagcggtgaa atgcgtagat attaggagga     600
acaccagtgg cgaaggcggc ctgctggacg atgactgacg ttgaggctcg aaagcgtggg     660
gagcaaacag gattagatac cctggtagtc cacgccgtaa acgatgacta ctaggtgtcg      720
ggtggcaagg ccattcggtg ccgcagcaaa cgcaataagt agtccacctg gggagtacgt      780
tcgcaagaat gaaactcaaa ggaattgacg gggacccgca caagcggtgg agcatgtggt      840
ttaattcgaa gcaacgcgaa gaaccttacc tgatcttgac atcccgatgc caaagcgcgt      900
aacgcgctct ttcttcggaa catcggtgac aggtggtgca tggttgtcgt cagctcgtgt     960
cgtgagatgt tgggttaagt cccgcaacga gcgcaacccc tatcttcagt agccagcatt    1020
ccggatgggc actctggaga gactgccagg acaacctgg aggaaggtgg ggatgacgtc      1080
aaatcatcat gccccttatg accagggcta cacacgtgct acaatggcgt aaacaaaggg    1140
aggcgaaccc gcgagggtgg gcaaatccca aaaataacgt ctcagttcgg attgtagtct    1200
gcaactcgac tacatgaagc tggaatcgct agtaatcgcg aatcagaatg tcgcggtgaa    1260
tacgttcccg ggtcttgtac acaccgcccg tcacaccatg ggagtcagta acgcccgaag    1320
ccggtgaccc aacccgtatg ggagggagcc gtcgaaggtg ggaccgataa ctggggtgaa    1380
gtcgtaacaa ggtagccgta tcggaaggtg cggctggatc acctcctttc tagggaagag    1440
aagaagtaag ggctgctgtc tattgttcag ttatcgagga atg                     1483
```

<210> SEQ ID NO 15
<211> LENGTH: 1615
<212> TYPE: DNA
<213> ORGANISM: Clostridiales bacterium VE202-27

<400> SEQUENCE: 15

```
aaccttgaca aataaacagt aatgcaaccc tgaaaattct aaaaagaaa attcagagaa        60
caagttttaa agcttcgtaa gaagaccttt aagacaccca aaaacagtaa gaaacgcttg      120
gaaacaagca acggttaaac attagctaga gttaatctta actgggttaa acacttaaac      180
aagagagttt gatcctggct caggatgaac gctggcggcg tgcctaacac atgcaagtcg      240
aacggagtta tgcagaggaa gttttcggat ggaatcggcg taacttagtg gcggacgggt      300
gagtaacgcg tgggaaacct gcctgtaccg gggataaca cttagaaata ggtgctaata      360
ccgcataagc gcacagcttc acatgaggca gtgtgaaaaa ctccggtggt acaggatggt      420
cccgcgtctg attagccagt tggcagggta acggcctacc aaagcgacga tcagtagccg      480
gcctgagagg gtgaacggcc acattgggac tgagacacgg cccaaactcc tacgggaggc      540
agcagtgggg aatattgcac aatggggga accctgatgc agcgacgccg cgtgagtgaa      600
gaagtatttc ggtatgtaaa gctctatcag caggaagaa aatgacggta cctgactaag      660
aagcccggc taactacgtg ccagcagccg cggtaatacg taggggcaa gcgttatccg      720
gatttactgg gtgtaaaggg agcgtagacg catgacaag ccagatgtga aaacccaggg      780
ctcaaccctg ggactgcatt tggaactgcc aggctgagt gcaggagagg taagcggaat      840
tcctagtgta gcggtgaaat gcgtagatat taggaggaac accagtggcg aaggcggctt      900
```

```
actggactgt aactgacgtt gaggctcgaa agcgtgggga gcaaacagga ttagatacccc    960
tggtagtcca cgcggtaaac gatgattgct aggtgtaggt gggtatggac ccatcggtgc   1020
cgcagctaac gcaataagca atccacctgg ggagtacgtt cgcaagaatg aaactcaaag   1080
gaattgacgg ggacccgcac aagcggtgga gcatgtggtt taattcgaag caacgcgaag   1140
aaccttacca agtcttgaca tcccaatgac gtgtccgtaa cggggcattc tcttcggagc   1200
attggagaca ggtggtgcat ggttgtcgtc agctcgtgtc gtgagatgtt gggttaagtc   1260
ccgcaacgag cgcaacccct atccttagta gccagcaggt aaagctgggc actctaggga   1320
gactgccggg gataacccgg aggaaggcgg ggatgacgtc aaatcatcat gccccttatg   1380
atttgggcta cacacgtgct acaatggcgt aaacaaaggg aagcgagaca gtgatgttga   1440
gcaaatccca gaaataacgt ctcagttcgg attgtagtct gcaactcgac tacatgaagc   1500
tggaatcgct agtaatcgcg aatcagcatg tcgcggtgaa tacgttcccg ggtcttgtac   1560
acaccgcccg tcacaccatg ggagttggaa atgcccgaag cctgtgacct aaccg         1615

<210> SEQ ID NO 16
<211> LENGTH: 1644
<212> TYPE: DNA
<213> ORGANISM: Clostridiales bacterium 1_7_47FAA

<400> SEQUENCE: 16
cctttggatt tgagaaaatt cagaacaaaa ccaagtaatg aaggttaaag ataactagcc     60
aagctaagta gtctgaaacc tggaatcagc ttttaatttg agagtttgat cctggctcag    120
gatgaacgct ggcggcgtgc ctaacacatg caagtcgaac gaagcatctt ataggaagtt    180
ttcggatgga atatgggatg actgagtggc ggacgggtga gtaacgcgtg gataacctgc    240
ctcacactgg gggataacag ttagaaatgg ctgctaatac cgcataagcg cacagtaccg    300
catggtacgg tgtgaaaaac ccaggtggtg tgagatggat ccgcgtctga ttagccagtt    360
ggcggggtaa cggcccacca aagcgacgat cagtagccga cctgagaggg tgaccggcca    420
cattgggact gagacacggc ccaaactcct acgggaggca gcagtgggga atattgcaca    480
atgggcgaaa gcctgatgca gcgacgccgc gtgagtgaag aagtatctcg gtatgtaaag    540
ctctatcagc agggaagaaa atgacggtac ctgactaaga gccccggct aactacgtgc    600
cagcagccgc ggtaatacgt aggggggcaag cgttatccgg atttactggg tgtaaaggga    660
gcgtagacgg cgatgcaagt ctgaagtgaa agcccggggc tcaaccccgg gactgctttg    720
gaaactgtgt ggctggagtg caggagaggt aagtggaatt cctagtgtag cggtgaaatg    780
cgtagatatt aggaggaaca ccagtggcga aggcggctta ctggactgta actgacgttg    840
aggctcgaaa gcgtggggag caaacaggat tagatacccct ggtagtccac gccgtaaacg    900
atgaatgcta ggtgtcgggg ggcaaagccc ctcggtgccg ccgctaacgc aataagcatt    960
ccacctgggg agtacgttcg caagaatgaa actcaaagga attgacgggg acccgcacaa   1020
gcggtggagc atgtggttta attcgaagca acgcgaagaa ccttaccaag tcttgacatc   1080
cccctgaccg gacagtaacg tgtcccttcc ttcgggacag gggagacagg tggtgcatgg   1140
ttgtcgtcag ctcgtgtcgt gagatgttgg gttaagtccc gcaacgagcg caacccttat   1200
ccttagtagc cagcatttcg ggtgggcact ctagggagac tgccagggat aacctggagg   1260
aaggtgggga tgacgtcaaa tcatcatgcc cttatgatt tggctacac acgtgctaca   1320
atggcgtaaa caagggaag caccctgcga aggtgagcaa atcccaaaaa taacgtccca   1380
```

```
gttcggactg tagtctgcaa cccgactaca cgaagctgga atcgctagta atcgcggatc    1440
agaatgccgc ggtgaatacg ttcccgggtc ttgtacacac cgcccgtcac accatgggag    1500
tcagcaacgc ccgaagtcag tgacccaacc gaaaggaggg agctgccgaa ggcggggcag    1560
gtaactgggg tgaagtcgta acaaggtagc cgtatcggaa ggtgcggctg gatcacctcc    1620
tttctaagga agaagaagta aggg                                           1644
```

<210> SEQ ID NO 17
<211> LENGTH: 184717
<212> TYPE: DNA
<213> ORGANISM: Lachnospiraceae bacterium 3_1_57FAA_CT1

<400> SEQUENCE: 17

```
ctcccctgaa tctcacagcg gcgtatcgct ccctttggta tgctcgtttc ggtcagggtt      60
cctccacatc cctgccaaaa gtcatggcac tacatcgccg gggaagcata tcccacacag     120
gctggtcatt cgattggaat aatccatcga tgaactacct gtatcataga acatttttgt     180
gccctgtgcc gtatgtccac aaagtaggaa ttaggggtaa aaatcagaaa tttccacgat     240
tgcggaaagt gtgatataat ccagttaagc ggcagcaatg aaaccgccgg aaaggagcgt     300
gtgcccatga aaggagcaac aagcatacag gaacgccttt gggaactccg caaggacaaa     360
ggcttaaatc tggaagaatt atcagagttg acgagtattt ccaaatcagc tcttggaagt     420
tatgaaaaag aggattataa ggaaatcaat catggcaacc ttatcacgct ggcagatttt     480
tatggggtgt ccctcgatta tctcttttgc cggacagaga accgggcgga gatcaacacg     540
ccattaaggg agctgcattt gagtgatgag atggtagcac ttctgaaaag cggtcggatt     600
aacaaccgtc tgctgtgcga acttgccacg cataaggact ttatcaagtt tcttgcggac     660
attgagattt atgtggatgg gattgccacc atgcagattc agaacctcaa cgcccttgtt     720
gataccgtcc ggcatgaaat cattgaacgg tatcgccccg gcgaagatga ccccatttg     780 aaagtgctgc aagccgccca tatcagcgat gatgaatatt tcagccacat ggtgctggat     840
gacctcaacc tcattatccg ggatattcgg gaagcccaca aaaaggacag cgagagtgcg     900
ccccagacca ccgttgccga tgaactgaaa gaaaatctgg aagcggtcga aaatttcaag     960
ggcagccggg atgaaaagct cgttgtcctt tactgtaaac agctcggcat caactataaa    1020
aatctgtcag atgaagaatt cgctggctg attcggattc tcaaaaaatc aaagaaaatg    1080
ggaacgccta tcagtcagag gaaaaaacgg taaaggaaaa ccgctgttgc atggtttgtt    1140
ggcttccatg tagcagcggt ttttgctggg attattcagt taaattttca gaacgacact    1200
ggaagttgtt tatccaaaat gaaatggaat aaccatatca agtaaaaatg caagaactat    1260
actaattgtt cccattagca cagaactttt caatgtgtcc ctcctcaaaa cagtaagtcc    1320
gataataaag actatcaatt ctaaaacaga gcgtgcttcg aaatatcccc atccatatac    1380
gaaagtcata ttaaacaata ctgctaaaat caatactgat agcataaatg caggtctgct    1440
ttttcctttc gcataccaac agacaaaagc caataatgga gaaacagctg taaatccaaa    1500
ccaaatcatc gcataacttc ttgggaaaaa tcctgcaata tagtttgaat acaaatagta    1560
gcttgcaacc ataccaacaa agaatacaaa acattgatg cttgctctta ttgcagaatt    1620
gctataaata gaaatacaca gtgcaatcaa tatccagatt gcaaacgcc caagaaaatt    1680 accaatatct aagactccat ttattgccat aagcacacct ggaagttcag tttgacgaaa    1740
atccagatat tttgagaaag ttcccaaagc tattccgaga acaatatcg ctatggtatt    1800 tataattttt ctattaccag atataggatt ttccgcactc cttatatcat tcaaaaactt    1860
```

```
cttcataggc atctcccaaa ttctaatttg tcataatcat tctatcatac cgttatgaat    1920
aaatcatctc atgcaaaaca atttcttctg ctcggttgtg aatgttattg caacgctgca    1980
cccattccat ttgacgggta cgcttcaatt cctcggtcac gccctcggca gctttcatct    2040
gctccatgat ggtgtctaac cgttcctgtg cctgttcgtt caggtctgca aggtatgtcc    2100
ataactcccc ggtcaaggtc aatgtgttca atctggctgg gtggacttct cttaaatatt    2160
cccggtgcat ccgtccgtac tttccgatgg ggcggtgttc ttccggcagc ttcaagtctg    2220
ggatgtagta atctccaaca aggatataat caattccgtt ttctgttatt cttggtttta    2280
attcgctcat gttccttacc tcctgtggaa gcaggctcgt ctggtactaa ctcaattaca    2340
tcggtaatct cacaattcag cgtttcgcag atacgggcta atgtgtccat gctgatgtgc    2400
tttccctctt tgctcatgtt ggcaatcata ttcgttgtca taccagcggc aagccttaaa    2460
tcttcttttc tcatattacg ctctaacagt gtgtgccaga gtggtttata gctgatgtgc    2520
atattatttt cctgccttc tatccatacc accggggcgg ctgccccggc aggaactttt    2580
ctcttattat aacaccaatc ttgtgaaatc acaatttatt cttgtagcct gccgctgata    2640
ccgtctggat tgtgcttttc ctttcttttt gttcccttta attagccatc aactgcttca    2700
tgccctgtga ttttgcttat gtgtgataaa gaagtaatag aagtgtaaaa aattttgccg    2760
ttcctatccg gcacatgagg tatgtcggat aggtcgggcg gttaggtgtc gggcagttct    2820
accttgccga caaaagaata atagatttcg atttcctgtc tgcgtaactt gccccggcgt    2880
ttcccgtcaa gggcaacgct ttcatggaca acgattttct ccacaaactc ccgcagcaga    2940
gtaggggtaa gttcttcaat ggtagtgtgc ctgcgtacca cattcataaa cttttcagcg    3000
tttgcggtgg cttcctgcgc tttggaaagt tcttcccgca gtctggcggc acgttctttc    3060 agttcttttct gctcggcttc atagtctgcc gacagctctg tgaaacgctc gtccgatatg    3120
cgcccggtta cgctgtcctc atacagccgc ttgaagatag cagataactc ggctatgcgt    3180
ttctcggcgg cttccagctc ctttttcttg gcggcgttcc tgcgtctgtc cccgtcctca    3240
ttctgctcga ttaaaagctt cataaaccgg gcttcatgct ttgccgcata gctggtaact    3300
ttccgcagat tggagagtac gccagcggtc aagaggtcag tgcggataaa gtgcgctgtg    3360
cagtcggcgg tgcgttttctt gtagcttccg cagatataac agtcctgctt gcgcttgtcc    3420
gtctggtatc gctgctggta catgacgctg ccgcagtcgg cacaaaagag tatgccggag    3480
aacaagccca cttcgtcata acggttgggg cgtttgcgct gcttgcgtaa ctcctgcacc    3540
cgttcccacg tttcccggtc aatgataggc tcatggtggt tctcaaaaac cgcctgcttt    3600
tccgggggat tttctatgct gtgtttcagc ttgtaggacg gcttctcggt cttaaagttt    3660
accagacagc ccgtatattc ccggtttcc agcagatgaa ccacggtatt ggtcgcccac    3720
ttgcactcat agccggggtg gtagcggcgg gtgctgcccg tcctgcggta ttccagcgtc    3780
cccggcgtgg ggatttgctg ctcggtcagc atacgggcta tcttggtcgg accgttcccg    3840
gcaaggcaaa ggctgtaaat ctgccgtacc accggggcgg cttcctcgtc aatgataaag    3900
ttttcgtcct cgtccatgag gtagccatag acgggcttgc ttgtgatggg ctttccgctc    3960
atgcccttag agcgttttac tgccttgatt ttcttgctcg tatctctcac cagccattcg    4020
ttaaaaatgt tccgcagcgg ggcaaaatca ttttccccct gtgcgctgtc cactccgtca    4080
ttgatagcga tgaagcggac acctttctgt gggaaaatca tttctgtgta cattcccacc    4140
tgtaagtagt ttcgccctaa cctcgacata tccttgacga taactgtccc gactttccct    4200
```

```
gcttcaatgt ctgcaagcat ggcttgaaat ccgggtcttt gaaagttcgc accggaataa    4260
ccgtcgtcgg tgtaccagcg cagattagaa aatccattct gtttggcata ggtttccaaa    4320
atcctctttt ggttggaaat ggaattgctc tcgccttgca gctcgtcctc atgggacagt    4380
cttgggtaaa gggcggtaat gagttgctgg gtggtctgtc ttaacataaa ttcctccgtt    4440
tccgacagcc agccccacta ttccgtacct tgattgtacc acatggggcg gctgtctgta    4500
tagcggcaaa agcgtcaaat ctgcttcttt acggtcggta aaaatgacgg tttttcaatc    4560
aggcttatca caggtcaaat atccggcggc ggcttctgct tccagcactt tcatcatctt    4620
gtcagcggcg tgtcggtcg ccccctcctt gaaaaagcca gacaccacaa ggattgtgtt    4680
gcctatcctc gtttcggtca cgcagtccgg gcggcgggca gggcgtttgt ttctctgggt    4740
gtcggtcata ggcaaatctc ctttccggca agcagccgtt tcagctgttc cattttcc     4800
tgtgcggcgg ctttcctcaa attctccccg gtaaagcaga gaggggaaca catttcaagc    4860
aggcggtcat aaatccgggc gtgggcggtg tcctccgggt gctgcaattc ctccagcgtg    4920
aggttggtcg tcacaatcag cggcttcctg ctccggtagc ggctgtcaat cacattgtag    4980
acctgttcca gaccgtattc tgtgccacgc tccattccaa aatcgtcaat gatgagcagg    5040
gggaagctgc aaaggcggga aatatattcg ttcctgcccg caaagctggc ggcaaggtcg    5100
tttaatattg ctgcaaagtt tgtcatgcac accgggactt cctgctccat gagggcgttt    5160
gcaatacacc cggcaaaata gcttttccca gtgcctaccc tgcccacaa gagcagcccg    5220
tagttcccgt cctttatctg ttcccagcgt gccacatatc cggcggcgtt cttcatctgc    5280
gggcagctgc cgttatcgtt ggcaaatgtc cagtcctgca tggtcttgtc tgtaaagccc    5340
tgccgtttca gccgttccac cgtttcaagg tggctgcgcc gcttctcggc ggcttcccgt    5400
tccttacggg ctgcccgctg gcagtcgcac tctgacgggt ggcggtcacg cccgaaaaag    5460
gtcttgccct ccgggaaata ggcttctttg ggtttccggc atttgccgca gtataaaagc    5520
ccgtcctccc cggtgtaatc ctccggctcg gctgtggtgt cggtcatagg cagtatggtg    5580
ttgtggattg tatcggtcat aggctttctc cctccttgaa tgaatagtcc ggtatgcctt    5640
tctttggctt ctctttggca gcgtcctcct gcgcccactt gtaaatggtg gctgcatggc    5700
tctggtactg cttcccggtg gaagcgatgt ggcaggaaag gcggtcaagg taatactccc    5760
acttgccggg gaagtcctgt tccagctcca aaagttctgt gtcagaaaga aatacatttt    5820
tatatctgcc ataagcggcg gggggctgcc cctcactcgc tccttttgtt tggctctcta    5880
ttaggttgtt tatattagtt tggttagggg acggttttcc gaccgtcata aggtcagttt    5940
tccggctgtc agttggtcgg tttcccgccc ttatgagggg cggttttccg tccgtcagtt    6000
ggtcggaaaa ctgtaccact gggataggcg gcactttcac atacagacgg ttggcggcag    6060
aaaagcccgt ccgtctgcgt tccagcagcc cggcagcgtc cagttcgttc agtgcgccct    6120
ttatggtggt gcagccttta tccagcattt ccgctatctc tgctatgggg tagacaatgt    6180
atgtccgtcc ctcgctgtcc tgccagccgt tcttctgcga aagggtggaa cggtctaaca    6240
gcagcgcata taactctctt gcggtgtggg ataggtctgt ttccagcagg aaacgggggt    6300
aaggcaggta agcgggcagc tccgttcctg cggtcatata atcagcgata gggttcacct    6360
ccttgtggtg tctgtctgtg ggtctgttta cgcttttagg gggcgttttt aagggaaaag    6420
gataaatgta tcacgcaccc tttgacaccc tccaaaaaag ccttgattta tgcgggtttg    6480
aaatgcccta aagcgtgaca tttctccctt tgtttccgct tccgtttggc ggcgtttatc    6540
cgcttcatgc gtccggcgca gtccgggcag tatttccccc ggttggattt tgggaagaag    6600
```

```
aacgccccgc agacagcgca gcgtttccgg cttcccggc gcaagagggc ggcttccagt    6660
gcttcatcaa ggggcaggac agcggcggta accagcggc agagcagcga atagctgata    6720
ctctgtacac acacgcaagg ctcgccgtcc tccaacagca ggcagttccc gctgtcatag   6780
ttgcagcact catgcacaag gcggcgggct gcccggtact ggcggtagtc catgcggggg   6840
atattaccgt tcatggctct gctcctttct gcgctgcggc tcgctccggc gtaaaatctg   6900
gtcgatattg cccttgacag tctgcaagcg gcggtactcc tcccgttttg cccggtaatc   6960
gttgtagccg ctgttttttct ctttgataag gctttcaatc tctgcttgca gggatttata  7020
gctcggcagc ttggaaatgc cgttctccct gaaatagcgg gcggctgcgt ctgctatgat   7080
aaagtcactt tcatgcttct gacggtaggc tgcttttgct ttggcgtttt tctgctgttt   7140
cagcccgtcc cggacagggc gggtcttgga ataggcaagc acctgccgtt gcagctcctt   7200
tttcccgttc agcgtctttt ccacctgctt caaccacgca aggctttcct gcatggcggc   7260
ataggcggca gaacaggctt cgtccagttc ctccggggag gaaaagccgt actgctgata   7320
ggcggtaacg gtagctgcca tttgctttag gttgtgcttt gccgcccagc ggtcatagcc   7380
cacgcccttg ccctcggctc gcttggcttc ccggtcaacc atgcgctgca aggtgttgtc   7440
tgccgggggtg gttttttgcag ctttttcccc ttgtaacggc ttttttaactg cggcagggta  7500
ttcgggtatg gctttggtct gttcggcagc tctgtgggcg ttctgcgtga gcagggcaag   7560
gacagcagcc ttgtcaaaat cgtccccag cttttcgggct gtgataggct ttgtcctgtc   7620
cggcgtgagg taggaaagcc gccccggct ctccttgacg gtcacaccct cccgcagcaa    7680
aagggaagaa aactcgtcaa agctgccagc ttgggaaagt gcctgccgta tcgtccggcg   7740
cagcttcgcc ttgtccgttt caaacttggt gggcttggtc ggctgtccgg cggcttctct   7800
ggcggcgttc tctttgtcaa gggcaagctg ccctttcttt gccgcccagt attcccgttc   7860
ggttatccgt tccttgctgc cgttcaagag gtcgatttgg taaagcccct cccggtggca   7920
catttccatg acttcgctct tgaaatattc catagcggcg ttggtgcagc ggtgcttgca   7980
gccctccagc gtgtcggctg gtctgtccat gtagggcaga agcgggactt cgtaaatccg   8040
cagggagttg atgacgatat gcacatggat attcccgctg tggttatgcc cgtccgggtg   8100
ggtgcagatt agggcttggt gtccggggaa atgctccttg cagaactgct cgcccagctc   8160
ctgcgcccgg tctacggtca agccgttgtc tgtcccgtcc cgtgggtcaa agctgatgat   8220
atagtggtgg cttttcacat cttcccgttt ttggttttttc tcatagcgga gattggctcg   8280
catacaggca acagcgaaat cctcgccccc gcagttgagg gaagaaatgc ggtaatcctc    8340
cctcggtatc agccgcccgt tttcatcaag ggtggctttc atggtaaact cgtcatgctc   8400
aaatgtgaga taggcttccg ctgcgccata gtcggcgttt ttagagctga tatgtttgaa   8460
tgttgccaac agcgtcaccc actttctgca agacttcaaa ctttagggca gcaaggtcgg   8520
aaaccgccgc ccgtacctcc ccggcaagct gcggataggg actgtgccac tcgttcagcg   8580
tccgggctat ctggtttaag ttgccgccga tcctcccgta ttcggcggtc agcttcccga   8640
cagcggcaag cagctcgtca ttgatggggg aaacggttat gatggggcgt atggctgccc   8700
cggttatggc ttgccggata aactcggctt ggctcatgtg gtaagcagaa agccgctggg   8760
caaactcggc gtattcttcc tcggtcatgc gtgttttgac tacccggctg cggtgcggcg   8820
tgttgtatcg tttcataggt ggttgacctc ctttctgtgc gtggtgtcct ctcactaata   8880
ggagaaaaac agggtgtgaa gcggaactgt ttttgaaaaa tccgaaaaat attttgaggg   8940
```

```
gtttttcagc ggcgcaagcc gcataagcag ggtttgggga aggcactccc caacaagatt    9000
cccgcagggg caaaatgagc gataagcgaa ttttggcacc tcggtagaat cttgctctaa    9060
gaaactgccg gcctgccgtt cacttgctac tgccacttt  tcagaaaatc tataaccagc    9120
tttttttata aaaggctgcg ggctggcgtt tttcccttac tccctacaaa ccacaaaaga    9180
gcagaatgga cggactttcc ggcaagaact tttccggcgg ctcggtcttt cccgacaata    9240
aggcgtttcg gaagctgcgt tttgcccgct gtctgaaaaa aatggcagcc ttttttggtt    9300
tcactgtcta atacggaact tttggaaatt tgccaaaaat ggacgcaaaa aaagcagcaa    9360 atcttttcg  gatttactgc ttcatgtgcc gctgcggtgc ggcgggatgg atattcagtt    9420
gaaataaaag aggatggtgg tactttagtc tatcgactct ttactaacta ttaggtaatc    9480
ttgaaagatt ttccttgaat ttatctaaag aatgttcatt gtttcccgca aaaataagtg    9540
gaattgtata ttcatatgat atgccatttt catagtccga taattgtatt tttatagtat    9600
catccctctc atctttaggt gctatatata tgaatgaatt tttatttata tcagatattt    9660 tcccttttc  agaagaaaca gtataacccc agtctgttaa atttgtcttt attgtaactt    9720
ctgtttctgt ttcttttcta gtctgcaatg ctgttttatc gatttggata tcaaaggag    9780 tcgaacctaa caattcactg tttatattta caagttcttc tccatttgtt ttagaaatat    9840
tagattcatc ttcataattt tgttgagatt catctttgg  tgtttctctg ttacatccta    9900 ataaaagca  taaataatt  agtactaata cagaaagttg ttttttttgc atttatttct    9960
cctttcatat tatcaaagaa agcactgaga gtactttcaa gaaatttga  aatattctca   10020 atgctttcta ttttttgatt ataaacttgc cggtaatgat actatgttaa tttatctctt   10080
tcgcgtaacc tttgttgcaa tatacacatg caccattcac ccatttgtga gacatttcaa   10140
tcgtctcaac ttcataaatg cttacttctc cacaaattaa acattgtttg taattatata   10200
catgacgtgt cgcacattta tcccagtcat catatatacc aggcatttca tcttcatatc   10260
catagtactg gggagaaccc caactatgag tatgagcggc aaatacagtc attggagcag   10320
ctacaattcc agctactact gaaagtgcta aaatagattt tcttaaattc ataagttcct   10380 cccttttcctt aaaaatacat agctcttgt  tacattgtca ttttaacata taattggta   10440 aaatgcaata atttattttc tatttacgag aaaatactgt gcatattatc ttatttagga   10500
atagttaagg cggctaccta aatcttttta ttactttacc gcacatgagc atttgcacca   10560
gggttgtcgt tgccgtaacc ttcgagcagg ttgataacgc cccagatacc gagaccggca   10620
ccgagcgcga taacgagggt ctgaagaacg gtgattgcct gttcaaaaaa tgccatatag   10680
tttgttagcc ggaatctgat taaaaatag  gtttgtcatg tttcataggc atacaaaagc   10740
cggaacaatc tgccgcccgg tttccggggg catgattccg gctgtcctcc tttttcatta   10800
tttttttctt gggattgtcc gctttgtacg ccaatggccc attagagggc aggtgcggcg   10860
aatagataag atcactccct tcaaaagcgg aacgaagtta agcgccctct gtgtctactt   10920
catatacatc gcagacctca ttgggcttga gtttcagcct tgcggacagg aatgcttcaa   10980
tgtcaaaagc gttcttatca tccgcgtcgg cagtgtactg gaaattgggg tgcttggtaa   11040
tgtcgtactt gtccgaaaga aaaggacgca caccgcgcag ctggagaata cacttgccgc   11100
catccataac agcaagctca tcctggctca tcagctcttt ccccaacttt tgatagttga   11160
gagagtggga agtttcacgc ccacggctct ctccggtgtt gtaggtgtcg atggtttcct   11220
tgcccagcac ggcagccagc tctttgaggg tggttggctc cttaccgccc aggaagatgg   11280
aagtatccat gttgccgatg atggtatctg cgttatcctt atagatcgcc ttcagctgac   11340
```

```
tctgtgcctg caacaccaga caggcggaaa tctcacggct tcggatggtg gcaaccagct    11400
tttccagctt ggggatctgg ccgatgttgg cgcactcgtc aatgagacag cgcacatgga    11460
ccgggagcct gccgccatac acatcgtcgg cttttcgca gagcaggtta aaaagctggg     11520
tataacacat ggaaataagg aagttgaagc tgtcgtcagt atcactcatg atgaggaata    11580
gggcagtttt cctatctccc agagtgtcta gctccagctc atcataagcc gtgacctcac    11640
gcagctctgc aatgtcgaac acggcaagac gcgcaccaca ggaaattagg atcgacttgg    11700 ctgttttcc agagacgaaa agtcaaggac ttttcatca aattcacaaa gaagtcacat      11760
tttgcggact tcctcacgga gcagacgctt gattttgtcc tccatcgtct cttttgcggt    11820
ctggctgaaa tggacacgga cgatataggt tgtcttgccg atctgctttc tgacagtcgg    11880
gcaagtggcg gtgttggttg cggtattgtt cattcaaaat cctcctgtaa atgaaaaata    11940
cccggtgact gttcatcatc gggcggtgtc ggtatgaggg aacaaggcaa ggtggcaaca    12000
ttaaggtatc tataaaaacc ttgccgtctt tgccatgctt gccgtgttcc tgttgtcagt    12060
ctcggagata gcagacccat gctgtgccgt cttctcggt cacaagtctg tccccgatac     12120
ggctctttgc cgttctcatg gtgcgtgagg aaatcccacg ctcattgact gccttttcca    12180
gttctgcgct cggcatacgc tttccgtccg caagcagttc cagaatgagc atttgcgcct    12240
gtgcggtctt gctctcggtc ttggcggtgt ccgtcccggc aagaagctcg tcagcggtaa    12300
tgtcataagc ccctatccac tcaaagcctt tctcgtctcc cagagaaaag gcaagggact    12360
gtccgggcgg cgcaagggag ctttctcat ggataagtac ccttgttgtg gggctgtcct     12420
tcagcttgcc gataaagagc agactgcgga ctgccgccgt aatgtcgata gaccctaatc    12480
cccggtaggt gctttgcgtt cctgcggctt tgttgagatg tccgatcagc acgatagcgc    12540
acccggtagc ctgtgcaatg tctcccagac tgcggaatat cgggcgcacc tcgtttgccc    12600
ggttcatgtc cacatctgcg cccagaaacg cctgtaccgg gtcaatgata accagccttg    12660 cgttgtttc cggattgcc cttgcgatgc gttcatcggc aagggtcagt ggtgtgtctc       12720
tatcgtcaat gacaagcact ttttcaaggt ctgcgtctgc ttccatcagt cggggcttga    12780
ccgtatcacc cagaccgtcc tcggcagtct ggtaaatgat attgaacggt tcaagggttt    12840
ccataccggg caagggcttt cggttggtgc aagccgccgc aagacgcatg gcaaagtagg    12900
tcttgccctc gccggggttg ccctgtatga tcgtcagctt tccaagggg atatagggaa      12960 accatagcca ttccacgctc gtcagctcca catctgccat gcggagcatg gaacaggct     13020 gggcggtggg cagctctcgc agcgtgattg tctcggctat gaatttgcgg ctcggaatgt    13080
ccccttgctg acggagaaca tcgttccagt cttccttgc cgggacaagg cgaatgacgg     13140
cgatctcgct gggaatggac tgtgccagtc gggtacaggc ttcgcttcct gcggtgtcgc    13200
tgtcaaggca gaggaacact tttcgggtgt ccttgcgttc agaaagaaaa cggtcaaggg    13260
ctttgcctga aacgccgccc agggcaaggt agctccttgt ctgccagtcc tgcggataaa    13320
ggcagataaa ggacaaaagg tcaatcggtg cttcaaagac aaagagctgg ttgccgtttc    13380
cctcatagtg gaacggatag gatttgtcag acccggcaat gtcctgtctg aatgggtctg    13440
ccgttcctcg cacatgggcg tatctcggcg taccgcttcg gtctctgccg acaaacacaa    13500
cattgtgccg cttgcgtcc tcgtaaatat ccccggaaag aagaaaagcc tcaacaagcg     13560
ttttgttgag acctcggctt tcgcaaagat attgaattgc tctgtcggct gttctgttgt    13620
gcaagggcaa gtgaaacgct gtgggcggtg ctgtgctggc ttcgctctgt ccctcagcgc    13680
```

```
tttcgccggt taagagctgg actgcttcgg gaaaggactt gccgtaaaac tccatgacaa   13740
aatcaatggg atagccgccc ttgctctggc tgtggcgaaa ccatttgttt ccccggacgg   13800
tcaggctgtc atgttctttc cagcggtatt cccgtccgct tttgataagt gtctctccct   13860
gtgtgcggag aaaatcttcc agactgacgg cgttcgcccg atcaatctgt ggttgggtgt   13920
aattcatcgg gatatatcct ccttttgtg tcgtgtttgg ggtcgatttt ggtgcatttg   13980
ttcctctgta cgctcgttaa atcgggcggc agtatctaca catgacttga ccttccaaag   14040
acggtgtaaa tcgtctctga cggtcttaaa ctcgccatag gtggtgttgt gcgcctgttc   14100
cagctcgtca tactcttcgg tcagcttttt catatccacc ttgccgtccg ggaactctcc   14160
ggtcagcttg cgtctggcgg cgtagaactg tttcagttcc gcttcatgct ctgccttgta   14220
cttggctctg gcttctcaa acttgatttt ctgcaagccg tcatagacag gcttcaagct   14280
ctggaaagca gcggagctgt catagagctg cttaattgct ttcattcggg cggtctgttc   14340
gtccagcgtt ttcttcaagc tctctgtggc agcactgtgt tcgctgacac ggctttccaa   14400
atcttcaagg gagtaaatgc cgtttgcccg gagataattg aaagtctcgt tcatctcctt   14460
tagattgctg accttgcctt tctgcgaata cgacccggct ctgcgctggg tgtaataggc   14520
gttcagcaga gaaacaaggt cgggtgcctg cggcttggca atctccgctt ttgcttcggc   14580
aatccaatcg aacaggagag cgattttctt cttgatgtcc cggataacgg cattggttgc   14640
cttgatccag cggttgaact cgcccttttc ggtgcgtatg cctttcttct ccattgcccg   14700
gacggttgcg ccttcatgga tagtaggaag taaatccacg ccttgccgtt catagctgcg   14760
gtggtcgata cgaacatcaa tacctttttc cgcaaacttg gcattgcata gctccgccca   14820
tgtctgccgc cagtattcca gcgtttcggg actgccccag tcggtagtgg aacggcgtt   14880
gaaaacaaat tcgccgttct ggtctcggat acggttgccg tcctcgtcca gctcatacac   14940
ccggcgttgc tttagtcccc atttgccgtt ctgctcgatg gggcggatgg ggcaaagcac   15000
atgaaaatgc gggtttggta tgccgccgtc ctccggtct ggctggtgta cggcaaagtc   15060
aaccaccatg ccccggctca caaagttctc caacaaaaat tgccttgcaa gagcgatgtt   15120
ttcctcaagg gaaaattcat tctgcaaggc aatgtcaaag ctgtatgcaa gctgggcgtt   15180
ctttccacgc tcggcttttt ccacggcgct ccatagggtc tggcggtctg cgtattcggg   15240
cggtgcatgg gacggcagga gaatgtcaga gcagatcacg ccgcccttgc gggtgtagtc   15300
gctgtattcg ccgtaatact cgctatacaa tcgctccccg gaacggtagg cggcagaagc   15360
aatagcggac tgtcctgcgc ttcgcttagt ctgcgtgacg ctcagatgaa atagtgccat   15420
cggctttcaa ctccttttct ctgtttgctt ggctgatgtg ggtaatcgcc atatggcgga   15480
tggctcgttg gacttctgcc agagaaaaga tgtactccat cagctctgtc atttcggtgc   15540
gtgtgagatc tttgatctcc ggggcaaggc tctcaaccgt gccgcccaga ttgcaaaggc   15600
ggtgggtgcg cttggtgcgt tcgcctttct ccagatactt ctttctgttc tccagacgct   15660
ccagcttgtg ctgttcctgt gcaagctgcg tctcggctcg ttccttttcg gtccgaagct   15720
gttcaagggt tttcggtttt gtcattgtga ttgacctcct tttttgattt tggggataaa   15780
aaaagaccgt caacttttcg catagtgcga ccagtcaacg gtctgatttt cggtattcgt   15840
tatgttctaa aatcagttct ttgaaagatg gcgttttca atctctaatg ttatgaaggt   15900
agcagtcatc agatagagga cggcgatgac acattccaaa gcaagcgaat tgatagggcg   15960
aggataaaaa tgtactaacg cacttaccaa cagtctaacc gggaagtatg tgcctaacca   16020
tgcagagact ttataaaacc gcttgcggaa ttgcactgtt ctctcattct gctcatttgc   16080
```

-continued

```
cttttttttga tatgcgtatt caaagcctcc aaccatagca ataaaaggaa taaaacttag   16140
gacaccaaag aaaatgtttt gcaggatcat aacagacatg aattgaatga tcaacaccat   16200
cacttcaaga gtgatcaaaa aaatcatgat ctggtggatg ccgtccgttt tgacttcctt   16260
aactttcggc aggtcattgt cgctttggta ttcatcattt agcaagtagt ctgttgtaac   16320
ctgaaacagc ctactgagtt gaagaatgtt tgttgcatct ggcatagctg ttcccatttc   16380
ccaacgggaa atggcttgcc ttgatacgcc cagcttatca gctaactctt cctgtgacat   16440
tccattggac tttctcaacc taacaatctt atctgataat ttcataatga aatcctcctt   16500
tgatttggtg atttcattat agcaatgaac gctttcagcc accaccactt caagtttaca   16560
tttccgcaac ataactttac gctgtgtttt tacttgctgg cggcaacag catttcatgc    16620 tgtttgcgga cggcaagtcc acaggggata gccgctttag cggcgcaagg gggtgtagcc   16680
accttgacgg aacgaagtga cgcaacattc tcggtcatgc agttttcttc tgctgacgga   16740
gaatgaagct ccgcaggacg cacgatactc ccgataggag agtatagaag tgcgcccttt   16800
agttcctaaa gggattttat cagttcgaca aacttgaatt ttctaattag tctttgcaaa   16860
taacctttaa accttcacaa tcaattacaa ttccctgaca agtcttgggc tttgatttag   16920
ggttataaaa tgcactctca atacgctttt cgtccaaata atccacgtat ttctggctgt   16980
acataggttc ttcacgaatt tgtagccgtt ttgtatccag ccattgtatt ttgtgaactc   17040
attcctcgaa cagatacaga agatatccgt aaccctctgc ttccatcttt gcgtaaggca   17100
caaagcgcag ggccgcactg ttgatgcagt agcgcacgcc atttggggac tccggatcgc   17160
cggtgaacac atgaccaagg tgagaatctc cggcacggct tctgacctct gtgcggcgca   17220
tgccgtggct caggtcctcc agttccacca cggcaggctc ttcaatgggc tttgtgaaag   17280
ccggccagcc gcagccgctc tcgtacttat ccgtggagga aaagagcggt tcgccggtga   17340
cgatatccac atagatgccc ttctcgaact gatcccagaa ctcattgctg aatggacgtt   17400
ccgtgccgtt ctcctggggtg atgcggtact gctcctccgt cagtttgtcc cgaatggact   17460
ctgctgcggg cttttggtag tcgcctggat cgatgcgaag cttggagaac agctccatct   17520
ccgcccgcgg gatgtggcag tagccgttcg ggttcttttc gaggtagttc tggtggtact   17580
cctcggcagg gtagtagttc ttgagtgggc cgatctccac gaagaacttt tcactgcgtc   17640
cccgctcgat ctccgcaatg cgctccaccg tttccttcgc gctttcgttg gtgtaataga   17700
caccggtctg atactggctg ccccggtcgt tgccctgccg gttctccacc gtggggtcga   17760
tcacatagaa gtaggccagc agcagggcgt cgagactcac ctgtccgggg tcatactcca   17820
cccgcacggc ctcccgaaag ccggtctcac ccttgcagac ggtcttgtaa tcggcgtccg   17880
cctcgcaggt gccgttggca tagccgctct cggcatcgat gacgccgggg atggactgca   17940
tcagctgttc catgccccag aagcagccgc ccgccagata gatgacattt tccgtggtat   18000
ccatatacat gcttccttca ccggacatat cagagggctg tccggtcctt tccttctcgt   18060
ccgttttctg cggaatattt ttctgcccgg cagtgcagcc gctcagcagc agtaccgcgg   18120
tgagcagaag cggcaatact ctccgataca tggtgtttcc ctccattctg agatgataaa   18180
ttcgtttgtc agcccatatc ggcggcaaga gcctggtcga tgagcttttg cagcgtctcc   18240
gcctgcttct tttccgtgat ggcgcctacg atggggtcgc ccacaatatt gccgctgcgg   18300
tcgaccacat aggtggtggg ataggcaaag atgttggtgg taaactttcc cgcctcacca   18360
tctgagtcaa aatacacatt ctgataggtg gcgtccttct tggccagtac atcttttgct   18420
```

```
tcggaaattg ccgcttcatc gccatccaat gtgaaggtgt tgacaccgat gagtgcgccg    18480
cccttcttcg caagctcctt gttcagcgcg tccagctcgg aaagctcgcc cacgcaggga    18540
ttgcaggtgg taaaccagaa attcactacg gtgacggcgt tgccggagaa cagctcgtcg    18600
ctcttcaccg tgttgccgtc caggtctttc ccctcaaagg cggggaactt ctgcatactg    18660
ccctgctcgg ccatcttgtc cgcgccgctc tgatcggacg gcatactcat atcatcgccc    18720
gcgggcatac tcatatcgcc gtccatggat ttctgcatga tctcgggata cttctcttcc    18780
aactcggtca gcttgttttc aatattgctg atctccgtgg ctgactcctt cagccactca    18840
tactccttgt cggcgaactg ctctttcgcg gtctcgatgg tatccagcag gaagtcgccg    18900 tagttttttcc cgtcctcgac catggccatg cccttgtcgg cctccataaa gaccttttcc    18960
cacagctcgg tattttccga caggatcgcg ttctcccgct ccagcagctc cttgtgcagg    19020
ctgagcgcct cctcggcgtt tttcggctcg ccggtcatgg cggagccgtt gccgctcatg    19080
tcacccatct tgtcattgtt cttcatgccg caggccgcca gggccagcac catcagcacg    19140
gcaaaagcca gtgcaaaaat tctcttcatg ttcattttga ttcctccatc gttgttttct    19200
ttggtgtttc tttcccgttg ccgaagccgt aacggaagca cacggcgttc gtcggacaag    19260
cgcggacgca cattccgcag cggatgcact cggtgtggtt gggcgttttc gtcacatcca    19320
catccatctt gcaggctctg gcacactttc cacaggagac gcacttactc ttgtccacct    19380
tcatctggaa gagggacacc cggttgaaca gcgcatagaa cgcgcccagt gggcagagcc    19440
acttgcaaaa cggccggtag aacagtacgc tcaacacgat caccgacagc aggatgctga    19500
acttccatgt aaacagcttg cccagcgccg cccggatgcc ggaattggca agggacagcg    19560
ggatggctcc ctccagcacg ccctgcgggc agaggtattt acagaagaac gggtcgccca    19620
tggctacatc atttacaagg aacgccggca gcaggaaaac catcaccagc agtacggcgt    19680
acttgaagta tcgcaggggc ttgagttttct ttgtggagag cttcttcgtg gggattttgt    19740
gcagcagctc ctgaaaccag ccaaaggggc acagaaaacc gcagatgaag cgtcccagca    19800
ggactcccag caaaatgagg aaacctgtga tataatagga gaagctgaac ttggatgagc    19860
ccaccactgc ctgaaacgcc ccgatgggac aggcaccgga ggccgctggg caggagtagc    19920
agttcagccc cggcacgcag acggttttcc ctgcgccctg atacaggcct cctttgagaa    19980
agttcggcag gtgcaggttg gtcaataagg ctgcccctgc ctgtatccaa ctccgaaagc    20040
gggacaggag ttgtgacgcg cccgaaaatt ttttacccaa tgcccacaca ctccagacat    20100
aatttaatcg ctttgctcag caccgtcgcc gcctcaccgc gccatacgcc gaagcacaac    20160
atggcgatac ccacaaccag caacaaggcc tgcgccgccg ttttttttac atggctcaat    20220
tccatcaccc tttcacttttt tctgctacca tcataacgca agagagttaa agtccttgtt    20280
aagaacgaaa atttaatgca aactttatct gggtttgcta taattaaaaa caacatgaaa    20340
atgaataaag aaggagggct cttatgcacc ttttagtaat tgaagatgaa cgcgccctgt    20400
gcgaaaccat cgtccgcagc ctgcgacgcc aggcatacag cgtggactgc tgctacgacg    20460
gggagaaggc ggtggagctt ctgggcgtgg agcgctacga tctggtactg ctggatctga    20520
acctgccggg gaaggacggc atgacagtgc tgcgcaccct gcggcagacc gaccgggaga    20580
caaaagtact gatcctctcc gcccgggtg aggtggagga caaggtggag ggactggacg    20640
cgggagccaa cgactatctg gcaaagccct tcatcttgc cgaactggag gctcgcattc    20700
gcagcctgac cctgcggcag ttcacccagc aggatgtgct gctgatctgc ggtgagctga    20760
cctttgacac ccgctcccgt accgccgccg tcaacgggca gacgctgacg ctcacccgca    20820
```

| | | | | | |
|---|---|---|---|---|---|
| aggaaacagg | gatacttgaa | tacctgatgg | tgcatcaggg | gcggcccgtg | agccaggagg | 20880 |
| agctgatgga | tcacgtttgg | gacaacagcg | tggacagctt | cagcaattcc | attcgcgtcc | 20940 |
| acatctccgc | cctgcgcaaa | aagctccgcg | ccgcgctggg | ttatgatccc | atccgcaacc | 21000 |
| gcatcggcga | gggctatctg | atgggggggcg | aggaagcatg | aagcatcttt | ccttgcaatg | 21060 |
| gcgcatcacc | ctgatgaccg | tcctgctcat | cggtgccacc | tgcgtaatca | tgaatctgct | 21120 |
| gctctgctcc | tccggcgtgt | actatatgga | caccattgcg | gacagcttac | agggcggcag | 21180 |
| cacggtaatc | ctgaatgagg | gcgaagcggc | gagctttgac | ccgcagctca | tagcgcccga | 21240 |
| cgaggagctg | accatcgtca | tcgatggggc | gcagggcgc | ttccgcacca | ccaactggta | 21300 |
| catcacggct | gcggtaacgc | tgctcagcgg | cattctgacc | tattttgtca | gcggacgtgc | 21360 |
| gctcaagccc | ctgcgcagtt | ttgcctcgca | ggtggagcag | gtgcagctga | caatcttgc | 21420 |
| cgatatgagg | atcgatgaag | acgtcattcc | agaatttcag | cagctgagcc | gctcgttcaa | 21480 |
| ccagatgctg | gagcggctga | acaatgcctt | tgccgcccag | cggcagttca | ccggcaacgc | 21540 |
| ggcccacgaa | ctgcgcacgc | cactggcact | aatgcaggcg | cagttggagc | tgttttccgc | 21600 |
| ggagcatcct | gatgtgcgac | cggagacggc | ggagttcctc | acgcttttgc | gtgagcagac | 21660 |
| ggaacggctg | atacagctga | ccaggacact | gctggagatg | agcaatctgc | ggcaggtggc | 21720 |
| gcggaacgag | cggatccagc | tcgctcccat | gattgaggag | atcttcacag | atcttgcgcc | 21780 |
| gctctcagat | aagctcggcg | tcacgctgac | ggcggagggc | gacggcatta | tgaccggcag | 21840 |
| cgatgcactg | atctaccggc | tgatcttcaa | cctgacggag | aatgctgtca | agtacaaccg | 21900 |
| gccgggcggc | tcggtgcggg | tctgtgtcac | acaggaaacg | gaaaaactcc | tgattcgcgt | 21960 |
| ttccgatacc | ggctgcggca | ttccggagaa | gtatcagcag | agcatcttcc | agcccttttt | 22020 |
| ccgggtggat | aagtcccgca | gccgcgagta | cggcggtgcg | ggactggggc | tctcgctggt | 22080 |
| atgggagatc | gccgacctcc | acggcggctc | cgtttgggtg | gaggaaagtt | ccgagaaggg | 22140 |
| cactaccatt | gcggtgggggg | tgccaacgca | acaatcaacg | aagccctaaa | acccttttat | 22200 |
| tcgttttcg | ccgcttcgct | cgccgcgctg | cggcgttcct | ctctgtatgg | ggcggtcagc | 22260 |
| cggaaagaga | agcgtcccctt | ttcaatctca | aattccttgc | agcccgtgtc | cgggtctacg | 22320 |
| tccgtcagct | tgcagacggc | gtgggaatga | atgcgacttt | cttgttatca | atttcttctt | 22380 |
| ttatcaaact | tcctacactt | gaaaagtgcg | aacataaaaa | cagcttcatc | catattctcc | 22440 |
| tttataaatt | tgttgctcaa | tttcgtgttc | aaattatacc | ataaaacttg | tgaacaattc | 22500 |
| tacctcaact | tttgtgagat | atgagaaaag | tccgaacagt | tttctgcccg | gacttcctcg | 22560 |
| ctcaatcata | aatcaattcc | gctttcacaa | cttcctctgc | ctgtgccttg | caagcgttca | 22620 |
| tctgccgtac | ccactccatc | tgattttcgg | ctttcagctg | ttcggtcacg | ccgttttgct | 22680 |
| ctgccagtga | ccgcacgatc | agctctattc | ggtttcgtgc | cgcttcgtca | atctcggcgc | 22740 |
| aatgctcaaa | aagcttatct | gataacacca | gctcattgaa | cagtatcgga | cggtgcattt | 22800 |
| tccagatacg | ccttgcgaag | tctgccgtag | tgtccgaggg | gcttggtctt | gcggataacg | 22860 |
| atgttcggga | taaggtaatc | tccgttctgt | gtgtaagtga | tattcatgct | gtttgtactc | 22920 |
| ctttcatcgg | ctctctctgc | ggtaaactgc | tgacaggac | gaacactccc | tttgcaatgt | 22980 |
| cctccgcacg | aatggcggct | ttcttggctt | cgatttccgc | cttttttccgc | ttcttgattt | 23040 |
| tgtcctcgta | tcgcttctgc | gctccgctgg | ctttccgctt | caagtagttc | tgatgaagcc | 23100 |
| tgtccttgcg | ttcctcacgc | ttgcggattt | cctctaattc | ttccggggtc | agctcaactt | 23160 |

```
ctccaaacgc cggggggaaca aatcgcccga caaaattgaa gtaaatctcg acctcctgtg   23220
tggtctgtat actgcctttg cggtcacgct catgcacaag gattttctcg ataaactcgt   23280
tgagcatggc aatggtcagc ttgtcgaagt tctcatattt gtcaatcaga gcgataaaac   23340
ggtcagcgtc cttttcatgc ttctcatagc tcttgactgc cttttccaga acagagattt   23400
cagcggtaag ctcggtctgt ccttttcgt attgagcgtc cagagtggcg tatctgctgt   23460
cggacagctt gcctaaaatg ttatcctcat agattttgca gagcaggact tccagctcgg   23520
aaactctctg ctttgctgtg gcaaggcgtg tccgctgttt cctgacctct gtggtctgct   23580
ggctggactg cgcttcctgc accacacgga caaactcggc tctgtcatgc ttcgcatact   23640
cggcaatggc tttcagcatt tcagagacaa gggacagtac cacatcttca ttgatacggt   23700
gctgggtctt gcagagcgtt ccgcaaggaa ctttggtgta ctgtgagcag gtgtattgag   23760
aaatgcgctt gccgttattg gtgcggtgga catacatctt gccgccgcaa tcggcacaat   23820
agagcaagcc cgtgagggga gctgcttcgc cccagccgtc cgggtagcgt ctgacattcc   23880
cacggatttt ctgcacaagg tcaaaggtct gctggtcaat gataggatca tgggtattct   23940
cgaaaattgt ccattcgtcc tccggaacat aatggctttt cttgtccttg aagtgctttc   24000
gggtcttgaa gttgatggtg tgtcccagat actcacgctt tcaagaatg ttgcagatgg   24060 tggaagaacc ccaaccgtac acatctttga aagtcttgtt tttgttcacg ccctcgccgt   24120
gccgggcaag gtaagcggac ggaatgagga cttttcttc tttcagcttg ctggcgatct   24180
gatacggacc gtagccgtca atcgtcatgg aaaagatgcg cttgaccacc tctgcggctt   24240
cggggtcaac cagccattgg tctctggctt cgttccagag atagccgtaa atgaccgtgc   24300
ctgtgaggtg cttgccggac ttgcctttgg actggaaagt ggaacggatt ttacggctgg   24360
tgtctctggc ataatactcg ttcatgatgt tgcggaaagg ggtaaaatca tcgtcccctc   24420
tggcactgtc cacgccgtca ttgatggcga taaggcgaac gccacgctga cgcaggattt   24480
ccataatctg accgactttc agatagtcac gacccatgcg gctcatgtcc ttgatacaca   24540
ggtactccac attcccggct tccacttctt tcatcattgc caaaaatccg ggacggtcaa   24600
agcaagtacc actaatgcca tcgtccgtga aatggacaat gtttgtaaag ccctgccggg   24660
cggcgaactc ttccaacata gcttttgat tggaaatgga attgctctca cgctgttggt   24720
catcatcttt gccaaagtca tcacggctca atcgttcgta cagagctgtg attttctcgt   24780
tttttctcat agcttgcgct cctttcttcg gttttaggtt gtgtgttcta agagacttcc   24840
caaccgattg attaagaagt cttttagagc atacaacacc tgccgccagc ttatattcct   24900
tatactggcg caccgcaaag tggttcggct tctcggcttc caatgcgtca aacatcagat   24960
ccacggatac cgataggtaa ggctctgact ttcgtctcgg ccttttcccc cggcccacac   25020
cggacgggca cctttcagcg catccggcgt accctcttac tttgtgaaga ttcccccatt   25080
ccaaaggggt ctcttgctca caagcaaac gacatattca caatcaatct ctttgcaagg   25140
aatcaataag tgctttttatt ctccgtatct ttctgggaaa aatggaataa agccgctccg   25200
gggtactgct gtgcagtatc gtatgttcca tttctgaaag cacacagagg ttttcaaaat   25260
catttgttcc gcctttgcta agtggtttga tatggtggca gtggtattcg tctacgggga   25320
caaaatttcc cgacagatag ctgacacctt tcatggaact gtatttactg attctgaaca   25380
tggctaaccg gctgttttg atgtattttg aagtgttgac taagtagctg atatccttca   25440
ttgatacacc gggattgtgc ttcttttcgc cgtaggcata aggatttta cggattacct   25500 tgcccttttc tgcagctatc agtttattgt cccaactggc ccattgaatc tcaatgaccg   25560
```

```
ggaactgatg gaagcagtaa tagccacgct ttccccatga gcggtattct ccgccctgaa   25620
agttatcctt gtaagcttgg tcttttatga atttaacatc tctgctcatt gtgtgataaa   25680
acaattcttt gattcgccaa cctattttc taaagctcaa acaaaacaga gacatgcctt    25740
tatagtagtt gtggactccc accacatagg cattccatgc gtgtattgtt tcaaatgacg   25800
gattgcgcct gatgtcatgt agcagttccc tgcatttctt aacaatcacg tcctctttgc   25860
tttttggaag ctcatttgtc accatcagct tcccctttg ctgtgggttc ttcgtctgct    25920
ttttataggc atagaagtca tcccagat acttcatctt tcccgggta aggtcatata      25980 tttttgtctt atcctcgttg atttccagct tcatgttccg tgtcaggtaa ttcgtaacac   26040
tgtatttgaa tttcacagcg tcctcataat ccttgcacaa taccagaatg tcatcagcat   26100
acctcacatg aatcccaact tttagatttg tgagtgcgag gttgcgtcgc ttgttcgcat   26160
agttgtgaaa ctttgcaacg cttctgtcat gccagcaatc accctggtca cggagccata   26220
catcaaatcg atgtagatat acattactga ttaacggccc caaaatcgaa ccttgtggag   26280
agcctttcgg attctccact ttacaggaat cctcatagta tccctttta atgaaacggt    26340 agatatagtt gaggattatc tggtctttta tcccgatatg ccacagttcc cggtatgcta   26400
tatccgggtc tatggttccg aagaaatctt tcatatccac ggacaggaca tagggcattg   26460
tctgacattg gcttttcacc tttgccagcg cattgtgagt gctgacctgt ttccggaatc   26520
cgaatgaact ctctacaaat tttgtttcac aatagggttc caccaccagt tgaatacatt   26580
tttcaaccag cttatcccaa atggagcaaa tcccaagagg ccgcttcttc ccattgcttt   26640
tcggtatgta cgttctccgt acataatcca ttcttttgtt tgtcagacgg tctttcacaa   26700
tctccgcaag ttcctgaata gagtagggtt ccagagtttt gatgtttgtt ttatccggcc   26760
ccagtgccat tcttcccgga cttttgctta attgacgcag tgcaagggct acgttatcag   26820
tgtcataaac catgacgtgg agtgcccgta ggtcaattct gttattctgg aaatcttcaa   26880
accgcttttc catgtccaca aaatagatgt tattggtact caattacttt tctttggttc   26940
ttcataggtt gtcgcctcat ttccgtaacg aatagtctct tgcgtctaat caggcgaatc   27000
ggaaatattg ttttattatt caaagcaaga ctaaggccct tcgctacccc ctgtttcttg   27060
acagggtatc tacgctacta tggccccgct gactacccgt tcataacctt tctggcctta   27120 cccttttcagt gcgggccgtc cccggctatt cctaaacgtc gggcagttcg cccttatcaa   27180
tatgactgcc ttaatactgc acttaggact tcctctgctc cgtaaacctg ggtctccccg   27240
atacgtttta cacgtattct atggcggcca taacgccatc ccccatagtg acaaaacgaa   27300
atcacgtgag gtagatttat tattccgtcc tctctgcaca gcagagcagg atagggttca   27360
taacgaagct ttagcaaatg cggaatgttg aatccatatg cagtggaacc cggggtgtgc   27420
tgtcaccagc agtgtccccg ccttcaccta tgcttcgcga ctgcctgtta ccagacagcc   27480
ggcaggagta ttagtcgagg tcggatacat ggaatatttg gcttccatgc cgcctccagt   27540
catatcaatt acctacaaga gtgtgccgct tttcacctcc ttagcacctc ttatcaggtt   27600
tgcagtggtg tcaccctact acgggagttt tacactgcaa ttagggtcgc acgattttg    27660 aactcctcgt catcctcccg gacttccata gcgttgatga actcaataag ggtggagaaa   27720
ttctgttcct ccaccggagc ctcatagtgg atatagccaa tgagcgcaca atagagaagc   27780
gtttctgcct tgacccagaa atcgtctccg gccttgcctt cgcctttggt attggcgatc   27840
agcgtcgtga ccagcttcaa gatgtccttt tcgctatgga tataggcgaa agggttatag   27900
```

```
tgcatggact tcttgaagtt gatggtattg aggaccttga tgcggtaagg ctcataaatg   27960
accttgccgt gtttatcctt cattggcttt ccgtccttcc ccagcttggg tgcgcccctt   28020
tggagcattt ttccgcactc caccaaaatg gttcccttcg ggtctgtgac cacataagaa   28080
ctgtgcatct gcatcagata tgaggtaggc accctgcgcc ttgctgactt tcatcagtag   28140
gtttcaggga gccgcctccc aaaccggacg tacacctctc agcgtatccg gctttccatg   28200
aatcaccttg attctttggt ttcgtgtaag agttcaaagc agtcagggca gagagccaga   28260
gattttcttc tcattttcag catttttctgc tcaaatatat ccctgccttt cagcgatttc   28320
agcgttctta cgtggtgcat acataaatag tctgcatgtt ccccgcaaat ctcgcatact   28380
ccggctttta tgcggtttac tatcgtgtgc ctgctgtcat atttcctata actcggcata   28440
acgtctgcca cattgtcata gccgtcgctg tgctttctga atccatcatg gtaaaattcg   28500
cagtatttac gtcccttagt tgtatcgtat gggattctca gtactccgtt taccatgtgc   28560
cgcttcttaa taacactgac attcgttctg tgctttcctg ccagagtttt taacatgctg   28620
taccgcacca tgtagtaata cttgtgcaat gcgcctacgt tttctgctat ccgatagaag   28680
ttatataacc ctcgaattttc ggaattgaaa gtagacacaa tctctgcatc gctgcggttc   28740
atcaggtctt tccttggcat aggacgccac atttctttgc ctgtgtcatt gttgcgtttc   28800
acctgtatcg ctccccgttc catcgctttt ttaatccatt tttctttcgg catatacagg   28860 aatactttttc cataccacac ccgtttcatg tcgccgtttt tacaacgctt catgttcttg   28920
gaatggatta ctttgaaatc gtaccccaga tagcgtaccg gcttactgga atgggtgact   28980
ttcgtctttt cctcggacat ttccaaatgc agttttttctt ggagaaagat ttttacatct   29040 tccttgatttt tttctgcgtc ctttttggag ccgataacgc caattacaaa atcatcggcg   29100
taacggttgt actggatttt cttgaagcct tcctcaaacg gattgtaata gtgctgattc   29160
atcttcttcc ttctggaatc cttaaattct tttaccagtt caggagttga ttttttctgcg   29220 cccattaacg ctttacgtgc ctttctgtat ctccgggacg cccgctcgta ttctctggtc   29280
gtccttctgc gttctggctc gcaatcatac ttttctttgt attcctgcat atagttgtcc   29340
agttcgctga ggtagatgtt tgcacatatc ggactgatac cgctgccctg cggaacaccg   29400
gagtaggtgc agttgtactg ccattgttcc atatatccgg ctttcaggaa cttccagatt   29460
agaccgataa aagcctcgtc tgaaatcctt ttccgcagta attcaaccaa cacatgatgg   29520
tcgaagttat caaagcacgc cttaatgtct ccctcgacaa tccatgtaac acctgtgaag   29580
tttttcttca cttgcgtaag tgccgtgtga cagcttcttt ttggtctgaa accgtgtgaa   29640
ttgttgctga atgtcggctc atagattgct tcaagaatca ttctgaccac ttcctgcact   29700
aacttatcat cagtagaagt gattcccaac gggcgaagtt tcccgttctt tttaggaatg   29760
tactttcttt ttgcaggctt tggctgatat gtcctgttgc gtatggattc aataatccgg   29820
ttaattctcg gcaggctcat gttgtccagc gtctgcccgt ctaccccctg tgtcatgctc   29880
ccctgcgatt tcgcaatgtt cgcatatgca aggagataga actctggatt gtataggttg   29940
cgatataatc tttcatattt gttgttactt acacttgcct tttcttcaag gcttttcaag   30000
acatgaatcg gatttctcat agtgtctcac acaccatcct ttctgttttg aaaatgattc   30060
actgttcccc tttgccatgt agacggcttt cccgtccgca gactactatg ggaactctgt   30120
tgccatggtg aatattcaga accccgcatt tcagcgtttt catagccttt cggcatttca   30180
ctttaggcaa tccccgttta gtacggtata aacaagcgtt ccacgttgtc ggtatgtgac   30240
gttcgccttt ttccactttc ccgtggctga acctgctccg agtatcagca gccgcatagc   30300
```

```
caaacaatgc gactgtcagg aacactgacg agtacaacct ctctacgtca ggggtacgct   30360
cttggtcccg atttcaggct gtcattcaag cagtctagct tccatcctca tacgtggatt   30420
ttcattccgt cacgccggcg cttctgaggc ttcagcgccc cgtgtcctcc gtcatgctat   30480
ggtcgccctc cagtttccct tttggggtaa gacgggaat gataggttgc ggcacaatgc   30540
cgcttgatac ttttacctac tacttgctca aggtaggatt tataccgccc ttacgggcgc   30600
actcggtttg agccagaagc gggtcttacc ggaaccggag ccgccgatca ccagcacatt   30660
tttgtttctg gcggtcttgg ggcccttggg gcggctgttc atggtcaggc tctcggtttt   30720
ggtcagaatc acattgttct ggaacaccgg gtcgatgtag ggtgcaatat cctcacgggt   30780
tccccaacgg gcagagccat actccatacc gtgacggtac ttcttggcgt ttttactttt   30840
gaggtacacc gccagacgca ggccagcacc gcagcacagc cctaccagca gatccaacgg   30900
gtgcaggctg ggccagaaac tttgcagcgc cccaggcagg acagcaaaca gggaaaggaa   30960
tttctctgaa gcatttgccc cctgagccag tcgccatgcc tccccgaagt tagtagcaaa   31020
cagccccatc aggagatagg gcaggttcag caaaacgagc ttttttgatgt caaactgctt   31080 tttcatcgtt ccagctcctt tcgcttggtg cggtccacca cggcattttt gaccatctct   31140
ttgaactgac tgagttttgc cagcacagac gggcgttccg ttttctcggc cttcttgacc   31200
tttttgctgg tgtactcggt aaatgcagcg gtcagcgcat cggcgtcacg gccttttgaaa   31260 aagatcaggt atttgggcgg ggagctgctg cggtctttct tcaccgcata gtccacacca   31320
tatttccggg cgatcttctc aaattccttg atggagggt ctgtgatctc gatattggag   31380 atccctgat tctgaccaat gagctgcttg acggtctgtt tgccgtgggg tgtcacaggg   31440
gcatcacggc ttctctgctt ttgcagcttc ttttccttgc agtgggccat gtacttgctg   31500
atggcggctt tgagcagcct gccggtgaac tttgttccgc tgacaaccag cgttaaagtc   31560
ctgttttcca cttcttcctg cattttcatc gcctcctatt acaataaatt tggacaggaa   31620
agccgggcag ccagtccggc tttctttcca tctcgtgcct aagctacaat aagaggagca   31680
actggctgac ccttgcctcc ttgggctttt atgtccgttg gaaagactgt tagccatcct   31740
cttgttgcag cgttcgattt gagcaggttg agccaccgga tgccggagag ttcgtgtcac   31800
ccaatagatt gaatcggcag cgagaaaaga tggatttccg gttgcagatt ctttgtgttg   31860
gaggaatgtg aatgaactgc gttggcatcg atgtttccaa aggtaagagc atgattgcag   31920
tcatgcggcc cttcggagag gtagtggttt caccctttga agtgcgccac accgccagcg   31980
aactgagcga gctggcaagg ctgctcaaaa acctggacgg tgagacccgc gtggtgatgg   32040
aatccacggg caattaccat gcgccggtgg cctggctgct ccacggcgcg gggttttatg   32100
tctccgtagt caatgcaatg ctggtgcacg actacgggaa caacagttta agacggggca   32160
agaccgacaa gaaggatgcc gtgaagctgg ccaactacgg ccttgaccac tggctcacac   32220
ttccgagata tgttccggaa gaggacaccc ggctcatgct gaagacctgc taccggcagt   32280
accagcagta ttccaaagta cagaccatgc tgaaaaacaa cctgatctcc ctgctggaca   32340
ccgctttccc agacgcaaac cgcctgttta ccagtccgcc ccgcgccgat ggcagtgaga   32400
agtgggtgga ctttgtcgcc actttttggc attgcgagtg tgtctgtggt ctgtctaaga   32460
aagcctttac cgccaagtac cagaagtggt gcagaaagca cggctacaat ttcagccaag   32520
ataaggcgtt ggatatttat gcctctgcct gtggacgctt cggtgtcatg ccgaaaacaa   32580
atacggcaaa acttttggta gaacaggcca tttcccaact ccagacaact tccgccgcat   32640
```

```
tagctgctct caagcaggag atgcagtctc tggcagcttc tctgccggag tatcctgtag   32700
tgatggaaat gtttggtgtt ggccctacac tcggccccca actcatagct gaaattggcg   32760
atgtgcgccg ttttcattcc aagaaagcgc tggtggcctt tgcaggcatt gacgcccgc    32820
cctaccaatc tggccaaata gatgtccgca gccgcagcat ttccaagagg ggatctgcct   32880
cactgcgcag gacactttc ctggtgatgg gcgtcctcct gcaatgtgcc ccaatggatg    32940
agccggtcta ccagttcatg aacaagaaac gctctgaggg caagccatac cgtgtctaca   33000
tgatggcatc cgccaacaag ttcttgcgta tctactacgc ttctgtgaaa gcctatttgg   33060
attccctgga acacgactga tttccctgcg ctataccatc tggctggccg ccgtttcgat   33120
tttgagttgc tcagcggctt gattttgtgt tgccttttc gctgctccca aaacctgaaa    33180
tttctacttg acttttgtta gcaggtcttt ccacaaaatg tgcaggggtg gtgcatttat   33240
ttctaaggcg ggaccaccag ccgccggaga aggtatttct tcatcgaacc gccctcaacg   33300
aatttgctca gaacggtcat agagcaaatc tccatttctg acctttgcat gactgagaat   33360
cttgatctgt ccctttgcct gactgtccag agctttttca tagcccttat ctgacaaaaa   33420
caggcgggtt cgttcacctt tccagcccac cggggagtca tgcgtcagca catcaaaaat   33480
aatcatgtgc cgggtgttct cagcaaatcg ctggagatcc atgtagtcat ggccgtgata   33540
gttctgcgct ccagctttct ggcgcatttc ttccatcagc tgaccgattg tttgccttc    33600
tggcataaaa ctcacttcct ttcccactct catacaacca tcaaaatcat gtctctcagc   33660
tgagcaaagt agagtttgcc ttgcggggtt atcagcgtat aggagccgat atgcccgtga   33720
ttgcagtagt ctttgacaca aaacagtcct tcattggctg ctttgcata gggcagtaca    33780
ttaccggatg cggtgcggta cacaaaacgc ttttccagaa ggaaacggac aaaccgacgc   33840
tccgggacaa gcaactcttt ggcggtggtg cggaggttgg tactgtgatt gaggtcgatg   33900
aacaaatcat aaaaggctgc cttactctcc agcagggcat tttcctctcg tagcgacgca   33960
ttttcttccc gctcagcaag cagctcggag cagagcttta tcagagcttc cggagaagtg   34020
gctatctccc acaacttctc ttttgtgaga taggctccgt gcttgcgaat gacaggtaga   34080
acttcatcaa acacccattg ttcaaaccgt tccgctgacg gcagtttact atgggcgatc   34140
agacgatata gatcaccttc ggggataaag agcatttcga ccatttgtac cgcggggctt   34200
ccatctgcct ttttcccagt ctggaccct atggaacatt tcgttccacc cctggtatgg    34260
tcgcggacgg ctttgcgtgg attggtatat cccagcgctg ttgccacatc tgtaccgcaa   34320
aataatactt tgccattctg ttccaaagtg cgaatgcttc cgaactctgg actattgaaa   34380
atttcaatct gattcatgct gtgcctcctt tggtgtaata caaaagcggc tgattaccag   34440
ccgcctgcgt gcatatcgtg atttaccagt gaagtgtagt ggttattcat ggtggtagga   34500
gcgttgaaca gcactgcaag caggtactgc ttgatgttgt gtacctgggt ggtgttcttt   34560
tgcagacagt ccatgacaaa ctcgatgtga gagctgtcca gcttcaaaaa gcgggagcgt   34620
acaatttcat gaggaaagtc cgcaccagag atccgggtgg tctttcgttt ggcacagacc   34680
gtttctacca acagctctac gatctcattc aggtcatcca ggtagagagg ataacgctgc   34740
ttcagacaat catactcgat attctccaaa atcaattccc gataattttc tatctctgtg   34800
acagacatcg catcccttcc tttccgttcc ggcggtatta ccgccgctgt ttcccggaag   34860
ggaatggaat cggtatttga tccatgagta ttttgttttt gggtatttga tttcttagta   34920
tttaattgtg ttggattttc cggtaacgga tttaccgctg acgggtttac cgttatcggg   34980
ttttccgaca acggcttatc caacatcggt tctccctcga tgggacgctc aaaaatggta   35040
```

```
tactcattgg ctgcgaattt accagaagca tcagttgtct gtctgcgccg aatgtatccg    35100
gctgtttcaa gctcattgac agcagagcgg attgcatctt tgctttctcg attgatatag    35160
ctgagtcctg acagcgtata atcccagtca tcaggcagag ataacatctg cgacaagaga    35220
ccctttgcct tcaaagaaag tcgtttgtct tttagatgaa aattgctcat aaccgtgtaa    35280
tcgccagtgc gttctacacg aaaaacagcc atttacttca ctcctttcat ttctcaggta    35340 tgaaaaagc cgcaattcat aaagaattg tggcagcggt tagggtctgt ctgtatcttt      35400
ttttcttgcg tcggtagggg cgttttggca ttggtggttt atcaaacaga tccctttcct    35460
gagaaaatgg taaggtttga aaaacacgat caatctcggt ggattccata tcacgctgtg    35520
agcggcaatc ttcttgaata gcttctcgga tttctcttac agtacacata ttcattcctt    35580
tcctttcgtt gtatcggtta tgaacgacgg tgttttttag gcttgaagtc gaggatatgc    35640
ccctcaataa catgggcata tctcttaatt ttgatttctc gacgctgctg gctttgcaga    35700
gctgactgat acccgtcctc tgtgagaaaa agcctcattt cgtcaccagg ttctccataa    35760
gcagtagggc gcaagacagt aaactcaatc atccagaaag tgctgtccca aaatcgctcc    35820
actgcaagaa tgttgtggcc tttcagttcc cttgctgcaa tatctttcat aggctctccc    35880
ttcatcgttc ctgatctcgt tggcgttttt tctgccattg ttccagcagt ttaataatgg    35940
tttcctgcat tttggccggt gtatagcttt tggggaaata ctttcgcaag gtatcgctgc    36000
tcaaggtcac tttatccaga tcacccttttt tttcctctga catgatggca agcatcacat    36060
cttctgacaa tttcccttcc tggctgaact ttttcattcg ctgagcctga gagagagaag    36120
gggtagcctg ctcatagtcc attgtttcca ccagcatttg ctgttcgtcc ggtttcaaaa    36180
aagagagttc ataggctggg ttaaatgcga ttttctttct atccaccata tccaaaagct    36240
ctggaatcag ttcagtcaaa cgaacatatc gcattacctg gataccgctt cgttcaccgg    36300
cttcttttgc cacctggtct ctggcgctca acttctgttc aacttgaaca gaagtcaggt    36360
ctgttcttgc tccttgatgt ttaatggctt ccagcttcat tttgtaggca aaagccctttt   36420 cactggggag cagattttct cgctgcaaat tgctgtcaac cataataatt gtggcagcat    36480
cgtcatccaa gtcgcgcaca atgacaggca tggtttcttt tccggccaat tcgctggctc    36540
tgcggcgtct gtgaccggct accagctcat aaccgccatc aggcagtggt ctggcaatcg    36600
caggaaccaa cacaccatac tttttgatgc tgtctgcggt ttctatcatt gcatcatcat    36660
ccttgacctt gaagggtga tccttgaacg gatgcagttc agataggga atttcctgaa      36720 ttttttccag ttgctcgtct tgccgacttt cttctgtaga aaacaggtca tctactgagg    36780
ccagctctat ttttttcgcg ctgcttttca agtttcaata cctccttcgt cagattttg     36840 tagccctcag ccactttgcc attaggatca tgggcataaa tgcttttcc ttcagcactg     36900 atttctttag ccctgacaga atgaggaatt tctgatgtaa acaccttgat cttactgcca    36960
taggtttcgc gcagaagagc ggagatttct ttggcaaaat tggttcggct gtctaccatc    37020
gtcagcagaa tccatcaat ttgcagcttg ggattgattt gtctgcgaac cttattgata     37080
gtttgcaaaa gctgctccaa acctttagct ggaagatact ctgcctggac ggggattata    37140
accctattag cggcagccag tgcattgacc gtaagcatac ccaggagggg ctggcaatca    37200
ataaggatat gggagtattg ccccttcagc gtgtccagat attgtcgcag aatggtttct    37260
cggctcatag cgtttaccag agatacctcc ataccagata gctggatgtc cgcaggcatc    37320
aggtctacgc cctcagggtg gtgcaggata ccctcgccgg gacgaattgg ttcatccatc    37380
```

```
aaaatacggc ccatagcgtc tgacagtgta aagggcagct tatcaggctg aggattgccc   37440
aagctgatgg tcaggcttcc ctgtgggtct ccgtcaatca aaggactttt cttcccggac   37500
tgcgccagac caattccaag attggcacaa gtggttgttt tgccgacacc accttttggg   37560
ttggctatgg caataatctg tgtattcatg atttcacctc atttctttct aagtttagat   37620
atgaaaaaaa gtgcctgctt tacctttcct gagaaagata aaacaggcac tttcactggc   37680
tcaatacctc ttgtaatgaa cctctatgta tggtaaacta tgtccacgat accatgaata   37740
taattaagtc tcgacgggaa ttgaactttt ggctaacgcc aaatttcgcg cctttgcaaa   37800
cagagtgcaa acaatagggg gctaaaatcc tttgttttg cttgattttg cttgtacaag    37860
gtttatagag aacatggaga aaagccttga tataactgca ttttctttat ccctgttgat   37920
agggaatata tgcactgggt ccatctccta aggggcagtt gagggttcga ttccccagg    37980 gaacgtagat ccgtacagaa agaataacgt cttttgtac ggattttttt atattaaatt     38040
atttatatac ggatgaaaaa tacagggcgg aacgattatg aaaagttaa agtttcattt     38100 tagaaagctg acaaatataa gacagcagct atataccata tattttgctg ctttatttct   38160
tcctatcatg attatcggta ttttctcct tatgaatacc tacactctgc ttgcaaacta    38220
tcacagggat ctcctggaat cagataatct ccgtgttaaa aatgttctgt ttgaaataac   38280
cactcaggtc tataatatct ccgagaacct tattttgat gaaacataa aggaaatatt     38340 atctacggac tatgagcaga ggaccaacct gatccaaaag gccggcaatc tgacagtggt   38400
tgacaataat gcgcagaatc atgcggaaat cgaagggata gagatatata ccgataatcc   38460
cacttttacg gattataaac agttctataa aaccgatgag gatatacaga agtcagattg   38520
gtatcagaaa gcaatcagcc aatccagtgt attctggata cctatgacta ctaccgataa   38580
atatgggaac gaatactgga atttgagcct ggtgcgcaga attccgctga ccgatgcgga   38640
atataatgcg gtactggtta tcaagatcag tgacaattat ttaaggacaa ggatcaacag   38700
ccaggaatat gctgccatgg tatcagtaaa tgaaggagag gtgttttta attctgacag    38760 aagccaatat ggaatcaaac aaaaggtatc cattgattat gatgaaaatt actaccaata   38820
tacagggaca aaaaagataa acggtgttac ctattttgtg gatgtttcca cgctgaacct   38880
gtatcagtca gattcccgtc tctatatatg taccatgaat gatcagggct atgtaagcat   38940
taaacggatt ttgacaatct gtgtcctgat cctggcggtg gctattctga taccgggtat   39000
tattattcac tattttacgg agtattttac atcccgtgtt cttatcttaa gaaaggccat   39060
gcatcaggcc agcaatgagg attatgatat acgaagcttt atccagggag aggatgaaat   39120
atcggaggcc ttctccgatt tggaaatcat gattcagaat attaaaaaga aggatgcgga   39180
tatgtatgaa gcccagatca ataaagcgga gcttctgaat aacagcagg tgatggaatt     39240 taaaatgctt gccagccaga ttaatcctca ttttctttat aatactctgg aaacgatccg   39300
tatgaaagct tttaaggcaa atgacaggga agtagccagg gcaatcaagc ttctgggtaa   39360
atccatgcgt tatgttctgg aaaatacggg tacctccttt actacgctga gtaaggagct   39420
ggaacacata aaagtctatc tggatattca gaagcttcgt tttacagata aattcgacag   39480
tgagatagaa gtaatggagg atattgatcc cggaaagctt ctcatcctgc ccctgttgct   39540
tcagcccgta gttgaaaatg ccatactgca tgggctggag gaaaaggaaa aggaagggtt   39600
aatccatata ttggtgagga agcagctggg agaggaagaa ctgctttgca ttgaagtatc   39660
ggataatgga aatggaatga cggaagaagc gcttgcattt ctgcaaagca cgattgaaga   39720
aaaggatata agcagaaata agagtatcgg gctgtataat atcaatcagc ggattaagct   39780
```

```
tacctatggg cagaaatatg gtgttaagat ttcttccaac atagaggaag gaacccgtgt    39840
cagtcttttt atccctatta accgtatgaa agagacagcg gttgtaacag caaatgaagg    39900
ttaaaccgga agaattcaaa aagtgaatgt acttttaggc agaattttac cgtattttc     39960 taatttaac taaattataa ttaatacatc ataaggattg aaaaatcctg tggtgtattt    40020
tttttactaa aaatacgaaa attttgttca ggaagggag gaataaaatg agcagtacaa    40080
agtcacgaaa ggaaattatt acggataagc tttattatcc cattcggatt gccattcttt    40140
tatctgtggt atttctgttt ataccaaatc tgaatccggc aagaataagc ggcatgataa    40200
ataaaaatat gtctttatt tcagcaggta tttcctattc atccttaacg gcggaattcg    40260
gccgggcctt caggaaagga tgggtggagg aaagctccat gcagctgtta ttcgtgtcat    40320
ccatggccat gtgtcttggg atcgttgctt tttgtgtaag cggatgcatg tcccttggta    40380
atttaaaatt caagaaaaca ggaaatatca tcggtacgat aggatgcgct gcagaactgg    40440
caggtatcgg aggaatttat attgcttatc tacagatatc gcagactgcg aaacctgata    40500
agatacagcc tgttttcct tccgggcttc ttctgatatt aataataacg ctgctcattc    40560
tgttgatttc agtcatacag ctggttttat ttccaaagct ttcaaaaaaa tccagatttg    40620
aaatgcccac aaaatacagg cttttctta tgctgatgcc ttttcttgca ttggtagccg    40680
tctttgccta tctgcccta tggggatggc gttatgcatt ttttgattat aaggtggggg    40740
attccataag catggaaaac tttgtaggct tcaagtggtt taccgagtta tttaaaaatc    40800
ccgccacggt aagggatatt gtgcgtgtat tgaaaatac gcttgccatg agcggacttg    40860
gaatcgcaac aagctggctt cccatggcct ttgccatatt cctgtcggaa ataaaaata    40920 taagattccg aagatttgta cagactctaa caacagttcc taattttata agctgggttc    40980
tcgtatatgc catagcgttc tgtatttct caacagacgg atttgtcagc agtattatgg    41040
tgaatctggg aatttgggat cagggtgtca atatgctgat gagcggggat catgtatgga    41100
tcaagatgct gggctggggc ctttggaagg gaatcggctg gagtgccatt attatatag    41160 cggcgatttc aggaatcgat cagcagctgt atgaagccgc aacagtagac ggcgcgggca    41220
gattccagag aatgtggcat ataacggtac cgggggctgat acctaccttc tgtgtattgc    41280
tgcttatgtc aattgccaat atcctcagca acggaatgga tcagtatctg gtattcgaaa    41340
atgcaaccaa ccagaacgct attatggttc ttgatctgta tgtttataag ctgggtatcg    41400
gaaaaggcgc cataccattg tctaccgtaa tcggtatggt taaatccata gtaagcgtga    41460
cgctgctgtt cgccgccaac ggtgtatcga agttgatccg cggtgaaagt attgtatagg    41520
aggttaagca tggcaaaatc agcacaggaa aaagcagacc tgaaggcaga aaaaatttat    41580 gagaaaagc acaggaaaaa atacagggcc agaccgggag acatccttt caatatgata    41640 aactatttgg tttttaccct gtttactgtg gcatgtattt ttccatttta ttatctgttt    41700
ataaatacaa tcagcgacaa cgatttggtc gtgaaagggg taatcaattt tatccccaga    41760
gggcttcatc tcgataatta caaatccctg ctgaatgtaa gtgatctttc caatgccttt    41820
cttgtttcac tgggaagaac cattatcgga acggcattca tggtggcggc ctccgcattt    41880
gtgggttacc tggtaacaaa gcaggagatg tggggcagaa aattctggta ccgcttcctt    41940
attatcacca tgtatttcaa tgcgggcctg attccctggt tcctgaacat gcagatgctg    42000
ggattgacca ataccttctg ggcttatatt attccgggaa ttgtagctcc ttataatatt    42060
atcctggtaa agacctacat agagtccatt cccgcggagc tggaggagag tgcacagatt    42120
```

```
gacggagcta cccatatgat gattttccgt aagatcatat ggccgctgag taaacctatt   42180
ctggcaacca tagccatttt cggcgccgta ggacactgga attcatttac ggattccctg   42240
atactgatgc agtcggcccc taatctgtat accctgcagc acagactgta tatttatctg   42300
aatacagctt ccaatctgag cgcattgatg gaatccggcg gacagatcag tgatacggtt   42360
cttaaatcag cgcttagtgc aaaggttatt aaatatacaa tttccatggt aacggtcatc   42420
cctattctgg tggtgtatcc gttcatgcag agatattttg aaaaaggtat catgctggga   42480
gccgtaaaag gctgagtctg accggaaatt ttatctgtat ttattgttgg tgtttatccg   42540 ttttacggt tatgtaacac aatcaaaaag gaggagaaag agaatgaaag caaaaaaagt   42600
cactgcactg cttatggcgg ccataatgac cctgtcattg gccgcatgcg gaaattcaag   42660
taaaacagct tcggagcctg tggcagacag cactgtccag gcaaatgctg aaacagatgg   42720
agaaacagcc ggagggata cccaggccgg tgaagagggg gattcctatg acgaacttct   42780
ggaagaaatc attcctgagg aaacagtcac tctggatgta tttgatcagc ttgccaacta   42840
ttccggagaa caaatcggat ggttcggtca ggttatgctg gaaaaattca atgtaaaact   42900
gaatatcatt cctgacccgg acggggtata tgaaacccgt atggaatccg gcaacctggg   42960
agatatcgtt atctggggaa acgattccga tgaatatcag caggcggttc agaagggtat   43020
gctgttcgac tggaatgagg atgatattct gaccgattac ggtccgtata ttaaagaaca   43080
tatgccttat gccctggaaa aaaatgcaaa ccttttccggc ggtactacct atggatatgg   43140
ttttgatgtg gcggtggatc ccagcgccag aggcgatatc atgtataccct gggatgtgag   43200 atgggatctt tataaagagc tgggctatcc ggaaataaag aatctggatg acatggtgga   43260
ggtcctggcg cagatgaagg aaatctgccc taaagatgac aatggaaaaa caacctatgg   43320
tgtatccctg tttaatgact gggatggtga tatggtaatg tttgtaaaat ccacagctac   43380
cgcatattat ggatacgatg aatttggttt cggtctttat gactccgagg aacagaaata   43440
ttatccctgt ctggaaaagg acggtcctta ccttacctgt ctgaaattct ataatgatct   43500
ttatcagagg ggacttctgg atccggattc acagacccag aaatatgacg gtatggtgga   43560
agactatcag aatggcaccg cattcctgaa tgtatttaat ttcctcggag cagccatgta   43620
taactctgac agtcatgcgg cagaaggaaa agccatgtat ccctgtcctc cggaggaagc   43680
aacgcccatc gcttacgggc tgaatgtata cggcggcaac agaatctggt ctattggcgc   43740
aaaaaccgaa tatccggaac tttgcatggc gatactgaac tggctttcca caccggaagg   43800
ccgtatgaca tcggaatatg gccccaagga tgtatgctgg tattatgatg aaaacggaaa   43860
aacctgtttc acggatttag gaagagctgc aaagcttgat atgaagacag aaatgacaga   43920
cggttattca ggaaccttg aagacggaga cttcaagatg aataatgaga cctgggctct   43980
tgatacgtta aatctggatt ccaacggaga tacctataat tacaagaaat gggacagctt   44040
catcagtgaa cccaactcgg aaatcgaggc tgactggaga gaatataccca agccagaac   44100 acctgatgaa tacatgggac agagacccta caagcttgcc cccggaacca cctattccgc   44160
aggaaccaaa tctgatgagc ttcttgtact ctggaatcag gttgcagact gtatcaaaac   44220
aaattcctgg aaagcaattt atgctacctc cgatgaagaa tttgataaaa tagtggatga   44280
aatgattgcc aaagcaaatg aatatggcta tgataagtgc atcgaattcc aggaaaatga   44340
agtgaaactg aaggcagcgg cagaagatgc tgtaaaataa caggttctga agctggactc   44400
aaaaacttaa tcaagggatt gtccgatgcg gcaatccctt ttcaggcttt gaaaggaacc   44460
accgtggaaa ggagaagcta ttaagaacat ggaaaactac ttaaaaagtc ctttatggaa   44520
```

```
taatcggctt cctgtagagg aacggctcga ttatctgatt ggagaaatga cgacagaaga    44580
aaaaattgcc tgcctgacca ccggctgccc ggatataagc agactgggaa tcagggcctc    44640
ctatatggga ggagaggcag cccatggaat agaagccaga catgatcagg cttttaataa    44700
aggagaaccg gaacccacaa catcctttac gcagcccatc ggaatgagtg ccagcttcga    44760
cagagagctt atcagggaat gcggacgctg cgtgggagaa gaggccagag ccttatttac    44820
ccgcaatggt tcgggagggc tttgcagatg gccccaacc gttgatatgg agcgggatcc     44880
cagatgggga agaaccgaag aagcctatgg agaagatccg tacctgacag gtgagatggc    44940
ttcttcctat atacagggaa tgaaggagac gatcccttc tatatcaggt gcggggcaac     45000
cctgaagcat ttttatgcaa ataatgtgga aaaggacagg atttccatct cttcttcatt    45060
ggatcgcaga aataaatatg aatattacct ggagcccttc cggaaagcca tagtggaagg    45120
gggagcggaa gcggtaatga cctcttacaa tgaaattaac ggaattcctg cgattgtgaa    45180
tgaggaggtc cgtaccatat taaaagaggc ctggggggctg cccggtcatg ttgtctgcga    45240
cggcggggac atgcagcaga ctgtttatga ccataaatac tttaaaaccc atgaggagac    45300
agtggcatat ggcctgaagg ccggagtgga ctgttttacg gatgataaat cagtggttat    45360
ggaggccgca cgtaaagccc tggaaaaagg gatgataaca gaggaagaca tcgaccggtc    45420
catacgtaat tccttccgca ctcgtatccg actcggattc tttgacgggg acggagaatg    45480
cccttatacg ggaatgggag aggagtatgt caataatcag gaacacaggg atatttgtgt    45540
gaaaatggcg gaagaatccg tggttctatt aaaaaatgaa aaaaatatcc ttccgttcct    45600
tcccgaaaaa accgaatccc tggcgattat aggccctctt gcggacgtat ggtacaaaga    45660
ctggtactgc ggaatccctc cctatacagt gactgtgctt gacgggataa aaaaggctta    45720
tccggatacg agcattgtct ccgtcagcgg cctgtcacgg atttatctgt gcagcggcgg    45780
aaagtatgtg ggtatggatg aatccggtca tctttatctg acggaaaagg ataaggcgga    45840
atgtttcacc tttacggact ggggctgcgg cagtacaaca ctggttgcct gcagcaatgg    45900
aaaatttgtc actctggaag aagaagatcc ctatatgaag gccggcaggg aggaagcctt    45960
ctcctggttc atcagggaat cctggaattt caggccggtt gggaaggaaa aggatatgcc    46020
ccgggagaca tattatcttg acagctggaa tggaatgaca gtgactgcag atagcagcgg    46080
attccttgta tgcggtacaa agaaggggga accggccgta tttaccatag aagtggaagc    46140
tgacggaatc aaggaagcgg tacatgctgc cgaaaatgca cagcgtgctg tgctggtatt    46200
gggctgtaat ccggtgataa acagcaagga agagatcgat cggagtacgc ttgcccttcc    46260
tccattccag caaaatctgg cggatgctgt aagaaaagct aatcccgaaa caatagtcgt    46320
tctgttgtcc aattatccct attccataaa ccgccttcag gaagaaatgc cgggtattat    46380
atggagtgct tccggcagtc aggagctggg aaccggtgtt gccagtatat tgagcggaaa    46440
agtttcccct gcgggccggc ttaatatgac ctggtatatc tccgacgaag atctgccgga    46500
tatgaatgat tatgatatca taaagggaaa gagaacctat cagtactttg acagagaagt    46560
attgtatcct tttggttatg gattatccta ttccgaattc acctatggaa agctgaatct    46620
ggaaaaaaag gaggataagg tgatcgcgcg ccttactgtt gccaataccg gaaaatatcc    46680
ggcggatgaa gtggttcagc tttatgtccg caaggaaact tcccgtgtga cagccaat     46740 cagccgtctg aaagggttca cgagggtgaa tctgaatccc ggtgagacca agaggtgga    46800 attcattgta aattgtgagg aactgaggat ttatgatgtg atttctgaag gcatgctgct    46860
```

```
ggaggatgga gagtatacct tcctggcagg tgcatcatcc cgggatatac gtcagaaggc   46920
ggttatctgt ctggagggaa aaaagaccgg tgtgagaagt ccatgggaag tgacggcagc   46980
ggacagatat gacgattatg acaattgctt tatacataaa gggacggacg gcttcacctg   47040
tgtaattccc ggaaaggcag gagacaatcc tgacatgccg gagcatactt ccggacagaa   47100
ggcaacagga gagctcttat atcatgattt cctgttttga cagaaatccct gcggaatggt   47160 attaaacatt tatgcactgg aagaaggaag catgagaata tccttctgtg cgcagggaat   47220
agaacccaaa agcctgacaa tacaaatcag ggaaggaaga gcctttgaag atatcagcat   47280
gtctttcccc tcaggtttcc gggtgccgga agaaccctgc acattgaaaa tagaaaccga   47340
agggaagata aaattgtgcc ggttttttctt tcgataagat cgtgtatcaa taattttcag   47400
acgaattatc gcgggggggg gggtaaaaat gcttttgcgg tattccgcag gctcattcc   47460 cgtatacttt ttaaattttt tatgaaagta gtccacatta ttatagccta cctgttcggc   47520
tatttcatat accttcaggc ggttttcctt taatagctcc ttggagtatt cgatctttct   47580
gtgatccaca taacagttga agcttctccc aaaggtctta ttaaagattt ttcccagata   47640
ggtactgctg tagccgaaga gggggcaat ccctccagc ttgatattat tccggaagtt   47700
gttgtcaatg taataaatga tatcatccag tatggtgtct ctggacggac gtccggtggc   47760
attcataatc atttctgtct gagcggaaat gaagagaatg atttcataca gataacggct   47820
ttgatcgatg cggcggataa tctccgagtt tgtgggaaaa ggaatttccg ccgaatggaa   47880
cgtatgattt accttttcct ttatacgcag gaataaatcc ttcaggaaca gctttacgga   47940
agaaatatca ttttttacat tatacagaaa ttcttccagg ctgaataagg tttccgctac   48000
cttattgcgc tggaaagcaa gcagataatc ggtcaggaga ttgctgtatt cctcaagcgt   48060
atcattattg atttccagag aaatctcatg aaatttgggg agctccccat agcccagggt   48120
atgctgcccc tgcatgcaga aaaacgtct tttccggaga gtggaagcct cctcatagga   48180
cagataaatc tcatccagat tggaaaccgg acggccatag gcaagaaaaa gggaatccag   48240
aggactgcct ttctgcggaa gatttttttc atagcgttcc agaaaaccgt taaatttgtt   48300
cagcgcaaag ctgcctttca ggagaatgac ttcattgctg tcctcattaa agtgttcaaa   48360
ggtatggttt ccccttatttg ttattttgag aagatctgcg aagctgtagc tggcatcctt   48420 cggatttttca ctgaatttttt cgtaaatcac tacctggtag cactctgcat acagattcat   48480
ctcctcgatt tcccgcgggg ataaaaggcc ttcttcaaga gtctgacagt ttccggtaac   48540
gatctcgtga aggatgacat ccttggcttt tgttttcagc aattccatat tttcggaaac   48600
ggcatgttct tcatccagtt cttttctttat tttgcagata gccagctgaa gctcatcctc   48660
atcaatgggt ttggtgatat agaaatcaac gccgtactgt atggctgtct gggcatatgt   48720
aaaatcggaa taaccgctca atatgataaa tctgccctgg aagccccttt cccgggccat   48780
tcgtattaaa tcagtcccat atattttggg cattcggata tccaggagaa ccagactcgg   48840 cttttttatcc aggatcaggc agagcgcttc ctctccattg gcggcttccg cgcatacctc   48900
aaagccaagt tcgttccagt caataatatt tttcagacct tcacggatat ttatttcatc   48960
gtctgcaatc agtacggttt ccaatttact accccgcttt atagttttgg ctgccttttct   49020 atgttggaaa tataaaaata acctgtattt taagtataaa agagcattga aagattgtca   49080
atgtatgtac gactctgcgt gctgtgtgat aaacccggat ttaaggagac aatgatatga   49140 aaaaagaat taagaaaacc ctgtctgttt tggctttgtg tactctggtt tttgcggtaa   49200
cgggatgtgc aaaagagaaa gaagcaaatc tgtatgagga attcatcgta gtggatgtgt   49260
```

```
ttgattctct tgccaatttc cagggaatac aatcaggctg gtttgctgaa attgtgaagg    49320
ataaattcaa tatggaactt aatatcattg cgcctaatgt ttccggcgga ggggataccc    49380
tgttcgagat ccgttcggcg gcaggcaatc tgggagattt ggtaatatgt tcggcggaaa    49440
acggtatatt gcaggatatg gttacagccg ggctgataat tgatatggaa ccttatttga    49500
aaaacaggca gattatgcgc tttaaagatg ccatatatga tctgaacaac aatgtcagcc    49560
agccgggtat ttatgccatt ccttccgaat tgtccatgaa ttccccgcag gtttccatgg    49620
aaacccggga tcccgtatat ggaccctata tccgctggga tctgtataaa gaactgggat    49680
atccccaaat cgatacgctg gaggatctgc tccctgttct gaaacaaatg caggaattgg    49740
aaccggctgc cgataacggg gagaaaacct atgcattttc ctttttaaa gactgggatt     49800 ccaatctgat gaatgcggtg aaacagccct gctgtttta tggctatgat gaatacggtt     49860
ttgtgcttgt gaaagcggac agcagtgatt atcagagtat tatagatccg gattccctat    49920
atgtaagagt attgaaatgg tactttgatg caaaccagat ggggctggtg gatccggaat    49980
caagtacgca gacgtttgaa agttttgaaa ccaaatataa agaaggccag ctgcttttt     50040 gtacatggcc ctgggtagcc cagcctgcat acaatacaca ggagaggaca aaagaaggaa    50100
agggatttat gatggcggat atcggggata tggttatta ttcctacggc tgcagccctg      50160
taggaaatca aaggtagtg atgtccatcg gctccaaggc ggaggatccg aaagactgg      50220 cggcattcgt tgactggctg tattcaccgg aaggaatacg gaataacagg cgcagacct     50280 cgggtggaat ggcaggaccc gaaggcttat gctgggaata tggggaagac ggcccttatt    50340
taacggattt tggtaaaaaa gccttgctgg gcgaggatgt ggaagttccg gaggaatggg    50400
ggaaaggtac ctggtcggaa ggaatatccg cattgaatta cagtaccgtt gcttcctgcg    50460
aactggatga aaaagggtat ccgtatgcgt atcttctatg ggattcggta aggaacatga    50520
atatttcccc gctggaaatc gattggagag aaaaaatggg ggcagaaaca accatggaat    50580
atctgcagaa aaacaataag atccttgttt ctccgggtac cggctatatg gctccccagg    50640
aaaattctga gatggctgct atccggcggc agtgccggaa ggttattcag gaatattcct    50700
ggaatatggt atttgcagca gatgaggcgg aattcaaccg tttgtatgaa caaatgtgca    50760
aggaagtgaa ggagctgggc tatgaaacca tgctggatat cgatctgtgg aacgcgaaga    50820
aaaaagaaga cgcgagatgg gaagctgtgc ggaattatga aaaataatta tgtttcttta    50880
ttcgttgaac gtttgtcttt ctgcaacggc tgcagcggat aaaaactaaa agacagaaga    50940
agatcttccc tgtcaggaac ccgtacccgg aaagaattct ggatacgggt tgtgatgatg    51000
ttcatatttt ccaaagctgc accgggcagc atggccagaa actgacagct gctgtaccgg    51060 gtataaaatat cgctggaacg aagggaactg cacaggcttt ctcttaatt ttccatcaga     51120 aaagccctgt tatcaagaga aataaaaacg ccgtcctgat cagtcatgga tacaagaatc    51180
atgtgaacac ttgatccggt tcgtgataaa ccccgtacta aaaaacggta tacgatata     51240 aatgcatcat aattctgaca ataagctcct tttgcaggat tagattcccg gagctgaaga    51300
ctgatagctt taatatcact tgcagcgact gaatgattct gtcttgtttc catgccggca    51360
tcacttgttt tcattgtggg cttataaaaa ttaagggcct tattccagtc cttttttcca    51420
attcgcatgg caatgtctgc ttttcatac aaggtctgaa aactgtcagt atcgcgtgaa      51480
aactctgcgc cgaccgtaac acaaagccgc ccatttatgc ccagttgttg tcctgcctgc    51540
ttaaatcggg aattgagact gcccacttta ttctttatca tgtcttcctt atattcacct    51600
```

```
ggcataaata ctgcatattc atcaccgcca atacgcccaa tcagatcttt tctgaagaaa    51660
cacaactcca taattcttga cagttcgact aatgtcctgt ctcctgtaag atggccatat    51720
ttgtcattaa tgtacttaaa ttcgtctata tccatcataa gaaatactcc ggaaattta     51780 tctgtgagca atttgtttac ttctgattca attgccctgc gattcaataa tcctgtcaaa    51840
gaatcctgct gtgttaattt ttggagacgt gaattttcca tttttaacac ctcaagttca    51900
ttagtatcgt caatcttttg taccatacct tcttcacaac tcttttttccg atttatgctc   51960 atgaatggct gctcctttat ataccottac cacatttaga acgagaatct atatatgatt    52020
tgttctataa gaataatgga tttataataa ttttatttta cagcctggta attttaaaat    52080
caataaaatt cgtaaacgga aaatatagtt cgtaaacaga atagaatgtt gcatgagacg    52140
aatatatcag ttataataaa ttcaatattt tcaaaaataa tacggtaata atataaaaga    52200
agacagagag aaaaaatgag atacagtaat tatacaaaac aggaaatttt ggaaaagacc    52260
cgtgaagcca tacatatgtt tatacgcaaa caggtcagac cgttcgctga attgctggat    52320
gacaatttcg tatggatcgg ggattttgaa ccactctaca tgaagggaat tcctgccttt    52380
ttggaaagtg taaagaaga gatccaggaa cagcctgtag atattacaga agaagagtac     52440
gctctattgt ctcatgaaag ccatatatgg ataacgtatg gacgttttac ggccacagct    52500
ttggggcttt cttccagaat ccatttcacc tttgtatgga gacaaaatgg taatgcttta    52560
cggctccttc atgccaatgc caaccatgcc aagaagatgc cgtatgaaaa tgcacagtcc    52620
aagatatttg aaaattgtaa ccagacagat catatgcttt atccggcaga ttccagtaag    52680
ctgacgatcc gtaatctgag cggaagtatt cattatctgc tgacagatga aatattattt    52740
atgaaagcga ataataagat ctgtgagatt gtaacacaga atggtattgt ttcctgtcgt    52800
atgactttaa cagaacttga aaatttccca ttcatccgga tccataagag ttatctggta    52860
aacaaggctt atatccgtga gatatgccgg tatacggcgg tattatcaaa cggaatacag    52920
cttcctatcg ggaaaaatg gtatatggac ttaaaaaagt gcttgaagga aagaggagag    52980
tagctgaaat tttctcttac ttaaaatata aaaacgctgc agattctaat cggatccgca    53040 gcgttttat atttttattc atagataata tttattgcgg agtgatggtt gccccgcaat    53100
gcccgcagaa ttttgagtcc ttgttcagcg gttccccgca tacaggacat tttgccgttt    53160
cctttttatc ctcttctttt actgcctttt ccggttcaag ggaagaaccg cattgcgtac    53220
agaacttcag ccctccgga tttacagcct gacaattggg gcatacgacc atagattccg      53280
gttccggctc ttttcgcag gcttctgcct cttcctttgc ctcgtcgtct ttttcggct       53340 cttcctgtcc ggaagactct tgtttacgc cgttttcttt tttaatccgt tctatttccg    53400
cctgcgcctg atcgatagcc tcataatggc tggctgcgtt gtcacagaat tcctggattt    53460
ccgtatcaat gggttcctca tcagcgaatt ttttatagta aaactctccg attttttca     53520 gatcctcagc caccgcactt ttttctgtag cgattttagc attcagcttt gtgatctcaa    53580
tagcatcatt tgttctgtca ccgatattct tagcgatatt tccaatctta tcaaataaat    53640
ccatattatc aatacctcct tttccaacat tctatgcgca gatttgggaa ataacaaggg    53700
actttagaaa tactttagaa agattaagaa tttcttttc tatgaaaaga gccgttgtcc     53760
aaaatgggca ccggctcttt cgtatagggg aaactcttag aaatctattt ctgcatcata    53820
gtagcatgcc ttcaggagct tttccatttc ctcctgtgtg ggaatacggg gattgcttcc    53880
tgtacaggca tcaccgatcg caagctctgc aacagtggga agcttatcca ggaattcctt    53940
ctcatcaatg atggaggtgt cggctataag gccgccttca ccataattct taattccgag    54000
```

```
aggaatattc agcatcctgt tcatattccg cagttcttca attaaagatt caatcagctc   54060
gtccgtggta ttgccgggaa ggctgataaa tctggcaatg tccgcataac gttctgcagc   54120
ttcttgattt ttggcattaa atttaataac cttgggaaga tacatggcat tggctgcacc   54180
gtggataata tgtcctccgg agaaggcagc gcctgtcttg tgggccatgg aatggacaat   54240
tcccaacagg gcgttggaga atgccatacc tgccaggcac tgtgcatcat gcatctgagc   54300
cctggcgtcc atatcgccgt cataggattt cttaaggtaa tcatgaatca ttttaatcgc   54360
atgaagcgcc aggggatccg tatagttgca atgtaaggtg aaacataag cctcaattgc    54420 atgggtcatg gcatccatgc ctgtatgcgc taccagcttg ggaggcattg tctccgccag   54480
ggcaggatca acgattgcca catcaggagt aatgttgaag tctgccagag gatatttgac   54540
acccttctgg taatcagtga taactgcaaa tgcggtaact tccgttgccg ttccggatgt   54600
agaaggaatc gcacagaaat gagctttctg acgcagttcc gggaaggaaa acggagtgat   54660
cagatcttca aaagttacat caggatattc ataaaatgcc cacatggttt tggctgcatc   54720
gataggagag cctccgccca tgcaacaat ccagtcgggt tcgaattcct gcatcatttt     54780
ggctccgcgc ataactgttt ctacagaagg atcagcttcc acaccttcaa aaagcttaac   54840
ttccatgccg gcttccttca gatactcttc agcctgtccc agaaatccgc ctctcttcat   54900
ggaaccgccg ccaactacaa taatggcttt ttttccttta agattcttca gttcagccag   54960
agatcctttt ccatgataca aatcacgcgg taaagtaaaa cgtcccattg caaatacctc   55020
cttaaaatat gtaatagtgt cgtaaccggg tatgtcatgc tccctcaat gtcattttat     55080 tatatgacgc cccgtttgtt aatattttaa cactattaac aaataatgtc aaatgaaata   55140
aaataactta cgattttgtg aatactgtgt ttcttgaatt attttccctc gtatagtatt   55200
cttgtatcaa aaggaaaaag gggggagaag aatggacatc agtattttaa ttgtagatga   55260
tgataagctg gtggtggaaa agctggtgga aggggttaac tggaagcagc tgggaatagg   55320
tatcgtactg acagcctata atatcagaca ggctaaggaa atcctggaag aggccagggt   55380
ggatattctt ctttctgata ttgaaatgcc tcagggagc gggctggagc tgctggaatg    55440
ggtcagaaat aaagagattc ccgtggaatg tatatttta agcagctatg cctatttgc      55500 ctatgcccag aaagcaatca acctcaaatc aagggaatat atgttaaaac cggtttccaa   55560
cagagaacta gaggaggcgc tgggaagcat agtggagatt ctgcagaaaa acgggaaga    55620 acagggagaa ggggaggaca aaaatcagc cttttgggag aggtatcttc tgcaggaaaa   55680
ctacagccgg tctctccttg agaaaggtta aaagaggg atatgcagtc cggagggga     55740 atatttctg gaaatcatac ggattttcc cgattctgat actaagaaaa agaagaatct     55800
tgttttgtat cattttatta ttcagaatgt tgccgcagaa ttcatggaag acaggcatca   55860
gaagctgatg gctgtcctcc gtgagagtga ttatgaatgg gttcttgtgg cggaagaaaa   55920
aggaagccag gaacaaagga aaatggattc ctgccagctg aaggaatgtc tggaaaaagc   55980
gctgcatatg cgcgtatgct tttatatggg agtgagttct tccgtggaag agctgggaaa   56040
aagccggagg aatctggaac agatggagca ggaagcggta cccggtaata acgggatgct   56100
ttttgaagag gaatgggata agaaggatat tgcctatgta tccccgccgt gggagatatg   56160
ggaaaaggaa atgtcggctt cggatatgat agccgatacc caggagaaaa tccttcatt    56220 tctggaggag ctctggaaca gcaatcaggt gacaatttcc acactggagc aattccggag   56280
ggaaatgatg cagatgatat acaggtatct gaataaacag gatgtgctga ttaccaggat   56340
```

-continued

| | | | | | |
|---|---|---|---|---|---|
| ttttgacgga | agagaatttg | atgagcatta | tgagagtgcg | gtggcaaccc | ttccggacat | 56400 |
| ggaaatttt | atccgatata | tttttgaaaa | gcttgcgggc | tttcagcatc | aggataaccg | 56460 |
| gcaggagtcg | gtggtagaac | agatcaagca | ctacataaat | gatcatctga | aggaggattt | 56520 |
| gtcccggaaa | accctggccg | gatccgtata | tttgtcagaa | gattatgttt | ccaagatatt | 56580 |
| tatgaatgtt | accggtattt | ccatcccaag | ctatgtagcc | tcctgcagga | tgcagaaagc | 56640 |
| gcaggaatat | ctgaagtatt | ccaccttttc | agtgagcaag | gtggcgctgg | aggtaggcta | 56700 |
| cagcaacttt | tcctatttca | gcaaaacctt | ccgggattat | accggctgta | ctcccaatga | 56760 |
| gtacagaaac | agggtaacaa | aaaagcaggg | ttaagaaagc | cgtataaaaa | gcaataatag | 56820 |
| cagatatatg | taatacaggg | ccccttttcc | attcggagta | tctgattcat | atatctgctt | 56880 |
| ttttttcggg | cagttatcac | attttttgtta | tcaggccgga | ataatgacag | atttatgttt | 56940 |
| atcccctcct | gttgactttt | atataaatta | tcattttttaa | gctgtaaata | acaaaattat | 57000 |
| ggccttcttt | acgaaactca | tataaagaag | accccgtatt | tttgttatgt | gctcagctta | 57060 |
| gaatttatag | attaatatta | cataaaaata | tacaatattt | acagaaagca | aaataaatat | 57120 |
| ttgtacaaaa | attaaaattg | acgaaaaagt | atggcataat | ccaaaaaaag | tagcacaagt | 57180 |
| aataaaaaaa | gaagttggga | gtgatgaaaa | gagtggcacg | acagaaaaca | gcagtaagca | 57240 |
| ctgcaaagcc | agtcagtatc | ggaaagaggt | tgaaagaag | cggttccctg | tatttgctga | 57300 |
| tgcttccctc | gctggtaatt | atgttccttt | ttacctatat | tccgatgtat | ggcgtaacca | 57360 |
| tagctttcaa | agattttaca | ccatcgcagg | gaatcatggg | gagcagctgg | gccggactga | 57420 |
| agtatttcag | acagtatttt | aattcctatc | agttctggat | aaccatcaaa | aatacgctgg | 57480 |
| taatcagctt | atacagcatt | gtggtaacct | tcccgctccc | gattgcactg | gcgcttatgt | 57540 |
| gcaatcagat | ggcaagaaag | ggattcaaga | agttttttca | ggtatccact | tatcttcccc | 57600 |
| actttatttc | cacagtggtt | atgtgcggta | tgatcatcct | gttcctttca | cccagccagg | 57660 |
| gaattattgc | aaagcttctg | agctttgtgg | gaattaccct | tcctaacctg | atgggccagc | 57720 |
| cctccgcttt | ttccagtatc | tatgtatgga | ccgaagcctg | gcagcatgtg | ggctgggaca | 57780 |
| gtatcccttta | catagcggcc | ctgtcggcag | tggatccttc | cctttatgag | gcggctacca | 57840 |
| tggacggcgc | cagcaaatgg | cagaagctgg | tgaatatcga | tattcccatg | ctgcttccta | 57900 |
| ccgcaaccat | catgtttatc | ctccgtacag | gcagcatcat | gagcgtaggc | tttgaaaagg | 57960 |
| tttatctgct | tcagaatacc | cttaacagca | gtgcgagtga | aatcatctca | acctatgtat | 58020 |
| ataagatggg | tctggtaagc | agccagtaca | gcctgtcagc | cgcaatcggc | ctgtttaaca | 58080 |
| atataataaa | tctggtattg | cttctttctg | tgaactatat | ctcaaagaag | atgagtgata | 58140 |
| cttcactggt | ataagggga | aacagaaatg | tccaataaaa | acggaactgc | cgggataagg | 58200 |
| gttaaaaagt | ctaaaaacga | caaggtattt | gatttcttcc | tttatcttct | ggctatcata | 58260 |
| atcatcatta | ttgttctata | tccgatgtat | tttattataa | ttgcatccat | aagcaaccct | 58320 |
| tcggatgtat | cggcgggaaa | tatcgtgttt | ctgcccaaag | gaattaattt | caagggttat | 58380 |
| ttgaaactgg | gtgaatattc | ccagctttgg | gtagggtata | aaacaccat | tttgtatacg | 58440 |
| gctctgggaa | cggttctttc | cctggttgtt | aatatacctg | ccgcttatgc | tctttcccga | 58500 |
| aaggatttgt | gcgggaaaaa | gctgtttacc | atttactatc | tgattcccat | gttttcacg | 58560 |
| ggcggcctga | ttcctaccta | tctggttatt | aaggatttca | acctgctcga | taatttctgg | 58620 |
| gttatggtag | tgccgttttc | cgtaattacc | tattatatta | tagttgccag | aaccttcttt | 58680 |
| aacaacagta | tccctgatga | tttatgggag | gccgcgcaga | tagacggctg | cggaaacctg | 58740 |

```
aacttttcct tcaaaatagt tcttcctctt tccaaggcgg ttattgcagt catagctctg    58800
tggacggcgg taggacagtg gaactcctat ttcaacgcat tgatttatct gcgcagtccg    58860
gagctgcagc ctctgcagct ggtattgagg aatatactta tcagcaacca gaagatcagc    58920
gccatgacaa ccggcgcggc agcagtggaa gccaagcaga tggctgatct gattaaatat    58980
gcggtaattg tggtatcctc cgcacctatt atgtgtatgt atcctttcgt gcagaaatat    59040
ttcaaccagg gcgttatgct cgggtctctg aagggataat gaaagctaag gtattcattg    59100
cttggaaagc aaaagtacat aaatatttat ttctaagaaa aggagagatg aaaatgagct    59160
attggaaaaa agcacttagt atcggactgg cagcagtgat gacagcatcc atgcttgcag    59220
gatgcggcgg cagcaataaa gataccgcgc aatcgggagg gaataccgcg gggacacagg    59280
cgtcagatac ggcggaagca gcagataacg gaacctctga agatatcact acttataaaa    59340
tcgcgactgt gcgctggacg gatgcatggc ctgtggattt cctggaaagc ggctttatga    59400
aagagctgga agaaaagcac ggaatcaaaa tcgaatggca ggtatattat gacaatgact    59460
ggcaggagca gaaatcccct ctgctggcat ccggagacct tcctgatgca ttttcggtt     59520
ctatctgtct gaaggatacc gacatttccc agaataagga ttatttcctg gagcttacgg    59580
atctgattga ccagaatatg ccgaatctga aggctgtttt tgaaaaagag ccggagttgc    59640
tggcaagggc aaaggatcgt aacgagaaa tttacagcct tgtgaaaaag cttcctttaa     59700
gaccggaggt atgcggcaat attctttata tcaacaagga atggctggat aacctgaacc    59760
ttgaggttcc cacaacctat gaagagctgg aaaatgttct ggaagcattc gtaacagagg    59820
atgcggacgg tgacggcgat cccaacaacg aattcggaat taccggcaat gcaggtttat    59880
atactttgag cggctgcctg cgtaattacc tgttcccttt cggaaccatg gtaagcagag    59940
ataacaatta catgagcctt gtagacggaa aacctgtttt catgccggta gaagagaatt    60000
ataaggaatc tgtaaaatgg ttcagcgata tgtatcagaa gggcatcatc gatcctgagt    60060
tcttcacgca ggaagatgcc atgagaagaa gcaagctgca ggcggaaggc ggttcccagg    60120
taggtctggt atcggcatgg acagctgatg cggaaacagg cctgaacgta ggtcagttcg    60180
ttcctctgga agcgattaca ggaccggacg gaaagcatca tgtggaaaat gcacagaatt    60240
tccttgatat ttcagacaga gaactgctta tcaccaaaaa ctgccagaat cctgaaaagc    60300
ttcttgcatg ggctgatgac ttctatacgg atttagcttc tctgcagacc ttctatggtt    60360
ccataccgga tcaggtacag gataacggcg acggaactta tgatgtgctc gttccttccg    60420
atggaagctc cctggatact tccgcatggt ccaattccat gcgtgacttc ggaccgaaat    60480
atatgaatcc tgaatttat gacaaggtaa gccttcctgc agatcagggt gacgggatca    60540
aactggctga ggatgccatc aacggcaaat atatagcaga tgacaatgtt gtcggattcc    60600
ctatggtaaa atatacggat gaagaactga cacagttaac aacgcttggc acggatattt    60660
ataaatatgt ggaagcacag tttgcacact gggtagtaga cggaggcatc gatgaagaat    60720
gggatgctta cctgaagcag ctggacagca tgggcttaca ggatctgatg aatattcaga    60780
acggagctta tgaagcatat ctgcagtcca tgggcaagta agacagccgg gtgcatatcc    60840
tgtaggatgt gcacccattt ttcagtaact taaactttgt ctctgcccct gttccctccg    60900
gcccgtactt ttgagactgc tgcccggttc ggctgcccct tcttccctca gccggctatg    60960
cagggatcct tacaggggaa cgactttagt cgttttgact tatcgttcgg ataaacacgc    61020
agcggtacta aggccgcaaa gtacgcggcc taaggaccgg cgagtttata cgccccttac    61080
```

```
aggataccct gcatagctgg ctgagggaag aagggGcagc cgaaccgggc agcagtctcg    61140
aaagtacggg ccggagggaa caggggcagg ggcgaaggtt gagataataa gaaaagaagg    61200
ggaaaaatat gattttcaaa aagataact gcctgatcta tcaatatgac aacgagacgg     61260
ttcagattga gccgtgggGg aatgatgcgg taagagtaag ggcttctatg aacgcttctt    61320
ttaccggaaa taactgggct tggaagaaaa aggcggaggg aaaaggcgag atagttgttt    61380
atgatgacca ggatgcttcc gcagtcgttt atgccaatat gtacagcggt aaaaatgagt    61440
ccttcggctc ccttactaac gggaaaataa ctgcagtggt gaatgcggac ggcgttcttt    61500
ctttttataa tcaggacaag aagctgctgc tgaaggagca gtggaagcgc cttaaggatt    61560
gtcccagtat gcctcttaat gtatatggac gggaattcaa ggccgtggca ggggattcct    61620
tccatgcggc tgccagattc atagcggatg atgaagagaa aattttcggt atgggtcagt    61680
atcagcagaa atatatgaat atgaaaggct gtatgctgga gctggcacag agaaattccc    61740
aggtgagcgt tccttttat gtatcgaata taggctacgg attctatgg aataacccgg      61800
ctgttggcaa ggttaccttt ggcgtgaacg gaacggaatg ggaagcggaa tgcacgaagg    61860
agcttgatta tcttgtgatt gcaggtgata cgccggcaga aatcgaagaa acttatatgg    61920
ggctggttgg caaagctccc atgatgcctg aatatggcct tggcttctgg cagtgcaagc    61980
tccgttacca gacacaggag cagctccttg cggtagctca taaatataag gaactgggac    62040
ttccgctgga tgtcattgtg gtggactttt ccactggac acagcagggg aatataaat      62100
tcgatgaaaa atactggccg gatgttccgg gtatgtgtaa ggaactggcg gacatgggaa    62160
tccgtgtgat ggtttcggta tggcctaccg tggattaccg gtcggaaaac ttccgggaaa    62220
tgatggaaaa gggttatctg gtcagaacgg aaagcggcgt gcgtatcgcc atgacctgtt    62280
tcggacagga gcttttcttt gatgccacca accctgatgc caggagctat gtatggcaca    62340
agatcaagga aaattattgg gataagggag cgcgcctttta ctggctggat gtggcggagc   62400
cggaatatac cacctatgat ttcagcaatt acagatatca gctgggcagt gtcatggagg    62460
tgggtaatat atatcccaaa ctctatacaa agggctttta tgacggcatg aaggcggaag    62520
gggatgaaaa tcccataaac ctggtgcgtt cggcctgggc gggaagcgcc aaatacggct    62580
ctcttgtatg gtccggggat attgacagta cctttgaatg cttccgcaga cagatgcggg    62640
caggactttc catggccatg gcgggaattc cctggtggac cacagatatc ggaggcttcc    62700
atggcgcgag cggagaggat cccacgttca gaaagctgtt catccgctgg ttccagtatg    62760
cctgcttctg ccctgtgatg cgcctgcacg gcaacaggga gcctcagaag ggctttgagg    62820
gagatatggt atcaggaatc ggcctgttcg gttccggcgc ggataatgaa gtctacagct    62880
tcggagagga agtctttgaa atatgtaaga aatacatgtt tttgagagaa acgcttaaac    62940
cttatataaa ggaacagatg cgtatcaccc atgaaaaagg gacgcccatc atgcggccgc    63000
tgttttatga tttcccggag gataaaaaag cctgggaaac agatgatgcc tatatgtttg    63060
gccctgactt ctgcgtagcg cccatgatgg aggaagattt atacgagaga gaggtttatc    63120
ttccggaagg atgcacctgg aaggatgtat tcagcggcag cagctacgag ggcggacaga    63180
cagtaaaggt ggatgctccg atagataaaa taccggtatt catgagggca gacagcagct    63240
ggagtataga tttctgaaag aaccgaaaga aaatgatccg ctgaatcaag gatatttcgg    63300
tgctttgctt tatagccata tagctatata ataaaaaaag gaaatgcctg gcgggaagcg    63360
aacgattgaa ttgcaaagtc ctgccaggct gtttgtataa acgggaggaa tagatatggc    63420
agggaaagcg gagaagaaaa ataaaagtat ggggaagctc accatacagg tcataattcc    63480
```

```
tgttatcatt ttattcctgg gtatcctggt agtcatgttc cagagcatgt ttgaagcaag    63540
gcagctggta taccgttata tcgaggatac cgccgcactg tatgtggagc agctcaatac    63600
cgatatcacc aaaatcaatt atgagatcat cactctgacc aataaaaaaa gagaaataaa    63660
ttccgttaag ggaatcaggc cggaagacag taagtattat ccggtcctga atgagatcca    63720
ggagcagaac cggaatctga aaatccgtta taaggaaccc agctgctttt ttgtgtatct    63780
ggaagaagcg gagctgctga taacggacag cggcagtata tttaaggaca gccagaagct    63840
gggcctgaac agtgcgctga tggaggccct ccgggagaag aaggggggaac gcactcctta    63900 ttcccagtgg tatttcatca atgacggcga acaggattat gtattcagcc gttttttccaa    63960 aaatggtatg acaatgggat gtgcaatccg cctggaggat ctgtttaaca ctctccgaat    64020
agacagcctt ggatacgaag gaattccgta tatacaggat aaggacggct ccatatttat    64080
ttcttccagg gacagggata aataagtgt ggaggatatc cggaatatct cgggaaaaaa    64140
ggcgggcatt tttacggaac aggtgattta ctcctttcct atcagcggaa ttatcggaga    64200
aaacagggtt tttcatatca tgataacccc cagcggcggc attctggaaa aaataatgcg    64260
ccttcaggtc attttggttt ttcttgccat aggaattatc gttggctgca tcctggtagt    64320
cagagtctat taccagcgta tcctgcgccc tatgaagcag ttcgtaaaca gcctgaaaaa    64380
tacggaagag aacagtggga ttaatgaaaa cggcagtaat aacatcctgg agctggaaat    64440
ggcaagcaag gaattcaagg gactgctgcg caaaattaaa tctctgaaaa ttgacatcta    64500
tgaaaaagaa ctggccaggc agaaaacaga gctggaagcc atgcaggtac agatcagacc    64560
gcatttttac cttaactgcc tgagcctgat ccacggaatg gcggatgtgg cgaaggaaga    64620
gaaaattgtg catatcacag aaatgctttc caattatgtg cgctatgtca tgagcgatac    64680 cttgagcca agatccctga aggaagaaat tgcatttata cgcaactatg tggaaatcca    64740
gcagatccgc tatggcaagg aagcattctc ctttgaagtg attatggaag ataccatcga    64800
tacctacctc gttcccacgc tcatcataca taatttcgtg gaaaatgcca taacccatgc    64860
ggtatctctg gataatcacg tggaaatcac cctctatata gtgaatgaaa attatgagga    64920
cggagagtac ctgtacatct gcatatcgga tacgggaaca ggctttcccc ctgatatcct    64980
ggaggccatc gaacaggata cgcctatata ttataatgac aggaagcata taggaatcca    65040
gaactccctg aaaaggctga agctgattta cggagaaaag gcaaaaatta ttttttccaa    65100
tatggatgaa ggatatgggg ctgtggttga aattacgatt cctgtacaga aggagcagaa    65160
tacaggcaca aataaagaca gggtttaaaa gccctgtttt tgtttgtgcc tttcggcgct    65220
gtgagctgaa tggtatgttt gactatacct gtaaattatt gtaaactgat tataactgtt    65280
ctgcagggca gcgcattcac tgcgttggcc gtaagaaagt gcttcaggaa tgcagaaaaa    65340
agtatgagac aggtacctgt gagataaaat aagaaaataa gatggaacag ctgaaaatga    65400
tagcttcagt tttccggaat caaacgcccc ttaaagcgga cagaggggag caaatatgaa    65460
attttcacaa atgccttacg aaagagtgga tttcaataaa gtggaagaag aattcactca    65520
gcttatgaaa gagtttaaag aggcccgaaa cggggaagaa cagtttgcag tgcaccggaa    65580
atattatgag ctgcgtgaca gggtggatac cctgatgaca attgcccata tccgccatga    65640
tgtgaatact gcggatgaat tttacagtgc cgagcaggat tactacgatg aggaaagccc    65700
tcgttacagc aatatggtaa ttaattacga gaagctgctg tacgagtccc cttaccgcaa    65760
tgttctggag gataagatag ggctggtagc ctttaaaaat atggaattgt cccagaaatc    65820
```

```
catgcaggag aagctgattc cccttgttca ggaggaaaat gccctgacga ccgcctacga   65880
gaaaatcccc gcttctgcgg aatttgactg ggacggggaa aaggtaaata tttcccggtt   65940
aaaagcctat ttgaaaaatc cggacaggaa tgtccgcaga aaagcgtggg aaaaattttc   66000
cgctttcttc aaagcgcatg aagaagagct ggacgatatt tatgataagc tggtaaagaa   66060
caggaccagg caggcaaaag agcttggcta tgaaaattat gtggaactgg gctattaccg   66120
aatgaaccgc aactgctata caagagaaca ggtagaagcc tttcgggatc aggtgaaaaa   66180
ggattttgtt cctttttgtgg agaagcttca tgacaggaga agggaacgcc tgggacttga   66240 caagcttttcc tttattgatg aaggagtata ttttaaagaa gggaatccca atcctgtcgg   66300
tactccggaa gaaattctgg aagcagggca gagaatgtac ggacagcttt ctccggaaac   66360
caaagaattc tttgatttca tgatggaaaa tgaactttttt gatgtgctgg ggcgcaataa   66420
taaaagagtg gggggatata tgacctatct tcccgtatac aggtctccct ttatatttgc   66480
caactttaac ggaacaagcg ccgatgtgga tgttattacc catgaatgcg gccatgcctt   66540
ccagggctat ctgtcaggaa tggatgaaat ccggagcat ggggatatca caatggaaac   66600
cgcggaatgc cattccatgt ccatggaatt cttcacggag aaatggatgg actggttctt   66660
cggggacaag gcggacgcgt ataggggaaat gcattttgag gacgccatga tgttcatacc   66720
ttatggctgt atggtggatg aattccagca tatcgtatat gccaatccgg atttgacgcc   66780
cgcccagagg aaagaagcat ggagcaggct ggaaaaggaa tacaagcctc atctggatta   66840 tgaagggggat gaattcttcg gaaagggagg atactggcag cagcagcatc acatttacag   66900 cttttcctttt tattatattg attatgttat cgcacagacg gttgcttttg aatataaact   66960
gtggatggat gaagattttg aggccgcatg gaagagctat ctgaagctct gccgcctgtc   67020
cgccgcagat ttctttaata acatgattaa agaagtggga ctgaagcttc cctttgagga   67080
aggctgtctg aaggaaatgg cagggaaact ggaaagaag ctgacgaaag aagcataata   67140
gtatatgaat tatatcatat tggatctgga atggaaccag gggaatgaac agaaagaaaa   67200
acagctgaag gaactgccgt ttgagattat agaaataggc gccgttaagt taaacagccg   67260
catggaaata tgcgacagct ttcatgaact tatacggccg caggtttata agaaatgca   67320 ttatatgacg aaaaagcttc ttcaccttga tatggaggag cttcagtcag ggcgcagttt   67380
tcttcaggta ataaagagct tccttgcctg gtgcggggag gactatatgt tcggaacctg   67440
ggggcctcag gatctgacgg agctgcagcg gaatatgaag ttctatggga tggagcctct   67500
tgataaaaag cccatgaaat tctatgatgt acagaagctt ttcagtatag ccttcgagga   67560
taagaaatca cgccgcaatc tggaatatgc ggttgatttt cttgccatat ccaaagatat   67620
accatttcac agggcactga gcgatgccta ttataccgga cgcgtactgg ccaaaatcaa   67680
ggatccccag gtactgcaga tgatatcctt tgacggcttt attgtgcctc ataacaaaaa   67740
agaagaggtt catattgtct ttgatgatta tgccaagtat atctccaggg attttgcgga   67800
taagcaggag cttcttgctg acaaggaggt ttcttccacc aaatgctatc tgtgccaccg   67860
caacctgaaa aagaagatcc ggtggttcac accaaacgga aagcattatt acagtgtatc   67920
ctattgtgaa aaacatggtt ttatgaaagg caaaatacgg gtccgcaaaa cggaggacga   67980
cagggtttat gcggtaaaga ccatgaagtt tattacggaa gaggatgcgg cggatatatt   68040 taaaagaaa gaaagagccc gcgaacttcg caggctcagg aagcataagg aaagctgaaa   68100
acggacggca cgtttggtgc cgtccgtttt tagctatact cctgaagtat ttcagccttt   68160
taccgctccg tttgtcagtc cgtctataat gtatctttga gcaaagatat aaaagataac   68220
```

```
aaggggagcc ataatcagta ccatggtagt catcataagc ggccagtcac tttgaaattc    68280
tcccacaccc cggtacattt ccagcataag agtggcgttg tttcttgtat gaagaaacag    68340
gaagggagtt acaaaatcat tccaggttcc cataacatgg aatattgtca tagttactgt    68400
aatcggcttc agcagaggga aggtaatctg gaagaacaca cgaagagggc ctgccccatc    68460
aataattgcc gattcctcca gttcgtaggg gacggtatta ataaagccct gatacatgaa    68520
gaatgcaaaa acacagcttc cggtggaaag gacaatcagt ccgtacagtt tattaatcag    68580
atgaaaacgc tgcatctgct gatacagagg aaccattgtg gtctggaacg gaaccatgaa    68640
gccgagaaga aaatagagca taaccagctt gtaaaatctg cttttccgcc ttgccaccgc    68700
ataagcagac atggaaccaa acaggattac cacaattaat gtagagaagg taataagcag    68760
ggtattaaaa aaagctctta caaaatgaat ctgtgcccag gcatttttaa aattctccag    68820
atacaatgat tccggaagtc ccagtggatt cagtcccatt tctcttggag ttttaaaaat    68880
actgataaca aggtagtaaa aaggcagcac tataatacag cataataaaa gcatgatgat    68940
ttccagaagg aatgttttcc aggtataacc cttaagatta gattttcttt tcatataagt    69000
ttttcctccc tcttttttcat cagggaaagc tgaatgatag tacagataca gataacaaaa    69060
aagaatacta ccgacatggc ggttgcttta ccgtacagct tttccgtaac gccccgtgta    69120
ataatgattt gtgttaccat aagagttgag tagccgggac ctccgttggt aagggaaaag    69180
ggcagatcga ataccttaag gctgccggtg agcagcagca taacgctgat agtcatagat    69240
ggagccagca tggggaaggt aatatggcgg aaaatatccc atccggaagc accgtcaatg    69300
cgggcggctt ctatatagga agaagggata ctctgcaggt tagccagata gatacatgca    69360
tgccatccaa tctgggacca tacgatacc ataatgatag aaaacatagc cagcatgggt    69420
tttcccagcc acagaacctt atctatgtgg aaaatagcga gaatggtatt tattaatcct    69480
cttccggtag ggctcagcat ataagaccac agatatccca gaatcagaac actgggaacg    69540
gacggaaaga aaaaaacagc tcttttgcaga ttacgggttt tcattttccc gtttagtaaa    69600
accgcaagag gaatggcaaa cagagtaacc agaagaggca cagaaaccgc ataaccagg    69660 gtattcatca aagcacgcat catgggtgca tccccgaaaa gatcaaggaa gttttttaaac    69720 ccaacaaatt cagctctgtt gaacccgtcc caatttgtaa acgcatattt aaagctgttc    69780
agcaggggaa ctatggtaaa ggttgtgtac cccaaaaaag caggcagtat aaacaggaga    69840
tagggaaatt cccttttcag agttttttttc aagacaggca gctcctttcg ttgaagatat    69900
cttcataaat tcagcggaat gcgtatccgc tattccgctg aatttaatca agcagtattc    69960
gcttttccct tactgttcag catccagttc agtccgtttt ttatccatat tttccactaa    70020
ctgttcgggc gtgatatttc ctgtgaggat ttcctgtgtt cctataagca tttcattgcc    70080
aagagcatct gaatacttcc actcaactgc ggggagatag aatttgcctt ctaacaggta    70140
aggatatccc tcttcaatag tgggatgaat ggggaagtca ataccgtcaa cagcaagcag    70200
tccgccggtc tgttcctgga atattttcaa tgattcatca ctggaaaggt attcaagaaa    70260
agctttggca gcaggcatat ttttttgcttt ggcattaatt gaccagccaa cccctgttgc    70320
acctgtcatc caggctactc catcttctgt tccgaaccag ggaagcatgc cgtattccag    70380
atcaggattc agttcatcta gagtggcaac agaccaggtg gcaccgatca tataggcaca    70440
ttcctcgaat gcaaacattt catttacctg atctccggta agtccaagag catcctgatt    70500
aatatatccg ggttcaaggt agtcagctgc ccaaaggcta accggttcgc tccacccatc    70560
```

```
tgcataggtc agttctccgt tatttacctg agagtcatag ctgccgtttt tatttatggt    70620
ctctgtggca acatagccct gaatgggatc atacagattt gtactgcaga aggcccaggg    70680
ctggattcca ttagccttca gggccgccat actggccaga tattcttcac ggtttgtggg    70740
aactgcaatt ccattatcct ctaatatttt tttgttatag aatatacctg caatccaggc    70800
atcgggtgcg aaagcatata ttttccgtc ttttgtataa gtctccttat ttttatcgga     70860
cattttttca aaagcgggca gataggaaat atccatggca atatcattat ccaggacttc    70920
tcctttgttt tccgcagctg ttacaaagac atccggtaaa tctcctgtgg agtacataat    70980 ctggaattt tcaacataat cctgtaccgg aggcgcatag atcaagtcca cgcttacatc     71040
cgggtatttc tctttgaaac cgttcagtaa aggctgcatt acggtttcat tctgccagga    71100
aagaaaagtc agtgtgccgc tggggcatc tccttcagtt acaggagcag tgctttctgc     71160
tgaagtttcc ggggcagctg cagatggggc agcagaggaa gcttccccgg aagagtccgc    71220
gccagcgcag ccggtaacgg aaaatgcgag tacggctgca agtgcggcag caaaaaactt    71280 tgaactttt ttcatattca taaccctcct tgataagatt gctttactaa gtttctatac     71340
tgcaggcgcc ggctcctgaa gcaattgaac tgtcatatat tacctttat gtgctttcta     71400 tacttaaaat tctagtcatt ttttgttcaa gtaaatgtg atataataca caaacttga     71460 attataatat ctttgcatag aaaacatgtg gattaaataa tattttttgta caaatatacg    71520 catgcctgct ttataatgtt actataaatt tgtcataaaa tcagtttttt cagggggtat    71580
tttatgctta agcatcacca tccacagcag tcctcaatta ttaccaaaac agcagtgagc    71640
gtagctaccg ttttctggc ggccatttc ctgcttatat ttggtatcac ctatctgaat      71700
agttactgga tgcatcaccg catacttacc gataagcagg aatttgttaa tgaaatctcc    71760
cgcagtatag atgatcagtt taaaagcctt acaacaccgc tggtatccct tgggaaccag    71820
tctgccgtgc atcggcttct taacagcaat gatacatatg attccagctg gctggctaat    71880
atacgggagg ttgaaacaag catatcccag attcatattt attatgacca tgttgttgat    71940
cttgtgatca tgaatacgga ttccaaaatc cttttttcag tcaccaatgc attaagccgg    72000
aactatgatt ttacaggcag cgattggttt cagaaggctc tggaacagcc gtcggccata    72060
aaatatgtcc ctcctcacgg agttgatcac tattccagac agaacgaaaa atacgcaaat    72120
gtattttctg ttatttatcc ggtgaaaaag gctgataaag tagagggata tattttatgt    72180
gaagtaaatg ccaataaaat ttcgagtctg ttttatggga cgagtattca ttcagccgaa    72240
ggttatatta tggtcgatga agacggtaag cttatttatg attatgtaaa cgaccgttct    72300
ccggatgaaa tcggagatat ctggacggca ataaacagga atagaaccac agatacaccc    72360
atgcagacta tactgaatgg aaatttatac accagtaaac agatacagac aacaagatgg    72420
tttatcatat cggaaacctc caacgaaata atcagaagtt ctgctaattc tatctggtcc    72480
tttgctattg ttattggatg tgctgcagta ggattttgca ttcttattct tcgttatatt    72540
acacgcaggc ttcagaaacc tgttgacagc gtaatcgaaa gaatatcctc atatgacgga    72600
tccggcgctg tcgcctttga cgatatggat aacagttttc gggaaataac ggttatccgc    72660
agtaaatttg aagaaatggc tggtaaaatc aattcactga tcaatgatgt atatgtggcc    72720
cagatgcacc agaaggatat tgaactggaa atgctggtca gtcagatcaa tcctcatttt    72780
ttatataatg ttcttcagac cattcatgga gaagccgtcc tgcatgggga ccgggaaatt    72840
gaagatatgc tttccgcttt gggggaaatt ctgcattata ccatagatca ttccgatgaa    72900
atgactacta tagccaggga aatacagcat gtaaataatt atctggggtt ttaccaaaag    72960
```

```
cgatttccac gtcttttttgt ttattctgta gattgtcctg aagatcttat ggatcatcag    73020
atactcaagt atcttcttca gccggtgata gaaaacagta ttaagcatgg ttttaaggac    73080
aggaaggaag gcggagagat aagactcctt attacccggg gacagggaga tattgtattt    73140
gaagtctttg ataacggaca tggtatcagt gcagaacgaa tggaggagat cagaacaaat    73200
atggaattag ccctgagaaa tccgggagtt ggaattgcaa atacaaatgc acggatcagg    73260
ctgaaatatg gtgcttccta tggcattgtg cttgatagtt tggaggaaga gtatacccgg    73320
gttatcatta caattccgga tgaggagagc aggtgatgaa tatgtataag gtatgttttg    73380
cggacgatga acctattatt tttaaggtgc tgaatgcgct tgtggattgg gcagacgttg    73440
gctgccagat tgtgggaaca gccacggacg gggtagaggc tctttcttta tatgaaaagg    73500
aaaaaccgga ctttattata attgatataa aaatgcctct catggatgga ttgagctgtg    73560
tgaagtatat tcgtgaaaaa gacaagagag tgaaaattgt acttctgaca gccagtgatt    73620
cttttgaatc agcccaggag gctttaaatc ttggagccaa tgggtatttg ctgaaaccgg    73680
tgagccgtga atccatcaat aaaattgtgt caaaaatcac agcagaactg aatcaggaaa    73740
ccagcagggc tgaagaatct tcctcaggga gtgaagagct gctattacag aaagagcttc    73800 agagactta tggagcaagt atgaatgcgg aagaaaacac ggcatggctg aatcacagca    73860
gactgatcca gggaaaatac ggactcattg atatttcttt tcgctggaat attcaggaaa    73920
aaccaggtga tacggaagtc ctttcggaaa tcttttccga atatataaga agggcaggta    73980
ttaagattta tgcccgcttt atatcagcga ataaccgtat tatttatgct gtttctccca    74040
tgaaggaaaa tacattggat tttctgcgga actatcataa agatatacccc ccggatttaa    74100 aatattctat atatttgctg caggaagccg gtggcaatat cagcccacag gctttatgca    74160
gcagtctgaa agcgaataaa atacatagtt tttatcattc ggaaaatcat atggacattt    74220
ttctgaaggg gattaaagag gaagattccc cacttcctat aaatgagatc aagaatattg    74280
tatccggtgc cctgcaggaa ttaagtataa caaaggtatc agattttcta agggatatat    74340
tttcctgtgc gcaggaggaa cttcgcagtc ccgggcagct gcagggtttc tgctataata    74400
tgatcatgca gctgaaaata catatgaagg atctagggct tttacagtct gcggaagaac    74460
tggataagat agggatagag agattcctgt caatagaatg tgcggaagag ttattaaaat    74520 atacccctcag ctgtattata aaatacctgg aggatttaga aaaagagag gaattcgccg    74580 gaaataaatc cattgtacta aaggcgaacg cttatgcaat ggaaaactac agggatccga    74640
agctttcact ggaaagcgcc gccgattatg tgggattgag taaaaattat tttatacgcc    74700
tatatggaaa ggagacagga atcagctttt ggacatatat tactagtttg cggatagaac    74760
gtgcaaagct tctgcttcga agtacacagc tttccatgat ggatatctgt gcacagatag    74820
gatatgatga tgtcagttat ttttcccgta aattcaagct ggaggtagga atatccccca    74880
ggaaataccg ggatggcaaa gaaaacatct gattacagtc agaagccgtc cggtcctttc    74940
gtatacctgt caaaatcaat cccatccttt ttacgccgtt tgcttcgttt caggctgatt    75000
ttcctgcgct ttccaaagct gtaatttctt atcagagaaa caatggatat cagcgcaaac    75060
agcgaaacaa ccacagcgat aacaataatc aggacatttt ttatattaat ataataaacc    75120
tgccccaagg cggttttttgc gctgtctcct gtctttgaaa cggcaggggt atcctgcaca    75180
atttccacag aagcgcttcc cacatacgag ccgttgtaag taaaattaat tatgcagcag    75240 gcttttttcgt ttccgccctc ataatccagt tccgattcca cgtccttata atcagcggta    75300
```

```
tttggaagta cgataatatc ggaagaattg atagccagaa gcggagcgga attaccgaaa    75360
acatcgctgt ccgattcaaa aaagctatta tttcccactg tatatttcgt atccgtctcc    75420
gaaatattaa cggcataaaa attgctgaac ccgtaattaa acagatctat ggtatcagta    75480
tattgagaag gcgattcttc cttcataatg acacagataa gcttcagccc gtctttctgg    75540
gcacaggata ccagcgtctg tctggcctcc gaggtatagc cggttttgct gccgaccaga    75600
tattcataag cataaggttt attggcaaaa agctgatttt tactgtgtac attcatttcc    75660
tggctaacag tggaggacac gggaatggtg taatttgccg tacttgccat tttgcacagc    75720
aggtcattgg aaaagaaggc ctgggcaatt aaagccatat cgtaagccga ggtataatgg    75780
ttctcatcaa aaattccgtt ggaagtaaca aagtgggaat cccggcaccc gagatctttg    75840
gcttttttat tcattaagtc cacgaaggaa tcaatgcttc cgctgatatg ttctccgata    75900
gcgtttcctg cttcattggc ggatccgacc agaagcccgt agagagactg ctccatggta    75960
atctgttcac ctgccttgat ccccatattg gaatcggtca gccagtcaat actgtttacc    76020
gcttcattgg aataggtgac gatatcatcc aggggacagc tttccatggc gatcagggct    76080
gtaagaattt tggttatgct ggcaggataa agcttgtcgt ggatattttt ttcataaagg    76140
atagccccgg tattggcttc catcaaaata gcggactggg cgccgatgag agggcctgcc    76200
ggccagtttt cccgtgcgtt ggattccaca ggcatctcct tgcgcgcctc tgcttcttcc    76260
tggaagctgt ttccggaagc gggtgcggca gctgcagaca aaggtatgga aaaaacaagt    76320
gccgggcata aaagaagaa ggtaagaaaa agtataaatt tatgttttgt tctgtggtgc    76380
attgccattt atttcacctt atatttctta tttaaactca aaatcgtatg attttgagat    76440
actcatatgt gtatgatacg ttttaccgt tatcatcata cactatctga tgataaaatt    76500
taagggattt aaggaaaaat tcataaaaag atcgtgttca cggaagcagt ttttgtttct    76560
gacatccatt tctgatatac cagaatcatt ccttcagaaa aaatttgttc cggtatcgaa    76620
aatgggatgg agctgctata ttgacatttt tgttcttatt gattataata aattgcagtt    76680
ttggcaataa ttaataaaaa tgccaaaact gcaaagcgat attagaggat gtgatattat    76740
ggaaatgaac caactgcaaa gtctgctacc gaagccagga tggatttta caaaaaatga    76800 atttgctgat ttgatacatg aagtcaatcc tcagtacagt gaacgttctg tctattggct    76860
gctgcggaag ctccagcagg aaaacaaaat acagaaacta gcaaaaaca ttttgaagc    76920 tgtctgtcag gagaaacaga agatgcctta taccctatgaa cactccagcg agtggaatca    76980
aattgtttct ggtattgaaa aagagtatcc tcttgtagat ttccaggcgt gggaactgat    77040
ccagctcaat gagtttgtaa accaccagat cgcacataac acagtattta tcgaagtgga    77100
agctatgttg gaggaagctg tattccatac tttaaaaagt aagtttccct gtgtgttgct    77160
tttcccatcg gaagagacat tttaccggta tagatctcca gaacagacca ttgttatttt    77220
aaaattgatt tcagaggcgc caaagcctgt cggacagccc tatagtgccc ccctggagaa    77280
actgctggtg gatttgttca gcaggaaact gaccggacac ctgattgaac gtgcggaata    77340
tccctctgtt tatgaggaga catttttccaa atacctgata gaccaaaaga aaatgttccg    77400
ttatgcaaga cgtagaggag tggaagagga aatgaaggag cttatccgta cgagcaccaa    77460
tatcaaattg attacaaaag aaaggtaaat atgctgcaaa aagagaattt ccgactggag    77520 aatatagga ggaaaacgat tgagatttat atcatcatac gctgtctgat ggtaatattt    77580
aaggaaaaat tcataaaaag atcgtgttca cggaaacatt gatgcttacg tgaacacgat    77640
cttatgtccg aagtacagaa aataaaaaat tactcaaatc ggaaataaca cagcttgata    77700
```

```
tctccatgca gccgtatctg cagtacggct tctccttcag aacattccgg gatatcctga    77760
agagaaattt tcacatccgt ataaacagga attctatatt ttgtccgttc tatggcttcc    77820
ttccgggcat tttcatccgg taaaaaggga ggtacagcct cgtaggttct tgtatcacct    77880
tcccattcac tcaccttttt cccatctatc catagctcca gacttccgcc ttttcactc     77940 tttaaatgga agaaggcatt ttttaatccg aattcgggcc tgcagctgcg gtatatcagg    78000
gtgcccgttt tctccgtgtt tacgggaaga gcggcggtga agccgaaatg cccttctgtc    78060
agagtgatat tttcgtaatc atcataatga tctgccggta tccgtttttt caaatcacgc    78120
agtccgggtt ttctgccggg aatctccaca aaagcctcca actgaggctg cgcgctggaa    78180
gggccggcaa atatccggta gcatccttcc tctaccatca tagttctgct gattacatca    78240
taaaaacgga attcttcaat cgatatcata aattctgctt tccgggtctc tccgggaagg    78300 ataccctctca ggcggcggaa cccaagaagc tgttttatcg gtttttttac ccggggaggct   78360 ggagcggttc cataaatctg agccacttca tcgctgaccc ggtcaccagt attggttaca    78420
cagaaggata cccgtagctt tcggttatcc tcaggcgctg cggaaaaatc cgtatatgta    78480
aaggaggaat aggtgaggcc atatccgaaa ggatacagta tatcaccatc aaaatagcgg    78540
taagttcgtt ttcccttatt gatatcgtaa tcatcaatat ccggcagctg ctcatccgaa    78600
cggtaccagg tcatattgag acgtcctgca ggcgcatttt tcccgaaaag tgtttctgcc    78660
atagctgtcc ccatatcctg gcttccggtt gcactccaca aaacagcggg cagcttttcc    78720
tgggccatat tgatagaata aggataatta gagaacagta cgagaataac gttaggattg    78780
atacggtaaa tttcttccag cagatgctcc tgtgccggag gaagggcaat ggtagtacga    78840
tccacttctt cctttgcatt gatcatggaa ttgcagccaa gggcaagaat gacttttcc     78900 tttccctgaa ccaggctgca ggccttttcc agtccgtttt ccacaatttc catccggaat    78960
tgtgcggcgg atccttctct catggaaaca agaaaatcct tttcatcaat ttccacggga    79020
gaatgaaaac ggttggtaag ctgtatcatg ccgttcccct gttccagtac atggaaaatc    79080
tccatgacaa accagtcaaa aggagcgtcc ttttccgcag caatccatcc cgtttccgag    79140
gattccttat cggattggcc cattcttgta ttcatatatt tccctgtacg ttcacagcgg    79200
aaggtatagc tgccttctcc ccagtcgtcc attacaaaga catccggttc ttccgacagg    79260
tacaatcttc cgtctgctgc cgtcgccaca cccttctggc cgcagcggaa tatcacccgg    79320
tcaagaccgt cggcaaaagg tacttgtgtt ccctgtatct ccttcattcc ctggcgcagt    79380
gtggttacat aaggaggagt tcccccatac cagtcctgat accagctgtc cgccagggga    79440
ccgaccagag ccatggtttc tgccgggaca gcaggatcca aaggaagcat tttattttca    79500
ttcttgagaa gaacaatggc ttcccgggac agctgcaggc agatttgctt attgagggga    79560
gaattcagat cttcttccgt caccctgtca taagggttgc agggctccct gtcataaata    79620
ccaagacgca gctttgtgcg gaatatattc cgcagggctt cgtcgatttc ctcctctgtt    79680
atgaggccaa gctcccaggc ctcccgggct gcctgagcta ctgcttccgg tcggtcggac    79740
ataccgtcta cgcctgcttt aaccgcattg gcaagagttt cggcatgaag gccgtaataa    79800
tgatgaagat tggccacaag ctccatagcg cctccgtcac agcaacatg  cccccttcagg   79860 ccgtattcct ttttcaggat ttccctcact tccgggttga gcattccggg aatgccgtta    79920
attttattat aagccgtcat tacgccttcc gcccggccgt tcattatggc tctccggaag    79980
ggttccagat acagctcctg ccggtttctg ggatctacgc aggaagactt ccatccccgg    80040
```

```
cccgcttcgg tgttattcgc ataaaaatgc ttgagggtag cagcgacacg aagatacttc   80100
ggatcatccc cctgcatgcc ctggatataa gcggaagaca tgacaccggt aagaaccgga   80160
tcttccccat agccttcctc cgttcttccc caccggggat cccgttccaa atcaacggta   80220
ggcgcccacc tgctcagccc gcgatcggga tgacggtgat aaataacccg tgcctccgtt   80280
ccggtcacct caccggcttt tttgataaga tccggatccc atgtggcgct catgccgata   80340
ggctggggga agaagtggt aggttccgca gcgcccaaat cattttgatc atttcttgcc    80400
tccacaccat gagcggcttc accgcctaca gaaaatcccg gtatccctaa tcgttccaga   80460
tcaggaaccc tggtagccat acaggacagc ttttcatcca ttgtcatttc tgataaaagc   80520
cagtccagcc gctcttcaaa aggaagggaa ggatcccaga agggcgtgtc cgttttcaca   80580
ttattcttca tattactccc ttctgcgcac attatgtacg cacgcggcat atgccgcata   80640
taaatcagag aggctgaaag aaaagctttt cagcctctta cctctcttgg aaaaaggcc    80700
tgacatcaca aggatatcag gcactctgtt ctttttcaa tgtacttgcg ttcatggact    80760
aatctataat tccgttatcg gcttctctga aaatatatta acgttgtttt aaaataaagt   80820
caacactta acgaatccat gtttacattg aaatcaaaat aagctataat gctttcatgg    80880
aggtgaagag gtggatatcc atgaaagact gcagtattta agaaaacaac taaagctgac   80940
aacacgggcc tttggcgcgt cgatcaatat gtcggcggt gcgataacca acatggaaaa    81000
gggacagaga aacattaccg atcggacggt caaagatata tgcagagaat ataatgttaa   81060
cccggactgg ctcatgtatg gaaagaacc catgtatatg gacgttctgg aagatctgga    81120
tattaatgat gatgtcaggc acctggcaag gcaatttacc caattgagtg aaaaggacag   81180
ggaacttgtg aaaaatatgg tggattccct gtgtgaaaag atagagcgaa agactgcgga   81240
tagagaggaa aacaaatgag acttaaaaat gtacccggct ccagggaggt tatcggagag   81300
agccgatttg tcatacatga accggaatta cagaagggaa aatggaaaga ggtcttcggg   81360
aatgagaacc ccattcatat agagattgga atgggcaagg gaagatttat tatgggaatg   81420
gccggacagc atccggaagt aaattttatc ggaattgaaa agtattccag cgtactgctg   81480
cgcgccatac agaaaatgga ggaagaagag cttcccaacg tacgttttat ccgtatggat   81540
gcagaggata tctgcaatgt atttgataaa gaggaggtca gcaggatata tctgaatttc   81600
tcggatccct ggcccaagga caggcatgcg aaaagacgcc tgccctccag acagttcctt   81660
gccagatacg acgagatctt aaaaaaggac ggaacactgg aattcaaaac agataacaga   81720
gtcctgtttg attttgcact ggaggagctg gagcctgcgg gctggaaagc cgatacagtc   81780
acctttgatc ttcatgcaga tgaggttctt gtccggggaa atatcatgac ggagtatgaa   81840
gagcggtttt ccgcggcggg caaccctatc tgtaagtatg tgatacgcg gtgacagaag    81900
cattcattcc tgcaatattc ctgtaatacg gtattagaaa gagaataaga gctgaattat   81960
atttaaagga tttctttgta aaatcaggaa aaatttaaat atatttcagc ttttttctata  82020
cattactgca aaaatgattg agaaaatatt gtgtattata tacattgaaa ccgttcccat   82080
tttatgttac tatgtgaaaa aggtgataac atgacaagta taattgatgt ggctaagaaa   82140
gccggagttt ccaagacaac cgtatcaaga gtttttattag gcagcgacaa ggttaagcct  82200
gcgacaaaag aaaagagttct gcaggttatt gaagaaatga attacagccc taatacagcg   82260
gccaggaccc ttgcatcgag aagaagtatg aatatcggtg tgatcagctg ttataccttc   82320
aatgatcctt tctattccat agtcagtgaa gagatttacc atatttgtga aaaagaggt    82380
tacagcactc tgttcgtggt aaaccgtgcc gatgaaagcg ggcacaagga tcctattgat   82440
```

```
atccttaatg gaaaagtgga tggattcatt tatctggggg aaggttcggt atccagaaaa   82500
cagctggaaa agcttgttaa aatgggaatg ccggcagcag cgtttaagac agggattcag   82560
gtggacggag taattgaggc agatatcgat aatgtaaagg cagcatatga cggcaccaat   82620
tatctcatag gccttggaca tagaagaata gcagttttaa caggaaaatg gaacaattat   82680
gaaacactgg gccgtttgga aggataccgc agggctttgg aggaaaatca tattccctat   82740
gaggaatctt tgattttcga tggtgaattt tcctatgaca taggacttga acgtgccaga   82800
gatatcatag atacaaaggc aacggcagta ttttgtttta acgatgttat ggcacatggc   82860
ttcgcaagag gagcaaagga tgcaaactac agggtgcctg aggatatatc cgttttggga   82920
tatgatgata ttatcttcat gaactatggc ccttatatca gctttccac tgtaaagcag   82980 ccggtaaggg aaatggggag atatcttgcg gaaacaatga ttgcagaggt ggaagggaaa   83040
agtgtggagt tacgtaaaat tttccctgct gtaatttcag agaagagac tacatgttcg   83100 gtgtagtttt ttcgtggcaa aaaatgggag cgctaccatt ttgcagataa atcattattc   83160
aagagaagga gaggcaagat gaaaaagaaa ctatgtgttt gtttagcagc attaatggta   83220
ttgggaagca tggccggctg tggaagcagc ccgtccaagg aaaaagaaac agcagctttt   83280
gaagcaaagg atccgtcgga gtacagcggc acaattacaa tatggtcctg gacagacgat   83340
cccaaatacc agatcgaagc atttaataag gtttacccta atgtaaaggt ggaatttacc   83400
cagattggtg aagattatga tgtcaagatg cagactattg tggataatga ggcagacggc   83460
cccgacattt tctgtgcgga cgccaaggta gtgaagaatt atctggaatc ggatgcctgg   83520
gaaaatttat cggccgaacc ctataatgcc acagcacttg cggaagacgt aataggctat   83580
accaaggaaa tcggttccga tgcccagggg aatctgagag ctttatgctg gcaggctacg   83640
ccgggcggac tctggtataa gcgcagcatg gcaaaagaat acctgggaac ggatgatccg   83700
gaagaggttt ccaaaatgct gtcaagcaca gagggaatgc tggatgtcgc caagacgatt   83760
catgataaaa gcgatggaaa gacagcgttc gtgacaaact tccaggattt atggatgatg   83820
tcctgctatg gacagcgtaa ggagccctgg gtaaaagacg gtaaattcat catggacgat   83880
tatgtgccgg aatttcttga tttgggaaaa acattccggg aaaacggtta tgatgccaaa   83940
ctggatgcat ggagtaccgc atggtatgcg gcagcagctg acgattctct gttcggttat   84000
gtcctgccta cctggggaat gcagtatgta atccagggaa gtgcgccgga ttccaaagga   84060
gactgggcga ttgcaagtat gcctgcatct tactttaacg gcggaaccta tgggaatt   84120 tacaaaaaga gcacccagaa ggaactggca tgggaatatc tgaaatttat cactctggat   84180
cctgattaca gcagacagta tgcgatagat aaatcggatt tcccggcgtt ggtatctgtg   84240
gaggacgagc tggtggaatc ctactcggat acatggtgcg gaggccagaa cacatttgca   84300
tttttcaaag aggaagccgg taaaataaat gcttcccttg taacaaagta tgatgatact   84360
atcaataatc tgctcctgca gaatgcagag ttatatgccc agggagaagt aacgaaggaa   84420
gaggccctgg aacaatttaa aaaagatgtg gcaaatgcat atcagtccat tacggtagag   84480
tagtaaacga aaggaaaagc agcccataaa tatgaactgc ttttcctttt tcaaacaagg   84540 taaggggta gtaaaaagta tggctaagaa aagggcccgg tatggctttc tctttgtttt   84600
accttatatc attgttttc ttatatttca gttatatccg attatttata cattctttt   84660 aagtatggaa gacggagcca cggcgggatt tattggcctg aagaattatc agcgtcttgc   84720
tgttgacgaa gtgttttgga aaagtgtggg aaacacctgg attatctggc ttggctgtat   84780
```

```
cataccgcag ataatatccg cgctggtgct ggccgtcctt ttatgccagt acaaactgaa   84840
aggcgccaat gtgtttcagg caatgtttta tctgcccaat ttagttacgg ctgcctcaat   84900
cggtattctg ttcagcgtgc tgcttgactg gcagacaggt accgtcaata aaatcttatt   84960
atccatgaat ctgatcaatg aacctgtaaa atggatggga aatccggtat ttgccagagg   85020
cctgacctct ctcatccaat ggtggatgtg gttcgggcac agcacgatca tccttacggc   85080
aggaatcaaa gcaatttcta cggatgtgat tgaagccgcc gtggtagacg gatccaacag   85140
cagacaaaga ttttttttaca ttacaatgcc tctgataaga cccactttat tatatgttgc   85200
agtcacttct ctgattggcg gaatgcagat ttttgatatc ccgatggccc tgacgggagg   85260
aaccggagaa ccccagaagt cgcttatgac aatggtttta tatttatata acaccgcttt   85320
taagaataaa aattatgcat acggggcaac ggtttcttat ggattattca taatcatcct   85380
gatagtatct gttctgtttt tcagagttct caaccctaag caggaaggag aggagtcatg   85440
aaaaagataa agctctccag aatcattatc tatattttgc tgatattgct tacagtcatt   85500
tgttttctgc ctttttatat catgatcatt aatgccacac attccagcaa tgagctgatg   85560
acaggcttgt atttacttcc ggagcctcc atctttcaga attatttgaa tatgagagaa   85620
atgatacaga tcggcagagg atttctgaac agcgtgatta tttcttttc ctccacgctg   85680 ctgagcgcct atttcggcgc gctgaccgct ttcggcctgt cgaaatacag gttcaaaggg   85740
cagggaattg tatttggtat cgtcatggtt tccatgatga ttccttcgca gctgggaatc   85800
atcgggttct tccggttatg taagttcatg ggaatcctgg atacctttt cccgcttatc   85860 ctgcccggga ttgccaatgc gagtacggtg ttttcatta tgcagtatat gaaatcctct   85920
ttaccggatt ctctgctgga aagcgccagg atagagggct gcaacgagtt tattatcttt   85980
aacagaatcg ctctgccgat ggtaaaaccg gctattgcaa cgatgtctat tttcaacttt   86040
gtgggaagct ggaataactt catgacgcct atgattgtgt tgtttaacca gaaaaatttt   86100
acgcttcccc tgcttattat gaatcttagg ggaaccttta acaggggatta cggagctacc   86160 tatctggcta tcgctatgtc aatagtcccc ataatgattg tatacgcatt tgtatcacgt   86220
actattacag aaggattgac ggcaggagcc gtaaaaggtt aatgaagaaa ggaattatat   86280
tatgaacccg atttaccgt cccagtatta tataccggat gttgaggctc gaaaagatga   86340
ggatggcaat atttatttat atggctcaaa ggactgctgc ggcaatgatg aatactgcag   86400
ctacgaatat caggtatttt ccagcagtga catgaagaat ttccgggcac atcctgtgtc   86460
ttttatttcc tatgatgagg cctcccacat ggcagcccat ggaaaaatgc ctttatatgc   86520
gccggattgt ctgaaaatca aggacagata ttgtctgttt tattgcttgt cggatggatc   86580
ggaaggcgtg gcttttcgg acagtcccgc aggccccttc acggatgcgg ttcctatagc   86640
cggagcggac ggaacacaga ttgatcccgc tgtatttaag gatgatgacg gccaggtgta   86700
ctatttttgg ggccagggaa gcctgagagg gggaaaattg tcggaggatt tatcggaagt   86760
ggttcccgag acaatggtta aggggatatt aacggaagac agagatggtt tcatgagggg   86820
aatatcaatc agaaaaagaa acgggatcta ttatctcgtc tatgcggaca gctcccgtgg   86880
gaagcccaca tgcctgggat atgcaatgag tgataagccg ctcggcccct atacgaaaaa   86940
agggattatc attgataata caggatgtga tccggcaagc tggaataacc atggatcgat   87000
cgaagaatat cagggaaaat ggtatgtctt ttatcatcgt tcctctcata acagtgaatt   87060
tagccgcaga gtctgtgtgg aagagatatt ttttgaagag gacggaacga taaaagaggt   87120
tctgatgacg agccagggaa cggaaccccc gatacccctgc aaaagaaaac tgcccgcatc   87180
```

```
ggctttgtgc cggctgtcgg ggaaatgcta ctttgacgcc tacagcagca gagatatgca   87240
ttatgaatat ttaactaata tccacaacgg cgactggggc gttatccggt atatggattt   87300
caactgtgaa atccggggta tttccctctc ctgttccagc agcacctatg gaggtactgc   87360
ggagatctat attgacagca tggaatcaga atgcctcgcc aaagtcgaga taagaggac    87420 aagcggaaaa tttgattttc agcaatttga cagtcctgtg cgtgtcccctt cgggagtaca  87480 tgcagtctac ataaaattca ccgggattgc cggaaagctg atggatctga aggatatcat   87540
gttttattaa tttaacatgt catataaaaa cttgaaagta catggataat gagtggatta   87600
tccatgtatt tttttgtcct ctcttttttac aattaacgta ccgaataaaa aaagaggagg  87660
aagaggaatg aagaaaaagt tattgagtat tttgttgagt gcggcgatgg tttcaggtat   87720
cctggccgga tgctccggaa gttctgccgg ctccgccccct gtggaatccg cagagaacca  87780
ggcggaaaca ccggcagcag gaacagagga agctgcggaa caaccgatg cgggggggctc   87840 ggaagctgcg ggaggagaat acgaatataa ggaagcaacc ataagcctac tgatcgataa   87900
ggattccacc cttgacgggc ttgaggcggt atgcgccctg gctaaagaaa aactgggcat   87960
aacggttgac gtgaaatcc gtgcaggcgg agcggacggg gataacattg taaaaacaag    88020
gctggcatcc ggggatatgg ccgatttgtg cgcttataac tcaggctgta agttcacgac   88080
actgaatcct tcggaatatt tcctggattt atcggatcag gcgtacctgt caaggctgga   88140
tgaatccttc ctcagcgctg ttacggcaga cggcaaggta tatgggtgc ctgcaggctt    88200 tgccagcggt gctggcgtcg tactttataa cagggacacc tatgagaaat acggacttga   88260
ggtgccgcat acatgggctg atttccttaa aaactgtgat gtgctgaaag aaaacgggga   88320
agtagccgta atcggaagct tgcagacag ctggaccaca caggtggttt atctgggcga    88380
tcattataat gtacaggcgg aaaatcctga ttttgccaaa gaattcgaag caggaacagc   88440
aaaatatgcg tcagaaccgg caggtcttaa gagctggcag aaatgtgtgg atctggttcc   88500
ttattacaat gaagactata ccgcaaccac ttaccagacg gcctgtgata tgctggtaaa   88560
cggggaagga acccattgga ttattaccag tgacggtgtg ctggcttata ttaacagcca   88620
gtacggagag gatgtcaaca agattggggc gttcggcgtt cccggggacg acgcagacaa   88680
tcacggaatt accacatggc cggcaggcgg gctttatgta aataaaaaca gtgaaaatat   88740
tgatgatatc cttcgtttcc tgaatttttg gatgagcgat gaagccataa atgcttatct   88800
ggcggtgcag cctccggcag gccccattat cattaaggga atggctcttc cggatgatgc   88860
cttccaggcg gtaaaggatg agcaggcata tattgatgcg ggcaaggcct gcacggccct   88920
ggagtatcag actgccgtaa agggcgcaag ctgtgagcag attcccagg aagcgggaac    88980 cggtcagatt tctgcggaag aagcggcgaa ggcctatgat gatgactgcc tgaagcaggc   89040
ggtgcagtta gggcttgact ggtaaacagt gagtaccggc agaagcaaag atatgtatgc   89100
ggggcaggcc gcctgtaaca caggcggcc tcctgatccg acagataag gaaaggattg     89160 cagatatgaa gaaaagaaa atgtattcca catggtttct tcttccggcc atgattgttt    89220
ttctcatcat ttttattatc cccaccgtca cttcgttttt tttcagtatg acggtatggg   89280
attttaaaac ctatcggttt ataggctttg ataattttaa aatgtttctc acggaacgtt   89340
ctttgaatat tggtattaaa aacactctga tatatgcctt tctaacctgc ggcattaagg   89400
ttctcctggc cttttttatc gctgttttttc ttaccggatc catacgtacc aagaatatac   89460
agcgttccat tatttctttc cccaatctgg tgagtaccat ggcaatcggc atcacttta    89520
```

-continued

| | |
|---|---|
| ccgcgatgat gcatcccagc aaaggcttaa tcaacaaagc cctggggctc tttggagcag | 89580 |
| cgaacataaa ctggctggga aatccggatt tggctctgta ttccattatc ggggtggatg | 89640 |
| tatggaaggg gctgagcatc gccaccgtca tctatgtggc agggatacag tctatagata | 89700 |
| agacgtatta tgaagcggct gaaatagacg gagccaacgc cagacagaag ctgttttcca | 89760 |
| ttacggcgcc ccttgcccgt ccggctatga attccgtcat tattctgtcc ttcatcgggg | 89820 |
| gcctgcgcag ctttgactta atttgggcca tgacaggagg cgggccggga tttgcaacgg | 89880 |
| acgtcatgtc atccatcgtt tataaacaat atgcggccgg attttacggt cttccacag | 89940 |
| ccggaaatgt gatcatgttt atcatgattg cgctgcttgc gtttcctttg cagaagtttc | 90000 |
| tgctgagcag ggaggtggat tcctgatgaa gaagaaaaaa ctgttgacga tctgcgggga | 90060 |
| cgtcatagga atggcggcct gccttgttat ttttgtcaca ccgttcctct atatgctggt | 90120 |
| caattcctta aaggggacca agaagcgaaa tctgatgtcg ctttcgcttc cgaaagaaat | 90180 |
| tcatccggaa aattacctgg aggtaatcaa ggcaaacaat tatatgcttg tcactgcatt | 90240 |
| taaaaacagc ctcatcctgg cactgtgctc cgttatcctg ctgattctca ccggttccat | 90300 |
| ggccggttat gtccttcaga gaaggaacga caggacaacc aggctggcta atgtgctgat | 90360 |
| tatgtcgggc cttatggtcc ctccggctat ccttcccaca atctgggtgc ttcagggcct | 90420 |
| gcatctttat aagacgcttc tgggaatgac aatcgtggaa gtggcgctga atattccttt | 90480 |
| caccatcatg ctgtaccggg gatttatggc aaccatcccc acagaactgg aagaagcggg | 90540 |
| ctttattgat ggctgcagca gaatacagct gttttccaga gtagtatttc ccctgttaaa | 90600 |
| acctgttacc tccacggtga ttatattgaa tgcggtgagt attttaatg attttaccaa | 90660 |
| cccgctctat ttcctgccgg gcaatgccaa tgctacggta cagttaaccc tttataattt | 90720 |
| caagggcaag tatgccagct cttacaacct gctgttcgcg gatgtgctgg tgattacgat | 90780 |
| tcctatgctg gttttgttta ttttcttcaa caaaaggata atagacggta tggtcgccgg | 90840 |
| agcggttaag gggtagtgtc agcctttgga aatcctaact tttaaatgct tgttccggga | 90900 |
| tctgcatttc tatataatca taatatgttt caaaaaacag ttatgaaaat atggaaatgc | 90960 |
| agatttttca taacagcctc gggaggaata tcaattgcgt tttcgatata agctgatcgt | 91020 |
| ttcctatgca gcgcttgcct ttatccttc cctgatatta ggcattgtat ggcagtatta | 91080 |
| caataccagg gaataccgtt ccaacgccca tgaaaatttg aaattcctgt cggagcagat | 91140 |
| gacgatacaa ttcgacaaca gctataacgc catgagccag gtgacgaatt atatcctgtc | 91200 |
| cgatcaggat atgctggggg cgatcagagg gctttccgat acagaaaaca gacggtatac | 91260 |
| ggaaatgata tcggagaatg aagcaattct gaaaaatggg atcagcaacg actacttcat | 91320 |
| gtccaatttc tatcgtgtta tcttttcaa tacatacggt aacatcatat acagcacgat | 91380 |
| gaatacggat atgggcgtaa tcaacagcaa gaccgcgata gaggattgtt actggctgga | 91440 |
| ggaggcccgt aatcttcacg gaaagcctct cctggtaggc atccatgagg ataactggaa | 91500 |
| ggccgacagt aaggagaagg ttttttccat ggtccgcgcc gtacagggac agcctcttgg | 91560 |
| atatatcgag gtccagcaga aaatcgacag gctggaggaa ttgttttcct ttccggaaag | 91620 |
| agaaataagg acaaccatac ttctggagga cggcagcctc ttttactcaa ccgatgagga | 91680 |
| aaatctggat acttacagaa catatgcatc ctcctgtgag gataatgctt atgaagataa | 91740 |
| gccttcggat ttattattat ccttaagcac ctccaaaaca ggcgcaaaaa tcattttatc | 91800 |
| ggaggatatg aggatcatac gggaagggat tccccagacc gcggtattct cgcttcttct | 91860 |
| ggtagtcact atttttttctc tttccatggt atttgtaatc cttatttcca cctatctgac | 91920 |

```
aaagcccata agggacatgc gcaagcagat cgaacagacg cagctcagca atctggatca   91980
ggagctcatc atcaacacat cggataatga aatagaagcc ttgaaccgct cctatagggg   92040
tctgctcaga cgtctcagtg aatcgctgga taaggaaaaa aagctgtccc ttttacagct   92100
tcaggctcag tttgataccc ttcaggccca ggtaaaccct catttccttt ataatgtgct   92160
gaatgtgata tccaacagag gaatggaaga cggggatgag aaaatatgtg acatctgcgg   92220
aaatctggca gccatgctcc gctattccac cagtacggtg gaacgctatg ccacggtgga   92280
gcaggagctg gactatctga gacaatacgt atatctgctg aaatcccggt ttgaagaaag   92340
gctggaggtg gaaatcacct gtgaggaatc catcagaaga aaaatcattc ccaaaatcgt   92400
tctccagcag ctggtggaaa acagtatgct ccatggctac aatcaaaaag atacggtcat   92460
gcgcataaag gtgaggggct ggatagagga aaacggatgg tatatcagtg tggaggataa   92520
cggagacggc atggaagaag ccgtccttca gaatctgctg gcgaagctgg aggagataag   92580
aaaaaagata cacatacaaa aaagcagcat tgagatggaa atagggcaga tggggctggc   92640
aaacctatac gccagaatgt atctgctgta tgtggacggc cttgtattcc gtctggaaaa   92700
taaacaggag agcggagtta tcataacaat cggagtgaag gaaggatcct gagaaggagg   92760
gtgaagaagg ggatgtattc ggtattagtg acagatgatg aacccactgc agtgaaacat   92820
atagaatcga taatagaaaa aaagtgcccg gattttacg tggccggaag agcccgcaac   92880
ggaaaagaag cgctggaaaa gacgctggat attcacccgg atatcttaat tacgacata    92940
cgcatgccgg ttatgacgg gatacagctg tcggaagctc tttacagcag cggggaggat   93000
acaaagatta tcatcgtgag cggttattct gaatttggtt atgcccagtc cgccataaag   93060
cttggcgtca gggattatat tctgaagcct gtggttcctt ccgaactgca ggctctgctt   93120
tttaagctta aagaggaact gaaggataaa tattatcagg gacgtaaaga gatcataagg   93180
aagctttccc tgggacaggc cccgaaggag ggggaaatgg aaaaatactt tccctatgcc   93240
ctttattatg cggctcttgt ccgcagaaat ggactgccgc ccagatttttc cggacagagg   93300
aatgtggaaa tattttcaga ttccaatgaa acaatattta tacggaaag agatgaatgc   93360
gaagccctgt atatctgtcc caaggaactg gtggacggga atgatttat caggctcatt   93420
gaacataagg tggaaaagga acagccgcag accgcatatt ttaccgcggt gtacggagat   93480
gagccggtac cctgcagccg gctgcaggag cttatgaaaa agctgtacag ggccctggac   93540
tgcggaattg tcttagggaa aaacaaggtg atccatctga agggagagga agaggacgga   93600
tgcggaaagg agccggaagt tcaggaggac ggactgtgcg gtttggaaaa gtactgtatg   93660
aaatccaatt tctccagagc aaaggaagag atgatccggc tgctgtacaa atgggataag   93720
gaagaacggc tcagatatg gtggaaggc atggttcaca agatctccta tatccttcag   93780
aaataccgca gcggcaaagg ctggaaccgg gaagaggaat ttttattgga ggatgccttt   93840
ctctattccg aaaacgtaca gcagctggcg gacaatctgg cggaaatcct atttaaaaca   93900
cccgaagagg aagcggactt tttgaaaatg gatacacagg aatactacaa taaaatcatg   93960
aagtacatct ccggacattt cgcccagcag ctgaccctgc agtccgcgag cagggcgctg   94020
ggaatatccc agacctattt aagcaagctg atacgcaaat acggcggcga gtcctttaac   94080
agctgcctta ccaggctgcg gatggaaaag gccatggaaa tcatgcggac cagcggatcc   94140
cggatctatg taaggatgt ggccgaacag gtagggtacc aggaccagtt ttatttcagc   94200
cgtatttcc gcgcccatac cggtatgtgc ccctctgatt tctggaatga ataatatgtg   94260
```

```
caattttttaa gcattttgt ccttgcaaag cacaaaaatg tgtaatatgc ttataccata    94320
aacttatgtc tccgttttat gctgacagag gcagctgatt gtatggaact cagaaaatgg    94380
tcaagaataa atagagagac agaaaataag aaggaggttt tatcatggaa tataaattta    94440
cgacaggaga ttttgaaaaa gaggtgctgc agtcggacaa gcctgtatta gttgattttt    94500
ttgcggactg gtgcggtccc tgtaagatga tggcgccggt tgtggagcag ctggctgaag    94560
aaatggatgg aaaagccaag gttggtaagc ttaatattga tgagaatatg gatattgccg    94620
agaaatacag tgtgatgaat atccccacct tcctgatttt caaggatggc caggaaaaag    94680
ccagaatagt gggcgcggta tccaaaaatg aattaataaa caaactggag cagacgttgg    94740
cttaacagcc agcgtccgtt ttctcatgat gtaattgtaa tccggatgac agatgaattt    94800
tttgattgat gaggggaagg cattttatgt acatactctt ttttttgctg tgggtaatct    94860
ttaacgggaa ggttacgctg gaaatagtac tgttcggaat tgtaatcgca ggggctgttt    94920
atgccttctg ctgtaagttc ctggattaca gtccccggaa ggactggctt atcatgcgta    94980
agttcggtta tattattgcc tatctgggcg tgcttatctg gaaatcgtc aaagccaatg    95040 cggcaactct taagctcgta gcatcccctc atatcagggt tcagcctgtt attgtccgct    95100
ttaaaacgga tttgaaaaca aaaactgcca gagtgcttct ggctaattcc atcacccttta   95160 cgccgggaac cattacggta gccctgcagg acaatgagta tacggtgcat tgtctggaca    95220
ggcgtttcag tgaagggctt tcggacgcg ttttgtgcg gcttctgcac aaaatagaag     95280
ggcaggtggc aggatgaacg gtttggaaaa tgcatatgaa gctgtgttta cagcagcgtt    95340 gattttctc ggctttatgc tccttctctg cctcataagg gctgtgaggg gcctcgtgt     95400 ggcggacagg ctggtggccg taaatatgat gggcaccatg gtcatggtta tgatagccat    95460
ccttgcgctt ttgctgcagg aaggctatct ggtggatatc tgtattatct acgccatgat    95520
aagctttctt gcagtcattg tgctgaccaa ggtatacatg ggagtttatc aggaaaccag    95580
gaaaaaagac aggaaaaagg atacgccgga ggaggaaaat gctcatgaat cttgaattgc    95640
tccgttttat aatcggaacg gtggttcttg cagcagggct gcttaccttt gcgatggagg    95700
tattcggatc ctaccgtttt gaatttgtac tgaaccggat gcatgctgcc gctctggggg    95760
acacgctggg gatcggaatt tccctgacag gccttatcat catttccggg ctgaatttta    95820
ccagcctgaa gatgctcctg gtaatcatgt ttctgtggtt cgcatcccct gtttcctccc    95880
atttgatttc ccgtctggag gttatgacgg acgaaaccct gaaggagcac tgtgaactgg    95940
actatgaaga ggatgacagg ctggatcggg aggagaaagg agaatgatat gcagacattt    96000
acttacctgc tgatgggctt tctggtagta tgtgctgttt cggtgagctt ctccaggaac    96060
ctgctgaatt ccattttgat ttttatgtcc tacagtctgg ttatgtcgat catatggatt    96120
cttctggaat ccccggatct ggcaattacg gaagcggctg tggggcagg agttaccagc     96180 gtgcttttct ttgtgacgct gaaaaagatc catgctatcc ggagggagga cgacgaagat    96240
gacagaaaag aagaatagcc gttttttccg ctggttttat ggggaagagg atccctgtt     96300 aggcaaggtg gaaatgaagc cgcagaagga atataaggaa gaggaagcca gcgtccagga    96360
aaggatgcgg gaataccggc agcttcagga aaaggtttat gatatggagc ataataagaa    96420
gctcctgctg tttaacaagg cttaccgggt gatgggcgtt atcttctgta tcagcctgat    96480
tgccattatg ctggtgacgg tttcttatct tcccaggacg ggaaacgcct ctaacccgga    96540
taataatgag gtgtcggagc ggtatattac caaagggctt caggaaacag gggcggtaaa    96600
cattgttacc ggcatgatcc tggattacag ggcctttgat acgtttgggg aatccaacgt    96660
```

```
tctgtttatc gccacggtca cggttcttat cttgctacgc attgacaaga cggataaaaa   96720
ggaaggggaa agcagggata atgctctgac ccgggctgaa gcggacgaga acgaccgtat   96780
ttatgagcca aaaatgatt tgatcctgca gaaggtggcg ggttttctgg tgccgctcat   96840
tattatattc ggcatttatg tcattctgaa cggccatctg tcccccggcg gcgggttttc   96900
gggcggcgcg attatcggcg cgggactcat cctgtatctg aatgccttcg ggtttgcgaa   96960
aacagaacgt tttttcacgg aaaagactta taaatggata tgcttttgtt ccctgacctg   97020
ctactgtctg gcgaaaagct attccttta tatgggcgcc aaccatctgc aagcgggat   97080 acccttaggg actcccggag ccatactgag cagcggcctg atactggtgc ttaatatttg   97140
cgtgggcctg gtggtaacct gtaccatgta cgctttttat gcgttgttca ggaagggggg   97200
attctaggat gggcggcaac cttttatcca attacgggga agcgattgcc atgatcctgt   97260
tcggtatcgg attctccaac ctgcttttgc agaagaacct gataaagaaa ataatcgggc   97320
tgaatatcat ggataccgcg gtttaccgtgt tccttgcaga aaaaggctat atcatgggac   97380
gtaaggctcc tatcgtggtg gatggggtcc agacggtggt aagctatatc aatccggttc   97440
ccagcgggct ggtactcacc ggcatcgtgg tgtcggtttc ggtaacggcg ctgatgctgt   97500
ctctgaccat ccgtctgtac cgcagatacc atacgctgga tctggacgag atttccgcca   97560
gactgaaaaa ggagggactg taaatggatt ttgtacagaa ctttcccttc ttctccatta   97620
ttttatccat gttttccggc acggtgagct cggttcttcc ggcaaaggcc gccaagtggc   97680
tgaatacggt tgttatcgga gccgtgggct gtatgtccgc cgtgctgctg gtgtacctca   97740
tgggtaaagg aaccagctat acctatatga tgggccattt tccggcgccc tggggaaatg   97800
aaatccgtgc gggagttctg gaagcgggta tggccctctt tttctgtatt atcatgctcc   97860
tttccctgat gggcgggcgc aagaagcttc tgggcgaggt ggaatacagc aagcacaatc   97920
tttattatat cctcacggat ctgctgctca gttcccttt ggcccttgta tataccaacg   97980
acctgttcac cgcctatgta tttgtggaaa tcaataccat atccgcctgc ggcctgatca   98040
tgatcaggca gaacggaagg acgattgaag cggcggtcag atatatgatc atgagccttc   98100
tgggcagcgg acttctgctg gtgggaatca gcatgctcta cgatatgaca ggccatctgc   98160
tcatgagcaa tatcaaggaa accgtgggag agatagtcgc ccaggggaa ttccggatgc   98220 cgctggtggt gaccatcggc ttaatctgcg tgggccttgc cataaaaagc gccctgtttc   98280
cctttcactc ctggctgcct gatgcctatg ctattccac cgtatcttcg gcggccatgc   98340
tttccagcct ggtttccaag ggttatattt ttctgctgat caagattatt tacagggtaa   98400
tcggctttga ttttattgcg gagaacaaga taatcaacgt attcttcgta ttcgggctca   98460
tggggatgat attcggctcc ctgagtgcta taaaggaaaa tgatatccga aggatgatct   98520
ccttttccag tgtggcccag attggatata tttacatggg cttcggactg ggtacggaga   98580
tcggcatggt tgccagtatt tttcatatcc tttcccatgc cgccaccaaa tccctcctgt   98640
ttatctccgc tatcggcctt acggatgttt ccaaaggcag caggaaattc caggatctta   98700
cgggggcggc ctacaggcat aaaatcgcgg gaatcggttt taccgtgggt tctttgtcca   98760
tggtaggaat gcctatgtta tccggcttcg tgagcaagct gctctttgcc caggcttcca   98820
tcggacatgc ttacaaaatg cttcccgccc ttatcgtact gggaatcagc acggtattga   98880 atgctatta tttcatgaaa acggtgatcc ggatttttgt tccggaaagg cgtacggact   98940
gtgaggtaat caccatcggc gcagaaaaaa cctatacggt taccattgtc cttttatct   99000
```

-continued

```
gccttaatat agccctgggc atgctgtccc agcccattgt gaaatggatc cagtcgggc    99060
tggctatgtt cggctgattt tatcaaattc ttaccaggcg cggaaacggc gcgcagacag   99120
gagctttata tgaaggaatc aggcatgctt ctctttccca tattttttcc gataatcatg   99180
ggaattctgt tgctgctttt gaaaaattca ataaaaaggt ctgccatgat aacccttacc   99240
gccataggcc ttttcgggac ggcgatagca gtcatcgggg taatcggcag cggagagact   99300
gcctttacgc tgtttcagct gaccatgcgg cttcctgtct attttaaggt ggatgcggtg   99360
gggcggctgt ttgtgtcggt ggtcacaatt gtctgggttc tcgccggtat ctatgcattc   99420
cggtatatgc agcacgagga ttgcaataaa agatatttcg gattttatct gattgtatac   99480
ggcgttcttg tagggctgga ttttttcggg aacctgatta ccttttacct cttttacgag   99540
tgcatgactc tgctgtccct tcctcttgta ttccataccc gcacaaggga ggcggttatg   99600
gcagggctga aatatctgtt ctattccctg gccggcgcat atctggcttt gtttggcctg   99660
tattttatca accgctatgg gaatacgctg acctttacag ccggcggagt gctggatttt   99720
tcacttgtgg aagggcatga aggattattg ttggtggttg ccttcctgat gcttatgggg   99780
ttcggtgtaa aagccggact gtttcctatg cagggctggc tgcctgcggc gcacccggta   99840
gcccctgccc ccgcatcggc tgtgctgtcc gggattattg tcaaatcagg tgtgctgggg   99900
ataatccgtg tggtttactt tattttcgga gcggagttcc tgaagggaag ctgggtacag   99960
aaggtatttc tgggactggc cctgggaacg gtattcctgg gttccatgct cgcttatctg  100020
gaaaaaggac tgaaaaaaag gctggcctat tcaacggtaa gccaggtttc ctatattctc  100080
ttcgggcttc ttctgctgaa tctggccggt atgacagggg cattcctgca tgtgattttc  100140
catgcggtca ttaaatccgg cctgttccta tgcgccggag cgatcatatt ccggacaggt  100200
aaaacgcggg tggacgagct gaggggaatc gggaaggaaa tgccggtaac catcggctgt  100260
atgacgcttc tgtcccttgc tttaataggt atccctcctg caagcggctt tgtcagcaaa  100320
tggtatctgg ctgtcggttc gctgtcctcg gaaaccggct tttacagctg gctggggccg  100380
gtggtactgc tgctgtccgc gctgctcacg gcgggctatc tgcttcccat aaccatgaag  100440
gggtttttcc ccggggaaga agaatcacga aaaggctttg tccggaagga agcggattcc  100500
gtaatgctgg ttcccatcct tctgctggct gtcctggctg ttgtgctggg tatgttcccg  100560
ggaggcctga tttcccttat cagcaacatt gcacagcagc tgttccagat gtaggcagac  100620
ggaagaaaac ggatggtaag tccgtaccag ggaaaaagaa aggtgttcat ctatgaaacc  100680
agaaatgatg cttgtggccg tactgctgcc tgtgctcggc ggcgctgtgg tgcccttgat  100740
acccttaaa aaaagaattt atatgacggt atacgttgaa tgcatagtgg tgacgaccag  100800
cctgattgtg gcggggctgc tggtaaacag gcctgtggat gcatttccta tcgtccggtt  100860
tgtgagcaat ctgtctctgt ccctgaaaat tgacgggtta tccatggttt ttgcgggtct  100920
ggtggccgcc ctgtggccgc tggcgacgct gtattccttt gaatatatga agcatgagaa  100980
aagagaacgg ttttttcttca tgtttttacac cattacctat ggtattacgc tgggtattgc  101040
tttttcagag gatatgctca ccatgtattt cttttatgag ctgctcacgc tggttaccgt  101100
acccttggtg ctgcatacgc tgaccagaga ggcgatcctt gccagccgga agtatctgta  101160
ttactccctg ggaggcgccg catttgcttt tctggggctg atcttcctgc tgacctatgg  101220
cacgaccatc aactttacct tcgggggagt cctggatgct tccgtgacag gaggagataa  101280
gagatccatg ctgctgctca tatactgcat cgccttctgc ggctttgggg taaaagcggc  101340
tgtctgtcct tttaattcct ggcttcccca ggcgggcgtg gcgcctaccc cggtcactgc  101400
```

-continued

```
gcttctgcat gcggtagccg tggtaaaggc gggagccttt gccatcatca gactgacctt   101460
ttacagcttt ggcccggact ttgtcagggg aacctgggcg cagaatgtgg tgatgggggat  101520 cgtgattttt accattgttt acggctgcag ccgcgcgctg aaggagacgc atttgaaaag   101580
gaggcttgcg tattccacca taagcaacct ttcctatatc cttttcggcg tatgcatcat   101640 gacgccctg ggtctggtgg gtgccttaag ccatatggta ttccatgctg ttatgaagat    101700
atgctccttc ttctgtgtgg gggcggtgat gtataaaacg ggaaagcagt atgtgcatga   101760
aatagacggt ttcggaaggc gtatgccggt ggtgttcgga atttttacca tagcgtccct   101820
cggactgatg ggagtgcccg gccttgccgg atttatcagc aagtggaatc tggcgacggc   101880
ggcggtaatg agcgataatg tcatggccta tgtggggatc ggggcccttc tgatatctgc   101940
gcttttaacg gccatctata tgctctctat cgttatccgg gccttttttcc ctgataagga  102000 gaagcagctg aacattccgg aggaagccag ggatccggga tggatgatgc tggtgccttt   102060
gtgtattttt gcgatagcta tccttatttt cggcctgcat tccgcaccga ttgtaaattt   102120
cttttcagga atagccggcg gaaatttgta aagagaggtt ggaggaacct gacatgactg   102180
gtgattatat gctgttatta atcctgtgtt ttccctttct gggggcattc gtggtagcgc   102240
tgctgggaag aggagaggga gcgggaaatg atacgtacag aaaagaaag acaactgcag    102300 atataggggc cggtctggta actgtttcag agatgctctg ctttgccgtt ttgttcggcc   102360
tgttctggaa gggcggcaat gagggaatcc ggtatgatta ccgttgggaa ggcttctgcg   102420
gaatggggct gcatctgtgt atggatgggt tccgtgccct gtatggcctg atcgcttctc   102480
ttatgtggat gatgacgacg ctgttttccg ccgaatatat gaaaagctac aggaacaggg   102540
gaagataccg ttttttttact ctgtttacgc tgggagccac catcggtgtg ttcctatcgg   102600
cagatctctt cactgttttt attttctttg aaatcatgtc ctttacttcc tatacatggg   102660
tggcgcatga agagacgaaa gaagccctgc gcgcggccga aacctatctg gctgtggcag   102720
tcatcggtgg cctggtaatg ctgatgggcc tgtttctttt gtacggggaa ctgggaacgc   102780
tggaatttac ccggctcgca caagcggcg agaagagccg tttaaatgga agcggaggat    102840
atgtacggat attcaccgcc tctgtctgcc tgctgtttgg cttcggggca aaggccggtg   102900
tcttccctct gcacatctgg ctgcccaagg cccatcccgt agcgccggcg ccggcatccg   102960
cccttctttc cggcatactt accaaagccg gtattttttgg tgttcttgtc atcagctgcg   103020
ctattctgcc ttttgatgcg gcgtggggca gactgctgct ggttttgggt gttctcacga   103080
tgtttaccgg tgcactcctt gccttattct ccgtgaatct taaaaggacg ctggcctgtt   103140
cctccgtgtc tcaaatcgga tttattctga tcgggatcgg catgcagggg cttatcggag   103200
aagagagcag cgtggccata cggggaagcc tgcttcacat ggtaaaccac tcctaatca    103260 agctggtgct tttttatggct gcaggcgtcg tatttatgaa ccttcatgaa ctgaacctga   103320
acaaaataaa aggattcggc agaaagaagc cgctgctgaa cttctgtttc ctgatggggg   103380
cgctgggtat cggcggaatg cctctgtgga acggatatac gagcaagacg ctgctgcatg   103440
aatccatcgt ggaatacagg catatgcttg cctcagcaaa tgcaggcggg gctggctgga   103500
tgcaggctgt ggaatggatt ttcctaatca gcggcggcat gacggtagcg tatatgctca   103560
agctttacat ctgtctcttt gtggaaaaaa ataatgacag gaagtgtcag gaacgattcg   103620
acggaatgaa gcattatatg aacgcctga gcggttttgc cctggcgggc agcgccgtgc    103680
tccttccgct gctggggctc ctcccccatc tgataacaga caggctggcg gatatgtccg   103740
```

```
ccgctttcct gaatgcggaa agcctgaaat ctgtggttgc ttatttctcc ctgatcaatt    103800 taaaggggc cggaatttcg attcttatag gtctgctgct ttatgtgctg gtggtacgca    103860
aatggatgga aacagtacag gacggaaaca ggatttaccg ggatcgctgg cccggctggc   103920
tggatttgga gaatctgctg taccggcctg tccttcttaa gatcctcccc ctgctattcg   103980
gaaccctgtg caggctggct gacagactga tggatacaat agtagtcctg ttaagaaaga   104040
ctatttacag ggacagcaga attccgcatg aaataaaaga aggcacaccc atgacccata   104100
tggtgggaat tgttctggac ggggttacgg agtatttcaa tcatcctgat gccacagagg   104160
aagagatagc tgaagatatc tatataaggc agcacgcaga aggcagatat gagcataagc   104220
ttgctatgat gcatgatgat ttacaggaaa atggaacgat tatcggaaga agcctgtcct   104280
ttggactttt ccttgcctgt ttgggacttc tgcttacttt gctgtatata ttgatcgatt   104340
aataccactt aagaaaaac gaagcccgct gacgatatac tgtcagatgg cttcgttttt    104400
tattatagtt ttgatgaaag gctatgcagc cggctggaga atcgcgtttt ttagttaggc   104460
ccggtctttt acaaggcaca ccaatacgga gcgtgggccc ataatataaa cattttcatc   104520
cagtatttcc tcacgggtaa tgactgctgc tgttcctctt gaggtatcta ctgcgggaat   104580
ccagtattta tcggggaca gctccggaag ctccactgtc agcggattcc agaaagtatt    104640
gatgccgata tacaggatat catccctgcc ggagggatag attccggcga acattacgcc   104700
caccattttg ctgttccagt caaaattatc atcccagggc ttcagagaat gaatactcat   104760
agacggaaaa ccaagactgc agggagcggt attatcccgt atcaccctgt gttcccggcg   104820
gaaggagatc atgtacctga aaaaatcatg aatttcttta ttttcctctg ctaaagtcca   104880
gtcaagccag atatttcat tgtcctggca ataggaatta ttattgccga actgcgtatt    104940
cccgaattcg tctccggcaa gaaacatggg agtgccgcgg ctgcacatga gaaccgcaca   105000
ggcatttttg atcatccgga acctcagctg ccggatttcc tcactgtcgg acgggccctc   105060
ctgtccgcag ttccagctcc ggttatcgac ggcgccatcc gtattgttcc agccgttcgc   105120
ttcattatgc ttgctgttat aggaataaag atcatataaa gtaaagccgt catggcaggt   105180
aagaaaatta acggatgcat tggagcctct ttttccgga ggataaagat ccggggatcc    105240
tataatacgc tgggcggcgg cagcagcata gccgtcatcc cctttcagga agctgcgcat   105300
atcatcccgg tatttccgt tccattccga ccaacggttc caggagggaa acgaaccgac    105360
ctgatacagg ccgcctgcat cccaggcctc agcgatcaaa tccacgcttc ccaggatagg   105420
atcataggca aggctttcca gaaggggagg gttgctcata ggagccgcat cctcattcct   105480
cccgagaata gaagccagat cgaagcggaa accgtccaca cggtaattga tgacccagta   105540
tcgcaggcaa tccagaatca gctgccggac gatagggtgg ttgcagttca gcgtattgcc   105600
gcagccgctg aaattatagt aatagccatc agggtgagc atgtaataaa tattattatc    105660
cagcccttta aaagaaaaga acggcccctg ttcattccct tctgcagtat ggttgaatac   105720
cacatccagg attacttcaa tcccattttc attcagggcc ctgataagcg ttttcagctc   105780
cagcccttcc tggttatatt caagctgtgc ggtataaccg gtattggggg caaagaaaca   105840
cacgggatta taccccagt aatccagaag catccgtccg tccacctccc ggcagccggc    105900
catttcatcg aattcaaaga taggcatcag ttccaccgcg ttgattccca actctttcag   105960
ataggggatt ttttccatta aaccggcaaa agtaccggga tgggaaaccc cggaagaggc   106020
atctttggta aaacctctta catgaagctc atagataata ttatccttta tggggatgag   106080
cggctgctta caattgcccc agtcaaagtt atttctcacc acacgggatt tgtacagaca   106140
```

```
gtccggctcg taaatccggc ggacgcccca ttcgctctgg ccggtaacag cctttgcata    106200
agggtcgaga atatatttgc ttttatcaaa tatcagccct ttttccggat cgtaagggcc    106260
atccaggcag taagcatatt cgaattcgtc tatcttcagg ccgaaaacaa tcatggaaaa    106320
gacattcccg atccgatagt gttccggaaa aggaatactg acgaacggcc ggaaggattt    106380
tctgtggaaa agcacaagct cacaggatgt ggcgttgtga gaagcaagag tgaaattaac    106440
cccgccgggc agggcagaag cgccgttaac ctcataaaat ccgggcctta cttcatatcc    106500
cctgatatta tccaggggct ttaaattggc agatatctcc tcgccggtaa tgctctccag    106560
cagtaaggtg ttttttcaata gtagtacctc cgtattggct gatttgtgat aaggtgtttc    106620
ttattcttct gattatatcc tgtggggaag tatggcacaa ccagtttttc tggtaacgga    106680
atacgcggct gtgctacttc ttcatttcat ctattttaat ctgttcggct gcatttaaga    106740
tccctaactg atattccgca atttctttca atatacgaaa tctttcattt ttattttttcc    106800 cttcgcgaat catttgtgca ttatgtgtct ctaaatttga gagtactgtc aattcattca    106860
ccgtagcaaa atctctgaca ttattcttc ccgccaattg aggattagcc tctctccagg    106920
cttttgccgt aaaaccaaag agcgcaacat ttaaaatgtc cgcttcctct gcataagcca    106980
gccattccag gttatctcta taattttttt taggaatcag gaagttttc acagcatctg    107040 tctgaatgat ataattattt tttgataaaa atcttttggc atcccattct atccgatcct    107100
tgttattttc ttcttcttc agtctctgaa attctttgat caggtataat ttgaatgtag    107160
ggctgattgc tgaagcaaac tcaaacgcaa tatccttgtg gcataggtg cctccatatt    107220 ttccccgttt tacatataat ccaacagctc cggtctgttc aatccattca gaaacacttg    107280
gggtaaatgt gagtaatcca gcctgctttt taaagtgttc agattcgaac actttaaaat    107340
tcggattata taactgttcc cacacagata gatattccaa agtggagcgg tttctcagcc    107400
agtttcttat gacatccgcc gccctggatc gatccgattt tgcatctgcg atatcagtaa    107460
tacagatata gtcatccatt tcctccgctg taacagcaat tgaaatattt tgaaccgtaa    107520
taatcctatt tttcgccata tggtaatcct cttatttatc tgtttatagt taattctcc    107580 gccttatact atggaattga ataaatattc tggtttctaa aacgttagct acaaggaatc    107640
gtttatgtat actattcata actggatgga tataaaacaa cagaaaaatg ggaatgaaga    107700
gtcgtaaata aagaaaataa attattagaa tattagattt aagatgatag aaataaataa    107760
aacaacacag aatatagtct gtctacatat acctgtaaaa atgagaaccc ggaaacatta    107820
agttcccggg ctttcccctaa gtcgaagcga cgtgattcga acacgcgacc tctgcgtccc    107880
gaacgcagcg ctctaccaaa ctgagccacg cttcgatctg gctttatata gccattcaat    107940
aatacaaaat ataagaaaa atgtcaatgg tttttcgaa aattatgttt ttcagaaat     108000 gtccataaca attcccatct gccctgtgcc tcgtatcctt cgccaaccgg tttgccttcc    108060
cgctgcagct tccccttcc gagggggctg tataccctgc gcaggcacgt agtgagtgct    108120
tgcactcgct ttcactctgc taaaaacgca gcggtactaa gattgcaaag gacgcaatct    108180
aaggaccggc gttttagaa ggcctttgca gggtatacag ccctctcgga taggggaaac    108240
cgcagcggga aggcaaaccg gttggcgaag gatacgaggc acagggcaga tgggaattgt    108300
tatggcagat caataattag aaggcagcac ccctgtatac ttctggaata ttttcgaaaa    108360
gtgcctcaca cttgtataac ccacggcttc agccgtctgc ttgacagaaa tattggcatt    108420
gctgcgtatc agttttttcg catttctat gcggacttcc gtcacgaagt caatatattt    108480
```

```
ctgtcccgtc ttttcgtgga acagcttgct gaaataggtg ggggacagat taaaatattc   108540
gctcacataa gcaatgctga catcctttgc ataattctgg tgtacaaaat ctttgataac   108600
tgttatatca aaattcctca gtggttcgat atgggataat tccgatgccg cggcttgcag   108660
ctctttgaca aagccggcaa agtcatccgc cgtaaatgaa tgagccagta cgtcctccag   108720
ataaagatac agggtactca ggcagatatt atcaaatatc ttttcattt tttggttttg    108780 tataaaagcg gcggaaagct gtcggatggt ttccctgctg ccaacaaggg cgttctggat   108840
aaagaggtca atttgttcac aaaaagacag aagatcatgt agtatgggga tttctgtcag   108900
tgaacggata tccgccgcgg aacggcagtc atatacaagg cggatttccg aaaggcggga   108960
gatccggcgg ctttcttcat agatttccga taaggaaccg gctgcggcgg taaacacgga   109020
aatcatgtca tgaggatagg agcgtatctg ggaattgata aaaaagtaa ggtgagaagg    109080 atcctttacg gaacagataa cacaaagctc cccgttggtg ttgaaaaata ccgcatgata   109140
aaataaaaat aagtttcttc gacaaaaatc atcaatactg cggaataaat catgcttgag   109200
catgtgctgc cgttcttttt cctgttcatc aatataaatc tgataaataa cgtaagggtt   109260
agttccgtaa ggaagaaaag ccgtctcatt actgcccagc tgatccgcca tattgaagga   109320
tcggatgaca tccaacgtaa ataatttatt gtcgtgttct ttctcctgat tctttaacac   109380
gacaatatca tccaccacct gcttcagcgt tgccagatcc accggcttga cagatagga    109440 ataagcggac agtgttatgg ccttctgagc atattcgaaa tcggcataac cgctgagaat   109500
aatccatttc gtggagggag atagcttacg gcaggtttcc agggcctcca gcccgttcat   109560
gagcggcatg cggatatcca gaaatgcgat atccggagga agcttttgca cctgtgctat   109620
ggcggcctgc ccattggaag catgaatata catgtgttca ttgggataaa gctcctccag   109680
catggactgc aggcttaaac gaatcatttt ttcatcatcg gcgatcagta taaacatgtc   109740 atttttccttt ctccgtatgg ggcttgggta tcattatggt gcatttggta ggtttatcga   109800
ttcctccccg gataataaag aaggaattag gagaaaaaat agtcagccgc tcttcaatat   109860
ttttaagtcc cacccgtttg taggatttat tttcaatata gggcaggccg ctgttaatta   109920
ctgtaatgac tgtaaaatcc tctccgttcc ggcttttgt agtaaaagcc gaaagctgaa    109980
taagttcgtt acggtccgaa ggttcaagcc catggacaat agcattttca attaacggct   110040
gtacaaggaa tttgggggatt tcgaaatcct ccagtcccgg ctctataaat atctggaaat   110100
ccagccgttc atcaaaacgg gtcttctgaa ggtacagata atcttttatg aaattaaatt   110160
catgctgaat ggtgctgtta aaattatgct cacaggtata ccggtacagg cgggaaaggc   110220
tgataatgga ctgttccagg cctttccgat cccccagccg gttcagcgca atcaggatat   110280
tcagtgtgtt atgcagaaaa tgaggattga tttccgactg cagcgtctgg tattccgcta   110340
ttttttgttc catctgaaat ttatattcgt tgtcaatgtg cgtatttatt ttttctatca   110400
tttcattcag gtttaccgca atcgtctcaa tttctgaaat actgcattgg gagatgtcac   110460
attggatatg ggaatcacct gcatgatatt tatccatggt atccaggaca gggctgatgg   110520
agctgcttaa gctgcgggag gtgcgtccga agataaaagc ggccattacg accatgccga   110580
aatagaatag caggaccagg cctgtggcaa acgcaggtt gcggtacagg tcatagcgag    110640
aggaaagata ataaaaggta aagccgaagt tcttatcccg ataagaatat aaatcataac   110700 ctcttttccgg ctgctttatg ccgttatccg atccgaggag ggaagagagg acaggagtga   110760
gcgcttcatt ggtggaaaaa agcagttcct gcttgggaga ttccaaaaag atcccggagt   110820
actggctcat ggaaatatcc ttcagggact caaaaataaa atccagggag atatccagaa   110880
```

```
tctcatatcc taccacctga cgtttatcaa tattttaaac cgtccgtatc aaagaaatgg  110940
tattcgccgc agaagcggta ttggaaggaa cgaatagggc ggcctggtta ttcctctgaa  111000
gctgtttgta ccagtcggag tccatatact cataatcttc gttgataaga agggtattat  111060 atttttcag gtaaaaaga gtatcgctgt tagacttgct ggggataaaa ccaatgccgg  111120
taatactgtt tccgatcaga gtcatacgat tatttaatgt ggcagtataa ttctgggaca  111180
gacgggtata agtaatcagg tcttcggtat aatctttttt gttcagataa aaaacatac  111240 ttgaaatctc aggatcaaac agataagtga gtgataatcc ggagttggcg tttatatgat  111300
tcaccagatg ggaggacaaa atgtttaagg tattttata ctcttttcc tgtgccttaa  111360 ttgttatctg tatatagcac acaaacaaaa gcaatataag cagaaaagaa ggaatgagga  111420
aggatacaat aaaggcaagc atagaagtgg attttaagga acggttttt ttcagagcct  111480 tttttatagt attcatatca tatgtcactc cctgataaaa tgaaacattc ataattatgt  111540
caggtgtaat tatatgcaca actaaaatgg tttgtcaaat taataaaaaa agtcctgtaa  111600
atggcaaaaa aaagtacaat atacacaaaa aaacagactt tagaatagtt ttccataatg  111660
ataaactgaa tacatccggt aagaaaacg aaattaaggc agtttaccta agtaaatctg  111720
caggttatgg gaaaggaagg gttaagttat gaaaaggcat gcaaagaaat tgacagctct  111780
gttatgtacg gcagcgatgt cggcagcatt actgtccggt tgttcatcgg gaggggacgg  111840
ccagactgca gatcaggccc cggccgcgca ggatgaggaa agcaaaaccg aagcagccgc  111900
acaaacagcc gattccgcag aacagacggc acagcccgct tctgatgtgg tattggagct  111960
ggagacaaca tggaccggtg aaatgctgga aggacttcag cagatcatgg atgattttac  112020
tgcggaaaca ggtatcgggg ttgaagtgat ttcacccggg gatgattacg aaaatgtaat  112080
gaaaacaaga atggcttccg gagatcttcc tgatttatgg gaaactcatg ggtggagcac  112140
tacaagatat tccgaatatc ttaccccttt aaatgacgag ccatgggtat ctcatgtgaa  112200
agaatccatc aaaaagacag tcaccgattc ccaggggaat atttatgtgg tcccgctgtc  112260
cattgatccg gcatccattt gttataacaa ggatattttt gatgaggccg gcgttgatgc  112320
gacaacaatc cgtacatggg cggatttcga agcggcatgt gacaagcttc ttacaaccgg  112380
aaaggtgccg gtatatgtag gcggaaaatc cgttaataac attgccaatc tgtttgaagt  112440
tatgcccccc ggattcctca ccaatgaaga tgttgcggat aaccagggag cggctctgct  112500
ggacggaagc tttgactggg aaaaatactg gacgcctctt gcacagatgc tggatgactg  112560
gcagcagaag ggatacttca ataaggacat tctgactgca agtgatgatg cctccattca  112620
ggcccttgcc aatggcgacg gcgctattgt aatcagcgga aatcatacga ttacacaggc  112680 tcttcctat aatcccgatg caaggcttgg aatcatggca attccttcac ccaatgaagg  112740
cggcaaagtt tatgtgtctt caggagaagg cgcctgctat ggtatttgga aggataccga  112800
atatccggag gaaagcagaa agctccttga atatctggca agagatgatg tctctgtaaa  112860
ggttgccacc ataaacggaa agattcccgc tatggaaggt gttaccaatg ataatgaata  112920
tgtgaccaaa gaatttaata tcatgatgaa tgccttcggc gatgatctcc tctatgtgaa  112980
ttattttgac agagaattcc ttcccagcgg tatgtggaat gatatgggag tagccggaaa  113040
tgaaatattt atgaatccgg gaaaaggaat tgaaaaatgt gtggaaacaa ttaagaccgc  113100
atatgatgaa aaaatcagcc agtaattttt cagatattat tttcagggcg ctggcttaag  113160
caggcgggcc gccgcgtgat ggactggttc atacgcggcg gcttacttgt gtcccggatg  113220
```

-continued

```
aaaaccggca gcacggctgc cggcggagct gagtcggaaa ggtatggtta tataatatga  113280
aaaaacgaaa cctaagaatg aatgtatttt atattcctgc actgcttctt atcctgtttt  113340
ttgttctgtg gccgctgata gaggcgttcc ggatttcttt cacacagtgg aacgggtatt  113400
cccaggatta taaatacata ggcttaaaaa actatcttaa attgtttaag gacagtaact  113460
tcctgatcgc cttccgtaac accatcatct atggttttgg cagtacgctg cttcagaatc  113520
tgctgggact cgcctatgca gtattcttaa attcccggtt taaaggtcat tccgtagtac  113580
gtacctttat atatatgccg gtcatgatat ccagtctgat catgggctat atcatttact  113640
tctttgttca atacaacagg ggtatattta atgaaatgat aggtattttc ggaatggcgc  113700
ccattgactg gatggcctcc ggaaccagag gtgttatcat cataacattg atgaattcct  113760
ggcagtatgt gggtattgcc atggtcattt acatggcggg ccttcagaat attccccaga  113820
tgtatctgga agcggcggaa atagacggcg cgagtccctg gcagcgtttc cggcacatta  113880
cctttccgct gctgcttccc tccatatcat cagcggttgt gctcaatctg atcggaggcc  113940
tgaagcttta cgacgttatc atatccctat ccggaggagg gccggattc tccacccatt  114000 ccctggcttc ctacgtgagc aaccagtatt ttaaagcgca gaatgcagga tattccgctg  114060
cggtgggaat attcaccttc ttatttatca tggtagtctc caatatcttc actaattatt  114120
tcagtaaaaa ggaggtggat atgtgatgaa aaagacactg ctgaaggact ggtggaaata  114180
tctgctgggc gtcgccatca ttattttcca tgtcctgccc atctatgtac tggtggtaat  114240
ggcattcaaa agcatgtcgg attcctcctc tctgctttcc ctgcctgaga aggtatatac  114300
ggctaatttt gtcaaggttt tccagtccgg gaacattccg tctgccctca ggaacacaat  114360
cattgtgacg gtctgtgtcc ttctgattga aattgtggtc ggcgggcttg cttcctatcc  114420
gctttccaga aataaaagca aatggaacgg gctcataaaa ggtattataa tggggattat  114480
gatgatacca tctttgagta tcctggtcgg tgtctattcc ctgcttgtat ccataaaagg  114540
aatatccact ctctggggaa ttatcctcgt gtcatccgcg ttcgggctcc ccatgaccat  114600
ttacctcttc accaacttca tcggggccat ccccccttcc cttgatgaag ccagcgctat  114660
tgacggctgc ggggtggcgc agaccttctt ttatattatt ctgccccagc tgaagcctgt  114720
aacggtaacc atcgtaatat taaacggggt ttccatatgg aatgaatacg catacagcct  114780
gtacattctc cagaaaccca aaatgtacac attgaccctg atgatatctc aatacttctc  114840
cgcaggaggg aaagacttaa atggtgcggc ggccgccgca tgtgttgcga ttttcccttt  114900
aatcatcgcc tacatattcc tccagaaaata ttttattcag gggaccattg acagcgcggt  114960
gaaaggatag gtattgatac agcagcaaat gccgtattta cggcaggatg agaggaaaca  115020
catgatcaga ccgaaaaaa tactgtcctg cggtatgcag ggaaatattt tgacaatgga  115080
atgcgcccag ggggtaatgc agattgttcc ttatgcagac aatatcctgc attttgtata  115140
ttacccacag aatgacagct cctgcctgac ggaggaaaca gacggcagag aaaaattgcc  115200
catgtgggga atagaagccg tgccgtccaa agacagccac tcggcactga cagaggaaga  115260
agacaagatc ctctacagcc tgtccggtgc aggacttgaa gtaagcagaa atgatgcgga  115320 aattacatttt accggggcca tgggagagaa gctgaccact cttttagact gccgtctgga  115380
accggcagtt gtcctgggcg aaaaaaacctt ccatatccgg gttgtttttt ccgcttcgga  115440
ggatgagaaa tattttggcc tgggacagca tcaggacggc agtctggatc tgggcggcag  115500
ggagcagatc ctgtggcatg attacagcca taagggcggt gaaatcgttg ccgtgcccctt  115560 ccttgttacg aataaaaat acggaatcat ctttgataat gcttcccgga tgaaggctgt  115620
```

```
acccggtgtg gaaggccata cagtttggca ggccgaggtg ggggaagcgg tttccttctt 115680
tctgataacg ggagagaaaa cggatgatat ttaccggggc tacagatgcc tttgcggagc 115740 ggcgccctg ccgccgagaa gagggctggg attcattcaa tgcaagcaga gatacgcctc 115800
ccaggaggag cttttggagg ttgcatccaa atataaggag aagggctgtc cctgcgatat 115860
ttttgtagtg gactggttcc attggaaggt tctgggagat ctgagcctgg atacgaagtt 115920
ctggcccgac agcgcgcaga tgaacccgga gcttgaggaa atgggctatg agacaatgat 115980
atcctgctgg ccgcggttta tgaaggaaag tgagaattat gaattcctgg aaaagaaggg 116040
ctggttcatg aaggatgccc ggggaaatac cgtttacgga acgccggagg atcagagagg 116100
cgcgctgatt gacaccacca atccggaatg cgggaaatgg tattttgata cgattaaaaa 116160
gaactatggt gatctgggat ataaatatta ttggacggat gaagacgaac cggatatcag 116220
ccctcatgaa tcctttctgc atgcaggaac cggagcgcgc attcataata tctaccctct 116280
tacccatact caatgtatct atgaaggcca cagagcagca ttttcccatc gctgcctgac 116340
actatccagg gccgcttatc tgggcgcgca gaaatacggt accaccttct ggtcgtccga 116400 tattttccg gagtgggatg ttctcaaaag acagataccc acagccctta atttctgtgc 116460
cagcggcatg ccctactggt catccgatat cggagggtgg caggcgcttc ccgatgagga 116520
cacggaggag gattacagca agcttctgat tcagacctcc ggttcgggta aaggagcagt 116580
caccaagaaa aattatacgg aactatatat cagatggttt cagtttggtg ttttctgccc 116640
caccttccgc acgcatggaa cccgcagaaa taatgaggta tggtcctatg ggaagaagc 116700 ggaaaaaatc ctggtgaaat atgtaaggct ccgctatcgt ctgatgccct acatttattc 116760
cctcgcattt tggacggagc agaccggtgc accgtttatg cgggctttgt ggatggactt 116820
ttccgacggg aaaagtgcgc ttaccgagga tgaattcatg ttcggcccgg cccttctcgt 116880
tgcgcctgta accgaacagg gggcggtttc ccgggaggtt tatcttcccg aaggaacaaa 116940
atggtacgac ttctggacag atgaaaaact ggacggcggt cagacgatca ccgtggatgc 117000
accgatagaa aagcttcctc tttttgtaaa ggaaggctcc ctgcttcctt tggggggaagt 117060 gcttccaaac agcaaagaag agcagacgga tatcgatata caaatttatc cgggaaagga 117120
tgcctcgttt tccctgtact cggatgacgg ggccagctat gcttatgaag agggagaata 117180
ttctctggtg aagctgattt gggaagaagg aaaacaggag ctgtccgtca cggaagaaca 117240
aacctcggag aagctgcgta aaaagaatta caggtggaca aagcactgaa cggtaaaaag 117300
aaaggaaaca gattatgcag gatttaagtt tttcttttcc aacccctcat ttccaactgg 117360
gaggatttga gttttccgtc ctgatttata ccttcaggaa tgtgtatgcg cccgatgagg 117420
cgcagatgac cgtcgaacag cccggagata cgctttgggc cgagggcaag ggcctgcggt 117480
gggcaggcgg ccagatggaa atgccgggcc gttttgaagt cagggcctgc atctgcagcc 117540
atggcatccg ggtgaaaacc acagcagaaa tacagaatcc cggagaagat atccgctgca 117600
ttaaagtcat tgttcacggg atcccggatg gaaagctggt taatttaatt aatgcgcagc 117660
cccgtgaaat cccgcaggaa ggcctgaacc tgaaatatcc ggagggctgg cgggatgtag 117720
gcacccccct agtggtcatg cagacaccgg agaatgagat gttttatttc cgttccctgg 117780
atgaaaaggt aagagacaaa cgctttgtct tcgtacgtac cggagataaa ctgaatgcag 117840
agcttatttt tgaagaagcg gcagtttcaa tgacgaaccg gattgatgct ccggaatggg 117900
aaatcggatg ggggaaaaac cttgcggaga tttatgagcc tcacagactg cacgtggaga 117960
```

```
agtgctacgg acttgtgcca tgggaggaaa gaacggacgt ccccggctgg gcaagagaaa 118020
tttccctggt ggcctccata cactgccagc actggaccgg atatattttc aatgactatg 118080
aacaggtatt ggaaaacctg aaaaaaattt gcaggcaggt ggaaggaaaa cgcgtgctcg 118140
cctaccttcc ggggtgggaa ggccgttatt actggaaata tgggaattat gtccctgacg 118200
aacggatggg aggaaaagaa ggcttccgga agctatgtga cggcgcgaag gagctgggag 118260
tccatgtcat gcccatgttc gggataaatg tggtgggcag ccatttcgaa aactatgagg 118320
aatgggggat tccttccgaa ttcagagggc cgggaggcag ccagtacgga ggcagtgtgg 118380
attgggacgg ctcccgccat tatgaccata attccaaccg taatctgaat cccgccgcgc 118440
cccggtggca gaaccgtctc tacgacaggt caccggctt aatggaggaa ttcgggtttg 118500
acgccgcctt ttttgatatt gcggcggtat ggatgaatga tcccagccac tacctgtatg 118560
acggcgtgaa acagcttatg gaaagattca aaaatataa tcccgatatg ctcctggccg 118620
gcgaaggctg gtatgacggt cttaccgcct gcattccgct tctgcagtgc ggtcatacgg 118680
acggcgtttt ccactggcat gacgaggcct atgcccccat gtttgacacc tatgcccgcg 118740
gcttcggcca tttatgtctg ggcgatgttt cccggggaag taccggagtc catgaactgg 118800
gatacaatcc gataaaaaaa tgcccgctgc gcaaggaat tatccccacg ataacgattg 118860
tggacggaac tctggaaaag gctccggacg ctgctgcgga aatatgtaag gatgccaatg 118920
cctatgcgga attatatctg aaggaatctc cggcaggttc ggaatggaga tagtaaatga 118980
gagacaataa aacgttatat ttagtatgta atgcacatct tgatctggtg tggcagtggg 119040
agtggcatga aagcctggca gaggcgctgt ccaccttccg tatagccgcc gcattttgtg 119100
aaacctatga cggatttatt ttcaaccata atgaagcaaa gctgtaccag tggattgagg 119160
aatatgatcc gcctctgttt caaaagatac aggatcttgt gcaaaaagga aaatggcata 119220
tcatgggggg ctggtatctg cagccggact gtgtgatgag cagcggagaa tcaattttca 119280
gacagatgga aaaggggctg aactatttca gagaaaagtt tgggtgccgc ccccgtacag 119340
ctataaatgt ggattccttc ggacatgacc gcggactggt acagcttctt cgcaaaagcg 119400
gatatacctc ctatctggtg ggacgcccat ctttggaagt gtgcaaggct cccggaccgg 119460
attttctgtg ggaaggatat gacggcacct gtataccggt tcatctggca gcggaaggct 119520
acaacagcgg acttggcaaa gtccgcagaa aactggaata ttaccgcagg caggaaggaa 119580
cagataattc tgtactggca ttatggggaa ttgggaatca cggggtgga ccgtctaagg 119640 aagatctgga tgaaatatca ctccttcaga aagagtggga aaagaaggc gtccagttaa 119700 tacacagcac tcctgaaatg tatttttgatt ccatttccgg atcagagctg cccctgttg 119760 acagggaaat aggtccctcc atgcccggct gctacacctc acaggtccgt atcaagcaaa 119820
cacattgtct tcttgaaaac atgctgtatc agacagaaaa gcttctggcg gccgcagaaa 119880
tctttaccgg tatggaaggg gattgggaat cgctgaaaca ggctgaagag attcttttgt 119940
ttaacgaatt tcatgatatc cttccgggca cttccgtcca acgggcagaa gatgcggcgt 120000
taagagaaat gggaggcgcg atttcccttc tggaaaaaga gaaacccgg gcgtttatgc 120060 acctctgccg ccagactgaa aagctggagc ctggtgtcat tcccatattt gcatgcaatc 120120
cgcatccatg gcctgtgaag gcggttctgg agtgtgaatt ccagcttcag gatcagggat 120180
gggattatac ctatactgat ttcgaggtga gatatcaagg ggaagtaatc ccgtcgcagc 120240
tggaaaaaga gggaagctcc ataccgttgg actggcggaa acgccttgta ttcatggctg 120300
atatccctcc gttttgccaca gcagccttgt acgcctatcc aaaggtgctt accgggaaac 120360
```

```
cggaattacc tcagacaatc gaatctgaga tccggctgga aggctccgga ggagagctga   120420
taattgataa aaagtcaggg ctaatcagtt cctacaggat tgacggaatc tcccttttct   120480
gcccgggagc tgcccgtctg gtagttattg cggacaatga ggatccctgg ggcatgacag   120540
taaacagctt ccctgaaatc atcggtgaat ttacgcctgc atctccagaa caggcgggta   120600
aaatctgtgg tttggataag gcaatagatc ctgtacatat aatcgaacat ggccccgtta   120660
gaacagtggt tgaagcaatc ttcctttata aacgttcggc tgccatagtc cattataaat   120720
ttcaaccgat tactaataag ctggatttgg agatacacct gcagtggaac gaacccaatc   120780
atatggttaa gctgtctctt ccgactccct ggaaggatgc ggaatgctgg ggacaaaaaa   120840
tgcttggcag agcccgttta tatgaaaatg gcacggaaaa tgtttcacaa aagtggattt   120900
ccgtatgtaa tgataaactg ggcctgacca tattaaacca gggaagctac ggcagcagct   120960
ttgaaaatgg ggaactgcgt ctcactctgc tgcgttcgcc tgcctatact gctcatccta   121020
ttgatgacag gataattctt ccccaggata gatttctatc ccgtatagat ataggagaac   121080
ggtcatttct gttttctatt catggagggg agcgggagtg tcagttgaac acggcagata   121140
aagaagcggc agtatataat gaagcaccct ttgcccgttc ttattttact aatgccagca   121200
agcccacagc cggaggaaat ataaaaatcg atgaagaaca gatacagctg ttatgtttaa   121260
agaggacgga cgcaggatat ctgatacatt tatacaatag ttcatcacag cctcggaaaa   121320
caaggtttac ttttatagaa agagagataa tggtggaatt agatcccttt gaactgaagg   121380
ctcttcacta ttcacaggga attctggaac cctgcggtct cataactttg caggatactc   121440
tgtaaaatat cttctttggc agatccttat attgtaattg actccccggg taaggaatgg   121500
cataataaac ctgaacccgg ggttttcccc ggctttcggg aactcaacgt tacgattggc   121560
taaaggaagg gacggataaa atgaaaacac cggagattgc agagagcgta ttcgttgcgc   121620
cggacgcggt aatactgggt gacgtacata taggagaaga ctgcagcata tggttccata   121680
cggtcatacg cgcggaggat gcctctgtcc ggatcgggga aggcaccaat atacaggata   121740
actcagtagt ccatgtggat aaagggcatc ccgtaaccat cggcaaccag gtaacagtcg   121800
gacatggggc catcatccac ggctgccgta tcggtgacaa taccctcata ggcatggggg   121860
ctatcctttt aaacggagca gtcatcggta aaaactgcat tataggcgca ggagcgctgg   121920
ttacccagaa caccatcgtt ccggataatt ccatggtcat cggaagcccg gcatccgtaa   121980
aacgccaggt tctggagcgg gaagtggaaa gcaactgcag aaatgcagaa atttacatca   122040
aagaaggaaa agattatgcc gatttcttcc gggaaaaaca ataacaccat caaagaacaa   122100
ttatccctgc tggcagaacc tgcctacagg gattttgcat cctccctgct tcccggcacg   122160
gaaaatatac tcggagtgag actgcccgcc ctccgcaggc ttgccaaaag gttagccaaa   122220
gaaaactggc tgcagaacct aaatctctgc acccaggaca gcttcgaaga atcatgctc   122280 cggggcttcc tgattggcta tgcaaaagca ccccttcccg tcattcttga ccagattaca   122340
caattccttc caaggataaa caactggtcc gtttgtgaca gcttctgcat cacactgaaa   122400
attgccgcac aataccccatc cgaattctgg gatttttcc agcccctcct gaacagtcag   122460
gaagaattca ccctccgctt tgttctcgtc atgcttctcg actactacat caatgatgaa   122520
tatatagaca gccttttccc gctctttgac cgcatcaccc accagggata ttacgtcaaa   122580
atggcgctcg cctgggccat ttccatgtgc tatgtccgat tccccgccca aaccaccatc   122640
tatctgcaga acaaccgcct ggacgatttt acctacaaca aatcccttca gaaaatcacc   122700
```

```
gaatcacaca gcgtttccgc agaatccaaa aagataatcc gatctatgaa aagaaactga 122760
cgcaggataa aagtctgccc ttttcccag cctaaactgt aatttcttcc tttaacgtag 122820
acaggcagat gatagtattg gcatcggtca cgcccttgat atccttcaga gtacaggaca 122880
gaaaatcctc gatatcctgc atatcccgga aaagcacctt aatagaaaa tccgcaggcc 122940
ccgcggtatg atggcattcc agcacctggg gaagctgcag gcagacatcc tgaaaagcct 123000
ccatattcct ggaataatcc attttacaa ggataaaagc cagaaggtta tagccggaag 123060
cgccgggatt cacacggatg gtatatttt caatcacccc tgtctgctcc agcttccgga 123120
tacgttccgt cacagcaggt acggacagag agacctgttt gctgatgtcg gaagcgcttg 123180
cccggctgtt ttctttaat atagaaagaa tggtggaatc agttatcc atagaaacct 123240
cccttagctt atttttttcc tggcaggagc gggcttaacc gcttctttt ttgtccggga 123300
agacggaagt gacagcttat aataaaacat atattgctgg attaccccg cgaagccctg 123360
atagcgttcg aaagggaaac ccttcgggta ataggcggcc agaatctgct ttacatgcgt 123420
atccactgga aaagcgccga tatgatgtaa ggcaaacagg cagatgcagt cggctacctt 123480
gcgcccaatc ccaaattccc cggtaagaat agcaatagcc tcttcataat ccgcattctg 123540
cagggaatgg aagaattctt ttccgctgcc gttgcagcac cgtttggcca tggcgagaat 123600
atatttgtcc cgatagccaa gccccagccc ctgcagccct tccagacctc cggcggcaat 123660
tttttccggt tcgggaaagg agtaaaaatc cttttcggac aaagactcct caccggtcag 123720
aaagccttcc ggctccagcc gctccccata ccggcggcac agggcatcca cactattgcg 123780
gatacgggta atattattat tctgggatat caggaaacaa aggatggttt cccacagatc 123840
ctgccgaaga atacgtattc ctccccccata ggaaatcgca gacgtcaaaa agctgtcttt 123900
cggatccacc gctttttttca tcgccccata atcagtggaa agatcgaaat aattatgcca 123960
ataggaatca aattcctgcg gggaacagga aaactccaca gaaaccccctt ccccggacat 124020
tccgaaagcc gacagagtcc cttcctttga aggcccgcag gctgtctgcc gtatccggac 124080
cagatgacgg ccggatgcaa ccgcatatgt attttccccg cagcagcaga tccggaacac 124140
ctgtcccgaa tccatcagca tacgcatatc aaaatcatga agtatcgtct ggtacataag 124200
agatatttcc cttcctcgca cgaattatga aagccggtaa cagttcagat aaccaggaac 124260
cattcctgat acctacagtt cctcacatac ctggaaaata taaaatttca gataatagga 124320
ttcatccgcc gcccagagta taggatgatc acagcactgc gtgcggaatt ccacctgacg 124380
aagcctctta tgggaaccgg cagcggcctc cctgatcgtt ttggaaaaaa gctccggatc 124440
cataaaatga gaacaggaac aggtaaccag aaaaccgccg ttttccacaa gcttcatgcc 124500
cctcaggttg atttcacgat accccttaac cgcattctta atggaatttc tggacttggt 124560
aaaggcagga ggatccagga taaccacatc aaattttcct ccctgtccct ccagccaggg 124620
aagaagctca aagacatcgg cacattgaaa atgaacccga tcctccagcc cgttcagcct 124680
cgcattttcc tcagcctgca aaatccccgt ctggaagaa tccaccccga aacactttc 124740
cgcccctgca attccggcat ttaaagcaaa agaccccggta tgagtaaaac aatccagaac 124800
cttttttcccc ctgcacagcc gctgaacagc cgcccgttta tacttctgat ccaggaaaaa 124860
cccctgttttc tgcccatcct ctatatctac gatatactta accccatttt cttcaatctg 124920
taccttcgta tcaaaaggag cgctgataaa tcccttaaaaa cgctccatcc cctcctgcag 124980
ccgtaccttg gcatcacttc gctcataaat tccccgtacc tcaatcccgt ccccttgcag 125040
tatccggcag agagcatcca gaatcacagc cttaagcctg tcaattccca gcgccaggga 125100
```

```
ctccaccaca agcacatccg aaaacttatc caccaccagc ccgggaagcc agtccgcctc   125160
cccgaatatc accctgcagc acccggtatc caccgtctgc ttccgatact cccacgcatt   125220
ttccacccgc ttctccagaa aagcttcatc gattaccgtc ccctttttcc gggaagaag    125280 cctcaccgta atcttcgatt gcatattaat aaacccaatc cccagaaaat accgtcaaa    125340 atcatgaacc gtaaccaaat ccccattttc aaaatcaccg gcaatacttt ctatttcatt   125400
atcataaacc cacatccccc cggatttcaa agtcctcccg gtccctttt ttaatgtaac    125460 aagagtatcg tacatatttc ctcacattcc gccgcttttt cgttatcacc caaactatca   125520
tgcccataac aaattttga ggcttttctg attattcttc ctttttgta ttgtaagtgt     125580 aacatatttt ctttataatt tacagtagca atgaaggttc ggccctccc catattctgt    125640 cagggttccc gtgcctgccc gcccttgct ccgcgcttc tgcctgccct gtttgccttc     125700
ccctcaggcg ttcctcccg gcgggtatgt gtaccctgca aaggccttcg aaaaacgccg    125760
gtccttagat tgcgtcctct gcaatcttag taccgctgcg tttttggcag agtgaaaacg   125820
tgcctgcgca gggtacacat acccgcccgg ggagggatag cctgagggga aggcaaacag   125880
ggcaggcagg aggcgcggag caaagggcgg gcaggcacgg gaaccctgac agaatatggg   125940
gcgtaccaaa agtataatct caaaaagagg agatggaacg tttgttccaa aggagagctt   126000
atgattctgg aaaaattcta tgaaaacccg gaaatactgc atgtcgggac agaagagaac   126060
aggtgttatt atgttcctct tgatgtgcag gaaaaggaga acgctagaaa cttaagcggg   126120
atcgactgga aattcggcta ttatcccaat gtggagtctg tgccggaatt ttacaaaaag   126180
gattttgacg aagaggcctt cggcaggctg gaggtgcctt cctgctggca gatgcttggc   126240
tttgatcaaa acaatatac caatataagg tatccttttc ccttcgatcc gccttttgta    126300
cccgacgaga atccctgcgg cgcctatatc aaatattttg atatcagtgc tgcggaggct   126360
aaaaaggaac agtacccttta ttttgaggga gtggattcct gcttttatgt gtggataaac   126420
ggaaagtttg tcggctacag ccaggtttcc cacagcccca gtgagtttca catcacaggg   126480
aaaaccaaaa ccggaatgaa taagctggcg gttctggtgc tgaaatggtg cgacggaagc   126540
tatctggagg atcaggataa gttccgtatg tccggtattt tccgtgatgt gcatctgctt   126600
ttcagacccg cagaacatgt cagggattat actgttacca cacctgttaa ttttgatgaa   126660
aacagggcgg aagtggaagt gaggatcaat gaggcggcgg gaaatccccg gattaccgtg  126720
gaattatggg ataaagacac ccttctgggg gaatgcgccg ttgaagacgg aaaagcgtcc   126780
ttcccggtga aggctcctgt cctgtggaat gcggaagagc cttatcagta catactgaaa   126840
ataaagaccc cggatgaaat cctgatccag agggtgggca tccgtacagt cgacatcaaa   126900
gacggcgtgg tgctcatcaa caacaggcct gtcaaattca aaggggtaaa ccggcatgac   126960
agcagcccgt ataccggggc cgtggtttcc cggatggatg ccatgtttga tctgcgcatc   127020
atgaaggagg ccaatatcaa tgccatccgc accagccatt atcccaatgc accctggttc   127080
ccggagctgt gcagcgaata tggttttat atgattgcgg aagcggatat tgaatcccat    127140
ggggcggcca ccatttacgg aggcagcacc gaaggaacct tcagctattt cgttcaggat   127200
ccttcctata aaatggccat cctggacaga gtgcagcgca gcgtgatccg tgataaaaac   127260
cagtgcggcg tcattttctg gtccctcggc aacgaatccg gcttcggaac caatatggaa   127320
gaggcgggac gctgggtaaa aaattatgat cccaccaggc tgcttcatta tgaaagcgtt   127380
catttccagc ctgaagggca cgaaaaagat gaatccatgc tggatgtgga aagccatatg   127440
```

```
tacgcatcca cgcagcatat cgatgaatat tttgcgaagc cgggagagaa aaagcccttc   127500
atccagtgtg aattcataca cgccatgggt aacggccccg gggatattga agactatatg   127560
cagcagatat accgttatga cggattctgc ggcgggtttg tgtgggagtg gtgtgaccat   127620
gccacctatg aaggcagagc ggaaaacgga aaggaaatgt tccattacgg cggcgatgcg   127680
ggagagtttc cccatgacgg aaacttctgc atggacggcc tcgtatttcc tgacagaagg   127740
cctcacgaag ggctttacga atggaaaaat gcgatccgtc cggtaagggc cgagctgctg   127800
gatcggaaaa agggtgttat ccgcctttac aacaagctgg atttcagaaa tttaaaagac   127860
tatatctata tccgttatga aatcaaagag gagggaatcc tcctggaaga aggaatgata   127920
gaggatctgg aggcagcccc tcacggcttc accgacatta ccctgaagct tccgggaaaa   127980
cccaaggatc actgctatct gaagctgacc tattatcaga aggcaaagga taagcttacc   128040
cagatcggcc atgagctggg ctttgatcag tttgtacttt ccgaagagaa ggatgtcagg   128100
ctgacactgc agaagaacgg cgagcctctt actctcacgg aaaccccgga ggttttccgg   128160
atggaaaaca gctccgtatg ctatgaattc gggaaaaagc agggaagctt cctgaagctg   128220
gagaaaaacg gaaaagcctg tataacagct cccgtagaat ggaatgttta ccgtgccccc   128280
acggataatg accgtaatat cgtccattcc tggaaagagg ccggatatga cagaagtgta   128340
gtaaaggtat acggctgtga ggccagggtg aaacagggca cggttgccat aacctgtgat   128400
ttttccatag cggctgttta tattcagcct ttcctgcggc ttcatgcggt atggagcata   128460
aacggcgaag gggaaatcaa ggtcgcggtg gatgggaaaa gagacacatc cttcccgttc   128520 cttcccggt tcggcctgaa attccagctt cctcaggaag aacaggaggt aacctatctg   128580
ggatacggac ctcatgaaag ctactgcgat aagcatcagg caagctatgt tgatgtattc   128640
cataccacag tgccccagct tcatgtggac tatgtgcgtc ctcaggaaaa cggaagccat   128700
tacagctgct cctccattca ggtgggaggg ctgcaggcgt ccggcagcag gcccttcagc   128760
ttcagtgctt cggaatatac catacaggag ctggaagcaa agcatcataa ctatgaactg   128820
gaaccgtcag gctcagtcat tgtatgcacc gattacaaac aaagcggcgt aggctccaat   128880
tcctgcgggc ctgagcttct gccccaatac aggctggatg aagatcagtt ccattgggaa   128940
atgctgtacc gttttgaata acggatggc tgctgcgtta ttcacatgac aaaaaaataa   129000
ggaggaacgg actatgtcaa aagtttccat gtcaggatcc aatgatttct gtccccagtg   129060
cctgtatctg tatggtacat acaaagaaaa cggggaaccc aattacgggc tgttctgctg   129120
ggcaacctat tgctgggatg aagggcttaa atttgtggcc tgtatcgggc aggataagct   129180
gacccgtgac agaataaggg ctgagggcgt attttccgct tccgtagtga gcgaagcgct   129240
tctgcccgcc gcggatttct gcggaaccca tccggatat gagttcgata agtcggagaa   129300
agtggaatct gaaaaaggcg gggtcctgaa tgtgccggtg ccgaaagcca gcccgtggac   129360
gttggagctt caggttgata aaccctgca tctggatgac aaaaaggaga gtgaaatata   129420
catttgcacg atcaaaaatg tgatggctga ggagtatctg gccggtgatg ccgactttga   129480
aaaacgcctc cgccaggccg cccctgtaat atccgtatcc gataaatatt tatccataaa   129540
cccggcgcct ttgggggact ggggaagcat gggataacgt tcctgtaaaa agaatataca   129600
ccgatagtaa caagaatgct gctcatttct gagcagcatt ctcgtcgttt tccggtgttt   129660
cgttctccaa ttgttccaga taattctttt ccccgcagtt gggacaatat aggatctgcc   129720
ccttccggct ccctacggaa aaaatcagct gcattaaggt aggcctgaag acctgtccgc   129780
aggcaggaca tttaaaggtg gcggtacgcc tgtaggcgag cctgcggaaa atcaggatca   129840
```

```
ggacaaacag cactatcagt ataagggcgg ttaccggtat catcttttgc agaaaatcca 129900
taaaaacctc cgttttcgta tgggcttcag ccaaggtaag ccttcagcag cctgaaagta 129960
ttctctacgc ccttcttatg gctccgctca taaccgtggg aggcatatac accggggccg 130020
atcagcccgt ggcgtacatc ataaccggcg gtgagagccg cgtccgcatc ggaaccgtaa 130080
aaaggatata catccaccgc aaagtccgcg ccggcctttt tcgccgcttc aatgagcgcg 130140
cttaccacat cataatgata aggccctctg ctgtcactgg cacagatgga aacctgatat 130200
tcatcacagc ccagtccttc tcccacgcag cccatatcca cggaaagaac ctccattaca 130260
tcctgcggaa tggaagcgca gccgccgtgc cccacttctt cgaacacggt aatatgatgg 130320
taaatcctgc gggcaggagt gatattttca tcctttacat atttggcata gcccagcaga 130380
actcccgtac tcagcttgtc atccagaaaa cggctcttga taaatccgga aggagtcacc 130440
actgtgcggg gttcaaagca gacaatatcg ccgggcagaa taccgagggc aagcacgtcc 130500
tctttggtgc gtaccacttc atccaggagg acttccattt ccgagtaagc tctcttggta 130560
ttgttatatt ccccgtttac atggatggaa gcattgcgaa gctggaaggt acctgtatat 130620
acgtttccgc ttctcgtaac gatgcggcag ttttctgctt ccgcattatt aggattcatg 130680
cccccctaacg gggtcaggtt caggtgcccc gcggaggtga tttccgatac cattgccccc 130740
agtgtatcca catgggcttc catgagaatc gggccggcag cgggatcgca tttttccctg 130800
tcttccgata cgccgtccgc tattttgaca aatacgccgc ctttggtggt aagctcaggt 130860
tcatacccca gttcggtata gaccttcatc agataagccg ccacattttt ggtatagcct 130920
gtagggctgt caatggaaag cagtttctgt gtctgctcca caatatactc tgtataatcc 130980
ttcatcagtg aatctccttt acgcatgatg tctgttatgt ctgatacaag attaccactt 131040
ttacgtaggt aaggccagtc cttccctcat tttattttaa taaaaagcat gatatactgg 131100
aaaacaaaag aggaatatgt ttcgtcagtc cggagcatgt tctcaaaaaa gccggaggat 131160
ggataccaat gaatcaaaaa ggcgaacaga agatgggtac ggaaagcata ccgaagttaa 131220
tggtgagtat ggcggttcca tccattatcg cacagataat taatatactt tataatattg 131280
tagaccgaat ttatatcgga catatccccg gtgtgggtgc ggcggcgctt accggcgtcg 131340
gcattacttt tcccatcatt accctgattt ccgcattttc agccttcgta gggatgggcg 131400
gagcgccgct tgcggcgatc tggctgggaa aaggggacag gaagcacgcg gaaagaatac 131460
tcggcagcgg aacctgtctg cttgttattt tcaccgtgct tctcatggcc gttttctatg 131520
gttttctccg gccgttccta tatatgttcg gcgcatcgga tgccaccatc ggctatgcca 131580
tggattacat gtacatatat ctgctgggaa ccctgtttgt ggagctggcc ctcgggctga 131640
atcccttat tatttcccag gccgctccc ggatcgccat gatatccatc gtgataggag 131700
cggtggtaaa tatagccctg gatcctctgt ttattttttgt atttggctgg ggagtgaagg 131760
gcgcggccat agcaactgtg ctttcccagg cggtaagcgc ggcctggaac gtaaaattcc 131820
ttatgagccc gaaatcctcc ctccgcctgt ctctgtgcca tgtgcgtccc tccttccgca 131880
ttatgtggca gatttgttcc ctgggtattt ccccctttat catgcgatcc acggaaagcc 131940
tgatcagtat tgtgctcaac cggggactgc agatatacgg aggagatttg tacgtaggtt 132000
ccctgacaat catgcagagt gtgcttcagc tcttttccgc tccgctctcc ggatttaccc 132060
agggagtgca gccgatcatc agctataatt acggcgcagg caattttgat cgggttaaaa 132120
aactatatcg gagcatgata ggaatcagct ttgccatttc ctttaccgcc aacctgaccg 132180
```

```
ccatgatatt tcccggagcc tatgccgccc tgtttacgaa cgacagggaa ttgatcggcc    132240
tggtatcgaa ggtcatgccg gtatttcttt tcggaatgct gttttttcggc ctgcagaacg   132300 ggatccagcc caccttcctc gctctgggac aggccaaaat atccctgttt atcgccatgt    132360
tccgaaaggt gatcctcctg gtgccccctgg cgcttgtgct tccccggttc tttggagtga   132420
tggggattta ttatgcggaa cccatatccg atattatttc tgcggctaca gcggaatac    132480 tgttttgtat aaatataaag aaaattctgt cgaaagaata tctggcaaga atccaatgag    132540
ggaataggac atgaatatta aaaaacagt taaggcactc ctcataatca acggacttca     132600
gtttgtggcg gcctttcttc tctggctggt cataggctcc caggtgctgg gcagggtgaa    132660
tcccgctatt tatcttacga taggtatcat gctgttaagc agccttctca ccattatggg    132720
cttatatatg gccagcaggt accagaatga cagctatcgg gagagtatga agaacctgga    132780
gaacctgaat ctgaagctgc gcgcccagag acatgattat atgaaccacc tgcaggtgat    132840
ctacggattg ctggagctgg gggaaatatga ggacgccagg gaatatatgg agccggtatt   132900
caaggatatc accagggtga cgagagccat gaaaaccctcc cagcccgcgg taaacgccct   132960
gcttcaggcc aaaatggaat ctgcggagaa aagggagtc gatatgattg tggaggtggg    133020 aacgccttttg aaggagatcc cgctggagcc gtgggagctg tgcaagcttc tcgccaatct   133080
catcgataac gggattacag ccctggaaga aaagaggga gaaaaaaagc tggcggtgga     133140
aatccgccag gacagcagat tctataccct tgccgtccgc aataacgggc cgctattcc    133200 cgaagagcat caggctctca ttttttaagca gggttttttcc accaaaaaag aagaaggcca   133260
cggtaccgga cttgccattg tttcccagat cgttaaagaa gccaaaggag aaatcagcct   133320
tttctccgat gaaaagagaa cccgctttgc gatccgcctg cccaggtaaa tgctgtttat    133380
ctgcaccctg tttttcatgt aacaggaagc aatatctgtg catgcatttg aaagcaggat    133440
attgacatta cagcccccgt tttgtataag ttgcggaata ccactttcct gaaatgagga    133500
aacggctata atcagacata gaaagggcgg tacgggatat tctttacag cagacgtaaa    133560 tccggtgccg gaaaggagga ataaaggaat ggatacattg atgatattgg gaattatcct    133620
tttcattgca ggctttatttt tgattgccat agaaatggta attcccgggt tcggagcgcc   133680
ggggatcagc ggaatcgcct gtcttattgc aggagttttc ctgactgcgg attccgtggc    133740
ggaaggagcg ttcattaccg ttattgtgct ggcgcttctg gaattatga tggcggtcat     133800 tgtgtggctg ctgtccaaag gcaagattca ctcaccgatt attctggagg aagagcagaa    133860
gaaggatgag ggctatatca gctccacgga tctggattat cttctgggaa aaagggaat    133920 tgcggagact gatttaagac ccacgggagt aggaaatttt gagggcgtta attttgatgt    133980
gatttcggaa ggaaaatata tatcaaaagg aacgaacctg gaaatcataa aggtaaacgg    134040
ttccaaatta attgtaaagg aacaatagta aaggggggctt tgtaatgagt aatataatag    134100
taatcagcat tatcggtatc atcggactgc ttattgtcct gttttttatt tttgtaccta    134160
taggtctgtg gatatcctcc ctggccgcaa atgttaaaat cagtatcttc aacctgatag    134220
gaatgaagct gcgccgcgtg gttccttccc gtatcgtcat tcctcttatc aaagcgagga    134280
aggctggact ggatctggga gtaaaccagc tggaagcaca ctatctggca ggcggaaatg    134340
tggataatgt ggtcaatgcc ctgatcgcgt cggaacgagc gggaatcgag cttccttttg    134400
aaaaagcggc tgccatcgac ctggcggggcc gtgacgttct ggaagcagta aagatgagcg    134460
taaatcccaa ggtaatcgaa accaccaatg tatcggcggt ggcaaaggat ggtatcgagc   134520
ttctggttaa ggccagagtt accgtgagag ccgatctgga acgcctggtg ggcggcgccg    134580
```

```
gagaagccac aatcctggca agaatcggtg aaggtatcgt aaccaccgtg ggttctgcca   134640
aatcccataa agaagtgctg gaaaacccgg atgacatttc aaaacgtgtg ttaagcaagg   134700
gtctggattc cggtacggct tttgaaatcc tttccattga tatcgcagat attgacgtgg   134760
gccgcaacat cggcgcccat ctccagtccc tgcaggcgga agcggataaa aatatcgccc   134820
aggccaaggc ggaggaaaga cgcgccatgg ctgttgcaaa ggaacaggaa atgcgtgcgt   134880
acgtggtgga agcggaggcg gaagttccca aagcccttgc ctatgccctg cgtgaaggaa   134940
aaatgggcgt gatggattat tatgaacttc agaatctgaa agcggatacc gatatgcgtt   135000
cgtctatttc cggaacagga atcgttgatt cggatttgac cggcgacgga aggaatgatt   135060
aggcaatgaa aaagagaagt ttgcaggaag agcttggaag gctgtccggc gtgcttatgt   135120
ccaataaatc ggcaggcagc aggtttgcgt ggaatcctta ttttcccccg ggggtatcac   135180
tcccggagga agaggcttcg gagattttct ccccggagga agaatcctca gaccctgccg   135240
tacagaaaac atggcaggaa cagcaggcac ccgggggcatt gccgggaaca gcggcaggaa   135300
caaaagggga gagccgggat agaattcctc gtccggaggc tgtgtcacag cgacggacgg   135360
ttctcaggaa agcggtagta ttaagcgaaa ttatcggcga accggtctgc agaaaaagaa   135420
aaaggaaagc atatggcaat cagggtaatc gtagtagagg atgaaagcgg aataaggaag   135480
cttcttagaa aaatcataga gcgcaacgat ggctttgaag tggccgggga atgcgataac   135540
ctggcggatg cggtgagtct tttcgccagg ctgaagccgg aggtggtctt ccttgatatt   135600
gaaatcaatg gggccagcgg cattgactgc gccaaaatca ttgcggacat ggagccaaag   135660
accaaaattg tctttgccac cgcccatgcg gagtatatgc cggaagcctt tgaggtttac   135720
gccttcgact atctggtaaa gccttttgat atcgaaagag tggatcgtac tctggcccgt   135780
atcctttccc tgaaggagca ggagccgcag gagcatccgg ataaaatcgt gcgctatgaa   135840
aaaggactgg accgcttcct tgtaaaaggc agggaaagca tgagttttgt ggatatccag   135900
gatatcgtcc tggtacagcg ggaaaacaac agcaccgtca tttacaccag acaggattcc   135960
tttaccacct cggcgggggct tggggatatc gaggcgaagc tggatccgga gctgttctta   136020
agaagccata aatcctatat tatcaatctg tccaaaatca aaaagataga accctacggg   136080
cgctggacct atatagttgc cttttaaggat ttggacaggg acgcgctgat tacggctgag   136140
aaatatgagg aaatcaaaaa aagattttcc tgaaattgtg gataaacatg aaaaagtgca   136200
gaaccgctgt ggataagata gcaatccatg cgggctgcac ttttttttgtg cggaaaccga   136260 cacatcggaa accccggagc ttaccgaagc ttctgccaga tttcctttac atcccggaac   136320
aggaaatccg gtttgatatc tccgtcttca atatctttca gagtagcttc gccggaaagc   136380
acacaaatgg catccacgcc cgcatttttg ccggtagcga tgtcagtata cagccgatct   136440
cccacaatga cggcttcccc ggctgaacag cctgtatttt tcagcacaca gtccaccata   136500
ataggctgcg gctttccgat aaagaagggc tcttgccggt tgcattttt cagcatgata   136560 ctcatggatc cgcagtcagg gataaagccg aagcttaccg gacagaccag atccgggttg   136620
gtggcaagat aaaccacatc ccgtcccagc ataatacagg tattccggat cttttccgag   136680
gtgttttccg tatcaaaacc gatgagtacg acagaagcac tctcatccgg ctctgtaacc   136740
acagaaagcc cgctttcccg aagctccgtt accaaagacc gggttcccat gcaatatacc   136800
gtctggtcgg gataatttc cctgatatac atggcggtag cctggctgga ggtgtagaaa   136860
tcttcgaaac ccgcctgaat gcccatgccc gttaccttct gcacataatc cgttacggat   136920
```

```
ttggaggaat tattggtaat gaaaatatac cttcccccgt tatcacggat ttgctgaagc   136980
aaatccaggg ttccttcaaa gatttcgttt tcattataaa tggtgccgtc catgtccagc   137040
agccacagct tttctttttt cagtatttcg gcattgcggc cattcaaatc ggttatcatc   137100
acagatcctt tcctctatta aagtttacag ttaccgtaaa cctactatat cagagcacat   137160
ccttggtggc aatgatattt acgcccgtat ccgcggcatt ttccaaaata atatcgccga   137220
tatgtacagg cgcttccacg cagatatccc tgagcgcctt cacacattcc ctatttttgc   137280
ccttggggat atcggaggct gtttttacgg aaacaacagg cagatggccg ccttttaccc   137340
tgacggtgga ggttacgata cgggtggggt tggtgcattc ctttctggcg taggcctctc   137400
cccggggaca ggtattgccg gtaaccttaa ccacatcctt gtcttccaac gtgacggtaa   137460
gggcacagcc taaagggcag ttaatacaga tgagttcacg ctgttccatt tgcttcacct   137520 cttctacct ggatcgtaat ggttttaagc cccggttggg aatgtccat ctgggacaga   137580 acatccttct ttttgagaat gacctgttcc atttctccgg gcgccagctt gttttttccgg   137640 atgcgggcta tctgccggtc atccagatat atgccgatat aacagttctt ataaatatcg   137700
cctacacgga accgcacggt gagcgtgtct tccatctggg aaggatgcag gttctgggga   137760
accgtatagc gcacgccgtt tttagcaacc agccgtactg tttcctctcc ggagggattg   137820
cggatctctc ctttgatata cagagccgca tatttgccgg cttttttccgc ctcctgggaa   137880 acatagtcca ccagatcatg gacatgaagc acatttccgc aggcaaaaac gccgggtata   137940 ctggttttcca ggctttcatt cacgtcgggg ccggaggtga cgggacacat atcaacaccc   138000 agcttttccgg acagttcgtt ttccgggatc agtcccacag aaagcagaag cgtgtcacag   138060
gggatatatt cctctgtacc cggaatgggt ttccgctttt catccacctt agccagggtc   138120
acgccctcta ctctttcctt tccgtggata tccaccacag tagtactgag cttcagggga   138180
atgccgaaat catccagaca ctgcacgata tttctctgca ggccgccgga atagggcatc   138240
agctccgcaa ccaccttgac cttcgcccct tccagggtca tacgccgggc catgataagg   138300
ccgatgtcac cggaacccag gatgacgatt tcctttcccg gcataaatcc gtccatattg   138360
acaaggcgct gggccgttcc ggcggaataa atgcccgcag gacggtagcc agggatattc   138420
agcgcccctc tcggccttttc ccggcagccc atggcgagga tgacggcttt ggcagtgagc   138480
gtcatcaagc cgtccttccg gttcatcgcc gtcactgttt tttccgaagc gtcatcggaa   138540
gcaggagaaa tatccagaac catggtgtgc agcttgcagg gaatttccaa ttccttaacc   138600
tgagtaataa aacgggctgc atattccggc ccgtcagct cctcctgaaa ggtatggagg   138660
ccgaagccgt tgtggataca ctggttcaga atgccgccca gctcgttatc ccgttccaga   138720
accaggattt tatcaatgcc gttttttacgg gcggagactg cggcagccag gcccgccggc   138780
cctcccccga taataatcaa atcataatca gccatagtaa acctttccgc atattccatg   138840
ctttatataa attccttggt ggtgccggtg agaagataag actcccctcc cgctttagtc   138900
agttccatgg gagatacctg cagctctctg gacaggattt ccattactct gggagaacag   138960
aagccggact ggcagcgtcc cattcctgcg cgggtgcggc gctttactcc atccagggat   139020
ttcgcgccca aaggcctgcg tacagcattt actatctcgc cctccgtaac catttcacag   139080
cggcagatca cattgccata agccggatcg gaggcgatga gagcggcgat ttcttccggc   139140
gtgctttccg cgacacaggg gatatccttc cgttcggaaa taaatccggt tttcttaacg   139200
gcattcagct tccctgcgat ctgctccgcc aggaaaagcc cgatgccgg agcgctggaa   139260 agtccgggag aatcgatgcc tgccgcgtta taaaagccct ccgcatcctc cgcttcgccc   139320
```

```
aggacaaaat cccccttttc ctcacaggca cgaaggcctg caaaagaagt gattgccata   139380
ttgagaggga ttttttccgc gctcagccgg gctttatcca caacctgggc aagaccttcc   139440
ccggttgtgc acacctcttc cttatcggtg atgtcttccg cagtggggcc agccaggaga   139500
tttccgtgta cggtaggagt gaccagtata cctttgccca gccgtgtggg ctgctggaag   139560
atggtatggg tcacgaaatc cccagccttt ttatccatca ggatatattc gcctttacgg   139620
ggagtgatat gcagcttatg ggcgctgacc atattgttga actgatccgc gtatacgcct   139680
gccgcattga caacacagcg ggcggcaaag tcacccttt cggtatggac cagataaccc   139740
tcagccgtcc tggtaatgtc ggtaacttct gtgttgaaat ggaaatccac gccgttcaca   139800
taagaatttt ccgccagggc aatcgtcatt ttaaaaggac agacaatacc gcctgtggga   139860
gcatagagaa cggcctttac atcaggtgac agattgggct ccagagcctt tatttcatct   139920
ccggcaacga tgcgtacatc agggactccg tttgcttcgg cccgttcccg cagctcctcc   139980
agaccgggga gattatcctc atcgaagcac aggacaaggg aaccatttct tttaaacgga   140040
aagtccagct ctttggaaag cgcatccatc atccggttgc cctgcacatt catgcgggcc   140100
tttaaagtcc ccggttcggc gtcataaccg gcatggataa tggcgctgtt tgccttggag   140160
gtcccgcagc acacatcctc ctccctttcc agaaccgccg ccttcaaatc ataccgggac   140220
agctcccttg ccgtggcaca gcctgtaaca cccgcgccga ttacaattac atccagcata   140280
ttttcctcca ttctgccgca caggcggcgt aagccaggta acaaaatcat atattataag   140340
aaaaagacag ccaaaaaaca catacccgac ggtacgtcct ttttgctgtc tcttttctc    140400 ctgcaaatac aatattcggt tatataagga aaccggaagc ggtcacatga accagacctg   140460
ccggtttgtt gttgaaatgg atatggcgcc tgcattcagg gcggccatga tatcttcccg   140520
atccgttatc agcccgccgg caatgaccgg gattctgctt tccgtgcaga tacgccgtat   140580
caccttgggc ataagcccgg gcagaacttc tatgatatcc ggatgtacgg attccgactg   140640
cctgcggata ttatcgaagg ccatggaatc aatggcaaaa aaacgcatca cggtaaagag   140700
attacattcc ttagcctgtc ggatgagagc cggttttgtg gatataatgc cgtcggcatc   140760
cgtggtattg cggataaagg taacggcgat ttcctttccg gacagcccgg atatcaaatc   140820
cagatgtacg attaccgttt tccccgcatc cttcagcctc ttcacaattc ctgaaatgct   140880
gcagatgtct ccgaagagga caaatacgat tcctatttcg gaatcaatac aggccttaag   140940
cccctcttca tcttttacag cagcgattac aggacagtcc tcaaactgtt ccataagtaa   141000
tttattcata ggaaaccctc tggaactta ttttagcata gtgaagtggg gaacgcaaga    141060
gctacatagt gggggagata aaaaacatcg ttgccgcctc tggcctgcgt taccctcccg   141120
gctgtgtccc ttgcctgtgt ctgccccgct ggctctggtg tccttggtgc cctccctta    141180 cggccgcagc acagcaaggt tccttgcagg ggacgcttcc gctcggataa tcacgcagcg   141240
gtactaaggc tgcaaaatac gcagcctaag gaccggcgtg tttataacgc cccttacagg   141300
aatccttgct gtgctgcggc cgtaaaggga gggcaccaag gacaccaggg gcagcggggc   141360
agacacaggc aagggacaca gccgggaggg taacgcaggc cagaggcggc aacgatgttt   141420
tttatagaca ctcttgaata agtgttgcca aatcagaatt tttattggca ctttcagccg   141480
gtattcattg acagggaggg gcttatgaaa tacgataaag aaaattgggt tttcttttgg   141540
gaaagggata agggttcgga tgcaggaaca gttgggaaag cggtacgta agcgataaa     141600 tattttgatt ggattgatgg ttgtggttgc cgcggccgtc ttttttgtcg tggggaatca   141660
```

```
atccggattg gagaatactg cagttgactt cggaaatacg gaggatttca gccggggggtg   141720
gtattatgag gaaaacgggc aggtaaaata cgtagaggaa ttgccttttta ctgcggaagc   141780
ggatgagatg atattttacc ataaactgcc agactccggg gaggagccgg tggttcttag   141840
cttcaggaac aggcagcaga aggtgacggt ccgggttggg gagaaatgcg tctatcagta   141900
tggcggcagc agtccgctgc ggggcagtct tcttccttcg atccaatgct ttgtttcgtt   141960
gggaatccag gacggtacgg aaacggctgt aatacaaatc gaaggaccg tgggtaaaaa    142020
aataatgctc tccgaaataa ggctgggaag ccaggggggcc gtcctgatgg gattttttcag  142080
ggagagctgg ggaattattt ttttcggcgt gcttatggtg gtattttcaa tgggattgct    142140
ggccggggga cttgttctgc gcatcaggag cggatataca gaatactcca tgtttctttc    142200
cgccggaatg tttgtactgc tgtcctcgct gtgggtgctt tcggattcac cggtcatgca    142260
gctgctgaca ggcagctccg aggttgtttt tatcgtctct tttttatgct ttatggtctt    142320
tcctatcccc atgtttttct ttgtggagag tatttgtgaa aagaaataca ggggattgtc    142380
tgtcttaaag cttttgttca gctttaattt ttttatccag gtattttat atatggctgc     142440
gggagtggaa ttctataaaa tgcttccgat cactcatatt ctgatagctg catccattat    142500
cttcactatt tactgtctgg gtaaggagtg tcggagaaac cggtcgtttt atgcgaggga    142560
aatccttatt gcccttttta ttttatggc aacggcattt ttatccttag ctgattttta     142620
tagtaacagg aaggattaca gcgtaattat gcggcttggg ctgctggcgt acgcattgat    142680
tttgatagtc atatccttca gaaagctcat cctttcagga gaggaacggg caaagctcaa    142740
ggtatacaga tccctggcct atgtggatat catgacgggg tgcaataaca gggcggcttt    142800
cgaaaaagcc ctggaaatcc tgagagccag agaggaagag tctgaattgg cgggaatggc    142860
catgattgat ttggatgggc tgaagagggt aaatgatacc tatggacaca gcatggggga    142920
tgaaatgatt ataggagccg gagacagcat aaagaaagca tttgccggca ggggagaatg    142980
tttttcgtatc ggcggggatg aattcacggt aatcctgaag gataaaaaac tgcaggaaaa   143040
ggaatacagg aggcttctgg aggaaatggt atcggcctat aacgactatc atgaaatacc    143100
catccggctg tcctgcgggct ttgccctgct cggaaccgaa aaaagagatg tggatgccct   143160
gtataaggaa gcagaccgga atatgtatcg tgaaaaacag aaaacaaagg ataaaaggta    143220
agggttcaga cctgtccggg ctgttacaaa aaaaagcttg acccttcccc gcaggggagg    143280
gcttatactt cttttaacag gaaaggagga gccgccggtg tacaaaatag gagagttttc    143340
caaaataacc agtctgacca taaaagcgct tcgttattat gaggaacagg ggattttgtg    143400
cccatcggag cgggataaga acggctacag gctgtataac gatcaggatt atgaaagggc    143460
gaggctgata gccctgcttc gcggactgga tttctccatt atggagatca gggatgttat    143520
ttccaattat gggggagaag aggatttgtc ctatttcctg aaagaaaagc aggcgcagat    143580
actgaacgg attgccggag aaaaggcgct tttgaagaag ctggaagaag ccctgccggg    143640
aggatctgcc gcagggatta tcaggcagga atacgacatc gtgataaagg aaatagagga    143700
aatgatagtg gtatccaccc gtttccgcgg agcctattcc gatgtgggca agtatatagg    143760
cagcctttat aaagcggcgg gaaataagtc cttcggctgt cccttcagcc tgtattacga    143820
tgaggaatac agggaagatg cggatgtgga gctgtgcgtt ccggtaaagg gtatggttca    143880
ggcgtcagga atcagctgcc gtaagctgcc gggctgcaga accataagta cgatccataa    143940
aggcggctat gatgagctgg gatttgcata taaggcgctt ctggatgcag cctatgaaag    144000
gaatcttcag cccgtatccc cctcaagaga gatttacaga aagggaccgg gacttatatt    144060
```

```
ccgcggaaac ccctctaact atgttacgga actcatgatt cccgtaaggg aaatggatat    144120
tccgatgcag gaacagaaag gataaatgat ggcagaacag aaatttgatt ttaagaagga    144180
atttaaaaac atttatttac agaaaaccca gccggtgatc gtggaagtcc ctcccatgac    144240
ttatctttgc gtggacggga aaggaaatcc caataccact caggaatata aggacgcgct    144300
ggcgattctg tacggactgt cctataccat aaaaatgagc aaaatggacg gaacccagcc    144360
ggtaggctat ttcgattatg tggttccccc tctggaaggg ctgtggtgga tggaaaacgg    144420
agaaggcttc gacgggatcc atatcacgga taagacccgg ttctgctgga cctccatgat    144480
cggcctccct tcctttgtca atgaaggat cctggaacag gccaaagaaa agctgcataa    144540
aaagaatccg gagctggatc tttcccgtgc ccatatggaa ataatggagg aaggtctttg    144600
cgcccagatc atgcaccttg gatcttacga tgacgagccc ggcaccatac tgcagatgaa    144660
ggagtttctg gaaaggaag gatatataac cgatataaat gaaaaagaa ggcatcatga    144720 aatctatttt aatgatccca gaaaaaccgc gccggagaaa ttaaagacga taatccggca    144780
tcccgtcaga aagtataat aaagaaaacc ggttcagagg cttttttatgg ccctggaccg    144840 gttttttagtt taaaaaagga attttcgtaa tgcgttctct tgatctgacg attatgccgg    144900
atttaattta tatcaggcac cacagagacg gcatctccgt aacctaaatc aaccgtccat    144960
gccccactcg atttgacctc taaatagcat gtggtatttt ccgggttacg caatactttc    145020
tgtcctgaat aatcaccaat cgtatttgct aacaactggc ttttttccatt ggaataatgg    145080 gcatatacta taaaattgct ttttccggta tagttcatgg taacagtggt gttcgtgccg    145140
ggcagaatga aaagcccgga gaccttatag cctgtacccg ataaagattt tgttgaaata    145200
ttcgtaatag ttgacacagt aagagtccag ttgccgctgg cgattatttc aaaaataccg    145260
gtccgtgccg ctgtgcttcc tcttttccaaa agggatgttc ctgcaaaaac accaatcgta    145320
ttggcaagaa gatttgactt gtctccattg taaaacttaa caataaaatt cctgtttcca    145380
tcatgtgtga gcgaaacctt ataagcagat ccttcaggaa gcaccacatc cggaataact    145440
gtgtcgcctg ttccggcata ctgaagaacc ggtacggcat acggaacgga tgtatcgctg    145500
aaatcggtac gcacagtaac aagggaagcg ggagacgccg cctgaattgg ctgcgttatt    145560
ccgcaaagca taatgcacga cagcatgaga acaaatattt ttcttgctct tttcatataa    145620
aaatacctcc catttaaata atattacctg ataccgctat tatagcacat atgaaaaagt    145680
attacagtaa tcaaaaaaca ggaggaaaag agagaagaca gaactgacgt aaatggaaac    145740
ggataaaaat agaaaaatca caaaaaaaag caccaacccc gaagctctgg atgtcttcaa    145800
aatcggtact ttcaaagtgc gccttcaggg gctcgaaccc tggacaccct gattaagagt    145860
caggtgctct accaactgag ctaaaggcgc ttaaattttc ttttgcaacg caggattcat    145920
tatattatat taattttcat tttgcaatag ttttttaaaa aaattttaag aaattttttat    145980 caacctttaa gaatagtaaa aaatatgata tgatccctat tgttttcaca gatttgctga    146040
tagaaagggg taagaggtgt tataatgatt tttgacagtc atgcccatta cgatgataaa    146100
gcctttgatg aagatcggga acagcttttg ggaagctttc cggaaaaagg gatcggttac    146160
gtggtgaacg cgggagccag cttcgattcc aatgaaagag gacttgagct tacgaaagaa    146220
tatccgtttt tgtatgctgc cgtgggaatc catcccgagc atgctcatac gctggatgat    146280
gcgggccttg aatggctccg cagccggttt tcggatccca aagcagttgc tgtgggagaa    146340
atcggcctgg attactattg ggacgagcct gcccgggata tacagaaaga ggcattcagc    146400
```

```
cgtcagatgg ccctggcaaa agaaatcggc aggccggtta tcattcattc cagggatgcg    146460
gcaaaggata ccctggatat gatgcgtgaa gaatatggaa aggacagacc tgccgtcatt    146520
cactgttttt cctatgcaaa ggagaccgcc agacagttcc tggatttggg atatatgatt    146580 ggataggcg gagtggtcac ttttaaaaat gcccgaaagg tgaaggaaac ggtggaatac    146640
gttcccatgg acaggctgct tctggaaacg gactgcccct acctggcgcc ggagcctcac    146700
agaggaacgc gcaacagttc cctgaacctt cccettgtag ctgcacagat tgcgactctg    146760
aaagggatat ccgaagagga agtgacggaa ataacctttc ggaatgcgaa acgcttttat    146820
ggaatcgact agaatctacg gaggatttat atgccaagat taggtacgcc cacaggaaca    146880
attgaagtac tgcataaata taattttaat tttcagaaaa aattcggaca gaatttcctg    146940
atagaaccca aagtgctgga aaccatagtg gaggccgcgg aaataggaga agaggactgt    147000
gtgctggaaa tagggccggg catcggcact atgacccagt atctggcaga gcaggccggg    147060
gaagtggtag ctgtgaaaat cgacaaggct ttgattccca tactgaagga taccctgtcg    147120
gcttattcca atgttacgat tatcaacgca gatatcctga agctggatat ggaggagctg    147180
gtaagggaaa agaacggagg gaagccggtt aaggtggtgg cgaatcttcc ctattacatc    147240
acgaccccca taatcatgca gctgtttgaa agccatgtcc ctctggaaag catcaccatc    147300
atggtgcaga ccgaggttgc ggagaggatg caggtggggc cgggaaccaa ggactacggc    147360
gccctttccc tagcggtaca gtattactcc aggccgaaaa ttgtcaccca tgtcccgccg    147420
tcctgcttca tgcccagacc caatgtggga agcaccgtca ttcgtcttaa cagatatgaa    147480
aagcccccgg tggaaacagc ggatgaagaa tttatgttca aactgatccg tgcgtccttc    147540
aaccagcgca gaaaaacgct tgtgaacgga ctgagcaatg cgtccggcct gaatcttacg    147600
aaggaggagg tcacggatgc attggaaaaa atgggactgc ctgccacgat acgcggggaa    147660
accttcaccc tggaacaatt tgcccgtctt ggcagccttt tatataaggg agggccggca    147720
tgattgaagc gattgttttt gatatggacg gcattctgtt cgatacgaaa aggctcagtg    147780
tggaaagctg gatcgaagtg gcaaagcggc tggggcttcc ggatattgat aagggagtat    147840
atggctgtat cggcctgaac cgcacggact gccgtatttt tctaaaagaa acctatggtc    147900
aggatttccc ctatgattat ttcagagaac agacagcagc cgttttttcag cggaagatgg    147960 caaaggacgg ccttcctgtt atgaaaggcg cgggagagct tcttgcatgg ctgcaggaaa    148020
aagggttaaa ggtggcactg gcctcctcca caagccataa aacggtggaa agccatctgc    148080
agcaggccgg gttaccggaa tttttccagg cggttatcgg cggggacatg gtggagcaca    148140
gcaagcccca gcccgatatt tacctgaagg cctgtcagct gcttgatgtg aaccgggca    148200 atgcggcagc catagaggat tctcccaacg gaatacgatc cgcatatgcg gcagggatgc    148260
tgcctgttat ggtgccggat ctggtgaagc ccgatccgga aatagagaaa atgctttacc    148320
ggaaatgcga cagtcttttt gctgttctgg aatttctgga agaaaaggat aaaaaaggtg    148380
aattatatca gccccgcatc taaaacgccg gctgaaagca gggagcggcg gataaggcat    148440
gtaccgggaa agcttttttcg gacagccgga ggtatagcgg gtccgttacg ggctgataat    148500
atggataacg gacagagcac agattttatt ttgaaaggag gtaatgcatg aaacaggcat    148560
taatatgggc gtccggcggg accggtttta catttctgat gaccacatta ggcgccgcca    148620
tggtattttt attccgcggc aaaataaata tgaaaataca gagggttttc ctgggattcg    148680
cggcgggagt catgattgcc gcttccgtat ggtcccttct cattcctgcc attgacgaag    148740
cggaggcggc aggaggtgtg gggtggatac ctgcggcggg aggatttgtc ctcggtattt    148800
```

```
tatttcttttt gctgatggat cagctgcttc cccatctcca cgcgggttcg gatgaaccgg  148860
agggtatttc gtcctcctgg aaaagaacga ctctgctggt tatggcggtc actctccata  148920
acattccgga aggaatggca gtggggctgg cgtttgccat ggcggcgcag aacatggggg  148980
ctgaggccgg tgcggcggca gcgttcgctc ttgccctggg aatcggtatc cagaacttcc  149040
cggaaggagc ggcgatatcc ctgccttaaa agcaggaagg gatgccttcc tggaaagcgt  149100
ttgtttacgg cagcctttcc ggaattgtgg aaccgatttt cggtattctg gttgttctga  149160
ttgccggagg aatccagccg cttatgccct ggcttctcag cttttgcggcc ggcgccatga  149220 tgtatgtggt agtggaggag ctcattcctg aagctcatct gggggagcat tccaatgtag  149280
gcaccctggg ggttatggga ggtttccta ttatgatgat tttagacgta gcattaggat  149340
aataacttaa atttcgcaca gacccctgtc ccctccggcc tctgctttcg gggcggctcc  149400
ccggtttgga tttccttccc tctgcgccag ccatgcagga atccttaaag gggacgctct  149460
cactcgtata aacacgcagc ggtcctaagg ccgcaaaaaa cgcggcctaa ggaccggcga  149520
gtttatacgc cccttacagg aaatcctgca tggctggcgc agagggaagg aaatccaaac  149580
cggggagccg ccccgaaagc aggggccgga gggacaggg ccctgtgcga aatttaggat  149640
aataatttaa ggagggaaaa gacatggaaa aatcaaaggt ttatttcaca acaatgaaga  149700
cttccttttc tgagaatctt cctcagaagc tgggagcgtct catcaaaacg gcaggtattg  149760
gcaatatcga ttttaccgat aaatatgccg ccatcaaaat gcacttcggt gagccgggga  149820
atctggcctt tttaaggccc aattatgccg ccgtagtggt taaggttatt aaggaactgg  149880
gggggaaacc gttccttacg gactgcaata cgctgtatgt gggaggaagg aaaaatgccc  149940
tggatcatat tgacgcggca taccagaatg gcttttctcc cttttccaca ggctgtcatg  150000
taatcattgc cgatggatta aagggtacgg atgaagaact ggtaccggta gaaggcggcg  150060
aatatgtaaa agaagcgaaa ataggacgcg ctattatgga tgcggatgtt ttcatcacac  150120
tcagccattt caagggccat gaagccaccg gtttcggcgg agcgctgaaa aacatcggca  150180
tgggctgcgg ttcccgtgcc ggtaagatgg aaatgcacaa tgcaggaaag ccctatgtgg  150240
agcaggagaa ctgtatcggc tgcggacgct gtattaaaat ctgtgcccat gacgcgcctt  150300
ccattaccaa tggaaaagcg tccattgatc acaagaaatg tgtgggctgc ggacgttgta  150360
tcggtgtgtg tccaaagat gcggtatgca ctcccgggga tgaaagtaat gatatcctga  150420
accgcaaaat tgccgaatac agcaaggctg tggtttccgg ccgtcctcat ttccatatca  150480
gcctggtggt ggatgtttcc cctaactgtg actgccattc tgaaaatgat attcctatcg  150540
tacccgatgt gggaatgttt gcttccttcg atcccgttgc tctggatgtg catgcgcgg  150600 atgctgtaaa taagcagcct gttatcgacg gaagccagct ggatcgtatg cctcatgtgc  150660
atcatgatca tttcattgat tccgcaccgg ataccaattg gcattcctgt atcgagcatg  150720
gagtaaagat cgggctgggc agtgatcagt atgaattaat cgagatctga cggcagtaca  150780
taatcattca aaaagttcc ggacaggctg cttataggcc tgtccggaac tttttactc  150840 cggcagaata tttttatttg ataacggcaa agccgccggg caaaagctgc ctgctttcca  150900
gcctgcgtga caaaagaaca cagccctccg gtacctctgt gcaggtgctg cctgcgttaa  150960
tgcatacggt aagtgaccgg ttatcctcct gcctgcggta agtgatcacc cgcgaattcg  151020
gttccggatc ggagaaaaca agaccgggac agcggcagag cggctcctgc ctgcgcagcc  151080
ggatgagcgc cttcaccata tcgcaggttt cctgataagc cccgctttcg atggcatccc  151140
```

-continued

```
agggcatgca cctgcggcag tccggatccg gccctccctc catggcgatc tcggttccat 151200
aaaagataca ggggcttccg ggcatggtat aaaggataca cagggcctgg aaaaaggaat 151260
cctcatccgg aagtttggtc ctcaggcggg ccgtatcatg ggaatccaga aggttgaaaa 151320
gaacctgatt ggtctgctcc atgtacatgc tgtagcattt gttgatccgg tactggaaat 151380
tcctgctgtc cgtttctttg tcccggaaga aattcatgac ggcattgtga aagggataat 151440
tcatgacaga atcaaactca tccccccctca gccatcgcat ggaatcctgc cagatttcac 151500
ccaggatata aaagtccggg cgcagggcct tcagacgcga ccgcaatgtc ctgcagaatt 151560
tatgggaaat ctcatgggcc acatccagcc gcagcccgtc aataccgaat tcttttatcc 151620
aatattcgca ggtttccgcc agatattccg caacctcatc attattggta ttcagctttg 151680
gcataaaagc cgtgaaatgg aaggaataat acttttttgtc gtaggtccag ggatccgttt 151740
gatcaaaggg ccatttattt accataaacc aattccagta agcggattcc gggccttttt 151800
ccagaacgtc ctgccaatag ggaaataat agccgcaatg attgaatacg ccgtccagca 151860
tgattcgtat acccgcttta tgggccgtat ccactaattc acgaaaatcc tcctccgttc 151920
caaaagcggg atcgatcttc cgatagtccg tggtatcgta tttatgggtg gtggaagctt 151980
caaaaacagg ggtcagatag ataccccgtaa tgcccaggtc tgccagataa ccgattttcg 152040
atgtgattcc cgggatatcc ccgccataaa actcatcatt tgtcacgctc ccctccgccc 152100
agggaagaat attcttttttg ggcagagaag ccttttttatt acagaagcgt tccggaagaa 152160
tctgatacca tacggtatcc ttcacccaat ccggcgtcac attgatatcc gcaggattca 152220
tccagggaaa agaaaatac tgcagcctta cattgcctgt cataaaggaa ccgtctgttc 152280
ggacccatc ctccagatag taacaggttt catccccgct cctgagctca aagaaataac 152340
cgcagcgttt ataaggagga aaaccgata tagtccacca tttgtggttt tccagttccc 152400
ttacctgcag catctcctca ggatgcccct tccacgtcca gggcccgccg aattcttccg 152460
actccatggg atcttcataa ttcaggaaaa cccgatccac ctccttttccg gtctggattt 152520
gtatcaccag ttccgattca tttttagcgt agcacatatt atcctggctt ctgtgataaa 152580
tacaacctaa attcatatgc aaacctcccc gattaaaaat aaatttgtaa atgttcagta 152640
ccttcacagt tacataaaat tctctatatc atgctaccat atgacgtttt ggagatatat 152700
caaatatatt actatctgta tatagaaatc tgtacaacat attaaaatat atacaaagta 152760
tataatggat attttttcaaa aaaagtaaaa acagtaatat tgattaggaa ataaatctta 152820
tataggcatc atgctataaa atgttactat gtacctgcag aaaaaaatctg ttaataaaag 152880
gaggaaatca ggtatgaaga aaaaagctgt ttcagtattg ctggcaattt ccatgctcgc 152940
agcaggaatg atgggctgcg gaaaacaggc tgccacggac agcacagggg ctgcggcgga 153000
aacaccggcc gcacaggctt ccgaaagtaa ggaggctgcg gatacagggg cttcatccgg 153060
cgctgtggaa attgaatttg taaaccagaa gagggaggct gcagatacct tccaggcagt 153120
gattgataag ttcagcgaac aaaacccgga tatcaaggta acgctgaata ccacccctga 153180
cggaagcggc gtgctcatga ccagagccag cagtgacaca ctgccggaca tccttatgca 153240
ctggcccaca gacgcacagt tcgtacagtt tgccaatgaa ggccttctgg ctgacttatc 153300
gggaaaagat tatacaggaa atatcgtaca gtcttatatc gaggatttga aaatggaaga 153360
cggggggcatt tattgtctgc ctatttccct gaactttatg ggtgtttact ataatgttga 153420
taaattcacc gaagccggct tttccgttcc ccagacctgg gacgaactga tcgcgctgtg 153480
tgataagatc gtggaaaaag gcgaagttcc cttcctcctt cccaataagg attcctggac 153540
```

```
cgtttcccag ctttgggaca atatcggcgg gaaagacaga ggcggatatg ctgatttta  153600 cgccggtctg gacgatggca gccagtctta tgccgcagat gcaatcgcca atgactccat  153660
ggaaaaaatg gttctgttaa ccgaaaagta ttcccagggg gatacgctgt ccctcggcta  153720
tgatcaggcg attaacgatt ttgcaaccgg agcagcctac atgtttatcc agggcagctg  153780
ggctcttccc tctatccagg cagccaatcc cgacgccaat gtggaaatgt tccccatgcc  153840
caacaatagc ggagacatga agcagccggt aggcgttgac tgcgcgatct gtgtcagcgc  153900
aaaggcagcc gcggatcctg caaaatcaga agcggtggat aaatttatgg cctatctttt  153960
ctccacggaa gcaggacaga tgtattcgga tatggatcat tctccttccg caatcacagg  154020
cgtgacggca gatattcccc aggataagct tgtacttgac ctgattgaca aggcgggcgt  154080
cctggatctg gcggtacctc ctaccggatt tgaagatacc aagcgttctg aaatccagaa  154140
tgtattcatg ggaacctccg ttcctgattt cctttcccag ctggatgaag actggaaaac  154200
cgcaagagag gcagaagcgc agtaacttgc aatagtctgt ccggggacag gcagtaaaca  154260
aaggctgccc acactctgtg ggccggcttt tgtccaagaa agacgggcag ggtgcgcata  154320
tcctgtccgt tttcaggtaa ggagaagaga gctatggata agaaaaaaaa gaaatatcc   154380 gaaagaacca gaacgctgtt cctgtttact ttgccgtctg tggtgatgta tactgttttt  154440
tttaccgtta cgatggctat cggcatttat tacagcttta ccgactggaa cggcatcagt  154500
gcgtcgtata aaatcatcgg tatcggaaat tacataaaag cgctgatgga ccgtaaattc  154560
caggctgccc tgaagtttaa ctttgtatac accttcctgt tcgtgctgat cctgattgtc  154620
atttccctgc tggtggcaat atgcctgaat aacctcacga agacatccac aatattccga  154680
tccatttatt ccttcccgc cgtgctttcc atggttacgg taggactgat atggaatgag  154740
ctgttctaca gagccctgcc cgtcatcggc aaggcgctga atataggctg gctttccaac  154800
agccttctgg gaaataaaac gaccgccatg ttcggcattc tgatcgtaaa cctgtggcag  154860
ggctgctcca ttcccattgt cctcttcctg gcagggctcc agagcgtacc atcggagctt  154920
tatgaggcgg cgaccattga cggagccaac cggtgggata aattcaaaag cataacattc  154980
cccttcctga taccggtgct gaatatggtt attatcaccc aggtgaaggc cgggctgacc  155040
attttcgatt atattatggc aatgaccaac ggagggccgg gaggcgccac acaggcggta  155100
ggtatattga tttacaacca ggcgatgaaa gggaacgcct acagccaatc cgtagccgag  155160
tccatgatct tgtttgttat tgtggccatt gtggctgccg ttaccttaaa aatgactaag  155220
aataaacagg taggtgatta gtatgggaaa atcaatatca tccagaattg cgaaagtagt  155280
tacagggctt gtcctgctca tcggcgcggt tattatcttg tttcccatgt atatcacgat  155340
aataacctct cttaagacac agcaggaatc cgccgccgat ttcttctccc tcccttcctc  155400
cttttacctg gggaattta tcagtgtatt tgagaaaagc gggtattgga catatgtgtg  155460
gaattctgcc aaaataacaa tcatatccgt cgtgctgatt ctggttttca tccccatgtg  155520
cgcttatgca atcgcccgca aaatggagga aaacaaatat tttaaaacta tctatttta   155580 tctgctcctg gggattttg tgcctttca ggttatcatg gttccgctgg tgcagtatct   155640
gactaaaatg aagcttttaa accagacagg gctgatctgt atgtgcctct ccctcgcttc  155700
ctcccaggga gtcttcctcc ttgccaatta tgtgaaaagc gttccccggg atctggagga  155760
agcggcctct attgacggct gtaccacctt ttccgcttat tggagggtag tccttccgtt  155820
aataaagcct atggtagcga ccatctttgt catgaatgcc ctgtgggtat ggaacgattt  155880
```

```
ccagatgccc ctgctgattc tgaaccagca gccgggtatg tggaccctgc ccctgttcca    155940
gtataacttt aaatcacaat ataccttga ttacaatctg gccttcgcct cttatctggt    156000
tgcaatgctt ccggtaatca ttgcctatat ttgtgcccag aaatacattg tcgcagggct    156060
tacccagggg gcggtaaaaa cctgaggcag cagatttaca gaattggtga aaggcctgcc    156120
gtccggggaa attgcaggaa ggagcagata tggctggaaa acaggggatt tacgaaaaat    156180
gggtgaaggg acgagaaga aaatccgtcc gtctggaggt actcaccata ttcctgatct    156240
ttatcgtcat catcatgggc gtgagcctta tgatctataa ccagaatatc agtgaactgc    156300
ggcaggctga catcaatcat cttacggaaa gcagcaagca gctggcctat tccgtggact    156360
ccattatcct ggatgtggga agcctgttca acctgcacta tcaggatcag aggatgtgca    156420
atattatcaa ccacagcaaa agccagtatg atgaggtgac ccgtttccag aataccactt    156480
atgtggaggg aaccatcaat catgtggttt ccaacagtaa atatatcaaa cgctgctgta    156540
tcttttcggc aaacggagat gtatacagca atatcagctc cgttttttcag gattataagg    156600 attatatatg ggggattgtt gacagcggga agctgggccg cagcattttt tatacggatc    156660
cggagatttg gagcatcggt caggtggatt ataaggtggt aacggctgtc aaggtgctgt    156720
acagctataa cggaaccctcc cctctggcct atgtgacact ggatatcggc tattcggagc    156780
ttgaccgcct cctcaattcc acggataacc ccgccggcac cctgctgttt tttgaggaca    156840
tgcagattta caacaacagg aaaggcggat tatacgggga acagcttacc gaggtgcagg    156900
aaaaagcaaa gcagatggta aatgacggcc atgaacagga tattcttcgg atcgacgggc    156960
tggattatct gatgaccgct atccgcagcg aaagctcggg ctggacggtg gtgcgctaca    157020
ttgctgagaa agaggccctc cgttccataa cggagcacaa aatcagggat attaccgtgc    157080
ttctggtcac aacggcggta gtctttatga tctattacta caggattaaa cagataatgg    157140 aaccctggc taaatggat gaagtgatcc ggcataataa aggcacttcc cttcaaaagg    157200
tgtatttatc cagggaggat gagtggctgc tgggaaataa tgaaatccgg aacgtgatac    157260
aaaattataa cagcatggca gaacgtatca atgaatatgc caggaaaacc cttctctatg    157320
aaattgagca gaaggaagcg cagatcaaaa tgctgaccta ccagatcaac ccgcattttc    157380
tatataatac gctgaatacc ataagcgcta ttgcggaaat agaaaacatg gaaaatattg    157440
tggaaattac ggacagcatt tccaacatat tccgctacaa tctgaagggt gactccatcg    157500
ttacgctccg ggaggaaatc ggccatgtaa aggactatgt acagattcaa aaataccgtt    157560
tccctgacca gtttgagatg atttatgaaa ttccggaaga aatttattcc atgaaggtca    157620
tgaaattcat tctgcagcct ctggtggaga acagtatatc ccatggactg tttgataagc    157680
cggaaggagg gcagataaca atcagcgcag cgcttacaga agaggagac atgcttctta    157740 cggtttcgga caacggaata gggattaaca aaaagcagct ggaggaaatg aaccaaaagc    157800
tgtttgaata cagggtaaac atgaattccg gaaaggattt cggcggggac ggaatcggca    157860
ttattaatgt aaatgcccgt gtgtccggtt attatggcaa ggaatacgga atcaccctgt    157920
atagcgaata tggccggtgg acccgggctg tcctgaggat aaaggcgctg cgcgacgagg    157980
agcctgagac cggccgggcg ggagaaacaa tatgaaaata ctgattgccg aggatgaata    158040
ttatgccagg cagaggctga taaagatcat cagggaatgt gacatggagg cggagctggc    158100
ttccgctgtg gaaaacggca gggaagcggt ggattttctg gaacagaata cggatgtgga    158160
tgtggtgctg acagacatta tcatgccaag gatgaacggc ctggagctgg cggaatatat    158220
ccatgtgaac atgccttata tacaggtggt tattgtatcc ggttatgaag aatttgatta    158280
```

```
tgccaggaag gctatcgaat acgaggtaaa gcaatacatt atcaagccgg tcaaaaggga   158340
gctgcttctg cgcgttctcc gtcagctgga ggaaaaacag gaaaacttcc gccgggaggt   158400
ggaggccggc gtgctggaaa ggctgaagaa gcttcccaac ggctataccT cgtccaagca   158460
ggtgctcacg aaaaaagaac tgatgcagat ccatatgccg caggctgcgg cgatgtccgg   158520
ggaaacaccc tgccgggtat tcgtcataca gctggagcgg acaatgaata cccgggatgc   158580
agggctcctg gacaaaatct gtgcccagaa actggacagc cggcttgccg gtaccttttt   158640
ctgtcagatg aatgatgaat atgtggcggc ggtcaggaca gaggaggatt cggaaggaag   158700
cgcgctgttc cgtgatctgg agggaatcct gaattactgc catgtacagc ttgagacggg   158760
agtggttgca gggatgagcc ggctttttta tggaacggcg agtatttatg atgcatataa   158820
agagtgtctg tacgccatga atatccgtct gatgaaaggc tggaataaga tatttgaata   158880
ccagcttccc catggcggaa acaattattt ccttccccgg gatgacaatg cccttgccgg   158940
cgcacttcag ctttccgatg ccgcaaaggc ggctgagctg gtgcacgcc tgctgaataa   159000 gcgggaaatg ttggaaagcg gagacgtgaa tgcctattac gacatgatat tgaacattct   159060
gcgcagcgtg aaccggtatt atcgttcttt atacaatgaa aatgaggcga tggactgcaa   159120
ggtggaaatc atgttttcac gcagatatga tctatatgtt ttcaagcatc cggaagagct   159180
ggaagaatat ttgatggata ttatccgtga aatctgcgat caggagcaaa attccctgaa   159240 aaacgggga aatgccataa tacgggatat ccttcattac gtggaacaga attaccagta   159300
tgatcttccc ctgcaggagc tggcggaaaa aaagtatttt atgaattcgt cttacctcag   159360
ccgtctgttc aaaagcgccg tgggacagac gttttcccga tatgtcatcg agcttcgtat   159420
taagaaggcc agggagctgc tgaaggataa aaccatgaaa atcaatgatg tcgccgcaca   159480
ggtgggctat aataacacgt cccatttat tcagtctttt aagaaactgt gcggctgtac   159540
tccggaggaa taccggaacc aactataact atttcgggag gttatctgat gaataagaaa   159600
gtagaagtga gctataaccc gcagctgggg tatctgaaaa cgatattcac ccataatttt   159660
gatttcctca caggtgtcct cggctatacc gaccggggag acggggtgga ggtgaagcg   159720 ggtacatacc ggaataaaac cgcaaaggtg atcatccgcc ctgtaagtgc agcggcatac   159780
cgtttccaga tgtatcctta tggaaaggaa ccagcggctg ccaatgaggt ttttttccatg   159840 gaacagacag ttccctatca ggtggaagag acggaagaat acctgtccgt ccgcactctg   159900
cgcatggaaa tccggataaa aaaactaccc tgggaggtaa gcacatatct ggacggcaga   159960
ctgcttacga aggaacagat cagagactcc aatgtggaca atatgtgcaa gtatcttccc   160020
atcggctttg actgtgacga agaaggaaag gtgatccgcg tccgggagag catgtacatg   160080
tattccgatg aggcctttta cggcttcggg gaaaagttca ccgaattcaa taaaagaggg   160140
cagaaaatcc actgctggca gaaagatgcc ctgagcacca acacggagga ttcctataag   160200
aaccatccct attttatgag cagcagaggg tattccgttc tggtgaacag ctataccaga   160260
atgacctttg atatggggtg cggctccaat gttacctacg gcatggaggt ggatgacagt   160320
tccctggatt atatcctgtt tgccgacagg gattataagg atctcctggc ggattatgta   160380
aacatgaccg gcagcatacc catgatacCC aggtgggcct ttgggctgtg gatgtccaaa   160440
tgtgtctaca aggatcagga ggaagtggta caggtagtaa agagggcaaa agaagaagag   160500
attgccatag atgtgattaa cctggatgcg tggcaggcat cggaggacag cggcgcatgg   160560
gtatgggaca ggaagcgttt tccggatccg gaaggcatga taacgtttct tctggaaaac   160620
```

```
cggatccacc tgtgcctgtg gatatatcct tatatcggag aagaatccga atacttccgc    160680
ctggccgggg agaagggatg gctggtgaag gacgggaacg ggaatcctct gaccttctat    160740
gcaaccgcgg ctgcagatcg caaggtagga tgctttgatt ttaccaatcc cggtttcagg    160800
gaatggtatt ttcccagggt aaaagaagtg attggaatgg gaatcggcgc ggtaaaaacg    160860 gattttccg aagcggttcc ggaaaacgcg gtttattatg acggctcaaa cggcttacag     160920
ggacacaata aactgaccta tctgtatgcg aaaaccatat atgaggcgat gaaggaggta    160980 aaggaaccc tgggagaacg tcccatgctc tggggaagaa gcggttatgc gggaagccat     161040
accattccgg cagcctgggc cggagattcc tccacccatc tgaataacca tgcctgcatc    161100
ctgcagggag ggctcagtat tgctttgagc ggcgttgcct attggggctt tgacatgggc    161160
ggcttttata atacggatca tgaaggctat gaatgcgtac ctgaagagga agaatatatc    161220
cgttccacac aattcggttt cttttcctct ctgagcaggt gccatgggaa aacacccagg    161280 gaacctgga attttgcacc ggaaaccagg aatatttttt cttattacaa tcagctccgt     161340
cacagactgg cgccgtatct gtattccgca gcatggcagg cctctctgga atccgtaccc    161400
atgatgaggc ctcttcttct ggagttccag ggggatcgca atgtgcggaa tataggccat    161460
gaatatatgc tgggagacag ccttctggtg gctccggttt tgaccagga cgagttttcc     161520 gtatatcttc cggaggggac atgggcggat ttcttcaccg gccgccagat cgaaggagga    161580
aggtggattt ctctgcagcc ggcgctggat cagattcccg tatatatcag gcccaatacc    161640
atagtcccca tgcttgcttc tgatgactgc cgcggtctgg aagaaccta taaagacctg     161700 actgtctgca tgaatttgaa agacaggctt tcctgtacct tttacgacga tgggtataag    161760
ggacatttca ccgcagagct gagaaacggg tgtctgagaa taaccacggg aatgcctgta    161820
aaggagataa ttctctatgg agtggagact gtggaagagg catcctgcaa cggccttccg    161880
gttacctgta taaaaaagga tgagtataca catctcttgc atttgtaagg aaaaataaag    161940 aaaccggag aaaggatctg ctgttttccg gcagcaggcc ttctccggtt tttgtattcc     162000
ctttaagaaa acagatatag taaaaagtac caaaaacaga atataaattt agtttattaa    162060
tgaagtttac aaactaaaat aaagtatcta taatgaggat ggaaagagaa ggattcaccg    162120
ggcattccgc ccggaagagg ctgtcagtac agcagaatgg agggaaaatg gcaatcgtaa    162180
gcgtaaagga aatcctggaa catgcatggg ggcataaata cggggttccg gcaattaatg    162240
tctttaatta tgaaacagtt aaatgggcta ttgaagccgc cgaggaagaa cggcttccca    162300
ttatcatcca attttatccc ggctttgcgg aacatattgc gttaaagtat gtcgcggact    162360
ttgcggtgga tatggcaaag aaggcccggg ttcccgtggc ggtccatctg gatcattccc    162420
cctcatatga atcgcggtg ggagggatca gggacggctt tccttccgtc atggtggatg     162480
gttcggtact gccctatgaa gaaaatgtgg agctcacccg tgcggtggtg agagtggccg    162540
aggtgttcgg tgtggacgtg gaagcggagc tcggacacgt gggaagcggt tccagcctgg    162600
atgatattgt caatgaaaaa aattatactt ccatagagga tgccgttgat ttcacagaga    162660
ggacaggatg cggctcccctt gctatcgccg tgggaaacgc ccatggagtc tatatcagag    162720
aaccccggct ggattttgac cggatccggg cgatccgcag cgcggtaaag gtgcctctgg    162780
tccttcacgg ctgttccgat atacctgatg accagcttaa ggaaagcgta atctcggcc    162840 tgagcaagtt caatattgcc acggaatatg accgggcatt ttatacgcc atcgctgcca    162900 gagccgataa aacagaacaa aaaggatcct ttttccggct tcaggaagag gcggcgaagg    162960
atatcagggc ctttgtggca ggaaagctga ggcttctgaa tcccaacggc tatgccctgt    163020
```

```
aaaggtggtg acggaatatg cattttgaca tagtgggcct ggaatcaccc tgcgttgact   163080
tgaatatcaa tgtggaaaat tttcccacgc cagacggagg agagcgggtc ctggagagca   163140
gctggcaggg cggcggcaag gtggctacgg gaatgatagc ggcggcgaga ctgcatgcca   163200 aagggggcatt tataggaacc gtgggagacg attcctatgg ggagttctgc agaagagact   163260
ttgaagcaca tggaatcgat acctgccatt tagtaaaaag agaaaaggaa accacactt   163320 tcgacgtggt tgtcagtgat aaaaaaagca tgggacgcag tatcctgtat tatcccggtg   163380
aagcgccggt ccgttttatg caggtggagg agctgcccga cgactatttg aagaatacca   163440 cataattttta tatttcccag ataaatgaaa ccacattgga agcctaaaag cgggcgaaaa   163500 gcgccgggc ctccatagtg atggatgcgg ataattattc tcccggcgat gaagaggcgt   163560
tcggcctgat agatgttatg atcggatcgg aattctacta caaagccctg ttcgggaatg   163620
aagattatga agcgaactgc cgcagcctca gagaaaggg gccgaatatc gtggtattca   163680 cccaggggaag caaggctgc ctgggcgtgg agaggaagg gttttcaca ctccccgcct   163740 atcaggtgga ggtggtcgac acggtggggg ccggtgatgt ttttcacgga gcgttcattg   163800
cggggctcct gcaggatat acaacaaagg aaaccgcccg tcttgccagc gccgtatcgg   163860
cggtcaaatg tacgagaatc ggtggaaggg cagggatacc ggattgggaa actgtgcgtg   163920
agttcatgga acaggcagg attgattatc gggaaattga agaacggata cagtattata   163980
aacggggatt atgttaagaa gggaagatgg ggatgtatac acaaaaatta atattgggag   164040
tagtacctgt aaaagaagc tttctgagca tggaagaagc cgtgagacag aaaaacaaat   164100
ttatgtccgt tatccgccgg gtaaaaccgg agctggtgga aatcgtggac gtggacgata   164160
ttgcggagca gggaatttta tatgaagcgg ataaagtgcc cgccgtggtg gataaattaa   164220
aaaaagcggg aattgatgcc ctgttcctgc ccttctgcga ttttggggag aacaggcgg   164280 cagcggcagt ggcggcagcc ttccgggtgc ccgtgctggt atggggagcc agggatgaaa   164340
ggcccaacac ctttgaggcc agaggcaggg acacccagtg cggcatgttc gcagccacca   164400
aggtgatgcg aagatatgga gtgacctaca gctacatatt caactgtgag acgaaaagcc   164460
cccgctttgc ctccggttat gaaaatttcc tcaggacggc ggcagtggta aaggctgtga   164520
agggcctccg cattgccaaa atcggagaca ggccggttcc ttcatgagc gtgatggcaa   164580 acgaagcgga tctgctcagc cggttcggca tggtatgtgt tcccatctca ccatccgcag   164640
tagtggggag aatgaagaca atcctggaag aaaacagcat ggttttccaa agctattgtg   164700
aaaatatcag ccaacgtatg gactgtactc agacaaaaga agaagatctg cgaaaggcgg   164760
cggcagtcaa aatggcggta cagcagctga tggaggaaaa taactgctcc gtgggagctt   164820
tcgaatgctg gtccgctttt ccgcccctgg cggatatctg ccctgcctg gtattggggg   164880 aaatggcgga tgagggcctg ccccttgcct gtgaaacgga tgtgaacggt gcggttacca   164940
tggcgatact ccgtgcctgc agcctgtatg aggatgtgga gttccttgcg gatctgacca   165000
tccgccatcc ggaaaatgac aatgccgagc tgctgtggca ttgcggcccc ttcccttatt   165060
ccctgaaaaa ggaggaaagc aaagccgccc tggtggaagg ccaggaaagc tttgaactga   165120
aggcgggaca gctgaccgta tgcagatttg atgaactgaa tggagagtac tatcttttg   165180 caggagaagc ctctaccaca gacgggccgg aaaccacggg cacctatgtg tggatggaga   165240
ctgataactg gcagcggtgg gaagaaaaat tgatgttcgg cccctacatt caccatctgg   165300
gcgtatgcta tggaaattat cttcctgttt tgagggaagc ggccagatat ctgggactgc   165360
```

```
acttcgacaa tgcccatgat cagggaatcc acagccttta acagacataa aaaggagat   165420 tagcgcatgc ttacaagccg caaacccaaa aatatcaagt atcataacca gaggctgatt   165480
ctggcgcttc tgcggagccg ggaggtcatg acggcgggag agctggccga gcaggcccat   165540
ctgagcgtac ccaccataac caagatactt gccgagctcc aggcaagagg gctggtaaga   165600
agcatgggga aggaaattc cacggaggag ggcggcaaga agcccgagct gtttgccctg   165660
aacggcgccc atcgctatgt gatttccata acagccggga gtgaaagaat aaagtgtgcg   165720
cttcttgacc tgacatgtaa ggtactggac aaaagaagcc tcccctatac ggatggcagc   165780
agctatgagt tatgcatgga cgatatctct gccctggtcc ttgcggcctg tgaagcagga   165840
aagctggaag aaaaggaaat ctgcgggata gccataggct ttgaagggat agtggatgcc   165900 cccagggggaa tcctccgttt tcccattcat aaccaggcat ggggaagaga tctgccggta   165960
aaggaggagc tgcaggcccg tcttcccggg tttgccggaa ttaccatcaa taatggaagc   166020
cgcttcgcag gctacgcaga gctttcggag catccggaat atgcctcctg ccgtgtagtg   166080
accatatcca ccgggacctc taccggcggc tgcgtcctgg aaaacggagt cctgatgcag   166140
ggggccaacg gcttcatcgg ggaactggga catattacgg tgagagagac tgaggaaaag   166200
gcctgtgcct gcgaaataa gggatgcttt gaaacagccg tttcccctga cgccctgtgc   166260
ggctatatgc aggaactgga aaagcatt ccgcgggaaa agaacctgc ggctgacaga   166320 agcggaagct gtgactatga aaagattctt cgccttgccg caaaaggaga tgcatgtgcg   166380
agaaaggccg tggaaaagtc cattgattat tatagtatat taatccgcaa tatcatgctg   166440
ctgtatgatc ctcatataat tgtcattcag ggaatttata cgcttgcggg agatttttc   166500 ctgaagcgtc tgcaggagct ggtgaagcag tctcctttt tccatattcc ccaggggctt   166560
tccatcgttt tttccggcct ggactttgac cgcgcggcag atctgggcgg cgcgctttat   166620
tccgttgacc ggtattttga aggagagcag ctgtttgagg aaatataagt acaggaatgg   166680
aaaacaggga aaaagcaaa aggataaaaa aataaatcag aaaagaacag aaaggagttc   166740
actatgaggt ataagcattt caaaaacgca gatgtaaagg tatcctgtct tgccgtggga   166800
acctgggcga tcgaggaaa aaattacggt ccggtggatc gggagggttc catccgcgca   166860
atccgcagaa tggtggattt gggagtcaac ctgattgaca cggccccatg ctatgggaac   166920
ggaaccgcag aaaaaatagt gggggaggcc atccgtacca tacccaggga taaaatcctc   166980
ctttccacca aattcggact ggtgccggat gtgtttaagg gagatttccg caaagaggct   167040
acctataaaa atgccatgag ggaggtgaaa agctctctca tgaatctgga taccgactac   167100
attgatttct atttcgtaca ctggccggac gtaaacaccc ccatctgcga gaccatgtcc   167160
gccctggcag atttaaaacg catggggtaaa atccgttacg tgggagtatc caattttacg   167220
caggaacaga tagaagaagc ggaaaaatat cttactgttg atgtacagca gcccccttt   167280 tccatggtgg aaagacagta tgaacagctg atgagctggg gcgcttcccg gggaattgat   167340
tccatgacct atggttccat gggagcggga atcctttccg gtaaatacag ggacacgccg   167400
gattttgaac ccggagatct gcgtctcacc ttctatgatt atttcaggga acccaaattc   167460
tccaaaatcc aggagctttt aaagaccatg gatgaaatag cagggaaaca taattgtcct   167520
gtatcccagg tggcattaaa ctggagtaca cagaaagatt tcgtgggaac ggctctggtt   167580
ggggtaagaa gtgaagccca tgcagatgag aactgcgtcg catttgaatg gaactgtct   167640 gaagcggaaa tccttcgttt ggacaacgaa ctggaacgtt tggattata aggaacagaa   167700 ataagtattc aatatattca atagaaagag agggaaacct gcgtacggga ttccctctct   167760
```

```
tttgtacgcc cggaggcgta tattcttttt caattgtctt ttataatttg gaacctgtgt  167820
tttgatgacc ggtattattc cctttcggca gcaaaacgtt ccgcctgctc ctgaatcaaa  167880
gcattgtcct caaaataatt gattttcata gccctttta catttgataa cgtattagcg   167940
gcttccgctt ccgccacatc gctgccttt ttcagaatat tataaatttc agggatatcc   168000 tttt caaatt cttttctccg tttccggata ggttccagtt cttcctgcat aacattattc 168060
aggaattttt taacctttac atccccaagg ccgcctctgg cataatgatc ctccatctcc  168120
tgaatattct ggtactcagg aagataacgg gcaaactgat cctcattgga aaatgcctcc  168180
agataaataa ataccggatt cccttccacc tttcccggat cctgaacccg gagatggccc   168240
ggatcggtaa acatggacat aattttctga cggacctctt cctccgtatc cgacaaataa  168300
atacagttat ttaaggattt gctcatttta gccttgccgt caatacccgg cagacgcatg  168360
caaaccttat tatccggaag aaggatatta ggatccgtaa gtgtttcccc ataaatggag  168420
ttgaatttgt ggacaatttc cttagtctgc tcaatcatgg gagcctgatc ctcccccacg  168480
ggaacggtag tggcattaaa agccgtaata tccgccgcct ggctgattgg ataggtaaag  168540
aagcccacag gtatgcttgt ctcaaaatta cgcatctgga tttccgactt caccgtagga  168600
ttacgctgca gcctggaaac cgtcaccaga ttcatataat agaacgaaag ctcacacagc  168660
tccggaatct gtgactggat aaacagcgtg gatttttccg gatccagccc gcatgccaga  168720
taatccagcg ccacctctat gatattctga cgcaccttct ccggattgtc cgcattatca  168780
gtcagagcct gggcatctgc aatcataata aaaattttat cgtattcacc ggaattctgc  168840
agctccaccc tgcgtttcag cgaacctaca taatggccca catgaagcct tccggtaggg  168900
cggtcgcccg ttaaaattac tttactcatg ttaaatctcc tgtcgcataa gaaatatatt  168960
ttactgcgtt ctatttact cgtattacgg gggatctgtc cagcaaatcc gcttatttt    169020 tccaaaaaca gttacagttc agccttcagc cgccgtctgt gccagtcccg cagcccttgc  169080
cgccctcctt ttcccagccc gcctgacctt gccctcccct gtggggcagc accctgcaag  169140
gttccttaga ggggacgctc ccgctcggat aatcacgcag cggtactaag gctgcacagg  169200
acgcagccta aggaccggcg cgcttataac gccccttaca ggaatccttg cagggtgctg  169260
ccccacaggg gagggcaagg tcaggcgggc tgggaaaagg agggcggcaa gggctgcggg  169320
actggcacag acgcggctg aaggctgaac tgtaaccaaa acaattgta ttcctgaccg    169380 gccggccgcg aaaagactc cggctgtccc ctctgtccgg atgtcccttc tttccggcgc   169440
cggaaatata tatggggcaa aaggtaaaaa cacgcaaaaa acaggtcgtt tgaagtgtag  169500
aaaatgaact ttgcggaata tataatttgt tttattaaat gtgtacagaa tattccaaaa  169560
taataaagct aagtatgcta tatgcacatc aaaataccga aaaggaggaa agggaatggt  169620
taaaaattct gctgacagga ggaaaaaagc agcaaaaact ttaaaattga tgtggaatct  169680
gaaatggatt tatctcatgc tgctccctgt tgtggcgtac tacatcatat tcaaatacat  169740
cccgatgtat ggcgtgacaa tcgcatttaa agattataac gttttcaagg gaatgctgga  169800
aagcccctgg gttggattta aagtgtttga aaaaatattt gccagcaaaa atttctggca  169860
ttccgtaaaa aatactcttg tgctgaacct gcttactctg gccgttaatt ttcccctgac  169920
gatctttgtg gcgctgatgc tcaatgaggt catccatctg cgttttaaaa agatgataca  169980
gtctattctg tatttacccc attttatctc ctgggtggta gtcgcgggaa tagccgccaa  170040
tatgtttacc caaagagacg ggacgattaa tctcgtactg aattccctgg gtatttccag  170100
```

```
cattcccttt ctgagtgatg agaagtggtg gattgtgact tatgtcatct gcagcgtttg   170160
gaaagagatc ggctggggga cgatcattta cctggcagcc ctgaccggcg tggacgaatc   170220
cttatatgag gcggcctatc tggacggcgc cagcaagctc cagagactga tttatgtaac   170280
ccttccgtcc atcaaatcgg tggtggttac catgctcatc cttcaggtct ccaaaatgat   170340
gaccattggc ctggacgctc ctctgcttct gggaaatgac aaggtcatgg ctgtttcaga   170400
ggttatcagt acctatgtat accggatcgg tatcgaaaat gccaagtaca gtgattccac   170460
cgccataggc ctgttccagt cggtggtcaa tatcctgata ctccttgccg cggaccggtt   170520
tgccaaggcg attggggaag aaggcattat atagaaaggg gaaagaaaa tgaaaaatcc    170580 cggaacaaaa acagggaaaa aacataaatt tacgatggga atggccgtgc tttatttct   170640 tttgactgct ctggtgttca tctgccttta tccgtttctg aacgtactgg catattccct   170700
gagcggctac aatgcggtgc tctccggaga tgtgacctt tatcccatag aattcaccct    170760
ggatgcctat aaacagatac tgggaagagc acagatatgg attgccatga gggtaaccat   170820
cttcgtcaca ctcatgggta cggctatcgg gcttgtgctc acgatctttg cggcatatgc   170880
cctgtcaaga aagaaccttc ccggcaaaaa gctgctttca ggactgattc ttttactat    170940 gtatttcagc ggcggcatca ttcccaccttt cctggtggta aaaaatctgg gaatgtatga   171000
ttctttgtcc tccctgtaca ttccgcaggc aatcaacgta tttaatttta ttgtaatgag   171060
gacctttttc cggcagctcc cggaaaagcct ggaagaagcc gccaaaatag acggagcctc   171120
cgacatggga gtgctgctga aaatcgttct tccgctttcg gttcccatta tcgcgactat   171180
cggcctgttt tatgccgtcc aatactggaa tggctacttt gacgctttga tttatatcca   171240
gtccccggat aaattcaccc tgcagctgag gctgcgcagc cttcttttg cggacgagct   171300 gaacaatgcg ggcggaggca atgtggaagg catcggcacc caggtgatga cccagtccct   171360
gaaaatggcc tgcgtcgccg tttcaacaat tcccatattg cttgtatatc catggctgca   171420
gaaatatttt gtcaaagggg taatgctcgg ctccgtcaaa ggatgattac ggcatcctga   171480
atgagacaaa gaaaataaaa tattcttata actagtaaaa cagaaaggaa ggaaagatat   171540
gaaaaagaaa aaaggaagtc ttacattcat ggccctgttc ctgacggcca gcatgcttgc   171600
aggctgcggc agcagcccgg caggaggcca ggcatcatcg ggggaggcat cttcttccgg   171660
tgatgaatcc ggaacccggg cggcagcagg agaggaagga acagcggagg ggtaccagac   171720
aacctatggc tccaagatgt ttgatgatgt taccatatca gtggagctct tgacaggag    171780 caatgccccg gaaggcagca cgatactgaa taacaaatgg gtggaatatg tgaatgaaca   171840
gatgggaaaa gtgggcatcc atgtggaatt cgtttccgtt ccccgttcag atgaagtaac   171900
caagatgcag acactcatgt cctccggcac agcgcctgac ataaccataa cttataccta   171960
ttcctatgcc gaggattact ttaaccaggg cggtatctgg gatttatcgg aattcatcga   172020
cggggaagga caggctcaga atatgaaggc atacctgggc gacagcgtta tcgtatatcgg   172080 cagaaataca gaaggaaacc tgtacggcat agttgccaaa cgcgccacaa cggctaattc   172140
caatattttt ctgcgcaaag actggctgga cgatctggga ctggagattc ccacgactgc   172200
ggatgagttc tacgatgtgg tcacacagat ggtgaggaac aacccggacg gcaaaaacg    172260 cgtggttgga atgtccttct ggggagtgaa taacggcgat aaccccagaa actgtatgtc   172320
ccttgccttt tcccaattgg caggagagcc caaggaaatt gacatagccc atggctttga   172380
ctattattac gaccccggaa tgcgtgaata tttcaggtat atcaataagt tttataacga   172440
agggctcatg gataaagaat actacaccat gactacggat acctttaaca gcgatattgt   172500
```

```
taccggctcc atgggcggtt ttgaatccaa tgtaaactac agcgtggatg tgctcagagg   172560
atcccttctg aaaacactgc aggaaaacga tccggatgcg gatattatct ccatccccgc   172620
attgaagaac gtaaacgatg gagtacagta cagcgcgacc tattccgaag gaggactgat   172680
cgccttctgt cccaaaacag ccgatgccga aatcgtggaa gcctgcatga cctatcttga   172740
ctggcagtgc acccaggaag gcggttttgt actctatcat ggctttgaag gggaacatta   172800
tgactttgat gatgccggaa taccggtagt caaggatgcc gcatacaaca gcgcagacaa   172860
agactggata cggacagata ttttcctggt gggaaatcag ggatattttg aaaccgtgga   172920
tgactttaat gcatgcacat ccaaagaagc ccccggctat gaagatcatg tgatagaaaa   172980
ctatgagaat tccatggcag ggacctgcat tcccgccacc ttctatacct cgccctccac   173040
acccgacctt cagacggatt tggcccttgt ccgcagcgaa tacatggtac agtgcataac   173100
ctgtccggaa tcggaatttg acgccaacta cgatgctttt atgaaagcca gtgaggacgc   173160
cggtataaaa acaataattg aagaacgtac agcttatttt acagaagtat acggatatta   173220
ataacaacag gcccgcggat atattatccc gggcctattc tgattcacat acggaaagag   173280
attcctgaaa atctgcgttt tccggcaggg acataatata gttctgatac ttttgggtg    173340 aaacacccac ctgctgggaa aaagtccgtg cgaaatgaga gtaattattg aagccggaca   173400
tccagcatac atccgtcaga aacctgcctt ccttcagata tttctgggca gcccgattc    173460 ttttattgag cagatactgc tgaatagtca gccccgtaac cattttgaaa cgcctgctta   173520
tataggaagg attgtggaaa aactgcctgg aaagatcctc cagcgtaaag ctgtccagaa   173580
gatgtccatc gatataaagc atgatatccc tgatcagcgg cggcatgata ctgcggcagc   173640
cctggtttcc acccgcccgg aaggcctgat ttaccattac aagaatttga aaagataag    173700 ataaggaaag cagatcatgc ccatattccg gactgctgtt cgcttccttc agatggttga   173760
agagcatgat aaactccccg atttgctgtt cattaagaaa agacagattg ttttggccgg   173820
ccggcctgtt gaaaaagcac gtggtcagat ccgtttcatg gctggaaagc gactgaaaaa   173880
agaattgctc cagatttatg gtaatccgtt cataatgctt tttatccacc agctccaccc   173940
gatggtactc ctccggctgt attacaagaa tatctcccct taccgaggga tagcagtgtt   174000
cttcgatata atagttgacc tttccattca ggaaaaggta tatttcgcag ccgttgtgcc   174060
gatggtaata aggatggatt gccaaatctg aaacatgacg gcaaagaata ttctgatcca   174120
ggaaatcaat tgttttaac atgatgaagt ttcctttccg gtattttacc aattttgaca    174180
cacttaataa taaatactat agcatataat ttactatatt tctatactat aaatatttta   174240
ttgcgttaaa agaacacttt cgtactcctg attcccggtt aaaattaagt tcacactttt   174300
tttataaatt aattagcact cacctcttga cagtgctaac aactagtgtt ataaatgtta   174360
tagaacaaca aaggaacggc agttaagccg gaagatttca atataaaatc aggaggaatg   174420
aactatgtta atcagaaata atttttttcaa cgacttttc ggagatatgt ttgatgaccc   174480 gttttcaac agaggctatg cgccccagac ccagctgatg aagactgaca tccgtgaaaa   174540
ggatggccag taccttctgg agattgaggt tcccggtttt acaaaggaag atgtaaaggc   174600
agaattaaag gacggctacc tcaccattac cgccgacagg aaagagcctg tgaaaatgc    174660 ggatgagaga accaaatatg taaggaaaga aagatattac ggaaccatga agagaacctt   174720
ctatttaggt gaaagagatt cagagaacga aatccatgcg gcattcaggg atggtattct   174780
tcggataatg attgacaagc cgcagcctaa gaaaatcgaa gaagagaaga ccatcattcc   174840
```

```
tatagagggc tgagatttat tgcccggatc atgttttatt tcctgattct gccggtatgg   174900
ccggttttat atagatgaaa gccgttataa acggataaaa taccctccct ttacccttac   174960
tgtattaaca aacgtccctg ctgttttaat aatagcaggg atatttgttt gtcaaaatct   175020
tatatagctg gatgaaagat ggtacaggaa tttatttagt gaataatatc ccatgatgct   175080
ttgcacccta ttctgtactc tgatacggaa tatagaacta aaaggaaga tattaccttta   175140 ttatacagta tatatgtttg tttgactttg cataaaaata ggggtataat ttacaaataa   175200
tatggcatat ttacaaaaaa cttatgagga gcggggatg ttatggctat tattaaatgt   175260
ccggagtgtg gacaagatat atctgataag gctaagagat gtattcattg tggaaaaatc   175320
tttgattcgg atccacagcc ggaggaaaaa agatgttctg agtgtgggga attattaccg   175380
gataatgttg aagtgtgtcc gagctgcggc tgcccggttg aagaagataa aaagccgtg   175440 gaaataaaac cccagcaggt agaagtggct ggcattacaa tgacacagaa aaccaaaaag   175500
ctgatcatcg gtataattat agctttgata gtttgtattg caggaggcgc tggttttaaa   175560
gtgtattccg ataagaaagc ggcgaaagaa tacagggaag cgtataatac ttacatagat   175620
gatttgaaaa aagcacagtc acttatgctt tcaggcggca gtgaggcaga gacattatgt   175680
aatcttacct taaggtatg gagtaattcc atttataaag aaaaagacag tgagacagat   175740
aaatacacaa gacaaaaaga cggtaccggt aggttttatg atgattttaa tgatgcacta   175800
agtattttat attctgattc cgggacatta accaccatat caaatataga aacaaaccag   175860
acatcgataa aaacattaat gaaaaaatta cagacaccac cggacggatt ggataagtgt   175920
tatgatacca tttctgattt atatgaagca tataaatcac ttaccgatat ggccatcagt   175980
ccatccggta attacaatgg cttcagttcc atgaaatctg atgcggtcaa tgattttatg   176040
tctgcctatg ataaattaga cagccagatg ccggaaaaaa tgaataaaaa gtaaaggaga   176100
acgtcgatat ggcacttatt aaatgttcag aatgtggggc agagatcagc gataaagcaa   176160
cggaatgtcc taaatgcggc tgtcctgtgg aagtgtctgc agcaactgaa acagcggaga   176220
ataagaaaaa aggacttgtt aaactaataa ttatcattgc tctggcatta cttctgctgg   176280
cggctgtcgg ctttggtgtt tttaagttga caaacaaacc ggatacgagt ggtctttata   176340
atggttttga atggggaatg acttacgatg aagtgttgaa acgtctgccc gaggatgcac   176400
tcaccaaaga tgaaaaaaat ttaatcgcag tcaataatat tgattatgaa ggcaagaag   176460 ggatagatgt cctagtctcc tataatttcc ctgatgttac tttaagcaag attacgctgt   176520
atattacgaa ttcagatgat agttcctata cggatgaggc gttgttggaa gaatacattc   176580
agcagatgga tagcctgtac ggcgatcatg ataaggatat cctttcttat aagtggaata   176640
ctcaaaagag caagattatg ttaacttatt tgtcggataa actctttatt ttatcatatg   176700
aagatattac aaaggcggac aattaattat attaagaaaa ggagcaccgt tgaatggtgt   176760
tccttttctt atatcaatta atctatttgc ttacttatag cagatccaga atgtcaatcg   176820
gccgggaaag cctgtaatcc gcagtgattt cctccggatt tttgcatccc cacaacgcca   176880
gcgctcgcgg aacacccgcg ccctccgcac atttcatatc ataaatactg tccccgatat   176940
acacagcctg ctcaggaaga attcccgctt tctccagata aaaagcatg ggcgccgggt   177000 caggcttatg ctctgaggta tccgtggcag taaccgtaat cgaaaataa tccgcgagcc   177060 ccagccgtat catatcataa tcgtattctt cctggttttt agaggttatt actccgagtg   177120
aaatcccatt ttccttcagt ttcttcagaa cctcaggaat atccgggtaa atggtaacat   177180
ccccgccatg cttgcaataa taggcatccc acttttaag gattgcagtg agatcgcctt   177240
```

```
ccacccccag ctgcttaaga gtaatggggc cggggatccc caggcagaaa tagagctgct 177300
ccggttcata aggaactccc ttaatctcca aaagaagctc ctgaagcccc tttatgatag 177360 cctttttccgt atttattaag gtcccgtcga tatcaaagat aaaatggcgt ttatccatca 177420 ggcatcccc ttcggtataa agttctcaaa aataaacagt ttaaaatctt tccggcacat 177480
atccatttcc tcctgggaac ggattgtcca tcccacaggc agggcatgat aaaaattaca 177540
gcatattttt ctggacaaat cattccggta aacccagttg taggctatga aatccggcct 177600
tgcagcaatg ttggaaagca ttttccccaa cagaaaaaaa ggaaggctgc agtttttatt 177660
ctctttgtta aaattggtgc acagctgtcc gcggaataca tccggccggt ttttcttata 177720
ccagataaga gccgaagggt ggaaggattc aatgcagtaa actcccttat agtcctttag 177780
cagacggttc acagcttccg gaatccggtc atcccttta tccatttaa tctcaataat 177840 cagaggaacc tgtccccta cgagatcgag aaattcctga aggtaggaa tctgttcctg 177900 ggtatccgcc agtatcagct ccttcagttc ccttaatgtc agctcgttta cccgtttatc 177960
aaccccgcac atccgtgtca gtgtggaatc gtggaaaacc acaggatatc cgtcactgga 178020
aagctggaca tccatttcca tgccgaagcc tttgtcaata gctctctgaa aggccttcat 178080
ggagttttcc ggtattcccg cagatagatc atgaagtccc ctgtgcgcat aataatgatg 178140
tagaagagcc ttacaatccg gcttacggaa ccgaggcata attaatacca tataaagtaa 178200
gaataagagt aacaaaataa tgattaatac aagaagtgct ttcatggaac aatctccttt 178260
ttcttttgcc tgaatatttc ttctgtcata ttcctagtat atagcggttt ctctgaattg 178320
tcattcataa aaaaactatt gcattccgca tacactccat ataaaatgca cataacagta 178380
aataataccg attcacagga ggtacctatg aaatttaagt ttgcccataa taattttaat 178440
gtaaaggatc ttcaaaaatc gcttcgtttc tacgaggagg cccttgattt gaagcccgtg 178500
cgcaccaaag aggctccgga cggaagcttc acgcttgcgt ttctttccga tggaaccaca 178560
cctcaccagc tggaattaac ctggctgaga gactgggaaa aagcttccta tgatttaggc 178620
gataatgaat tccatctggc ctttaccgta gatgatatgg aggcagccca ttcccgtcat 178680
aaagaaatgg gatgcatctg ttttgaaaat gaagccatgg gaatttattt cattcaggat 178740
cccgacggtt actggattga aatcgtaccg gcctgatccg ccgttccttc cgtaagcccg 178800
aacatgtccc tgcatatgct ttttccgctt tctgtgcgga agatacgctg cagggcgtgt 178860
tccgcggctt cacgggatgc attgtcttca tataaattca caagaaaatc agcctcaaca 178920
agaatctgat aatcaagccc gttaatatcc tgataagtat gatgatgggc aaccaggtaa 178980
catactctgt caataacaga gtcctcaaag cccaggggtt ccagcatcgt tcttgcgata 179040 accggaccctt ccagctcctg atgcttaccg ctgcagtccc catactttc ttcactcact 179100 ttaatgccga tgtcatggac aatagcggca atttccagaa tattctgctc atcatcctca 179160
agcccctcca attttcctat catgcctgca aaatcatgaa ccttgataaa atgctgaatc 179220
cttttgggat ccctggcata atagcgtatc atttctttta gcagaagcac atttctatcc 179280
ataaaataac catcctttct tatagaattc cacacatact gtcctgtcta tttatgata 179340 ggaaaagccg gtatacaagg gaaatgaaa aagatatcag actgcagcca aaaggttca 179400 ttctttcgtc aggctattca tcgtctgcgc tgtgacctta tgctcctatt atccttcgct 179460
ccgcatccgt ccgtgcgcca tcctgtccgg cagccggcag tatcttcggt ttatcccgcc 179520
ccaacagggg aaaacgctgg tgacaaagaa aagaaactat actataatga agagaatcag 179580
```

```
agcagtgacg ttacgggaaa ggatgaaaag caaatgagaa cagtgcaggt atccgagata  179640
actgaaaata taaaggaaat gtgcatagaa gccaaccata ctctcacaga agatatggaa  179700
caggccctga accatgcggt caccaaagaa caggcggctt taggaaagca ggttttggga  179760
cagctccagg agaatctgcg cattgcaagg gaggatacaa tccccatttg ccaggatacc  179820
ggaatggcag tggttttat ggaaataggc caggatgtcc atttcgaagg cggggcgctt  179880
gaggatgcgc taaatgaagg aatccgccgg ggatataagg aaggctacct ccgcaaatcc  179940
gtggtaggcg atcctctgct ccgtgaaaat accggagata acaccccagg aatcatacac  180000
tataccattg taccgggaga aaagataaag attacggtag cgcccaaagg cttcggaagc  180060
gaaaacatga gccgtgtttt catgctgaag cctgcagacg gaatggaagg ggttaaaaat  180120
gcggtgctca ctgcggtgaa agaagccggc cctaacgcgt gcccgcccat ggttgtggga  180180
gtgggaatcg gaggaacttt tgaaaaatgc gctctaatgg cgaaacaggc attgaccagg  180240
cctttaaatg aacattccga aatccctat ataaggaaa tggaggagga gcttctggaa  180300
aggataaatc gatcagggat cggtcccgga ggactgggag gaaccaccac cgcgctggga  180360
gtaaatatca ataccctatcc cacacatatt gcaggcctgc ccgttgctgt aaatatctgc  180420
tgtcatgtga acagacattc cgtaagaacc ctgtagaacc ctttatatgg tagttcttaa  180480
tctaagtaat accatatctg cagataaagt atcatatata ataagaagaa agccgtttga  180540
ccggaggaag aacagaatgg aaaaacatat gagagtgccc tttaccagac aggaagcggc  180600
caccctgaaa tcgggagatt acgtctatct tacagggacc atatacacgg ccagggatgc  180660
cgcccataaa agaatgtatg aagcccttat gaaaaaggaa gcccttccgt ttgatatcag  180720
aggaaatgta atatactata tggggccgtc gcccgcaaga aagggcggc ctattggttc  180780 cgcaggcccc accaccgcaa gccgtatgga taaatatacc cctgcccttc tggatttggg  180840
gatgcaggga atgataggaa aaggaaaacg tacggaagaa gtgagagaag ccatgatccg  180900
caatggcgcc gtatattttg cagcggtagg aggcgccggc gcccttcttt ccaaatccat  180960
cctcagctcg gaggtcatcg cttatgatga tttgggaacg gaagcggtaa gaaagctttc  181020
cgtaaaggat tttcctgttg ttgtggtaat ggacagccag ggaaataatc tttacgaaac  181080
cgccataaag caatattgta agaataaaa aggaaagag aatcaaatat gcgtagaata  181140
gccttgatgg tcttccggct tttctttaaa gccatttatt atttcagcca catctggtgg  181200
tgcagtatcc atgaaagcat cagctatgag gaaggcttca ggtggtgtaa aaagacaacc  181260
ctcgccgcca ataaggcagg ccgtgtgaca attgaagccc atggcgtgga aaacctgccc  181320
gaaaaagacg ggttcattat gttttcccaac catcagggcc tttttgacgg cctcgtattc  181380
ctggaatcct gtccgaaggt ctttttccttt gtaatgaaaa aggaagccgc caatgtcatt  181440
cttctcaaac aggtgcgcaa ggctctggga gccctcgtta ttgatcggga agatctgaga  181500
cagtccatga agataatcca ggcaatggca gaagaagtaa aaaaaggccg caactttatt  181560
atttttccgg aagggaccag gagccgacag ggcaaccata cccttgaatt taaggggagc  181620
agctttaaag cggctatgaa agccaaatgt cccatagtgc cctgtgccct gatagattct  181680
ttcatcccct ttgatgaaaa cagcatcagg agggttaccg taaagatatt ctatctgaag  181740
cccatgtact atgaagaata taaggatatg aaaacaacac aaatagcaga agaagtaaaa  181800
agacgtatag atgaaacaat tgccggatat actcagaaag agcctctcgc ataagaagtt  181860
cccgggtata tgaaaaaact tggtaaaaac ttaccaaaaa gaattgacaa acagttacgc  181920
cttatgtata ataacatttg cgctaccgaa tgggacgcgc acttcatatt ggtagaggat  181980
```

```
agttcagttt tgtggagaaa tactcaagag gctgaagagg cgccctgct aagggtgtag   182040 gtcgtttata gcggcgcgag ggttcaaatc cctctttctc cgttcccttt accgataaa   182100 aggggagctt gattatagct tcgcgggaaa agaatcttaa gagattgaga tttctttttt   182160
ttcgcacttt tgccggatga aaagaacgag taaaacttat ggaaaatata ggttaaaaaa   182220
gttgttgaca tttgacaaaa tatggtgcta taatgaaagt ccaccgcgaa tggcgatgga   182280
acagagattt aaagaaata aaaaagtta aaaagtgct tgactggcag aacaacatgt   182340
gataagatat caactgttgc ggctgagaaa gcagcacaca gaaccttgac aaataaacag   182400
taatgcaacc ctgaaaattc taaaaagaa aattcagaga acaagtttta aagcttcgag   182460
agaagacctt taagacaccc aaaaacagta agaaatgttt ggaaacaaac aaacggttaa   182520
acattagcta gagttaatct taaccggatt aaacacttaa acaagagagt ttgatcctgg   182580
ctcaggatga acgctggcgg cgtgcctaac acatgcaagt cgaacgaagt tacacagagg   182640 aagtttcgg atggaatcgg tataacttag tggcggacgg gtgagtaacg cgtgggaaac   182700
ctgccctgta ccgggggata acacttagaa ataggtgcta ataccgcata agcgcacgga   182760
ttcacatgaa gcagtgtgaa aaactccggt ggtacaggat ggtcccgcgt ctgattagcc   182820
agttggcagg gtaacggcct accaaagcga cgatcagtag ccggcctgag agggtgaacg   182880
gccacattgg gactgagaca cggcccaaac tcctacggga ggcagcagtg gggaatattg   182940
cacaatgggg gaaaccctga tgcagcgacg ccgcgtgagt gaagaagtat ttcggtatgt   183000
aaagctctat cagcagggaa gaaaatgacg gtacctgact aagaagcccc ggctaactac   183060
gtgccagcag ccgcggtaat acgtaggggg caagcgttat ccggatttac tgggtgtaaa   183120
gggagcgtag acggcatggc aagccagatg tgaaaaccca gggctcaacc ttgggattgc   183180
atttggaact gtcaggctgg agtgcaggag aggtaagcgg aattcctagt gtagcggtga   183240
aatgcgtaga tattaggagg aacaccagtg gcgaaggcgg cttactggac tgtaactgac   183300
gttgaggctc gaaagcgtgg ggagcaaaca ggattagata ccctggtagt ccacgcggta   183360
aacgatgatt gctaggtgta ggtgggtatg gacccatcgg tgccgcagct aacgcaataa   183420
gcaatccacc tggggagtac gttcgcaaga atgaaactca aaggaattga cggggacccg   183480
cacaagcggt ggagcatgtg gtttaattcg aagcaacgcg aagaaccta ccaagtcttg   183540 acatcccaat gacgcacctg taaagaggtg ttccccttcgg ggcattggag acaggtggtg   183600
catggttgtc gtcagctcgt gtcgtgagat gttgggttaa gtcccgcaac gagcgcaacc   183660
cttattctta gtagccagca ggtaaagctg ggcactctaa ggagactgcc ggggataacc   183720
cggaggaagg cggggatgac gtcaaatcat catgcccctt atgatttggg ctacacacgt   183780
gctacaatgg cgtaaacaaa gggaagcgag acagtgatgt ggagcaaatc ccagaaataa   183840
cgtctcagtt cggattgtag tctgcaactc gactacatga agctggaatc gctagtaatc   183900
gcgaatcagc atgtcgcggt gaatacgttc ccggtcttg tacacaccgc ccgtcacacc   183960
atgggagttg gaaatgcccg aagtctgtga cctaaccgaa agggaggagc agccgaaggc   184020
aggtctgata actggggtga agtcgtaaca aggtagccgt atcggaaggt gcggctggat   184080 caccccttt ctaaggcgaa gaagtagggg ttgtattact gtttagatgt taaggagcc   184140 ggaaggctct gggaacatca ggaaaaaagg attccggtgg cgatacgctt aggggagaca   184200
cccgttctca tcccgaacac gatggttaag acttaagcgg ccgatggtac tatgctgaa   184260 acggtatggg agagcaggtg gctgccggat tacaacaaaa acaagctgaa caagctttat   184320
```

-continued

```
atacactggt tttaccagtg attcaaaatt aggaacaatc ctgattttga atgactgata  184380
aaatatgcag tcaagaatgt accttgaaaa ccgaatattg aaaataatct taaagtatca  184440
acgtctaaaa ggaaggtttt gtaaaaggaa ccaaccggat agaagaagat aaacgagaag  184500
acatccaaaa caagcaataa cccattcgaa agaatgggaa gaaataccaa aaagagcata  184560
caacgctatg tatgccgtaa cgagaccaag taaggacgag ttacaaacag gttaagctgt  184620
aaagagcaca aggtggatgc cttggcacta agagccgatg aaagacgtga taagctgcga  184680
aaagctgcgg tgaggagcaa atatcctatg acccgca                           184717
```

<210> SEQ ID NO 18
<211> LENGTH: 22
<212> TYPE: DNA
<213> ORGANISM: Artificial sequence
<220> FEATURE:
<223> OTHER INFORMATION: DNA Probe/Primer

<400> SEQUENCE: 18
ccacagtcca tgccatcact gc                                            22

<210> SEQ ID NO 19
<211> LENGTH: 22
<212> TYPE: DNA
<213> ORGANISM: Artificial sequence
<220> FEATURE:
<223> OTHER INFORMATION: DNA Probe/Primer

<400> SEQUENCE: 19
gcccaagatg cccttcagtg gg                                            22

<210> SEQ ID NO 20
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 20
gctggatttg catccgtaat                                               20

<210> SEQ ID NO 21
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 21
tgggactggt tgacaccata                                               20

<210> SEQ ID NO 22
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 22
cacggcctac atcctcatct                                               20

<210> SEQ ID NO 23
<211> LENGTH: 20
<212> TYPE: DNA
<213> ORGANISM: Artificial sequence

```
<220> FEATURE:
<223> OTHER INFORMATION: DNA Probe/Primer

<400> SEQUENCE: 23
ttggtaggta ccagcggaag                                              20

<210> SEQ ID NO 24
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 24
tgcctcccat tgttgatcct                                              20

<210> SEQ ID NO 25
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 25
actcgttgca ggtgtagaca                                              20

<210> SEQ ID NO 26
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 26
tggacggaag cggaaatcta                                              20

<210> SEQ ID NO 27
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 27
cggccaagct caatacactc                                              20

<210> SEQ ID NO 28
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 28
cagatggatc gcacagagag                                              20

<210> SEQ ID NO 29
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 29
tctgtgtacc acgaattggc                                              20
```

```
<210> SEQ ID NO 30
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 30
actaaagtgc ccgagctgat                                               20

<210> SEQ ID NO 31
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 31
atggtcactg tctgccatgt                                               20

<210> SEQ ID NO 32
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 32
tcatagtgac ccgagactgc                                               20

<210> SEQ ID NO 33
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 33
tgttgcaaag aagcctgaca                                               20

<210> SEQ ID NO 34
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 34
actgctcaat ctgacgtcca                                               20

<210> SEQ ID NO 35
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 35
atagggagct gtgatctggc                                               20

<210> SEQ ID NO 36
<211> LENGTH: 20
<212> TYPE: DNA
<213> ORGANISM: Artificial sequence
<220> FEATURE:
<223> OTHER INFORMATION: DNA Probe/Primer
```

```
<400> SEQUENCE: 36
ctctcagcca gcgtactctt                                              20

<210> SEQ ID NO 37
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 37
ctccatagcc acctccgtag                                              20

<210> SEQ ID NO 38
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 38
cctgtcttca acccaagcac                                              20

<210> SEQ ID NO 39
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 39
caacaacgaa ctgctggtca                                              20

<210> SEQ ID NO 40
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 40
tggggctggc aaaggcaagt                                              20

<210> SEQ ID NO 41
<211> LENGTH: 23
<212> TYPE: DNA
<213> ORGANISM: Artificial sequence
<220> FEATURE:
<223> OTHER INFORMATION: DNA Probe/Primer

<400> SEQUENCE: 41
gaccactgca ctaggctgga aca                                          23

<210> SEQ ID NO 42
<211> LENGTH: 21
<212> TYPE: DNA
<213> ORGANISM: Artificial sequence
<220> FEATURE:
<223> OTHER INFORMATION: DNA Probe/Primer

<400> SEQUENCE: 42
agctctggca acgtcagcac t                                            21

<210> SEQ ID NO 43
```

-continued

```
<211> LENGTH: 22
<212> TYPE: DNA
<213> ORGANISM: Artificial sequence
<220> FEATURE:
<223> OTHER INFORMATION: DNA Probe/Primer

<400> SEQUENCE: 43
aagtggggcg actgagcctt ct                                              22

<210> SEQ ID NO 44
<211> LENGTH: 23
<212> TYPE: DNA
<213> ORGANISM: Artificial sequence
<220> FEATURE:
<223> OTHER INFORMATION: DNA Probe/Primer

<400> SEQUENCE: 44
gctagcatgt gcatgtggaa cac                                             23

<210> SEQ ID NO 45
<211> LENGTH: 22
<212> TYPE: DNA
<213> ORGANISM: Artificial sequence
<220> FEATURE:
<223> OTHER INFORMATION: DNA Probe/Primer

<400> SEQUENCE: 45
tgagagcctg gtgtgtctgg ct                                              22

<210> SEQ ID NO 46
<211> LENGTH: 22
<212> TYPE: DNA
<213> ORGANISM: Artificial sequence
<220> FEATURE:
<223> OTHER INFORMATION: DNA Probe/Primer

<400> SEQUENCE: 46
tgcacctttg cctcagagca cg                                              22

<210> SEQ ID NO 47
<211> LENGTH: 21
<212> TYPE: DNA
<213> ORGANISM: Artificial sequence
<220> FEATURE:
<223> OTHER INFORMATION: DNA Probe/Primer

<400> SEQUENCE: 47
tggctgcctg gttgcttcag t                                               21

<210> SEQ ID NO 48
<211> LENGTH: 24
<212> TYPE: DNA
<213> ORGANISM: Artificial sequence
<220> FEATURE:
<223> OTHER INFORMATION: DNA Probe/Primer

<400> SEQUENCE: 48
tagcagccaa acatgccaag caga                                            24

<210> SEQ ID NO 49
<211> LENGTH: 25
<212> TYPE: DNA
<213> ORGANISM: Artificial sequence
<220> FEATURE:
<223> OTHER INFORMATION: DNA Probe/Primer

<400> SEQUENCE: 49
```

```
atgctcatag cggtgccaag agaaa                                           25

<210> SEQ ID NO 50
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 50
cctactctgc ctggctcttt                                                 20

<210> SEQ ID NO 51
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 51
acccttctga gtccctgaga                                                 20

<210> SEQ ID NO 52
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 52
cacagcacag ccttctttgt                                                 20

<210> SEQ ID NO 53
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 53
tccagttcac agtccaggtc                                                 20

<210> SEQ ID NO 54
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 54
tgccgggatt aaaagcatgg                                                 20

<210> SEQ ID NO 55
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 55
acagggacag caggattagg                                                 20

<210> SEQ ID NO 56
<211> LENGTH: 20
<212> TYPE: DNA
```

```
<213> ORGANISM: Artificial sequence
<220> FEATURE:
<223> OTHER INFORMATION: DNA Probe/Primer

<400> SEQUENCE: 56
ctgcagtact gtggggaggt                                                     20

<210> SEQ ID NO 57
<211> LENGTH: 20
<212> TYPE: DNA
<213> ORGANISM: Artificial sequence
<220> FEATURE:
<223> OTHER INFORMATION: DNA Probe/Primer

<400> SEQUENCE: 57
caaaggcgga gttaccagag                                                     20
```

COMPOSITIONS AND METHODS FOR TREATING AND PREVENTING GRAFT VERSUS HOST DISEASE

CROSS-REFERENCE TO RELATED APPLICATIONS

This application is a U.S. 371 national phase entry of International Patent Application No. PCT/US2017/022456, filed Mar. 15, 2017, claims priority to provisional patent application 62/308,603, filed Mar. 15, 2016, each of which is herein incorporated by reference in its entirety.

STATEMENT REGARDING FEDERALLY SPONSORED RESEARCH OR DEVELOPMENT

This invention was made with government support under grants HL090775, HL128046 and CA173878 awarded by the National Institutes of Health. The government has certain rights in the invention.

FIELD OF THE DISCLOSURE

Provided herein are compositions and methods for administering bacterial strains to reduce Graft-versus-host disease (GvHD) and improve survival after allogeneic Bone Marrow Transplantation (BMT).

BACKGROUND

Graft-versus-host disease (GvHD) is a medical complication following the receipt of transplanted tissue from a genetically different person. GvHD is commonly associated with stem cell transplant (bone marrow transplant), but the term also applies to other forms of tissue graft. Immune cells (white blood cells) in the donated tissue (the graft) recognize the recipient (the host) as foreign (non-self). The transplanted immune cells then attack the host's body cells.

Intravenously administered glucocorticoids, such as prednisone, are the standard of care in GvHD. However, the use of these glucocorticoids, an immune suppressant, has many side effects and new treatment methods for GvHD are needed therefore.

SUMMARY OF THE DISCLOSURE

Provided herein are compositions and methods for administering bacterial strains to reduce GvHD and improve survival after allogeneic BMT.

In one aspect, the present disclosure provides a method of treating Graft versus Host Disease (GvHD), the method comprising administering to a subject in need thereof a therapeutically effective amount of a bacterial composition, the bacterial composition comprising at least two (e.g., at least 3, at least 4, at least 5, at least 6, at least 7, at least 8, at least 9, at least 10, at least 11, at least 12, at least 13, at least 14, at least 15, at least 16, or at least 17) bacterial strains selected from VE202-1, VE202-3, VE202-4, VE202-6, VE202-7, VE202-8, VE202-9, VE202-13, VE202-14, VE202-15, VE202-16, VE202-18, VE202-21, VE202-26, VE202-27, VE202-28, or VE202-29. In some embodiments, the bacterial composition comprises VE202-1, VE202-3, VE202-4, VE202-6, VE202-7, VE202-8, VE202-9, VE202-13, VE202-14, VE202-15, VE202-16, VE202-18, VE202-21, VE202-26, VE202-27, VE202-28, and VE202-29.

Further embodiments provide a method of treating Graft versus Host Disease (GvHD), the method comprising administering to a subject in need thereof a therapeutically effective amount of a bacterial composition, the bacterial composition comprising at least two (e.g., at least 3, at least 4, at least 5, at least 6, at least 7, at least 8, at least 9, at least 10, at least 11, at least 12, at least 13, at least 14, at least 15, at least 16, or at least 17) bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17. In some embodiments, the bacterial strain comprises 16S rDNA sequences of at least 96%, at least 97%, at least 98%, or at least 99% homology. In some embodiments, the bacterial composition comprises bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17.

Yet other embodiments provide a method of increasing survival following bone marrow transplant, the method comprising administering to a subject in need thereof a therapeutically effective amount of a bacterial composition, the bacterial composition comprising at least two (e.g., at least 3, at least 4, at least 5, at least 6, at least 7, at least 8, at least 9, at least 10, at least 11, at least 12, at least 13, at least 14, at least 15, at least 16, or at least 17) bacterial strains selected from VE202-1, VE202-3, VE202-4, VE202-6, VE202-7, VE202-8, VE202-9, VE202-13, VE202-14, VE202-15, VE202-16, VE202-18, VE202-21, VE202-26, VE202-27, VE202-28, or VE202-29. In some embodiments, the bacterial composition comprises VE202-1, VE202-3, VE202-4, VE202-6, VE202-7, VE202-8, VE202-9, VE202-13, VE202-14, VE202-15, VE202-16, VE202-18, VE202-21, VE202-26, VE202-27, VE202-28, and VE202-29.

Still further embodiments provide a method of increasing survival following bone marrow transplant, the method comprising administering to a subject in need thereof a therapeutically effective amount of a bacterial composition, the bacterial composition comprising at least two (e.g., at least 3, at least 4, at least 5, at least 6, at least 7, at least 8, at least 9, at least 10, at least 11, at least 12, at least 13, at least 14, at least 15, at least 16, or at least 17) bacterial strains comprising 16S rDNA sequences of at least 95% homology to SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO: 13, SEQ ID NO: 14, SEQ ID NO: 15, SEQ ID NO: 16, or SEQ ID NO: 17. In some embodiments, the bacterial strain comprises 16S rDNA sequences of at least 96%, at least 97%, at least 98%, or at least 99% homology. In some embodiments, the bacterial composition comprises bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17.

In some embodiments, the bacterial strain does not have an antibiotic resistance gene. In some embodiments, the antibiotic resistance gene renders the bacterial strain resistant to vancomycin. In some embodiments, the bacterial strain produces butyrate. In some embodiments, the method does not include the administration of an antibiotic. In some embodiments, the bacterial composition is administered prior to, after, or both prior to and after bone marrow transplant. In some embodiments, the subject has chronic GvHD or acute GvHD. In some embodiments, the administration results in an increase in the amount of butyrate in the intestine of the subject. In some embodiments, the method further comprises determining the amount of butyrate in the intestine of the subject prior to and/or after administration of the bacterial composition. In some embodiments, administration results in an increase in the amount of histone acetylation in the intestine of the subject. In some embodiments, the method further comprises determining the amount of histone acetylation in the intestine prior to and/or after administration of the bacterial composition. In some embodiments, administration results in an increase in the amount of butyrate producing bacterial strains in the intestine of the subject. In some embodiments, the method further comprises determining the amount of butyrate producing bacterial strains in the intestine prior to and/or after administration of the bacterial composition.

In some embodiments, the bacterial composition is a pharmaceutical composition (e.g., comprising a pharmaceutical acceptable excipient). In some embodiments, the pharmaceutical composition is formulated for oral or rectal administration. In some embodiments, the pharmaceutical composition is formulated for delivery to the intestine or colon. In some embodiments, one or more of the bacterial strains is lyophilized. In some embodiments, the pharmaceutical composition is in the form of a capsule. In some embodiments, the pharmaceutical composition further comprises a pH sensitive composition comprising one or more enteric polymers. In some embodiments, the bacterial composition is a food composition product further comprising a nutrient.

Yet other embodiments provide a method, the method comprising determining the amount of butyrate in the intestine of a subject, wherein if the amount of butyrate in the intestine of the subject is lower than the amount of butyrate in the intestine of a healthy individual, administering to the subject any one of the bacterial compositions provided herein.

Certain embodiments provide a method, the method comprising determining the amount of histone acetylation in the intestine of a subject, wherein if the amount of histone acetylation in the intestine of the subject is lower than the amount of histone acetylation in the intestine of a healthy individual, administering to the subject any one of the bacterial compositions provided herein.

Other embodiments provide a method, the method comprising determining the amount of butyrate producing bacterial strains in the intestine of a subject, wherein if the amount of butyrate producing bacterial strains in the intestine of the subject is lower than the amount of butyrate producing bacterial strains in the intestine of a healthy individual, administering to the subject any one of the bacterial compositions provided herein.

Additional embodiments are described herein.

DESCRIPTION OF THE FIGURES

(FIG. 1B) Fatty acid levels (short and long chain) in the intestinal luminal contents (stool) and (FIG. 1C) in the intestinal tissue of animals in experimental groups.

FIG. 2. (FIG. 2A) Expression level of SLC5A8 (transporter) and (FIG. 2B) GPR43 (signaling receptor) in CD326+ purified intestinal epithelial cells (IECs) of syngeneic (BALB/c→BALB/c) or allogeneic (C57BL/6→BALB/c) BMT recipients. (FIG. 2C) Level of acetyl-histone H4 (FIG. 2D) levels of histone deacetylase (HDAC) and (FIG. 2E) histone acetyltransferase (HAT) enzymes in IECs (CD326+) of syngeneic and allogeneic transplant recipients.

FIG. 3. (FIG. 3A) Acetylated histone-H4 of CD326+ purified intestinal epithelial cells of syngeneic (BALB/c→BALB/c) or allogeneic (C57BL/6→BALB/c) BMT recipients treated daily with intragastric vehicle or butyrate (10 mg/kg) for 21 days. (FIG. 3B) Weight loss on day 21 (FIG. 3C) GVHD clinical score (FIG. 3D) survival and (FIG. 3E) intestinal histopathology of recipients of bone marrow transplant receiving intragastric butyrate or vehicle.

(FIG. 4B) Level of FITC-dextran translocation across the GI-barrier into blood serum. (FIG. 4C) Total intestinal cell recovery (FIG. 4D) intestinal immunophenotypical analysis and (FIG. 4E) ratio of Treg (FoxP3+) to effector cells (FoxP3-) in recipients of allo-BMT treated with vehicle (▬) and butyrate (▨).

FIG. 5. (FIG. 5A) CD326+ purified intestinal epithelial cells (IECs) cultured in the presence or absence of butyrate and withheld (left panel) or subjected to (right panel) irradiation (6 Gy). (FIG. 5B) Allogeneic CD8+ T cell killing assay. CD326+ IECs incubated with or without butyrate overnight followed by co-culture with allo-primed CD8+ T cells. (FIG. 5C) Chromatin immunoprecipitation (ChIP) of primary CD326+ IECs treated in the presence or absence of butyrate overnight. qPCR analysis of the promoter region of the BCL-B gene. (FIG. 5D) Culture of intestinal stem cells in the presence or absence of butyrate. (FIG. 5E) mRNA expression of claudins. (FIG. 5F) Expression level of pro-apoptotic proteins BAK (left) and BAX (right) (FIG. 5G) anti-apoptotic protein BCL-B, and (FIG. 5H), junctional proteins in CD326+ purified IECs isolated 21 days following allo-BMT.

(FIG. 6A) 16S rRNA-encoding gene sequencing of stool for percent of 17 Clostridal strains in total GI community on day −1 and day +35, relative to BMT on day 0. (FIG. 6B) GVHD clinical score and (FIG. 6C) survival following syngeneic (BALB/c→BALB/c) and allogeneic BMT (C57BL/6→BALB/c) with vehicle or 17-strain administration. (FIG. 6D) Obligate anaerobes of C57BL/6 (H-2b) mice were targeted with antibiotic mixture (ampicillin 5 mg, metronidazole 4 mg, clindamycin 5 mg, and vancomycin 5 mg) by intragastric gavage for 6 days followed by colonization with cocktails of indicated bacteria, 4 and 6 days later. Animals received BMT from donor B10.BR (H-2k) mice and (FIG. 6E) followed for survival.

FIG. 7. SEQ ID NOs:1-17.

DEFINITIONS

Figures 1, 1A:
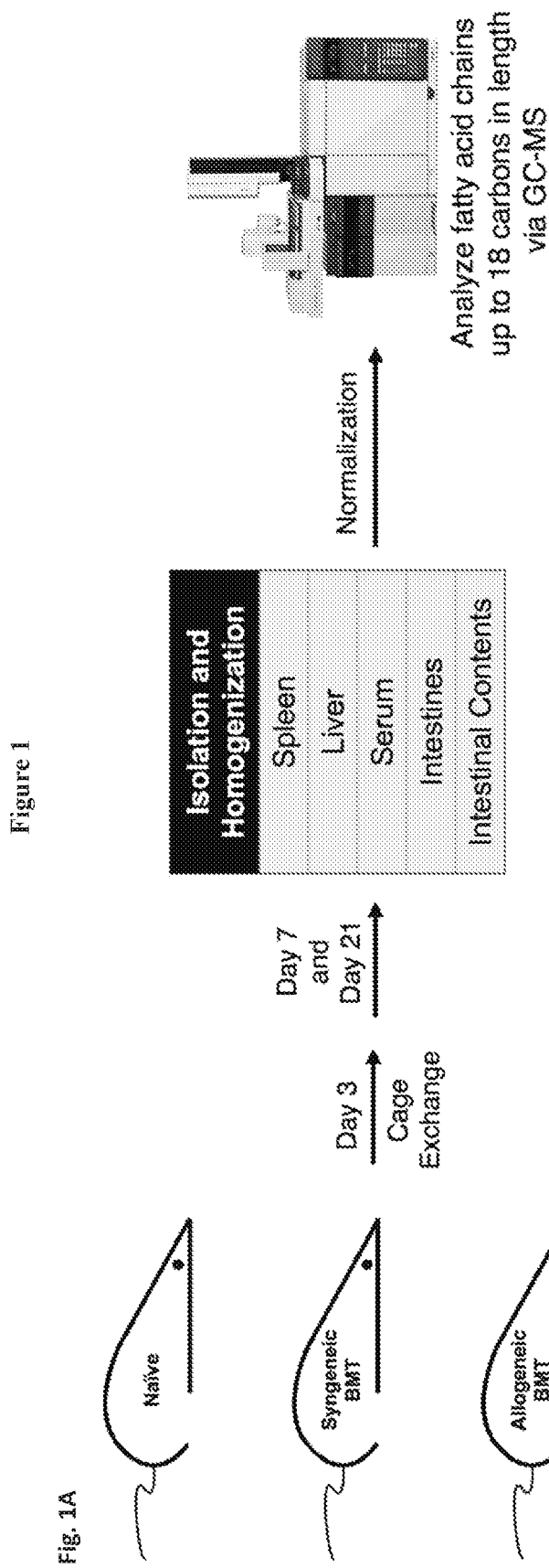
FIG. 1.
(FIG. 1A) Schematic of fatty acid analysis.
Figure 1:
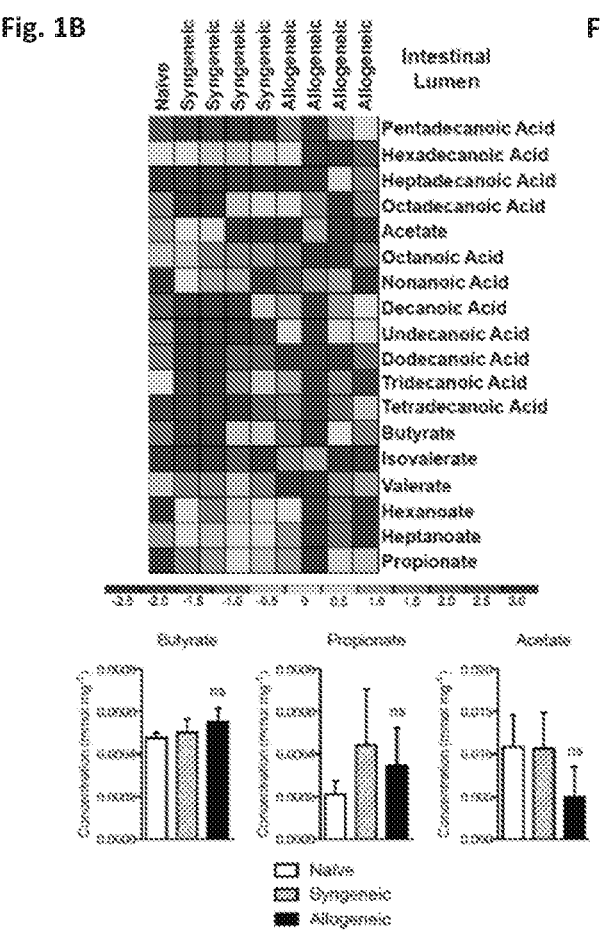
Figure 1:
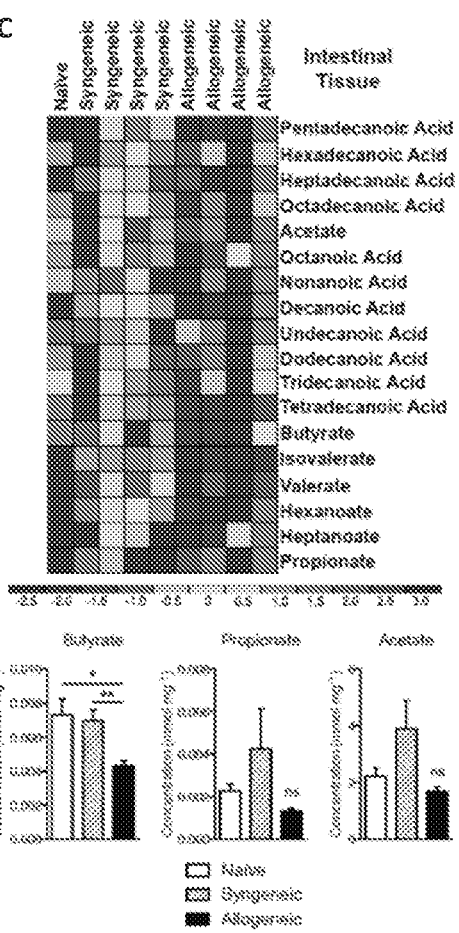

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

As used herein, the term "prokaryotes" refers to a group of organisms that usually lack a cell nucleus or any other membrane-bound organelles. In some embodiments, prokaryotes are bacteria. The term "prokaryote" includes both archaea and eubacteria.

As used herein, the term "subject" refers to individuals (e.g., human, animal, or other organism) to be treated by the methods or compositions of the present disclosure. Subjects include, but are not limited to, mammals (e.g., murines, simians, equines, bovines, porcines, canines, felines, and the like), and most preferably includes humans. In the context of the disclosure, the term "subject" generally refers to an individual who will receive or who has received treatment for a condition characterized by the presence of biofilm-forming bacteria, or in anticipation of possible exposure to biofilm-forming bacteria.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "effective amount" refers to the amount of a composition (e.g., a composition comprising bacteria described herein) sufficient to effect beneficial or desired results. An effective amount can be administered in one or more administrations, applications or dosages and is not intended to be limited to a particular formulation or administration route.

As used herein, the term "administration" refers to the act of giving a drug, prodrug, or other agent, or therapeutic treatment (e.g., compositions comprising bacteria described herein) to a physiological system (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.), topical administration and the like.

As used herein, the term "co-administration" refers to the administration of at least two agent(s) (e.g., bacteria described herein in combination with an additional agent) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

As used herein, the term "pharmaceutical composition" refers to the combination of an active agent (e.g., bacteria described herein) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also can include stabilizers and preservatives. For examples of carriers, stabilizers, and adjuvants. (See e.g., Martin, Remington's Pharmaceutical Sciences, 15th Ed., Mack Publ. Co., Easton, Pa. (1975), incorporated herein by reference). In certain embodiments, the compositions of the present disclosure may be formulated for veterinary, horticultural or agricultural use. Such formulations include dips, sprays, seed dressings, stem injections, sprays, and mists. In certain embodiments, compositions of the present disclosure may be used in any application where it is desirable to alter (e.g., inhibit) the formation of biofilms, e.g., food industry applications; consumer goods (e.g., medical goods, goods intended for consumers with impaired or developing immune systems (e.g., infants, children, elderly, consumers suffering from disease or at risk from disease), and the like.

As used herein, the term "therapeutic agent," refers to compositions that decrease the infectivity, morbidity, or onset of mortality in a subject (e.g., a transplant recipient) or that prevent infectivity, morbidity, or onset of mortality in a host. As used herein, therapeutic agents encompass agents used prophylactically, e.g., before transplant. Such agents may additionally comprise pharmaceutically acceptable compounds (e.g., adjuvants, excipients, stabilizers, diluents, and the like). In some embodiments, the therapeutic agents of the present disclosure are administered in the form of topical compositions, injectable compositions, ingestible compositions, and the like. When the route is topical, the form may be, for example, a solution, cream, ointment, salve or spray.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc. Also included within this term are prokaryotic organisms that are Gram-negative or Gram-positive. "Gram-negative" and "Gram-positive" refer to staining patterns with the Gram-staining process, which is well known in the art. (See e.g., Finegold and Martin, Diagnostic Microbiology, 6th Ed., CV Mosby St. Louis, pp. 13-15 (1982)). "Gram-positive bacteria" are bacteria that retain the primary dye used in the Gram-stain, causing the stained cells to generally appear dark blue to purple under the microscope. "Gram-negative bacteria" do not retain the primary dye used in the Gram-stain, but are stained by the counterstain. Thus, Gram-negative bacteria generally appear red.

The term "non-pathogenic bacteria" or "non-pathogenic bacterium" includes all known and unknown non-pathogenic bacterium (Gram-positive or Gram-negative) and any pathogenic bacterium that has been mutated or converted to a non-pathogenic bacterium. Furthermore, a skilled artisan recognizes that some bacteria may be pathogenic to specific species and non-pathogenic to other species; thus, these bacteria can be utilized in the species in which it is non-pathogenic or mutated so that it is non-pathogenic.

As used herein, the term "cell culture" refers to any in vitro culture of cells, including, e.g., prokaryotic cells and eukaryotic cells. Included within this term are continuous cell lines (e.g., with an immortal phenotype), primary cell cultures, transformed cell lines, finite cell lines (e.g., non-transformed cells), bacterial cultures in or on solid or liquid media, and any other cell population maintained in vitro.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Such examples are not however to be construed as limiting the sample types applicable to the present disclosure.

DETAILED DESCRIPTION

Provided herein are compositions and methods for administering bacterial strains to reduce GvHD and improve survival after allogeneic BMT.

Graft-versus-host disease (GvHD) is a medical complication following the receipt of transplanted tissue from a genetically different person. GvHD is commonly associated with stem cell transplant (bone marrow transplant), but the term also applies to other forms of tissue graft. Immune cells (white blood cells) in the donated tissue (the graft) recognize the recipient (the host) as foreign (non-self). The transplanted immune cells then attack the host's body cells. GvHD can also occur after a blood transfusion if the blood products used have not been irradiated or treated with an approved pathogen reduction system.

Whereas transplant rejection occurs when the host rejects the graft, GvHD occurs when the graft rejects the host. The underlying principle (alloimmunity) is the same, but the details and course may differ. In the classical sense, acute graft-versus-host-disease is characterized by selective damage to the liver, skin (rash), mucosa, and the gastrointestinal tract. Newer research indicates that other graft-versus-host-disease target organs include the immune system (the hematopoietic system, e.g., the bone marrow and the thymus) itself, and the lungs in the form of immune-mediated pneumonitis. Biomarkers can be used to identify specific causes of GvHD, such as elafin in the skin. Chronic graft-versus-host-disease also attacks the above organs, but over its long-term course can also cause damage to the connective tissue and exocrine glands.

Acute GvHD of the GI tract can result in severe intestinal inflammation, sloughing of the mucosal membrane, severe diarrhea, abdominal pain, nausea, and vomiting. This is typically diagnosed via intestinal biopsy. Liver GvHD is generally measured by the bilirubin level in acute patients. Skin GvHD results in a diffuse red maculopapular rash, sometimes in a lacy pattern. Mucosal damage to the vagina can result in severe pain and scarring, and appears in both acute and chronic GvHD. This can result in an inability to have sexual intercourse.

Acute GvHD is staged as follows: overall grade (skin-liver-gut) with each organ staged individually from a low of 1 to a high of 4. Patients with grade IV GvHD usually have a poor prognosis. If the GvHD is severe and requires intense immunosuppression involving steroids and additional agents to get under control, the patient may develop severe infections as a result of the immunosuppression and may die of infection.

In the oral cavity, chronic graft-versus-host-disease manifests as lichen planus with a higher risk of malignant transformation to oral squamous cell carcinoma in comparison to the classical oral lichen planus. Graft-versus-host-disease-associated oral cancer may have more aggressive behavior with poorer prognosis, when compared to oral cancer in non-hematopoietic stem cell transplantation patients.

In the clinical setting, graft-versus-host-disease is divided into acute and chronic forms, and scored or graded on the basis of the tissue affected and the severity of the reaction. The acute or fulminant form of the disease (aGvHD) is normally observed within the first 100 days post-transplant, and is a major challenge to transplants owing to associated morbidity and mortality.

The chronic form of graft-versus-host-disease (cGvHD) normally occurs after 100 days. The appearance of moderate to severe cases of cGvHD adversely influences long-term survival.

Intravenously administered glucocorticoids, such as prednisone, are the standard of care in acute GvHD and chronic GvHD. The use of these glucocorticoids is designed to suppress the T-cell-mediated immune onslaught on the host tissues; however, in high doses, this immune-suppression raises the risk of infections and cancer relapse and has other undesirable side effects.

I. Compositions

In one aspect, the disclosure provides methods comprising bacterial compositions, wherein the bacterial composition comprises one or more bacterial strains selected from the group consisting of VE202-1, VE202-3, VE202-4, VE202-6, VE202-7, VE202-8, VE202-9, VE202-13, VE202-14, VE202-15, VE202-16, VE202-18, VE202-21, VE202-26, VE202-27, VE202-28, and VE202-29. The VE-202 strains have been described in detail, for instance in Atarashi et al. *Nature* 2013, 500: 232-237 and supplemental materials, Narushima et al., *Gut Microbes* 2014: 5(3): 333-339, and PCT published application WO2013/080561, all of which are incorporated by reference in their entirety. A summary of the seventeen VE-202 strains is provided in Table 1. The genomes of the VE-202 strains have been deposited in the NCBI database, and the Genbank Assembly Accession ID of each of the VE202 strains is provided in Table 1. In addition, Table 1 provides the SEQ ID NOs of the 16S rDNA sequences determined from the Genbank Assembly Accession ID nucleotide sequences and/or through targeted sequencing. The 16S rDNA sequences are a subsequence of the Genbank Accession IDs, also depicted in Table 1.

In one aspect, the disclosure provides methods comprising bacterial compositions, wherein the bacterial composition comprises at least two bacterial strains selected from the group consisting of VE202-1, VE202-3, VE202-4, VE202-6, VE202-7, VE202-8, VE202-9, VE202-13, VE202-14, VE202-15, VE202-16, VE202-18, VE202-21, VE202-26, VE202-27, VE202-28, and VE202-29. In some embodiments of the methods provided herein, the bacterial composition comprises at least 2, at least 3, at least 4, at least 5, at least 6, at least 7, at least 8, at least 9, at least 10, at least 11, at least 12, at least 13, at least 14, at least 15, at least 16, or at least 17 bacterial strains.

In one aspect, the disclosure provides methods comprising bacterial compositions, wherein the bacterial composition comprises VE202-1, VE202-3, VE202-4, VE202-6, VE202-7, VE202-8, VE202-9, VE202-13, VE202-14, VE202-15, VE202-16, VE202-18, VE202-21, VE202-26, VE202-27, VE202-28, and VE202-29. In one aspect, the disclosure provides methods comprising bacterial compositions, wherein the bacterial composition essentially consists of VE202-1, VE202-3, VE202-4, VE202-6, VE202-7, VE202-8, VE202-9, VE202-13, VE202-14, VE202-15, VE202-16, VE202-18, VE202-21, VE202-26, VE202-27, VE202-28, and VE202-29. As used herein, "essentially consist of" refers to bacterial compositions that do not include any additional clostridial strains (Such compositions may include additional non-clostridial strains, such as e.g., *E. coli* or *Bacteroides*). In one aspect, the disclosure provides methods comprising bacterial compositions, wherein the bacterial composition consists of VE202-1, VE202-3, VE202-4, VE202-6, VE202-7, VE202-8, VE202-9, VE202-13, VE202-14, VE202-15, VE202-16, VE202-18, VE202-21, VE202-26, VE202-27, VE202-28, and VE202-29. As used herein, "consist of" refers to bacterial compositions that do not include any additional bacterial strains.

In one aspect, the disclosure provides methods comprising bacterial compositions, wherein the bacterial composition comprises one or more bacterial strains selected from the group consisting of VE202-1, VE202-3, VE202-4, VE202-6, VE202-7, VE202-8, VE202-9, VE202-13, VE202-14, VE202-15, VE202-16, VE202-18, VE202-21, VE202-26, VE202-27, VE202-28, and VE202-29. The closest relatives of the VE-202 sequences have been determined, e.g., by comparing the 16S rDNA sequences and/or the whole genome of a particular VE-202 sequence against bacterial sequences available in public databases such as the NCBI (See e.g., Atarashi et al. *Nature* 2013, 500: 232-237 and supplemental materials). The closest relatives of VE202-1 are *Clostridium saccharogumia*, *Clostridium ramosum* and *Clostridium spiroforme*. The closest relatives of VE202-3 are *Flavonifractor plautii*, *Pseudoflavonifractor capillosus* and Lachnospiraceae bacterium. The closest relatives of VE202-4 are *Clostridium hathewayi* and *Clostridium saccharolyticum*. The closest relatives of VE202-6 are *Blautia coccoides*, Lachnospiraceae bacterium and *Blautia producta*. The closest relatives of VE202-7 is *Clostridium bolteae*. The closest relative of VE202-8 is Clostridiacieae bacterium. The closest relatives of VE202-9 are *Clostridium indolis* and *Anaerostipes caccae*. The closest relative of VE202-13 is *Anaerotruncus colihominis*. The closest relatives of VE202-14 are *Ruminococcus* sp., Lachnospiraceae bacterium and *Coprococcus comes*. The closest relatives of VE202-15 are *Clostridium lavalense* and *Clostridium asparagiforme*. The closest relatives of VE202-16 is *Clostridium symbiosum*. The closest relative of VE202-18 is *Clostridium ramosum*. The closest relatives of VE202-21 are *Eubacterium contortum*, *Eubacterium fissicatena* and *Clostridium* D5. The closest relatives of VE202-26 are *Clostridium scindens* and Lachnospiraceae bacterium. The closest relative of VE202-27 is Lachnospiraceae bacterium. The closest relatives of VE202-28 are *Clostridium* bacterium and *Clostridium aldenense*. The closest relative of VE202-29 is Lachnospiraceae bacterium. Thus, in some embodiments, the disclosure provides methods comprising bacterial compositions, wherein the bacterial composition comprises one or more bacterial strains selected from the group consisting of *Clostridium saccharogumia*, *Clostridium ramosum*, *Clostridium spiroforme*, *Flavonifractor plautii*, *Pseudoflavonifractor capillosus*, Lachnospiraceae bacterium, *Clostridium hathewayi*, *Clostridium saccharolyticum*, *Blautia coccoides*, *Blautia producta*, *Clostridium bolteae*, Clostridiacieae bacterium, *Clostridium indolis*, *Anaerostipes caccae*, *Anaerotruncus colihominis*, *Ruminococcus* sp., *Coprococcus comes*, *Clostridium lavalense*, *Clostridium asparagiforme*, *Clostridium symbiosum*, *Eubacterium contortum*, *Eubacterium fissicatena*, *Clostridium* D5, *Clostridium scindens*, *Clostridium* bacterium, and *Clostridium aldenense*. In some embodiments of the methods provided herein, the bacterial composition comprises at least 2, at least 3, at least 4, at least 5, at least 6, at least 7, at least 8, at least 9, at least 10, at least 11, at least 12, at least 13, at least 14, at least 15, at least 16, or at least 17 bacterial strains.

In one aspect, the disclosure provides methods comprising bacterial compositions, wherein the bacterial composition comprises seventeen bacterial strains (1) *Clostridium saccharogumia*, *Clostridium ramosum* or *Clostridium spiroforme*, and (2) *Flavonifractor plautii*, *Pseudoflavonifractor capillosus* or Lachnospiraceae bacterium, and (3) *Clostridium hathewayi* or *Clostridium saccharolyticum*, and (4) *Blautia coccoides*, Lachnospiraceae bacterium or *Blautia producta*, and (5) *Clostridium bolteae*, and (6) Clostridiacieae bacterium, and (7) *Clostridium indolis* or *Anaerostipes caccae*, and (8) *Anaerotruncus colihominis*, and (9) *Ruminococcus* sp., Lachnospiraceae bacterium or *Coprococcus comes*, and (10) *Clostridium lavalense* and *Clostridium asparagiforme*, and (11) *Clostridium symbiosum*, and (12) *Clostridium ramosum*, and (13) *Eubacterium* contortum, *Eubacterium fissicatena* or *Clostridium* D5, and (14) *Clostridium scindens* or Lachnospiraceae bacterium, and (15) Lachnospiraceae bacterium, and (16) *Clostridium* bacterium or *Clostridium aldenese*, and (17) Lachnospiraceae bacterium. In one aspect, the disclosure provides methods comprising bacterial compositions, wherein the bacterial composition essentially consists of seventeen bacterial strains (1) *Clostridium saccharogumia*, *Clostridium ramosum* or *Clostridium spiroforme*, and (2) *Flavonifractor plautii*, *Pseudoflavonifractor capillosus* or Lachnospiraceae bacterium, and (3) *Clostridium hathewayi* or *Clostridium saccharolyticum*, and (4) *Blautia coccoides*, Lachnospiraceae bacterium or *Blautia producta*, and (5) *Clostridium bolteae*, and (6) Clostridiacieae bacterium, and (7) *Clostridium indolis* or *Anaerostipes caccae*, and (8) *Anaerotruncus colihominis*, and (9) *Ruminococcus* sp., Lachnospiraceae bacterium or *Coprococcus comes*, and (10) *Clostridium lavalense* and *Clostridium asparagiforme*, and (11) *Clostridium symbiosum*, and (12) *Clostridium ramosum*, and (13) *Eubacterium* contortum, *Eubacterium fissicatena* or *Clostridium* D5, and (14) *Clostridium scindens* or Lachnospiraceae bacterium, and (15) Lachnospiraceae bacterium, and (16) *Clostridium* bacterium or *Clostridium aldenese*, and (17) Lachnospiraceae bacterium. In one aspect, the disclosure provides methods comprising bacterial compositions, wherein the bacterial composition consists of seventeen bacterial strains (1) *Clostridium saccharogumia*, *Clostridium ramosum* or *Clostridium spiroforme*, and (2) *Flavonifractor plautii*, *Pseudoflavonifractor capillosus* or Lachnospiraceae bacterium, and (3) *Clostridium hathewayi* or *Clostridium saccharolyticum*, and (4) *Blautia coccoides*, Lachnospiraceae bacterium or *Blautia producta*, and (5) *Clostridium bolteae*, and (6) Clostridiacieae bacterium, and (7) *Clostridium indolis* or *Anaerostipes caccae*, and (8) *Anaerotruncus colihominis*, and (9) *Ruminococcus* sp., Lachnospiraceae bacterium or *Coprococcus comes*, and (10) *Clostridium lavalense* and *Clostridium asparagiforme*, and (11) *Clostridium symbiosum*, and (12) *Clostridium ramosum*, and (13) *Eubacterium* contortum, *Eubacterium fissicatena* or *Clostridium* D5, and (14) *Clostridium scindens* or Lachnospiraceae bacterium, and (15) Lachnospiraceae bacterium, and (16) *Clostridium* bacterium or *Clostridium aldenese*, and (17) Lachnospiraceae bacterium.

TABLE 1

| VE-202 strain # | Genbank Assembly Accession ID | 16S rDNA Seq ID NO | Genbank Accession ID | closest relatives | notes |
|---|---|---|---|---|---|
| VE202-1 | GCA_000508865.1 | 1 | BAHP02000171.1 | Clostridium saccharogumia; Clostridium ramosum; Clostridium spiroforme | Vancomycin resistant* |
| VE202-3 | GCA_000508885.1 | 2 | BAHQ02000607.1 | Flavonifractor plautii; Pseudoflavinofractor capillosus; Lachnospiraceae bacterium | Vancomycin resistant* |
| VE202-4 | GCA_000508905.1 | 3 | BAHR02000208.1 | Clostridium hathewayi; Clostridium saccharolyticum | |
| VE202-6 | GCA_000508925.1 | 4 | BAHT02000283.1 | Blautia coccoides; Lachnospiraceae bacterium; Blautia producta | Vancomycin resistant* |
| VE202-7 | GCA_000508945.1 | 5 | BAHU02000044.1 | Clostridium bolteae | |
| VE202-8 | GCA_000508965.1 | 6 | BAHV02000026.1 | Clostridiacieae bacterium | Vancomycin resistant* |
| VE202-9 | GCA_000508985.1 | 7 | BAHW02000064.1 | Clostridium indolis; Anaerostipes caccae | Strong butyrate producer* |
| VE202-13 | GCA_000509005.1 | 8 | BAIA02000175.1 | Anaerotruncus colihominis | |
| VE202-14 | GCA_000509025.1 | 9 | BAIB02000026.1 | Ruminococcus sp.; Lachnospiraceae bacterium; Coprococcus comes | |
| VE202-15 | GCA_000509045.1 | 10 | BAIC02000310.1 | Clostridium lavalense; Clostridium asparagiforme | |
| VE202-16 | GCA_000509065.1 | 11 | BAID02000318.1 | Clostridium symbiosum | Strong butyrate producer* |
| VE202-18 | GCA_000509085.1 | 12 | BAIE02000084.1 | Clostridium ramosum | Vancomycin resistant* |
| VE202-21 | GCA_000509105.1 | 13 | BAIF02000133.1 | Eubacterium contortum; Eubacterium fissicatena; Clostridium D5 | |
| VE202-26 | GCA_000509125.1 | 14 | BAII02000026.1 | Clostridium scindens; Lachnospiraceae bacterium | |
| VE202-27 | GCA_000509145.1 | 15 | BAIJ02000227.1 | Lachnospiraceae bacterium | Strong butyrate producer* |
| VE202-28 | GCA_000509165.1 | 16 | ABQR01000074.1 (1) | Clostridium bacterium; Clostridium aldenense | |
| VE202-29 | GCA_000509185.1 | 17 | ACTP02000021.1 (2) | Lachnospiraceae bacterium | Strong butyrate producer* |

*Narushima et al., *Gut Microbes* 2014: 5(3): 333-339
(1) *Clostridiales bacterium* 1_7_47FAA
(2) Lachnospiraceae_bacterium 3_1_57FAA In one aspect, the disclosure provides methods comprising bacterial compositions comprising one or more bacterial strains comprising nucleotide sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17. In some embodiments, the bacterial strain has at least 80%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or up to 100% homology.

In one aspect, the disclosure provides methods comprising bacterial compositions comprising one or more bacterial strains of at least 95% homology to nucleotide sequences found in bacterial strains defined by the Genbank Assembly Accession IDs GCA_000508865.1, GCA_000508885.1, GCA_000508905.1, GCA_000508925.1, GCA 000508945.1, GCA 000508965.1, GCA 000508985.1, GCA 000509005.1, GCA_000509025.1, GCA_000509045.1, GCA_000509065.1, GCA_000509085.1, GCA000509105.1, GCA000509125.1, GCA000509145.1, GCA000509165.1, or GCA 000509185.1. In some embodiments, the bacterial strain has at least 80%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or up to 100% homology.

In one aspect, the disclosure provides methods comprising bacterial compositions comprising one or more bacterial strains comprising 16S rDNA sequences of at least 95% homology to nucleotide sequences found in bacterial strains defined by the Genbank Assembly Accession IDs GCA_000508865.1, GCA_000508885.1, GCA_000508905.1, GCA_000508925.1, GCA_000508945.1, GCA_000508965.1, GCA_000508985.1, GCA_000509005.1, GCA_000509025.1, GCA_000509045.1, GCA_000509065.1, GCA_000509085.1, GCA_000509105.1, GCA_000509125.1, GCA_000509145.1, GCA_000509165.1, or GCA_000509185.1. In some embodiments, the bacterial strain has at least 80%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or up to 100% homology.

In one aspect, the disclosure provides methods comprising bacterial compositions comprising one or more bacterial strains comprising 16S rDNA sequences of at least 95% homology to nucleotide sequences found in bacterial strains defined by the Genbank Accession IDs: BAHP0200017.1, BAHQ02000607.1, BAHR02000208.1, BAHT02000283.1, BAHU02000044.1, BAHV02000026.1, BAHW02000064.1, BAIA02000175.1, BAIB02000026.1, BAIC02000310.1, BAID02000318.1, BAIE02000084.1, BAIF02000133.1, BAII02000026.1, BAIJ02000227.1, ABQR01000074.1, or ACPT02000021.1. In some embodiments, the bacterial strain has at least 80%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or up to 100% homology.

In one aspect, the disclosure provides methods comprising bacterial compositions comprising one or more bacterial strains of at least 95% homology to nucleotide sequences found in bacterial strains defined by the Genbank Accession IDs BAHPOi20001711, BAHQ02000607.1, BAHR02000208.1, BAHT02000283.1, BAHU02000044.1, BAHV02000026.1, BAHWO2000064.1, BAIA02000175.1, BAIB02000026.1, BAIC02000310.1, BAID02000318.1, BAIE02000084.1, BAIF02000133.1, BAII02000026.1, BAIJ02000227.1, ABQR01000074.1, or ACPT02000021.1. In some embodiments, the bacterial strain has at least 80%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or up to 100% homology.

In one aspect, the disclosure provides methods comprising bacterial compositions comprising one or more bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17. It should be appreciated that SEQ ID NOs:1-17 correspond to the 16S rDNA sequences of VE202-1, VE202-3, VE202-4, VE202-6, VE202-7, VE202-8, VE202-9, VE202-13, VE202-14, VE202-15, VE202-16, VE202-18, VE202-21, VE202-26, VE202-27, VE202-28, and VE202-29 respectively (See Table 1). Additional nucleotide sequences that correspond to the 16S rDNA regions of the VE202 strains are found in WO2013/080561; herein incorporated by reference in its entirety. Bacteria with similar 16S RNA sequences are closely related to each other. Furthermore, closely related bacteria are expected to have similar genes and properties. For example, a bacterial strain that has a 16S RNA sequence that is similar to SEQ ID NO:1, which is the 16S RNA sequence of VE202-1, is expected to have properties similar to VE202-1. Similarly, in another example, a bacterial composition comprising 16S rDNA sequences of at least 95% homology to SEQ ID NO:1, SEQ ID NO:2, SEQ ID NO:3, and SEQ ID NO:4 is expected to have the same properties as a bacterial composition comprising VE202-1, VE202-3, VE202-4, and VE202-6.

In one aspect, the disclosure provides methods comprising bacterial compositions, wherein the bacterial compositions comprise bacterial strains. It should be appreciated that the terms bacteria, strains, and bacterial strains are used interchangeably herein. The bacterial strains of the bacterial compositions disclosed herein can be identified by their 16S rRNA (or 16S rDNA) nucleic acid sequence. In some embodiments, the bacterial strains have 16S RNA sequences corresponding to SEQ ID NO: 1-17. In general, bacteria are classified as belonging to a specific species and/or genus based on their 16S rRNA nucleic acid sequence. Bacteria, such as bacteria derived from the microbiome, may also be classified into phylogenetic clusters with other closely related strains and species. (See e.g., Rajilic-Stojanovic, M., and de Vos, W. M. (2014). The first 1000 cultured species of the human gastrointestinal microbiota. *FEMS Microbiol Rev* 38, 996-1047). Methods for determining the identity of specific bacterial species based on their 16S rRNA (or 16S rDNA) nucleic acid sequence are well known in the art (See e.g., Jumpstart Consortium Human Microbiome Project Data Generation Working, G. (2012). *Evaluation of 16S rDNA-based community profiling for human microbiome research*. PLoS One 7, e39315).

In one aspect, the disclosure provides methods comprising bacterial compositions comprising one or more bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO: 17. In some embodiments of the methods provided herein, the bacterial composition comprises at least 2, at least 3, at least 4, at least 5, at least 6, at least 7, at least 8, at least 9, at least 10, at least 11, at least 12, at least 13, at least 14, at least 15, at least 16, or at least 17 bacterial strains.

In one aspect, the disclosure provides methods comprising bacterial compositions comprising at least two bacterial strains comprising 16S rDNA sequences of at least 95% homology to SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO: 17. In some embodiments of the methods provided herein, the bacterial composition comprises at least 3, at least 4, at least 5, at least 6, at least 7, at least 8, at least 9, at least 10, at least 11, at least 12, at least 13, at least 14, at least 15, at least 16, or at least 17 bacterial strains.

In one aspect, the disclosure provides methods comprising bacterial compositions comprising bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO:12, SEQ ID NO:13, SEQ ID NO:14, SEQ ID NO:15, SEQ ID NO:16, and SEQ ID NO: 17. In one aspect, the disclosure provides methods comprising bacterial compositions comprising bacterial strains essentially consisting of 16S rDNA sequences of at least 95% homology to SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO:11, SEQ ID NO:12, SEQ ID NO:13, SEQ ID NO:14, SEQ ID NO:15, SEQ ID NO:16, and SEQ ID NO: 17. In one aspect, the disclosure provides methods comprising bacterial compositions comprising bacterial strains consisting of 16S rDNA sequences of at least 95% homology to SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO: 17.

It should be appreciated that for all compositions provided herein, in some embodiments, the bacterial strains are purified. Thus, for example the disclosure provides purified bacterial strains comprising a 16S rDNA sequence with a nucleic acid sequence selected from the group consisting of SEQ ID NOs:1-17. In addition, for example, the disclosure provides bacterial compositions comprising purified bacterial strains comprising a 16S rDNA sequence with a nucleic acid sequence selected from the group consisting of SEQ ID NOs: 1-17. The bacterial strains disclosed herein originally may have been obtained and purified from the microbiota of one or more human individuals or obtained from sources other than the human microbiota, including soil and non-human microbiota. As provided herein, in some embodiments, bacteria isolated from the human microbiota, non-human microbiota, soil, or any alternative source are purified prior to use in the compositions and methods provided herein.

It should further be appreciated that the bacterial strains disclosed herein that have a 16S rDNA sequence with a nucleic acid sequence selected from the group consisting of SEQ ID NOs: 1-17, are also homologous to other strains based on their whole genome sequence, or subset of their whole genome sequence. Thus, it should be appreciated that, in one aspect, the disclosure also provides compositions and methods comprising bacterial species with close homology to the bacterial strains that have a 16S rDNA sequence with a nucleic acid sequence selected from the group consisting of SEQ ID NOs: 1-17.

In one aspect, the disclosure provides methods and bacterial compositions comprising bacterial strains with 16S rDNA sequences that have homology to a nucleic acid sequence of any one of the sequences of the bacterial strains or species described herein. In some embodiments, the bacterial strain has at least 60%, at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or up to 100% homology relative to any of the strains or bacterial species described herein over a specified region or over the entire sequence. It would be appreciated by one of skill in the art that the term "homology" or "percent homology," in the context of two or more nucleic acid sequences or amino acid sequences, refers to a measure of similarity between two or more sequences or portion(s) thereof. The homology may exist over a region of a sequence that is at least about 50 nucleotides in length, or more preferably over a region that is 100 to 500 or 1000 or more nucleotides in length. In some embodiments, the homology exists over the length the 16S rRNA or 16S rDNA sequence, or a portion thereof.

Additionally, or alternatively, two or more sequences may be assessed for the identity between the sequences. The terms "identical" or percent "identity" in the context of two or more nucleic acids or amino acid sequences, refer to two or more sequences or subsequences that are the same. Two sequences are "substantially identical" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% identical) over a specified region or over the entire sequence, when compared and aligned for maximum correspondence over a comparison window, or designated region as measured using one of the following sequence comparison algorithms or by manual alignment and visual inspection. Optionally, the identity exists over a region that is at least about 50 nucleotides in length, or more preferably over a region that is 100 to 500 or 1000 or more nucleotides in length. In some embodiments, the identity exists over the length the 16S rRNA or 16S rDNA sequence.

Additionally, or alternatively, two or more sequences may be assessed for the alignment between the sequences. The terms "alignment" or percent "alignment" in the context of two or more nucleic acids or amino acid sequences, refer to two or more sequences or subsequences that are the same. Two sequences are "substantially aligned" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% identical) over a specified region or over the entire sequence, when compared and aligned for maximum correspondence over a comparison window, or designated region as measured using one of the following sequence comparison algorithms or by manual alignment and visual inspection. Optionally, the alignment exists over a region that is at least about 50 nucleotides in length, or more preferably over a region that is 100 to 500 or 1000 or more nucleotides in length. In some embodiments, the identity exists over the length the 16S rRNA or 16S rDNA sequence.

For sequence comparison, typically one sequence acts as a reference sequence, to which test sequences are compared. Methods of alignment of sequences for comparison are well known in the art. See, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman. Proc. Natl. Acad. Sci. USA 85:2444, 1988, by computerized implementations of these algorithms (GAP, BESTFIT, FASTA, and TFASTA in the Wisconsin Genetics Software Package, Genetics Computer Group. Madison. Wis.), or by manual alignment and visual inspection (see. e.g., Brent et al., Current Protocols in Molecular Biology, John Wiley & Sons, Inc. (Ringbou ed., 2003)). Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively.

In some embodiments of the compositions provided herein, one or more of the bacterial strains are human-derived bacteria. In some embodiments of the compositions provided herein, all of the bacterial strains are human-derived bacteria. In some embodiments of the compositions provided herein, the bacterial strains are derived from more than one human donor.

The bacterial strains used in the compositions provided herein generally are isolated from the microbiome of healthy individuals. In some embodiments, the compositions include strains originating from a single individual. In some embodiments, the compositions include strains originating from multiple individuals. In some embodiments, the bacterial strains are obtained from multiple individuals, isolated and grown up individually. The bacterial compositions that are grown up individually may subsequently be combined to provide the compositions of the disclosure. It should be appreciated that the origin of the bacterial strains of the compositions provided herein is not limited to the human microbiome from a healthy individual. In some embodiments, the bacterial strains originate from a human with a microbiome in dysbiosis. In some embodiments, the bacterial strains originate from non-human animals or the environment (e.g., soil or surface water). In some embodiments, the combinations of bacterial strains provided herein originate from multiple sources (e.g., human and non-human animals).

In one aspect, the disclosure provides methods comprising bacterial strains wherein the bacterial strains produce butyrate. In some embodiments, the bacterial strains produce butyrate when introduced in the intestine of the subject. Butyrate producing bacterial strains are known in the art. In addition, butyrate producing bacterial strains can be identified, for instance, by sequencing the genome to identify the presence of a set of genes that allows for butyrate production and/or assessing if a particular strain produces butyrate upon introduction in the intestine (e.g., by detecting the presence of butyrate in the stool).

In some embodiments of the methods comprising compositions of butyrate producing bacterial strains, the composition comprises one or more bacterial strains selected from the group consisting of VE202-1, VE202-3, VE202-4, VE202-6, VE202-7, VE202-8, VE202-9, VE202-13, VE202-14, VE202-15, VE202-16, VE202-18, VE202-21, VE202-26, VE202-27, VE202-28, and VE202-29. The VE-202 strains have been described in detail, for instance in Atarashi et al. *Nature* 2013, 500: 232-237 and supplemental materials, Narushima et al., *Gut Microbes* 2014: 5(3): 333-339, and PCT published application WO2013/080561, all of which are incorporated by reference in their entirety. The combination of the seventeen VE202 strains produces butyrate. In addition, it has been shown (See e.g., Narushima et al.) that each of the 17 strains individually is able to produce butyrate. Thus, in some embodiments, the methods disclosed herein provide for the administration of a composition of butyrate producing bacterial strains, wherein composition of butyrate producing bacterial comprises one or more bacterial strains selected from the group consisting of VE202-1, VE202-3, VE202-4, VE202-6, VE202-7, VE202-8, VE202-9, VE202-13, VE202-14, VE202-15, VE202-16, VE202-18, VE202-21, VE202-26, VE202-27, VE202-28, and VE202-29. In some embodiments of the methods provided herein, the composition of butyrate producing bacterial strains comprises at least 2, at least 3, at least 4, at least 5, at least 6, at least 7, at least 8, at least 9, at least 10, at least 11, at least 12, at least 13, at least 14, at least 15, at least 16, or at least 17 bacterial strains. As further shown in Narushima et al., VE202-9, VE202-16, VE202-27, and VE202-29 are strong butyrate producers (See also Table 1). Thus, in some embodiments, the methods disclosed herein provide for the administration of a composition of butyrate producing bacterial strains, wherein the composition of butyrate producing bacterial comprises one or more bacterial strains selected from the group consisting of VE202-9, VE202-16, VE202-27, and VE202-29. In some embodiments, the composition of butyrate producing bacterial strains comprises VE202-9, VE202-16, VE202-27, and VE202-29. In some embodiments, the composition of butyrate producing bacterial strains comprises VE202-9, VE202-16, and VE202-27. In some embodiments, the composition of butyrate producing bacterial strains comprises VE202-9, VE202-16, and VE202-29. In some embodiments, the composition of butyrate producing bacterial strains comprises VE202-9, VE202-27 and VE202-29. In some embodiments, the composition of butyrate producing bacterial strains comprises VE202-16, VE202-27 and VE202-29. In some embodiments, the composition of butyrate producing bacterial strains comprises VE202-9 and VE202-29. In some embodiments, the composition of butyrate producing bacterial strains comprises VE202-16 and VE202-29. In some embodiments, the composition of butyrate producing bacterial strains comprises VE202-27 and VE202-29. In some embodiments, the composition of butyrate producing bacterial strains comprises VE202-9 and VE202-27. In some embodiments, the composition of butyrate producing bacterial strains comprises VE202-16 and VE202-27. In some embodiments, the composition of butyrate producing bacterial strains comprises VE202-9 and VE202-16. In each of the compositions of butyrate producing bacterial strains provided herein, in some embodiments, the composition may include additional bacterial strains selected from the group consisting of VE202-1, VE202-3, VE202-4, VE202-6, VE202-7, VE202-8, VE202-9, VE202-13, VE202-14, VE202-15, VE202-16, VE202-18, VE202-21, VE202-26, VE202-27, VE202-28, and VE202-29. It should further be appreciated that in some embodiments, in each of the compositions of butyrate producing bacterial strains provided herein, the composition may include additional bacterial strains that are known butyrate producers, wherein the additional bacterial strains are not VE202 strains.

In some embodiments of the methods comprising compositions of butyrate producing bacterial strains, the composition comprises one or more bacterial strains selected from the group consisting of VE202-1, VE202-3, VE202-4, VE202-6, VE202-7, VE202-8, VE202-9, VE202-13, VE202-14, VE202-15, VE202-16, VE202-18, VE202-21, VE202-26, VE202-27, VE202-28, and VE202-29. The closest relatives of VE202-1 are *Clostridium saccharogumia, Clostridium ramosum* and *Clostridium spiroforme*. The closest relatives of VE202-3 are *Flavonifractor plautii, Pseudoflavonifractor capillosus* and Lachnospiraceae bacterium. The closest relatives of VE202-4 are *Clostridium hathewayi* and *Clostridium saccharolyticum*. The closest relatives of VE202-6 are *Blautia coccoides*, Lachnospiraceae bacterium and *Blautia producta*. The closest relatives of VE202-7 is *Clostridium bolteae*. The closest relative of VE202-8 is Clostridiacieae bacterium. The closest relatives of VE202-9 are *Clostridium indolis* and *Anaerostipes caccae*. The closest relative of VE202-13 is *Anaerotruncus colihominis*. The closest relatives of VE202-14 are *Ruminococcus* sp., Lachnospiraceae bacterium and *Coprococcus comes*. The closest relatives of VE202-15 are *Clostridium lavalense* and *Clostridium asparagiforme*. The closest relatives of VE202-16 is *Clostridium symbiosum*. The closest relative of VE202-18 is *Clostridium ramosum*. The closest relatives of VE202-21 are *Eubacterium contortum, Eubacterium fissicatena* and *Clostridium* D5. The closest relatives of VE202-26 are *Clostridium scindens* and Lachnospiraceae bacterium. The closest relative of VE202-27 is Lachnospiraceae bacterium. The closest relatives of VE202-28 are *Clostridium* bacterium and *Clostridium aldenese*. The closest relative of VE202-29 is Lachnospiraceae bacterium. Thus, in some embodiments, the disclosure provides methods comprising butyrate producing bacterial strains wherein the bacterial composition comprises one or more bacterial strains selected from the group consisting of *Clostridium saccharogumia, Clostridium ramosum, Clostridium spiroforme, Flavonifractor plautii, Pseudoflavonifractor capillosus*, Lachnospiraceae bacterium, *Clostridium hathewayi, Clostridium saccharolyticum, Blautia coccoides, Blautia product, Clostridium bolteae*, Clostridiacieae bacterium, *Clostridium indolis, Anaerostipes caccae, Anaerotruncus colihominis, Ruminococcus* sp., *Coprococcus comes, Clostridium lavalense, Clostridium asparagiforme, Clostridium symbiosum, Eubacterium contortum, Eubacterium fissicatena, Clostridium D5, Clostridium scindens, Clostridium bacterium*, and *Clostridium aldenense*. In some embodiments of the methods provided herein, the bacterial composition comprises at least 2, at least 3, at least 4, at least 5, at least 6, at least 7, at least 8, at least 9, at least 10, at least 11, at least 12, at least 13, at least 14, at least 15, at least 16, or at least 17 bacterial strains. As further shown in Narushima et al., VE202-9, VE202-16, VE202-27, and VE202-29 are strong butyrate producers (See also Table 1). Thus, in some embodiments, the methods disclosed herein provide for the administration of a composition of butyrate producing bacterial strains, wherein the composition of butyrate producing bacterial comprises one or more bacterial strains selected from the group consisting of *Clostridium indolis, Anaerostipes caccae, Clostridium symbiosum* and Lachnospiraceae bacterium. In some embodiments, the composition of butyrate producing bacterial strains comprises *Clostridium indolis, Anaerostipes caccae, Clostridium symbiosum* and Lachnospiraceae bacterium. In some embodiments, the composition of butyrate producing bacterial strains comprises *Anaerostipes caccae, Clostridium symbiosum* and Lachnospiraceae bacterium. In some embodiments, the composition of butyrate producing bacterial strains comprises *Clostridium indolis, Clostridium symbiosum* and Lachnospiraceae bacterium. In some embodiments, the composition of butyrate producing bacterial strains comprises *Clostridium indolis, Anaerostipes caccae*, and Lachnospiraceae bacterium. In some embodiments, the composition of butyrate producing bacterial strains comprises *Clostridium indolis, Anaerostipes caccae*, and *Clostridium symbiosum*. In some embodiments, the composition of butyrate producing bacterial strains comprises *Clostridium indolis* and Lachnospiraceae bacterium. In some embodiments, the composition of butyrate producing bacterial strains comprises *Anaerostipes caccae* and Lachnospiraceae bacterium. In some embodiments, the composition of butyrate producing bacterial strains comprises *Clostridium symbiosum* and Lachnospiraceae bacterium. In some embodiments, the composition of butyrate producing bacterial strains comprises *Clostridium indolis* and *Clostridium symbiosum*. In some embodiments, the composition of butyrate producing bacterial strains comprises *Anaerostipes caccae* and *Clostridium symbiosum*. In some embodiments, the composition of butyrate producing bacterial strains comprises *Anaerostipes caccae* and *Clostridium symbiosum*. In each of the compositions of butyrate producing bacterial strains provided herein, in some embodiments, the composition may include additional bacterial strains selected from the group consisting of *Clostridium saccharogumia, Clostridium ramosum, Clostridium spiroforme, Flavonifractor plautii, Pseudoflavonifractor capillosus*, Lachnospiraceae bacterium, *Clostridium hathewayi, Clostridium saccharolyticum, Blautia coccoides, Blautia product, Clostridium bolteae*, Clostridaceae bacterium, *Clostridium indolis, Anaerostipes caccae, Anaerotruncus colihominis, Ruminococcus* sp., *Coprococcus comes, Clostridium lavalense, Clostridium asparagiforme, Clostridium symbiosum, Eubacterium contortum, Eubacterium fissicatena, Clostridium D5, Clostridium scindens, Clostridium bacterium*, and *Clostridium aldenense*. It should further be appreciated that in some embodiments, in each of the compositions of butyrate producing bacterial strains provided herein, the composition may include additional bacterial strains that are known butyrate producers, wherein the additional bacterial strains are not *Clostridium saccharogumia, Clostridium ramosum, Clostridium spiroforme, Flavonifractor plautii, Pseudoflavonifractor capillosus*, Lachnospiraceae bacterium, *Clostridium hathewayi, Clostridium saccharolyticum, Blautia coccoides, Blautia product, Clostridium bolteae*, Clostridaceae bacterium, *Clostridium indolis, Anaerostipes caccae, Anaerotruncus colihominis, Ruminococcus* sp., *Coprococcus comes, Clostridium lavalense, Clostridium asparagiforme, Clostridium symbiosum, Eubacterium contortum, Eubacterium fissicatena, Clostridium D5, Clostridium scindens, Clostridium bacterium* or *Clostridium aldenese*.

As noted above, SEQ ID NOs:1-17 correspond to the 16S rDNA sequences of VE202-1, VE202-3, VE202-4, VE202-6, VE202-7, VE202-8, VE202-9, VE202-13, VE202-14, VE202-15, VE202-16, VE202-18, VE202-21, VE202-26, VE202-27, VE202-28, and VE202-29, respectively (See Table 1). Thus, in some embodiments, the methods disclosed herein provide for the administration of a composition of butyrate producing bacterial strains, wherein the composition of butyrate producing bacterial comprises one or more bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17. In some embodiments of the methods provided herein, the composition of butyrate producing bacterial strains comprises at least 2, at least 3, at least 4, at least 5, at least 6, at least 7, at least 8, at least 9, at least 10, at least 11, at least 12, at least 13, at least 14, at least 15, at least 16, or at least 17 bacterial strains. As further shown in Narushima et al., VE202-9, VE202-16, VE202-27, and VE202-29 are very strong butyrate producers (See also Table 1). Thus, in some embodiments, the methods disclosed herein provide for the administration of a composition of butyrate producing bacterial strains, wherein the composition of butyrate producing bacterial comprises one or more bacterial strains comprising 16S rDNA sequences of at least 95% homology to SEQ ID NO:7 SEQ ID NO:11, SEQ ID NO:15, and SEQ ID NO:17. In some embodiments, the composition of butyrate producing bacterial strains comprises bacterial strains comprising 16S rDNA sequences of at least 95% homology to SEQ ID NO:7, SEQ ID NO:11, SEQ ID NO:15, and SEQ ID NO:17. In some embodiments, the composition of butyrate producing bacterial strains comprises bacterial strains comprising 16S rDNA sequences of at least 95% homology to SEQ ID NO:7, SEQ ID NO:11, SEQ ID NO:15, and SEQ ID NO: 17. In some embodiments, the composition of butyrate producing bacterial strains comprises bacterial strains comprising 16S rDNA sequences of at least 95% homology to SEQ ID NO:7 SEQ ID NO: 11, and SEQ ID NO: 15. In some embodiments, the composition of butyrate producing bacterial strains comprises bacterial strains comprising 16S rDNA sequences of at least 95% homology to SEQ ID NO:7, SEQ ID NO:11, and SEQ ID NO: 17. In some embodiments, the composition of butyrate producing bacterial strains comprises bacterial strains comprising 16S rDNA sequences of at least 95% homology to SEQ ID NO:7, SEQ ID NO:15, and SEQ ID NO:17. In some embodiments, the composition of butyrate producing bacterial strains comprises bacterial strains comprising 16S rDNA sequences of at least 95% homology to SEQ ID NO: 11, SEQ ID NO: 15, and SEQ ID NO: 17. In some embodiments, the composition of butyrate producing bacterial strains comprises bacterial strains comprising 16S rDNA sequences of at least 95% homology to SEQ ID NO:7, and SEQ ID NO: 17. In some embodiments, the composition of butyrate producing bacterial strains comprises bacterial strains comprising 16S rDNA sequences of at least 95% homology to SEQ ID NO:11 and SEQ ID NO: 17. In some embodiments, the composition of butyrate producing bacterial strains comprises bacterial strains comprising 16S rDNA sequences of at least 95% homology to SEQ ID NO:15, and SEQ ID NO:17. In some embodiments, the composition of butyrate producing bacterial strains comprises bacterial strains comprising 16S rDNA sequences of at least 95% homology to SEQ ID NO:7, and SEQ ID NO: 15. In some embodiments, the composition of butyrate producing bacterial strains comprises bacterial strains comprising 16S rDNA sequences of at least 95% homology to SEQ ID NO:7, and SEQ ID NO:11. In some embodiments, the composition of butyrate producing bacterial strains comprises bacterial strains comprising 16S rDNA sequences of at least 95% homology to SEQ ID NO: 11, and SEQ ID NO: 15. In each of the compositions of butyrate producing bacterial strains provided herein, in some embodiments, the composition may include additional bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO: 17. It should further be appreciated that in some embodiments, in each of the compositions of butyrate producing bacterial strains provided herein, the composition may include additional bacterial strains that are known butyrate producers, wherein the additional bacterial strains do not include 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO: 11, SEQ ID NO: 12, SEQ ID NO:13, SEQ ID NO:14, SEQ ID NO:15, SEQ ID NO:16, or SEQ ID NO:17.

In one aspect, the disclosure provides methods comprising compositions of bacterial strains. In some embodiments of the compositions provided herein, one or more of the bacterial strains does not have an antibiotic resistance gene. In some embodiments of the compositions provided herein, the bacterial strains do not have an antibiotic resistance gene that renders the bacterial strain resistant to vancomycin.

In some embodiments of the compositions provided herein, the compositions do not include bacterial strains that are resistant to one or more antibiotics. It should be appreciated that it may be desirable to have a mechanism to remove the bacterial compositions provided herein from the body after administration. One such mechanism is to remove the bacterial compositions by antibiotic treatment. Thus, in some embodiments, the compositions do not include bacterial strains that are resistant to one or more antibiotics. In some embodiments, the compositions do not include bacterial strains that are resistant to one or more antibiotics selected from the group consisting of penicillin, benzylpenicillin, ampicillin, sulbactam, amoxicillin, clavulanate, tazobactam, piperacillin, cefmetazole, vancomycin, imipenem, meropenem, metronidazole and clindamycin. In some embodiments, the compositions do not include bacterial strains that are resistant to vancomycin.

In one aspect, the disclosure provides methods comprising bacterial compositions that do not include bacterial strains that are resistant to vancomycin. As shown in Narushima et al., VE202-1, VE202-3, VE202-6, VE202-8, and VE202-18 are resistant to vancomycin. Thus, in some embodiment, the disclosure provides methods comprising bacterial compositions that do not include bacterial strains that are resistant to vancomycin, wherein the composition does not include VE202-1, VE202-3, VE202-6, VE202-8, and VE202-18. In some embodiments of the methods comprising compositions that do not include bacterial strains, the composition comprises one or more bacterial strains selected from the group consisting of VE202-4, VE202-7, VE202-9, VE202-13, VE202-14, VE202-15, VE202-16, VE202-21, VE202-26, VE202-27, VE202-28, and VE202-29. In some embodiments, the composition comprises one or more bacterial strains selected from the group consisting of VE202-4, VE202-7, VE202-9, VE202-13, VE202-14, VE202-15, VE202-16, VE202-21, VE202-26, VE202-27, VE202-28, and VE202-29, and in addition the composition does not include any bacterial strains that are resistant to vancomycin. In some embodiments, the composition comprises bacterial strains VE202-4, VE202-7, VE202-9, VE202-13, VE202-14, VE202-15, VE202-16, VE202-21, VE202-26, VE202-27, VE202-28, and VE202-29. In some embodiments, the composition essentially consists of bacterial strains VE202-4, VE202-7, VE202-9, VE202-13, VE202-14, VE202-15, VE202-16, VE202-21, VE202-26, VE202-27, VE202-28, and VE202-29. In some embodiments, the composition consists of bacterial strains VE202-4, VE202-7, VE202-9, VE202-13, VE202-14, VE202-15, VE202-16, VE202-21, VE202-26, VE202-27, VE202-28, and VE202-29.

In one aspect, the disclosure provides methods comprising bacterial compositions that do not include bacterial strains that are resistant to vancomycin. As shown in Narushima et al., VE202-1, VE202-3, VE202-6, VE202-8, and VE202-18 are resistant to vancomycin. The closest relatives of VE202-1 are *Clostridium saccharogumia, Clostridium ramosum* and *Clostridium spiroforme*. The closest relatives of VE202-3 are *Flavonifractor plautii, Pseudoflavonifractor capillosus* and Lachnospiraceae bacterium. The closest relatives of VE202-6 are *Blautia coccoides*, Lachnospiraceae bacterium and *Blautia producta*. The closest relative of VE202-8 is Clostridaceae bacterium. The closest relative of VE202-18 is *Clostridium ramosum*. Thus, in some embodiment, the disclosure provides methods comprising bacterial compositions that do not include bacterial strains that are resistant to vancomycin, wherein the composition does not include *Clostridium saccharogumia, Clostridium ramosum, Clostridium spiroforme, Flavonifractor plautii, Pseudoflavonifractor capillosus*, Lachnospiraceae bacterium, *Blautia coccoides, Blautia* product, Clostridaceae bacterium and *Clostridium ramosum*. In some embodiments of the methods comprising compositions that do not include bacterial strains, the composition comprises one or more bacterial strains selected from the group consisting of *Clostridium hathewayi, Clostridium saccharolyticum, Clostridium bolteae, Clostridium indolis, Anaerostipes caccae, Anaerotruncus colihominis, Ruminococcus* sp., *Coprococcus comes, Clostridium lavalense, Clostridium asparagiforme, Clostridium symbiosum, Eubacterium* contortum, *Eubacterium fissicatena*, *Clostridium* D5, *Clostridium scindens*, *Clostridium bacterium*, and *Clostridium aldenese*. In some embodiments, the composition comprises one or more bacterial strains selected from the group consisting of *Clostridium hathewayi*, *Clostridium saccharolyticum*, *Clostridium bolteae*, *Clostridium indolis*, *Anaerostipes caccae*, *Anaerotruncus colihominis*, *Ruminococcus* sp., *Coprococcus comes*, *Clostridium lavalense*, *Clostridium asparagiforme*, *Clostridium symbiosum*, *Eubacterium* contortum, *Eubacterium fissicatena*, *Clostridium* D5, *Clostridium scindens*, *Clostridium bacterium*, and *Clostridium aldenese*, and in addition the composition does not include any bacterial strains that are resistant to vancomycin. In some embodiments, the composition comprises bacterial strains *Clostridium hathewayi*, *Clostridium saccharolyticum*, *Clostridium bolteae*, *Clostridium indolis*, *Anaerostipes caccae*, *Anaerotruncus colihominis*, *Ruminococcus* sp., *Coprococcus comes*, *Clostridium lavalense*, *Clostridium asparagiforme*, *Clostridium symbiosum*, *Eubacterium* contortum, *Eubacterium fissicatena*, *Clostridium* D5, *Clostridium scindens*, *Clostridium bacterium*, and *Clostridium aldenese*. In some embodiments, the composition essentially consists of bacterial strains *Clostridium hathewayi*, *Clostridium saccharolyticum*, *Clostridium bolteae*, *Clostridium indolis*, *Anaerostipes caccae*, *Anaerotruncus colihominis*, *Ruminococcus* sp., *Coprococcus comes*, *Clostridium lavalense*, *Clostridium asparagiforme*, *Clostridium symbiosum*, *Eubacterium* contortum, *Eubacterium fissicatena*, *Clostridium* D5, *Clostridium scindens*, *Clostridium bacterium*, and *Clostridium aldenese*. In some embodiments, the composition consists of bacterial strains *Clostridium hathewayi*, *Clostridium saccharolyticum*, *Clostridium bolteae*, *Clostridium indolis*, *Anaerostipes caccae*, *Anaerotruncus colihominis*, *Ruminococcus* sp., *Coprococcus comes*, *Clostridium lavalense*, *Clostridium asparagiforme*, *Clostridium symbiosum*, *Eubacterium* contortum, *Eubacterium fissicatena*, *Clostridium* D5, *Clostridium scindens*, *Clostridium bacterium*, and *Clostridium aldenense*.

In one aspect, the disclosure provides methods comprising bacterial compositions that do not include bacterial strains that are resistant to vancomycin. As shown in Narushima et al., VE202-1, VE202-3, VE202-6, VE202-8, and VE202-18 are resistant to vancomycin. VE202-1, VE202-3, VE202-6, VE202-8, and VE202-18 correspond to SEQ ID NO:1, SEQ ID NO:2, SEQ ID NO:4, SEQ ID NO:6, and SEQ ID NO:12, respectively. Thus, in some embodiment, the disclosure provides methods comprising bacterial compositions that do not include bacterial strains that are resistant to vancomycin, wherein the composition does not include bacterial strains comprising 16S rDNA sequences of at least 95% homology to SEQ ID NO:1, SEQ ID NO:2, SEQ ID NO:4, SEQ ID NO:6, or SEQ ID NO:12. In some embodiments of the methods comprising compositions that do not include bacterial strains, the composition comprising 16S rDNA sequences of at least 95% homology to SEQ ID NO:3, SEQ ID NO:5, SEQ ID NO:7, SEQ ID NO:8, SEQ ID NO:9, SEQ ID NO:10, SEQ ID NO:11, SEQ ID NO:13, SEQ ID NO:14, SEQ ID NO:15, SEQ ID NO:16, or SEQ ID NO:17. In some embodiments, the composition comprises one or more bacterial strains comprising 16S rDNA sequences of at least 95% homology to SEQ ID NO:3, SEQ ID NO:5, SEQ ID NO:7, SEQ ID NO:8, SEQ ID NO:9, SEQ ID NO: 10, SEQ ID NO: 11, SEQ ID NO: 13, SEQ ID NO: 14, SEQ ID NO:15, SEQ ID NO: 16, or SEQ ID NO: 17, and in addition the composition does not include any bacterial strains that are resistant to vancomycin. In some embodiments, the composition comprises bacterial strains comprising 16S rDNA sequences of at least 95% homology to SEQ ID NO:3, SEQ ID NO:5, SEQ ID NO:7, SEQ ID NO:8, SEQ ID NO:9, SEQ ID NO:10, SEQ ID NO:11, SEQ ID NO:13, SEQ ID NO:14, SEQ ID NO:15, SEQ ID NO: 16, and SEQ ID NO: 17. In some embodiments, the composition essentially consists of bacterial strains comprising 16S rDNA sequences of at least 95% homology to SEQ ID NO:3, SEQ ID NO:5, SEQ ID NO:7, SEQ ID NO:8, SEQ ID NO:9, SEQ ID NO:10, SEQ ID NO:11, SEQ ID NO:13, SEQ ID NO:14, SEQ ID NO:15, SEQ ID NO:16, or SEQ ID NO: 17. In some embodiments, the composition consists of bacterial strains comprising 16S rDNA sequences of at least 95% homology to SEQ ID NO:3, SEQ ID NO:5, SEQ ID NO:7, SEQ ID NO:8, SEQ ID NO:9, SEQ ID NO: 10, SEQ ID NO: 11, SEQ ID NO:13, SEQ ID NO:14, SEQ ID NO:15, SEQ ID NO:16, or SEQ ID NO:17.

In some embodiments, the compositions include bacterial strains that are susceptible to at least four antibiotics that are efficacious in humans. In some embodiments, the compositions include bacterial strains that are susceptible to at least three antibiotics that are efficacious in humans. In some embodiments, the compositions include bacterial strains that are susceptible to at least two antibiotics that are efficacious in humans. In some embodiments, the compositions include bacterial strains that are susceptible to at least one antibiotic that is efficacious in humans. In some embodiments, the compositions include only bacterial strains that are susceptible to at least four antibiotics that are efficacious in humans. In some embodiments, the compositions include only bacterial strains that are susceptible to at least three antibiotics that are efficacious in humans. In some embodiments, the compositions include only bacterial strains that are susceptible to at least two antibiotics that are efficacious in humans. In some embodiments, the compositions include bacterial strains that are susceptible to at least one antibiotic that is efficacious in humans. (An "antibiotic that is efficacious in a human" as used herein is an antibiotic that has been used to successfully treat bacterial infections in a human).

In some embodiments of the compositions provided herein, the composition includes one or more anaerobic bacteria. In some embodiments of the compositions provided herein, the composition includes only anaerobic bacteria. In some embodiments of the compositions provided herein, the composition includes one or more facultative anaerobic bacteria. In some embodiments of the compositions provided herein, the composition includes only facultative anaerobic bacteria. In some embodiments of the compositions provided herein, the composition includes one or more obligate anaerobic bacteria. In some embodiments of the compositions provided herein, the composition includes only obligate anaerobic bacteria.

In some embodiments of the compositions provided herein, one or more of the bacterial strains is a spore-former. In some embodiments of the compositions provided herein, one or more of the bacterial strains is in spore form. In some embodiments of the compositions provided herein, one or more of the bacterial strains is a non-spore former.

In some embodiments, the compositions described herein comprise spore forming and non-spore forming bacterial strains. In some embodiments, the compositions described herein comprise spore-forming bacterial strains. In some embodiments, the compositions described herein comprise only spore-forming bacterial strains. In some embodiments, the compositions described herein comprise only non-spore forming bacterial strains. The spore-forming bacteria can be in spore form (i.e., as spores) or in vegetative form (i.e., as vegetative cells). In spore form, bacteria are generally more resistant to environmental conditions, such as heat, acid, radiation, oxygen, chemicals, and antibiotics. In contrast, in the vegetative state or actively growing state, bacteria are more susceptible to such environmental conditions, compared to in the spore form. In general, bacterial spores are able to germinate from the spore form into a vegetative/actively growing state, under appropriate conditions. For instance, bacteria in spore format may germinate when they are introduced in the intestine.

In some embodiments, at least one (e.g., 1, 2, 3, 4, 5, or more) of the bacterial strains in the composition is a spore former. In some embodiments, at least one (e.g., 1, 2, 3, 4, 5, or more) of the bacterial strains in the composition is in spore form. In some embodiments, at least one (e.g., 1, 2, 3, 4, 5, or more) of the bacterial strains in the composition is a non-spore former. In some embodiments, at least one (e.g., 1, 2, 3, 4, 5, or more) of the bacterial strains in the composition is in vegetative form (As discussed above, spore forming bacteria can also be in vegetative form). In some embodiments, at least one (e.g., 1, 2, 3, 4, 5, or more) of the bacterial strains in the composition is in spore form and at least one (e.g., 1, 2, 3, 4, 5, or more) of the bacterial strains in the composition is in vegetative form. In some embodiments, at least one bacterial strain that is considered able to form spores (i.e., a spore-former) but is present in the composition in vegetative form. In some embodiments, at least one bacterial strain that is considered able to form spores is present in the composition both in spore form and in vegetative form.

It is envisioned that the bacterial strains of the compositions provided herein are alive and will be alive when they reach the target area (e.g., the intestines). Bacterial spores are considered to be alive in this regards. In some embodiments, bacteria that are administered as spores may germinate in the target area (e.g., the intestines). It should further be appreciated that not all of the bacteria are alive and the compositions can include a percentage (e.g., by weight) that is not alive. In addition, in some embodiments, the compositions include bacterial strains that are not alive when administered or at the time when the composition reaches the target area (e.g., the intestines). It is envisioned that non-living bacteria may still be useful by providing some nutrients and metabolites for the other bacterial strains in the composition.

In any of the compositions provided herein, in some embodiments, the bacterial strains are purified. In any of the compositions provided herein, in some embodiments, the bacterial strains are isolated. Any of the bacterial strains described herein may be isolated and/or purified, for example, from a source such as a culture or a microbiota sample (e.g., fecal matter). The bacterial strains used in the compositions provided herein generally are isolated from the microbiome of healthy individuals. However, bacterial strains can also be isolated from individuals that are considered not to be healthy. In some embodiments, the compositions include strains originating from multiple individuals. As used herein, the term "isolated" bacteria that have been separated from one or more undesired component, such as another bacterium or bacterial strain, one or more component of a growth medium, and/or one or more component of a sample, such as a fecal sample. In some embodiments, the bacteria are substantially isolated from a source such that other components of the source are not detected. As also used herein, the term "purified" refers to a bacterial strain has been separated from one or more components, such as contaminants. In some embodiments, the bacterial strain is substantially free of contaminants. In some embodiments, one or more bacterial strains of a composition may be independently purified from one or more other bacteria produced and/or present in a culture or a sample containing the bacterial strain. In some embodiments, a bacterial strain is isolated or purified from a sample and then cultured under the appropriate conditions for bacterial replication, e.g., under anaerobic culture conditions. The bacteria that is grown under appropriate conditions for bacterial replication can subsequently be isolated/purified from the culture in which it is grown.

In one aspect, the disclosure provides bacterial strains and mixtures of bacterial strains with unique biological properties. In some embodiments of the compositions provided herein, the composition of bacterial strains produces butyrate when introduced in the intestine.

In one aspect, the disclosure provides methods comprising pharmaceutical compositions comprising the bacterial compositions provided herein. In some embodiments, the pharmaceutical compositions provided herein comprise bacterial compositions. In some embodiments of the pharmaceutical compositions provided herein, the pharmaceutical composition comprises a pharmaceutical acceptable excipient. In some embodiments of the pharmaceutical compositions provided herein, the pharmaceutical composition is formulated for oral administration. In some embodiments of the pharmaceutical compositions provided herein, the pharmaceutical composition is formulated for rectal administration. In some embodiments of the pharmaceutical compositions provided herein, the pharmaceutical composition is formulated for delivery to the intestine. In some embodiments of the pharmaceutical compositions provided herein, the pharmaceutical composition is formulated for delivery to the colon. In some embodiments of the pharmaceutical compositions provided herein, one or more of the bacterial strains is lyophilized. In some embodiments of the pharmaceutical compositions provided herein, the pharmaceutical composition is in the form of a capsule. In some embodiments of the pharmaceutical compositions provided herein, the pharmaceutical composition further comprises a pH sensitive composition comprising one or more enteric polymers.

Any of the bacterial compositions described herein, including the pharmaceutical compositions and food products comprising the compositions, may contain bacterial strains in any form, for example in an aqueous form, such as a solution or a suspension, embedded in a semi-solid form, in a powdered form or freeze dried form. In some embodiments, the composition or the bacterial strains of the composition are lyophilized. In some embodiments, a subset of the bacterial strains in a composition is lyophilized. Methods of lyophilizing compositions, specifically compositions comprising bacteria, are well known in the art. See, e.g., U.S. Pat. Nos. 3,261,761; 4,205,132; PCT Publications WO 2014/029578 and WO 2012/098358, herein incorporated by reference in their entirety. The bacteria may be lyophilized as a combination and/or the bacteria may be lyophilized separately and combined prior to administration. A bacterial strain may be combined with a pharmaceutical excipient prior to combining it with the other bacterial strain or multiple lyophilized bacteria may be combined while in lyophilized form and the mixture of bacteria, once combined may be subsequently be combined with a pharmaceutical excipient. In some embodiments, the bacterial strain is a lyophilized cake. In some embodiments, the compositions comprising the one or more bacterial strains are a lyophilized cake.

The bacterial strains of the bacterial compositions provided herein can be manufactured using fermentation techniques well known in the art. In some embodiments, the active ingredients are manufactured using anaerobic fermenters, which can support the rapid growth of anaerobic bacterial species. The anaerobic fermenters may be, for example, stirred tank reactors or disposable wave bioreactors. Culture media such as BL media and EG media, or similar versions of these media devoid of animal components, can be used to support the growth of the bacterial species. The bacterial product can be purified and concentrated from the fermentation broth by traditional techniques, such as centrifugation and filtration, and can optionally be dried and lyophilized by techniques well known in the art.

In some embodiments, the composition of bacterial strains may be formulated for administration as a pharmaceutical composition. The term "pharmaceutical composition" as used herein means a product that results from the mixing or combining of at least one active ingredient, such as any purified bacterial strains described herein, and one or more inactive ingredients, which may include one or more pharmaceutically acceptable excipient.

An "acceptable" excipient refers to an excipient that must be compatible with the active ingredient and not deleterious to the subject to which it is administered. In some embodiments, the pharmaceutically acceptable excipient is selected based on the intended route of administration of the composition, for example a composition for oral or nasal administration may comprise a different pharmaceutically acceptable excipient than a composition for rectal administration. Examples of excipients include sterile water, physiological saline, solvent, a base material, an emulsifier, a suspending agent, a surfactant, a stabilizer, a flavoring agent, an aromatic, an excipient, a vehicle, a preservative, a binder, a diluent, a tonicity adjusting agent, a soothing agent, a bulking agent, a disintegrating agent, a buffer agent, a coating agent, a lubricant, a colorant, a sweetener, a thickening agent, and a solubilizer.

Pharmaceutical compositions of the disclosure can be prepared in accordance with methods well known and routinely practiced in the art (see e.g., Remington: The Science and Practice of Pharmacy, Mack Publishing Co. 20th ed. 2000). The pharmaceutical compositions described herein may further comprise any carriers or stabilizers in the form of a lyophilized formulation or an aqueous solution. Acceptable excipients, carriers, or stabilizers may include, for example, buffers, antioxidants, preservatives, polymers, chelating reagents, and/or surfactants. Pharmaceutical compositions are preferably manufactured under GMP conditions. The pharmaceutical compositions can be used orally, nasally or parenterally, for instance, in the form of capsules, tablets, pills, sachets, liquids, powders, granules, fine granules, film-coated preparations, pellets, troches, sublingual preparations, chewables, buccal preparations, pastes, syrups, suspensions, elixirs, emulsions, liniments, ointments, plasters, cataplasms, transdermal absorption systems, lotions, inhalations, aerosols, injections, suppositories, and the like.

In some embodiments, the bacteria are formulated for delivery to the intestines (e.g., the small intestine and/or the colon). In some embodiments, the bacteria are formulated with an enteric coating that increases the survival of the bacteria through the harsh environment in the stomach. The enteric coating is one which resists the action of gastric juices in the stomach so that the bacteria which are incorporated therein will pass through the stomach and into the intestines. The enteric coating may readily dissolve when in contact with intestinal fluids, so that the bacteria enclosed in the coating will be released in the intestinal tract. Enteric coatings may consist of polymer and copolymers well known in the art, such as commercially available EUDRAGIT (Evonik Industries). (See e.g., Zhang, AAPS PharmSciTech, 2016, 17 (1), 56-67).

The bacteria may also be formulated for rectal delivery to the intestine (e.g., the colon). Thus, in some embodiments, the bacterial compositions may be formulated for delivery by suppository, colonoscopy, endoscopy, sigmoidoscopy or enema. A pharmaceutical preparation or formulation and particularly a pharmaceutical preparation for oral administration, may include an additional component that enables efficient delivery of the compositions of the disclosure to the intestine (e.g., the colon). A variety of pharmaceutical preparations that allow for the delivery of the compositions to the intestine (e.g., the colon) can be used. Examples thereof include pH sensitive compositions, more specifically, buffered sachet formulations or enteric polymers that release their contents when the pH becomes alkaline after the enteric polymers pass through the stomach. When a pH sensitive composition is used for formulating the pharmaceutical preparation, the pH sensitive composition is preferably a polymer whose pH threshold of the decomposition of the composition is between about 6.8 and about 7.5. Such a numeric value range is a range in which the pH shifts toward the alkaline side at a distal portion of the stomach, and hence is a suitable range for use in the delivery to the colon. It should further be appreciated that each part of the intestine (e.g., the duodenum, jejunum, ileum, cecum, colon and rectum), has different biochemical and chemical environment. For instance, parts of the intestines have different pHs, allowing for targeted delivery by compositions that have a specific pH sensitivity. Thus, the compositions provided herein may be formulated for delivery to the intestine or specific parts of the intestine (e.g., the duodenum, jejunum, ileum, cecum, colon and rectum) by providing formulations with the appropriate pH sensitivity. (See e.g., Villena et al., Int J Pharm 2015, 487 (1-2): 314-9).

Another embodiment of a pharmaceutical preparation useful for delivery of the compositions to the intestine (e.g., the colon) is one that ensures the delivery to the colon by delaying the release of the contents (e.g., the bacterial strains) by approximately 3 to 5 hours, which corresponds to the small intestinal transit time. In one embodiment of a pharmaceutical preparation for delayed release, a hydrogel is used as a shell. The hydrogel is hydrated and swells upon contact with gastrointestinal fluid, with the result that the contents are effectively released (released predominantly in the colon). Delayed release dosage units include drug-containing compositions having a material which coats or selectively coats a drug or active ingredient to be administered. Examples of such a selective coating material include in vivo degradable polymers, gradually hydrolyzable polymers, gradually water-soluble polymers, and/or enzyme degradable polymers. A wide variety of coating materials for efficiently delaying the release is available and includes, for example, cellulose-based polymers such as hydroxypropyl cellulose, acrylic acid polymers and copolymers such as methacrylic acid polymers and copolymers, and vinyl polymers and copolymers such as polyvinylpyrrolidone.

Additional examples of pharmaceutical compositions that allow for the delivery to the intestine (e.g., the colon) include bioadhesive compositions which specifically adhere to the colonic mucosal membrane (for example, a polymer described in the specification of U.S. Pat. No. 6,368,586) and compositions into which a protease inhibitor is incorporated for protecting particularly a biopharmaceutical preparation in the gastrointestinal tracts from decomposition due to an activity of a protease.

Another example of a system enabling the delivery to the intestine (e.g., the colon) is a system of delivering a composition to the colon by pressure change in such a way that the contents are released by utilizing pressure change caused by generation of gas in bacterial fermentation at a distal portion of the stomach. Such a system is not particularly limited, and a more specific example thereof is a capsule which has contents dispersed in a suppository base and which is coated with a hydrophobic polymer (for example, ethyl cellulose).

A further example of a system enabling the delivery of a composition to the intestine (e.g., the colon), is a composition that includes a coating that can be removed by an enzyme present in the gut (e.g., the colon), such as, for example, a carbohydrate hydrolase or a carbohydrate reductase. Such a system is not particularly limited, and more specific examples thereof include systems which use food components such as non-starch polysaccharides, amylose, xanthan gum, and azopolymers.

The compositions provided herein can also be delivered to specific target areas, such as the intestine, by delivery through an orifice (e.g., a nasal tube) or through surgery. In addition, the compositions provided herein that are formulated for delivery to a specific area (e.g., the cecum or the colon), may be administered by a tube (e.g., directly into the small intestine). Combining mechanical delivery methods such as tubes with chemical delivery methods such as pH specific coatings, allow for the delivery of the compositions provided herein to a desired target area (e.g., the cecum or the colon).

The compositions comprising bacterial strains are formulated into pharmaceutically acceptable dosage forms by conventional methods known to those of skill in the art. Dosage regimens are adjusted to provide the optimum desired response (e.g., the prophylactic or therapeutic effect) . In some embodiments, the dosage form of the composition is a tablet, pill, capsule, powder, granules, solution, or suppository. In some embodiments, the pharmaceutical composition is formulated for oral administration. In some embodiments, the pharmaceutical composition is formulated such that the bacteria of the composition, or a portion thereof, remain viable after passage through the stomach of the subject. In some embodiments, the pharmaceutical composition is formulated for rectal administration, e.g. as a suppository. In some embodiments, the pharmaceutical composition is formulated for delivery to the intestine or a specific area of the intestine (e.g., the colon) by providing an appropriate coating (e.g., a pH specific coating, a coating that can be degraded by target area specific enzymes, or a coating that can bind to receptors that are present in a target area).

Dosages of the active ingredients in the pharmaceutical compositions of the present disclosure can be varied so as to obtain an amount of the active ingredient which is effective to achieve the desired pharmaceutical response for a particular subject, composition, and mode of administration, without being toxic or having an adverse effect on the subject. The selected dosage level depends upon a variety of factors including the activity of the particular compositions of the present disclosure employed, the route of administration, the time of administration, the duration of the treatment, other drugs, compounds and/or materials used in combination with the particular compositions employed, the age, sex, weight, condition, general health and prior medical history of the subject being treated, and like factors.

A physician, veterinarian or other trained practitioner, can start doses of the pharmaceutical composition at levels lower than that required to achieve the desired therapeutic effect and gradually increase the dosage until the desired effect (e.g., treatment of a pathogenic infection, reduction of bacterial burden of pathogenic infection, reduction or inhibition of toxin production) is achieved. In general, effective doses of the compositions of the present disclosure, for the prophylactic treatment of groups of people as described herein vary depending upon many different factors, including routes of administration, physiological state of the subject, whether the subject is human or an animal, other medications administered, and the therapeutic effect desired. Dosages need to be titrated to optimize safety and efficacy. In some embodiments, the dosing regimen entails oral administration of a dose of any of the compositions described herein. In some embodiments, the dosing regimen entails oral administration of multiple doses of any of the compositions described herein. In some embodiments, the composition is administered orally the subject once, twice, 3 times, 4 times, 5 times, 6 times, 7 times, 8 times, 9 times, or at least 10 times.

The compositions, including the pharmaceutical compositions disclosed herein, include compositions with a range of active ingredients (e.g., live bacteria, bacteria in spore format). The amount of bacteria in the compositions may be expressed in weight, number of bacteria and/or CFUs (colony forming units). In some embodiments, the pharmaceutical compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more of each of the bacteria of the composition per dosage amount. In some embodiments, the pharmaceutical compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more total bacteria per dosage amount. It should further be appreciated that the bacteria of the compositions may be present in different amounts. Thus, for instance, as a non-limiting example, a composition may include $10^3$ of bacteria A, $10^4$ of bacteria B and $10^6$ of bacteria C. In some embodiments, the pharmaceutical compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more CFUs of each of the bacteria in the composition per dosage amount. In some embodiments, the pharmaceutical compositions disclosed herein contain about $10^1$, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more CFUs in total for all of the bacteria combined per dosage amount. As discussed above, bacteria of the compositions may be present in different amounts. In some embodiments, the pharmaceutical compositions disclosed herein contain about $10^{-7}$, about $10^{-6}$, about $10^{-5}$, about $10^{-4}$, about $10^{-3}$, about $10^{-2}$, about $10^{-1}$ or more grams of each of the bacteria in the composition per dosage amount. In some embodiments, the pharmaceutical compositions disclosed herein contain about $10^{-7}$, about $10^{-6}$, about $10^{-5}$, about $10^{-4}$, about $10^{-3}$, about $10^{-2}$, about $10^{-1}$ or more grams in total for all of the bacteria combined per dosage amount. In some embodiment, the dosage amount is one administration device (e.g., one table, pill or capsule). In some embodiment, the dosage amount is the amount that is administered in a particular period (e.g., one day or one week).

In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ of each of the bacteria of the composition per dosage amount. In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ total bacteria per dosage amount.

In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ total CFUs per dosage amount.

In some embodiments, the pharmaceutical compositions disclosed herein contain between $10^{-7}$ and $10^{-1}$, between $10^{-6}$ and $10^{-1}$, between $10^{-5}$ and $10^{-1}$, between $10^{-4}$ and $10^{-1}$, between $10^{-3}$ and $10^{-1}$, between $10^{-2}$ and $10^{-1}$, between $10^{-7}$ and $10^{-2}$, between $10^{-6}$ and $10^{-2}$, between $10^{-5}$ and $10^{-2}$, between $10^{-4}$ and $10^{-2}$, between $10^{-3}$ and $10^{-2}$, between $10^{-7}$ and $10^{-3}$, between $10^{-6}$ and $10^{-3}$, between $10^{-5}$ and $10^{-3}$, between $10^{-4}$ and $10^{-3}$, between $10^{-7}$ and $10^{-4}$, between $10^{-6}$ and $10^{-4}$, between $10^{-5}$ and $10^{-4}$, between $10^{-7}$ and $10^{-5}$, between $10^{-6}$ and $10^{-5}$, or between $10^{-7}$ and $10^{-6}$ grams of each of the bacteria in the composition per dosage amount. In some embodiments, the pharmaceutical compositions disclosed herein contain between $10^{-7}$ and $10^{-1}$, between $10^{-6}$ and $10^{-1}$, between $10^{-5}$ and $10^{-1}$, between $10^{-4}$ and $10^{-1}$, between $10^{-3}$ and $10^{-1}$, between $10^{-2}$ and $10^{-1}$, between $10^{-7}$ and $10^{-2}$, between $10^{-6}$ and $10^{-2}$, between $10^{-5}$ and $10^{-2}$, between $10^{-4}$ and $10^{-2}$, between $10^{-3}$ and $10^{-2}$, between $10^{-7}$ and $10^{-3}$, between $10^{-6}$ and $10^{-3}$, between $10^{-5}$ and $10^{-3}$, between $10^{-4}$ and $10^{-3}$, between $10^{-7}$ and $10^{-4}$, between $10^{-6}$ and $10^{-4}$, between $10^{-5}$ and $10^{-4}$, between $10^{-7}$ and $10^{-5}$, between $10^{-6}$ and $10^{-5}$, or between $10^{-7}$ and $10^{-6}$ grams of all of the bacteria combined per dosage amount.

In one aspect, the disclosure provides a food product comprising any of the compositions provided herein and a nutrient. Also with the scope of the present disclosure are food products comprising any of the bacterial strains described herein and a nutrient. Food products are, in general, intended for the consumption of a human or an animal. Any of the bacterial strains described herein may be formulated as a food product. In some embodiments, the bacterial strains are formulated as a food product in spore form. In some embodiments, the bacterial strains are formulated as a food product in vegetative form. In some embodiments, the food product comprises both vegetative bacteria and bacteria in spore form. The compositions disclosed herein can be used in a food or beverage, such as a health food or beverage, a food or beverage for infants, a food or beverage for pregnant women, athletes, senior citizens or other specified group, a functional food, a beverage, a food or beverage for specified health use, a dietary supplement, a food or beverage for patients, or an animal feed. Non-limiting examples of the foods and beverages include various beverages such as juices, refreshing beverages, tea beverages, drink preparations, jelly beverages, and functional beverages; alcoholic beverages such as beers; carbohydrate-containing foods such as rice food products, noodles, breads, and pastas; paste products such as fish hams, sausages, paste products of seafood; retort pouch products such as curries, food dressed with a thick starchy sauces, soups; dairy products such as milk, dairy beverages, ice creams, cheeses, and yogurts; fermented products such as fermented soybean pastes, yogurts, fermented beverages, and pickles; bean products; various confectionery products such as Western confectionery products including biscuits, cookies, and the like, Japanese confectionery products including steamed bean-jam buns, soft adzuki-bean jellies, and the like, candies, chewing gums, gummies, cold desserts including jellies, cream caramels, and frozen desserts; instant foods such as instant soups and instant soy-bean soups; microwavable foods; and the like. Further, the examples also include health foods and beverages prepared in the forms of powders, granules, tablets, capsules, liquids, pastes, and jellies.

Food products containing bacterial strains described herein may be produced using methods known in the art and may contain the same amount of bacteria (e.g., by weight, amount or CFU) as the pharmaceutical compositions provided herein. Selection of an appropriate amount of bacteria in the food product may depend on various factors, including for example, the serving size of the food product, the frequency of consumption of the food product, the specific bacterial strains contained in the food product, the amount of water in the food product, and/or additional conditions for survival of the bacteria in the food product.

Examples of food products which may be formulated to contain any of the bacterial strains described herein include, without limitation, a beverage, a drink, a bar, a snack, a dairy product, a confectionery product, a cereal product, a ready-to-eat product, a nutritional formula, such as a nutritional supplementary formulation, a food or beverage additive.

II. Therapeutic Methods

In one aspect, the disclosure provides bacterial compositions and methods of treatment for disease (e.g., GvHD) in a subject. In one aspect, the disclosure provides bacterial compositions and methods of increasing survival following bone marrow transplant. In some embodiments, survival after bone marrow transplant is increased because the methods provided herein decrease the risk of GvHD. In one aspect, and without being limiting, the bacterial compositions disclosed herein can treat disease and/or increase survival because their administration results in an increase in the amount of butyrate in the intestine of the subject. In one aspect, and without being limiting, the bacterial compositions disclosed herein can treat disease and/or increase survival because their administration results in an increase in the amount of histone acetylation in the intestine of the subject. In one aspect, and without being limiting, the bacterial compositions disclosed herein can treat disease and/or increase survival because their administration results in the increase in the amount of butyrate producing bacterial strains in the intestine of the subject.

In one aspect, the disclosure provides methods of treating a disease in a subject and/or increase survival comprising administering any of the bacterial compositions provided herein to the subject in an effective amount to treat the disease and/or increase survival. In some embodiments of the methods provided herein, the administration of the bacterial composition to the subject results in an increase in the amount of butyrate in the intestine of the subject. In some embodiments of the methods provided herein, the amount of butyrate is increased by at least 10%, at least 20%, at least 30%, at least 40%, at least 50%, at least 100%, or at least 200% when compared to the amount of butyrate present in the intestine of the subject before the administration of the bacterial composition. In some embodiments of the methods provided herein, the administration of the bacterial composition to the subject results in an increase in the amount of histone acetylation in the intestine of the subject. In some embodiments of the methods provided herein, the amount of histone acetylation is increased by at least 10%, at least 20%, at least 30%, at least 40%, at least 50%, at least 100%, or at least 200% when compared to the amount of histone acetylation in the intestine of the subject before the administration of the bacterial composition. In some embodiments of the methods provided herein, the administration of the bacterial composition to the subject results in an increase in the amount of butyrate producing bacterial strains in the intestine of the subject. In some embodiments of the methods provided herein, the amount of butyrate producing bacterial strains is increased by at least 10%, at least 20%, at least 30%, at least 40%, at least 50%, at least 100%, or at least 200% when compared to the amount of butyrate producing bacterial strains in the intestine of the subject before the administration of the bacterial composition. Without being limited to a specific mechanism, it is thought that an increase in the amount of butyrate producing bacterial strains in the intestine will result in an increase in the amount of butyrate in the intestine, which, is correlated with an increase in the amount of histone acetylation in the intestine.

In one aspect, the methods provided herein comprise the administration of the bacterial compositions to a subject in a therapeutically effective amount to treat or prevent a disease (e.g., GvHD) and/or increase survival. The terms "treat" or "treatment" refer to reducing or alleviating one or more of the symptoms associated with a disease. The terms "prevent" or "prevention" encompass prophylactic administration and may reduce the incidence or likelihood of the occurrence of the disease. Accordingly, "increasing survival" is defined as a reduction in the likelihood that a subject will die from the consequences of a specific event (e.g., bone marrow transplant). In some embodiments, administration of the compositions provided herein result in a healthy microbiome that results in an increase in the amount of butyrate in the intestine thereby increasing protection of a subject against disease (e.g., GvHD) and/or increasing survival (e.g., following bone marrow transplant).

As used herein, a "therapeutically effective amount" of composition, such as a pharmaceutical composition, is any amount that results in a desired response or outcome in a subject, such as those described herein, including but not limited to prevention or treatment of GvHD and/or increasing survival following bone marrow transplant. It should be appreciated that the term effective amount may be expressed in weight (e.g., gram or milligram), number of bacteria or CFUs (colony forming units) to be administered. It should further be appreciated that the bacteria can multiply once administered. Thus, administration of even a relatively small amount of bacteria may have therapeutic effects.

In some embodiments, the therapeutically effective amount of any of the compositions described herein is an amount sufficient to treat the disease, e.g., prevention or treatment of GvHD and/or increasing survival following bone marrow transplant.

Aspects of the present disclosure are related to methods for treating a disease or condition in a subject by administering a therapeutically effective amount of any of the compositions described herein. In some embodiments, the subject is a mammalian subject, such as a human, non-human primate, rodent, rabbit, sheep, pig, dog, cat, horse, or cow. In some embodiments, the subject is a human subject.

The compositions and methods described herein may be utilized in conjunction with other types of therapy (i.e., combination treatment), such as additional therapeutic agents. Examples of additional combination therapies include, without limitation, surgery, radiation, gene therapy, and administration of additional therapeutic agents, such as chemotherapeutics, antibiotics, antivirals, anti-fungals, anti-parasitics, immunomodulatory agents, anti-inflammatory agents. In general, combination therapies can be administered simultaneously or sequentially (in any order) with the compositions and methods described herein. In some embodiments, any of the compositions described herein is administered simultaneously with one or more additional therapeutic agents, for example in a single dose or in multiple doses that are administered at substantially the same time.

In some embodiments, the compositions described herein are administered to a subject concomitantly with one or more additional therapeutic agents. In some embodiments, the compositions described herein are administered to a subject followed by administration of one or more additional therapeutic agent. In some embodiments, any of the compositions described herein is administered at least about 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 3 months, 4 months, 5 months, 6 months or more prior to administration of the one or more additional therapeutic agent. Alternatively, in some embodiments, one or more therapeutic agent administered to a subject followed by administration of any of the compositions described herein. In some embodiments, one or more therapeutic agent is administered at least about 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 3 months, 4 months, 5 months, 6 months or more prior to administration of any the compositions described herein.

In some embodiments, the one or more traditional therapeutic agent is an immunosuppressant such as a topical or systemic corticosteroid (e.g., prednisone, prednisolone or methylprednisolone) or ciclosporin. Additional treatments include, but are not limited to, infliximab (Remicade), entanercept, sirolimus, mycophenolate mofetil (MMF), and/or extracorporeal photopheresis.

In some embodiments, the subject has not received a dose of an antibiotic prior to administration of the bacterial composition. In some embodiments, the subject has not been administered an antibiotic at least 1, at least 2, at least 3, at least 5, at least 10, at least 15, at least 20, at least 25, at least 30, at least 60, at least 90, at least 120, at least 180 or at least 360 days prior to administration of the compositions provided herein.

In some embodiments, the subject may be administered one or more doses of an antibiotic prior to or concurrently with a bacterial composition. Antibiotics may be administered for a variety of reasons. For instance, antibiotics may be administered to remove bacterial species from the colon and/or intestine prior to administration of the bacterial compositions provided herein. Antibiotics may also be administered to suppress unwanted infections in the case of cancer treatment. In some instances, antibiotics may be administered as a treatment method for an infectious disease.

In some embodiments, the subject is administered a single dose of an antibiotic prior to the bacterial composition. In some embodiments, the subject is administered multiple doses of an antibiotic prior to the bacterial composition. In some embodiments, the subject is administered at least 2, 3, 4, 5 or more doses of an antibiotic prior to the bacterial composition. In some embodiments, the subject is administered a dose of an antibiotic at substantially the same time as the bacterial composition. Examples of antibiotics that can be administered include, without limitation, kanamycin, gentamicin, colistin, metronidazole, vancomycin, clindamycin, fidaxomicin, and cefoperazone.

III. Additional Methods

Also within the scope of the present disclosure are methods of assessing the amount of butyrate present in the intestine of a subject. In some embodiments, the methods provided herein will result in an increase in the amount of butyrate present in the intestine of the subject. In some embodiments, the disclosure provides methods of administering bacterial compositions, wherein the administration results in an increase in the amount of butyrate in the intestine of the subject. In some embodiments of the methods provided herein, the method comprises determining the amount of butyrate in the intestine of the subject prior to administration of the bacterial composition. In some embodiments of the methods provided herein, the method comprises determining the amount of butyrate in the intestine of the subject after administration of the bacterial composition. In some embodiments of the methods provided herein, the method comprises determining the amount of butyrate in the intestine of the subject prior to and after administration of the bacterial composition. In some embodiments, the disclosure provides methods comprising determining the amount of butyrate in the intestine of a subject, wherein if the amount of butyrate in the intestine of the subject is lower than the amount of butyrate in the intestine of a healthy individual, administering to the subject any of the bacterial compositions provided herein. In some embodiments, the amount of butyrate present in the intestine of the subject is determined prior to administration of any of the bacterial compositions disclosed herein. In some embodiments, if fewer than a threshold amount of butyrate is present in the intestine of the subject, any of the compositions described herein are administered to the subject to increase the amount of butyrate in the intestine of the subject. In some embodiments, the method comprises identifying the subject as a candidate for a treatment of the disease (e.g., GvHD), or needing an increase in survival following bone marrow transplant, based on the amount of butyrate present in the intestine. Thus, for instance, if the amount of butyrate present in the intestine of an individual is lower than the threshold amount, the individual is identified as a candidate for treatment, wherein, in some embodiments, treatment comprises administration of the bacterial compositions according to the methods provided herein. In some embodiments, the threshold amount is the amount of butyrate present in the intestine of a healthy individual (i.e., an individual not having, or being at risk of having, GvHD). In addition, the art can be relied on to provide the amount of butyrate in a healthy individual (See e.g., Huda-Faujan et al., *Open Biochem J.* 2010, 4: 53-58). Methods for determining the amount of butyrate in the intestine are known in the art and may include gas chromatography analysis of the metabolites and/or other components of a stool sample.

In one aspect the disclosure provides methods of assessing the amount of histone acetylation present in the intestine of a subject. In some embodiments, the methods provided herein will result in an increase in the amount of histone acetylation present in the intestine of the subject. In some embodiments, the disclosure provides methods of administering bacterial compositions, wherein the administration results in an increase in the amount of histone acetylation in the intestine of the subject. In some embodiments of the methods provided herein, the method comprises determining the amount of histone acetylation in the intestine of the subject prior to administration of the bacterial composition. In some embodiments of the methods provided herein, the method comprises determining the amount of histone acetylation in the intestine of the subject after administration of the bacterial composition. In some embodiments of the methods provided herein, the method comprises determining the amount of histone acetylation in the intestine of the subject prior to and after administration of the bacterial composition. In some embodiments, the disclosure provides methods comprising determining the amount of histone acetylation in the intestine of a subject, wherein if the amount of histone acetylation in the intestine of the subject is lower than the amount of histone acetylation in the intestine of a healthy individual, administering to the subject any of the bacterial compositions provided herein. In some embodiments, the amount of histone acetylation present in the intestine of the subject is determined prior to administration of any of the bacterial compositions disclosed herein. In some embodiments, if fewer than a threshold amount of histone acetylation is present in the intestine of the subject, any of the compositions described herein are administered to the subject to increase the amount of histone acetylation in the intestine of the subject. In some embodiments, the method comprises identifying the subject as a candidate for a treatment of the disease (e.g., GvHD), or needing an increase in survival following bone marrow transplant, based on the amount of histone acetylation present in the intestine. Thus, for instance, if the amount of histone acetylation present in the intestine of an individual is lower than the threshold amount, the individual is identified as a candidate for treatment, wherein, in some embodiments, treatment comprises administration of the bacterial compositions according to the methods provided herein. In some embodiments, the threshold amount is the amount of histone acetylation present in the intestine of a healthy individual (i.e., an individual not having or being at risk of having GvHD). Methods for determining the amount of histone acetylation are known in the art and include Western blot and ELISA to determine the amount of acetylation on one or more histones isolated from one or more cell types in the intestine.

In one aspect the disclosure provides methods of assessing the amount of butyrate producing bacterial strains present in the intestine of a subject. In some embodiments, the methods provided herein will result in an increase in the amount of butyrate producing bacterial strains present in the intestine of the subject. In some embodiments, the disclosure provides methods of administering bacterial compositions, wherein the administration results in an increase in the amount of butyrate producing bacterial strains in the intestine of the subject. In some embodiments of the methods provided herein, the method comprises determining the amount of butyrate producing bacterial strains in the intestine of the subject prior to administration of the bacterial composition. In some embodiments of the methods provided herein, the method comprises determining the amount of butyrate producing bacterial strains in the intestine of the subject after administration of the bacterial composition. In some embodiments of the methods provided herein, the method comprises determining the amount of butyrate producing bacterial strains in the intestine of the subject prior to and after administration of the bacterial composition. In some embodiments, the disclosure provides methods comprising determining the amount of butyrate producing bacterial strains in the intestine of a subject, wherein if the amount of butyrate producing bacterial strains in the intestine of the subject is lower than the amount of butyrate producing bacterial strains in the intestine of a healthy individual, administering to the subject any of the bacterial compositions provided herein. In some embodiments, the amount of butyrate producing bacterial strains present in the intestine of the subject is determined prior to administration of any of the bacterial compositions disclosed herein. In some embodiments, if fewer than a threshold amount of butyrate producing bacterial strains is present in the intestine of the subject, any of the compositions described herein are administered to the subject to increase the amount of butyrate producing bacterial strains in the intestine of the subject. In some embodiments, the method comprises identifying the subject as a candidate for a treatment of the disease (e.g., GvHD), or needing an increase in survival following bone marrow transplant, based on the amount of butyrate producing bacterial strains present in the intestine. Thus, for instance, if the amount of butyrate producing bacterial strains present in the intestine of an individual is lower than the threshold amount, the individual is identified as a candidate for treatment, wherein, in some embodiments, treatment comprises administration of the bacterial compositions according to the methods provided herein. In some embodiments, the threshold amount is the amount of butyrate producing bacterial strains present in the intestine of a healthy individual (i.e., an individual not having or being at risk of having GvHD). In general, the amount of butyrate producing bacterial strains in the intestine (e.g., presence or absence of one or more butyrate producing bacterial strains may be determined by assessing a sample obtained from the subject, such as a fecal sample. Such a fecal sample may be subjected to 16S RNA analysis, whole genome sequencing and additional methods to determine the amount and nature of the butyrate producing bacterial strains present in the intestine.

EXAMPLES

Example 1

The impact of alterations in intestinal microbiota on microbial metabolites and on disease processes, such as graft-versus-host disease (GVHD), is not known. Experiments described herein used unbiased analysis to identify novel alterations in gastrointestinal microbiota-derived short chain fatty acids (SCFA) after allogeneic bone marrow transplant (allo-BMT). Alterations in the amounts of only one SCFA, butyrate, were observed only within the intestinal tissue. The reduced butyrate in CD326+ intestinal epithelial cells (IECs) after allo-BMT resulted in decreased histone acetylation, which was restored upon local administration of exogenous butyrate. Butyrate restoration improved IEC junctional integrity, decreased apoptosis, and mitigated decreased GVHD. Furthermore, alteration of the indigenous microbiota with 17 rationally selected strains of high butyrate producing Clostridia also decreased GVHD. These data demonstrate a heretofore unrecognized role of microbial metabolites and indicate that local and specific alteration of microbial metabolites has direct salutary effects on GVHD target tissues and can mitigate its severity.

Alterations in the intestinal microbiome are associated with several disease processes (David, L. A. et al. Diet rapidly and reproducibly alters the human gut microbiome. Nature 505, 559-563 (2014); Turnbaugh, P. J. et al. A core gut microbiome in obese and lean twins. Nature 457, 480-484 (2009); Mathewson, N. & Reddy, P. The Microbiome and Graft Versus Host Disease. Curr Stem Cell Rep (2015); Jenq, R. R. et al. Regulation of intestinal inflammation by microbiota following allogeneic bone marrow transplantation. Journal of Experimental Medicine 209, 903-911 (2012); Eriguchi, Y. et al. Graft-versus-host disease disrupts intestinal microbial ecology by inhibiting Paneth cell production of α-defensins. Blood 120, 223-231 (2012)). However, the effect that changes in the community structure of the microbiome have on the production of microbial-derived metabolites is poorly explored. Microbial metabolites influence disease severity, but whether these alterations in microbial metabolites can impact outcomes after allogeneic bone marrow transplant (allo-BMT) are not known. Allo-BMT is a critical interventional therapy for patients with aggressive hematological malignancies (Jenq, R. R. & van den Brink, M. R. M. Allogeneic haematopoietic stem cell transplantation: individualized stem cell and immune therapy of cancer. Nature Reviews Cancer 10, 213-221 (2010); Choi, S. & Reddy, P. Graft-versus-host disease. Panminerva Med 52, 111-124 (2010)). Although allo-BMT is a curative and widely used treatment, approximately 40-50% of patients experience severe gastrointestinal damage from graft-versus-host disease (GVHD), which leads to high transplant-related mortality (Choi et al., supra; Ferrara, J. L. M., Levine, J. E., Reddy, P. & Holler, E. Graft-versus-host disease. Lancet 373, 1550-1561 (2009)).

Studies have revealed that the intestinal microbiota is significantly altered in patients with GVHD and the alterations correlate with GVHD severity and pathogenesis (Jenq, R. R. et al. Regulation of intestinal inflammation by microbiota following allogeneic bone marrow transplantation. Journal of Experimental Medicine 209, 903-911 (2012); Taur, Y. et al. The effects of intestinal tract bacterial diversity on mortality following allogeneic hematopoietic stem cell transplantation. Blood 124, 1174-1182 (2014)). Nevertheless, the direct causality of the changes in the host microbiota on GVHD severity is unclear. More relevantly, whether changes in the microbiota result in alterations in levels of microbial metabolites and by-products that have biological impact on allogeneic-BMT remain unknown. Microbial metabolites such as short chain fatty acids (SCFA) are exclusively derived from the GI microbiota and are not made by the host. Some of these fatty acids (FAs), specifically the histone deacetylase inhibitor (HDACi) butyrate, is a preferred energy source for intestinal epithelial cells (IECs) (Ganapathy, V., Thangaraju, M., Prasad, P. D., Martin, P. M. & Singh, N. Transporters and receptors for short-chain fatty acids as the molecular link between colonic bacteria and the host. Curr Opin Pharmacol 13, 869-874 (2013); Fleming, L. L. & Floch, M. H. Digestion and absorption of fiber carbohydrate in the colon. Am. J Gastroenterol. 81, 507-511 (1986); Sealy, L. & Chalkley, R. The effect of sodium butyrate on histone modification. Cell 14, 115-121 (1978); Cook, S. I. & Sellin, J. H. Review article: short chain fatty acids in health and disease; Aliment. Pharmacol. Ther. 12, 499-507 (1998)) and administration of exogenous HDACi regulates GVHD (Reddy, P. et al. Histone deacetylase inhibitor suberoylanilide hydroxamic acid reduces acute graft-versus-host disease and preserves graft-versus-leukemia effect. Proc Natl Acad Sci USA 101, 3921-3926 (2004); Reddy, P. et al. Histone deacetylase inhibition modulates indoleamine 2,3-dioxygenasedependent DC functions and regulates experimental graft-versus-host disease in mice. J. Clin. Invest. 118, 2562-2573 (2008); Choi, S. W. et al. Vorinostat plus tacrolimus and mycophenolate to prevent graft-versus host disease after related-donor reduced-intensity conditioning allogeneic haemopoietic stem-cell transplantation: a phase ½ trial. Lancet Oncol. 15, 87-95 (2014)). But the impact that host indigenous microbial metabolites that function as HDACi have on GVHD remains Unknown (Fleming, L. L. & Floch, M. H. Digestion and absorption of fiber carbohydrate in the colon. Am. J Gastroenterol. 81, 507-511 (1986); 12. Sealy, L. & Chalkley, R. The effect of sodium butyrate on histone modification. Cell 14, 115-121 (1978); Cook, S. I. & Sellin, J. H. Review article: short chain fatty acids in health and disease. Aliment. Pharmacol. Ther. 12, 499-507 (1998)).

Methods

Reagents:

RPMI, penicillin and streptomycin, and sodium pyruvate were purchased from Gibco (Grand Island, N.Y.); FCS from GemCell (Sacramento, Calif.); 2-ME from Sigma (St. Louis, Mo.); murine GM-CSF from Peprotech (Rocky Hill, N.J.).

All antibodies (Abs) used for FACS were purchased from eBioscience (San Diego, Calif.). DMSO and butyrate was obtained from Sigma (St. Louis, Mo.), and lipopolysaccharide (LPS) from InvivoGen (San Diego, Calif.).

Mice:

Female C57BL/6J (H-2b; CD45.2+), BALB/c (H-2d) mice were purchased from National Cancer Institute and FoxP3.DTR (DREG) (H-2b) mice and C3H.sw (H-2b) mice were purchased from The Jackson Laboratory (Bar Harbor, Me.). The age of mice used for experiments ranged between 7 and 12 weeks. All animals were cared for under regulations reviewed and approved by the University Committee on Use and Care of Animals of the University of Michigan, based on University Laboratory Animal Medicine guidelines.

Cell Isolation and Cultures:

Primary intestinal epithelial cells (IECs) were obtained from C57BL/6J mice as described previously (Lefrangois, L. & Lycke, N. *Isolation of Mouse Small Intestinal Intraepithelial Lymphocytes, Peyer's Patch, and Lamina Propria Cells.* (John Wiley & Sons, Inc., 2001)). Briefly, luminal contents of intestine were flushed with CMF solution. Intestine was then minced into 0.5 cm pieces, washed with CMF four times, transferred to CMF/FBS/EDTA, and incubated at 37° C. for 60 minutes (shaking tubes every 10 minutes). Supernatant containing IECs was then transferred through 100 µM cell filter followed by incubation on ice for 10 minutes to allow sedimentation. Supernatant was again transferred through a 75 µM cell filter. CD326+ IECs were next purified utilizing either FACS or anti-APC magnetic microbeads (Miltenyi Biotec Ltd., Auburn, Calif.) and an autoMACs (Miltenyi Biotec). For viability assay, CD326+ IECs were seeded on gelatin coated 100 mm culture dishes and treated in the presence of absence of indicated butyrate concentrations overnight. Cells were then subjected to or withheld from irradiation (6 Gy) and cultured for another 24 hours.

Bone Marrow Transplantation (BMT):

BMTs were performed as previously described (Reddy, P. et al. A crucial role for antigen-presenting cells and alloantigen expression in graft-versus-leukemia responses. *Nat. Med.* 11, 1244-1249 (2005); 15). Briefly, syngeneic (BALB/c→BALC/c or C57BL/6J→C57BL/6J) and allogeneic (C57BL/6J→BALB/c or C3H.sw→C57BL/6J) recipients received lethal irradiation. On day −1, BALB/c recipients received a total of 800 cGy of irradiation (split dose separated by 3 hours) and B6 animals received a single dose of 1000 cGy. Donor splenic CD90.2+ T cells were magnetically separated using an autoMACs (Miltenyi Biotec; Bergisch Gladbach, Germany) and $0.5 \times 10^6$ to $2.5 \times 10^6$ T cells were transferred to BALB/c and C57BL/6J recipients. $5 \times 10^6$ donor whole or TCD bone marrow was transferred to all recipients. Survival was monitored daily and the recipient body weight and GVHD clinical scores were determined weekly, as described previously42. Histopathologic analysis of the gastrointestinal (GI) tract was performed as described (Reddy, P. et al. A crucial role for antigen-presenting cells and alloantigen expression in graft-versus-leukemia responses. *Nat. Med.* 11, 1244-1249 (2005)). Animals received vehicle (sterile PBS, 0.0004 g Na+ per dose) or sodium butyrate (10 mg/kg, 0.00004 g Na+ per dose) by flexible 20G-1.5" intragastric gavage needle daily for 1 week, then every other day thereafter.

For BMTs performed at MSKCC, C57BL/6J mice were treated with an antibiotic cocktail to target obligate anaerobes (ampicillin 5 mg, metronidazole 4 mg, clindamycin 5 mg, and vancomycin 5 mg) gavaged daily for 6 days (BMT days −18 to −13) followed 4 and 6 days later by oral gavage with indicated bacteria (BMT days −9 and −7) or PBS. Clostridial bacteria were cultured individually on plates and resuspended in anaerobic PBS at a final OD (600 nm) of 0.02 to 0.06. One week later, mice were irradiated (12 Gy single dose) and transplanted with B10.BR BM ($5 \times 10^6$) and T cells ($0.5 \times 10^6$ CD5 MACS), and followed for development of clinical GVHD.

Gas Chromatography Mass Spectrometry (GC/MS):

To determine targeted fatty acid quantitation, samples (plasma, spleen, liver, intestine, and intestinal fecal content) from mice 7d and 21d post-transplant were harvested, homogenized, and snap-frozen in liquid N2. Equal volumes of plasma and homogenized tissue were utilized, while fecal content was weighed at necropsy. Samples were dispersed in acidified water spiked with stable isotope-labeled SCFA standards and extracted with diethyl ether. The ether layer was immediately analyzed by gas chromatography/mass spectroscopy using a Phenomenex ZB-WAX column on an Agilent 6890 GC with a 5973MS detector. Quantitation was performed by calibration to internal standards. The tissue levels were normalized by protein concentration of the homogenized tissue. Heatmap data was generated using GenePattern software from the Broad Institute (Cambridge, Mass.). Metabolomic data, mass spectral analytical parameters and spectral raw data from the study and meta data is available in the National Institutes of Health Metabolomics Data Repository Coordinating Center (DRCC) at the University of California San Diego Metabolic Flux Analysis (MFA) Assessing Label Incorporation into Luminal and Intestinal Tissue Butyrate Pools:

Animals were intragastrically gavaged with a bolus (2 g/kg) of either labeled $^{13}C2$-Butyrate or non-labeled $^{12}C$-Butyrate. The small and large intestines were then harvested 6 hours later and prepared for analysis as above. The incorporation of $^{13}C2$ labeled Butyrate (Sodium butyrate-1, 2-$^{13}C2$) in the butyrate pools in the lumen and the intestinal tissue were measured using GC/MS as described previously (Mathew, A. V., Seymour, E. M., Byun, J., Pennathur, S. & Hummel, S. L. Altered Metabolic Profile with Sodium-restricted Dietary Approaches to Stop Hypertension Diet in Hypertensive Heart Failure with Preserved Ejection Fraction. *J. Card. Fail.* (2015); Mell, B. et al. Evidence for a link between gut microbiota and hypertension in the Dahl rat. *Physiol. Genomics* 47, 187-197 (2015)) and unlabeled (m/z 145) and labeled butyrate which is 2 a.m.u higher (m/z 147) were detected. The ratio of the labeled to unlabeled peak areas were adjusted to incorporate natural distribution of $^{13}C$ label and expressed as percentage of $^{13}C$ incorporation into the butyrate pool in the luminal contents (Lumen) and intestinal tissue.

MFA Assessing Label Incorporation into Tricarboxylic Acid (TCA) Metabolite Pools:

The incorporation of 13C2 labeled Butyrate (Sodium butyrate-1, 2-13C2; Sigma) into the TCA cycle metabolites in the intestinal tissue were measured using LC/MS performed an Agilent 6520 high resolution Q-TOF (quadrupole-time of flight instrument) coupled with an Agilent 1200 HPLC system (Agilent Technologies, New Castle, Del.), equipped with an electrospray source. The extract was subjected to hydrophilic interaction chromatography using Phenomenex Luna NH2 column (particle size 3 m; 1×150 mm) at a flow rate of 0.07 mL/min. Solvent A was 5 mM ammonium acetate with pH 9.9 and solvent B was acetonitrile. The column was equilibrated with 80% solvent B. The gradient was: 20-100% solvent A over 15 min; 100% solvent A over 5 min; 20% solvent B for 0.1 min 20% solvent A for 15.9 min. Liquid chromatography electrospray ionization (LC/ESI) MS in the negative mode was performed by Q-TOF instrument using the following parameters: spray voltage 3000 V, drying gas flow 10 L/min, drying gas temperature 3500 C, and nebulizer pressure 20 psi. Fragmentor voltage was 150 V in full scan mode. Mass range between m/z 100 to 1500 was scanned to obtain full scan mass spectra. Two reference masses at m/z 121.050873 and m/z 922.009798 were used to obtain accurate mass measurement within 5 ppm. All chromatograms and corresponding spectra of TCA metabolites: citrate, succinate and malate and their corresponding 13C labeled counterparts were extracted and deconvoluted using the MassHunter software (Agilent Technologies, New Castle, Del.).

Retention time consistency were manually rechecked and compared to authentic compounds that were injected under similar chromatographic conditions. For tissue extracts, metabolite concentrations were normalized to protein content, which was determined by the Bradford-Lowry method. For the flux analyses, peak area of the labeled compounds were normalized to natural abundance of the label and represented as ratios to the total compound peak area.

16S Deep Sequencing:

On indicated days, fecal pellets were collected from mice and stored at −80° C. DNA was extracted and purified with phenol-chloroform following bead-based lysis. Sequencing and analysis was performed as described (Koenigsknecht, M. J. et al. Dynamics and Establishment of *Clostridium difficile* Infection in the Murine Gastrointestinal Tract. *Infect. Immun.* 83, 934-941 (2015)). Briefly, the V4 region of the 16S rRNA gene was sequenced using Ilumina MiSeq technology. Sequencers were trimmed and analyzed using Mothur (Schloss, P. D. et al. Introducing mothur: open-source, platform-independent, communitysupported software for describing and comparing microbial communities. *Appl. Environ. Microbiol.* 75, 7537-7541 (2009)). The 16S rRNA gene sequence from each strain in the 17 strain cocktail was added to the version 9 trainset sequences from the Ribosomal Database Project (Cole, J. R. et al. The Ribosomal Database Project: improved alignments and new tools for rRNA analysis. *Nucleic Acids Res.* 37, D141-5 (2009)). The resulting sequences were classified by comparing to described trainset with the requirement that the confidence score is 100%.

MSKK 16S experiments were analyzed using the Illumina MiSeq platform to sequence the V4-V5 region of the 16S rRNA gene. Sequence data were compiled and processed using mothur version 1.34 (Schloss, P. D. et al. Introducing mothur: open-source, platform-independent, community supported software for describing and comparing microbial communities. *Appl. Environ. Microbiol.* 75, 7537-7541 (2009)), screened and filtered for quality (Schloss, P. D., Gevers, D. & Westcott, S. L. Reducing the effects of PCR amplification and sequencing artifacts on 16S rRNA-based studies. *PLoS ONE* 6, e27310 (2011)), then classified to the species level (Wang, Q., Garrity, G. M., Tiedje, J. M. & Cole, J. R. Naive Bayesian classifier for rapid assignment of rRNA sequences into the new bacterial taxonomy. Appl. Environ. Microbiol. 73, 5261-5267 (2007)) using the Greengenes reference database (DeSantis, T. Z. et al. Greengenes, a chimera-checked 16S rRNA gene database and workbench compatible with ARB. *Appl. Environ. Microbiol.* 72, 5069-5072 (2006)).

17 Strain Mixture:

The 17 strain mix was prepared as described (Atarashi, K. et al. Treg induction by a rationally selected mixture of Clostridia strains from the human microbiota. *Nature* (2013)). Briefly all strains were grown in 5 ml of EG media for 24 hours at 37° C. under anaerobic conditions. Each strain was grown to confluence, with the exception of St 3, 8, 13, 26, and 29. Cells were scraped from EG agar plates and added to the 5 ml culture to obtain the same approximate optical density as the other strains. All cultures were then mixed and glycerol was added to a final concentration of 20%. Aliqouts (1 ml) were individually frozen and stored at −80° C.

Transmission Electron Microscopy (TEM):

Samples were stained as previously described (Soler, A. P. et al. Increased tight junctional permeability is associated with the development of colon cancer. *Carcinogenesis* 20, 1425-1431 (1999)). Briefly, the intestines from mice that received butyrate or vehicle treatment were harvested 7 days and 21 days following syngeneic and allogeneic BMT and flushed with 0.1 M Sorensen's phosphate buffer (pH 7.4) to remove luminal contents using a 20G needle. The intestines were next gently flushed with 0.1% ruthenium red (RR) containing 2.5% glutaraldehyde fixative in Sorensen's buffer and immediately placed in a dish containing the stain/fixative. Cross sections were immediately sliced (2 mm wide) from the duodenum, jejunum, and illium. The tissue was then rinsed three times with Sorensen's buffer, containing 0.1 percent RR and post-fixed for one hour in one percent osmium tetroxide in the same buffer containing RR. The samples were again rinsed with Sorensen's buffer containing RR. Next, the tissue was dehydrated in ascending concentrations of ethanol, treated with propylene oxide, and embedded in Epon epoxy resin. Semi-thin sections were stained with toluidine blue for tissue identification. Selected regions of interest were ultra-thin sectioned (70 nm thick) mounted on copper grids, and post stained with uranyl acetate and lead citrate. The samples were examined using a Philips CM100 electron microscope at 60 kV. Images were recorded digitally using a Hamamatsu ORCA-HR digital camera system operated using AMT software (Advanced Microscopy Techniques Corp., Danvers, Mass.).

FITC-Dextran Assay:

Food and water was withheld from all mice for four hours on day 21 post bone marrow transplant. FITC-dextran (Sigma-Aldrich; St. Louis, Mo.) was administered by 20G-1.5" flexible intragastric gavage needle (Braintree Scientific; Braintree, Mass.) at a concentration of 50 mg/ml in PBS. BMT recipients received 800 mg/kg (~16 mg/mouse). Four hours later, serum was collected from peripheral blood, diluted 1:1 with PBS, and analyzed on a plate reader at excitation/emission wavelength of 485 nm/535 nm. Concentrations of FITCdextran experimental samples were determined based on a standard curve.

Western Blot:

CD326+ purified IECs were harvested from animals that received syngeneic (BALB/c→BALB/c) or allogeneic (C57BL/6J→BALB/c) BMT. Whole cell lysates were next obtained and protein concentrations determined with Pierce BCA Protein Assay (Thermo Scientific). Equal amounts of protein (20 µg) were separated by SDS-PAGE gel electrophoresis (120V, 1.5 h) and subsequently transferred to polyvinylidene difluoride (PVDF) membrane using a Bio-Rad semi-dry transfer cell (Hercules, Calif.) (20V, 1h). The following antibodies were used to analyze the membranes with dilutions in accordance with the manufacturers specification sheet: α-tubulin (Cell Signaling, clone 11H10), Acetyl histone H4 (Lys5/8/12/16) (EMD Millipore, clone 3HH-4C10), SLC5A8 (abcam), GPR43 (abcam), Occludin (abcam, clone EPR8208), JAM (abcam, clone EP1042Y), and Claudin 5 (abcam). Secondary anti-rabbit antibody conjugated to HRP (Jackson ImmunoResearch, Cat No. 111-035-003) was used to detect primary antibodies, where needed. Densitometric analysis was performed using ImageJ software (National Institutes of Health; Bethesda, Mass.).

Quantitative PCR:

mRNA was isolated from samples using RNeasy kit following manufacturers instructions (Qiagen; Venlo, Netherlands). Using 1 μg of each mRNA template, cDNA was synthesized using SuperScript VILO (Invitrogen; Carlsbad, Calif.). qPCR primers were designed for murine targets. All primers were verified for the production of a single specific PCR product using a melting curve program and are shown below in Table 2.

ward: CCTACTCTGCCTGGCTCTTT (SEQ ID NO:50); Reverse: ACCCTTCTGAGTCCCTGAGA (SEQ ID NO:51)), Slc5a8 (Forward: CACAGCACAGCCTTCTTTGT (SEQ ID NO:52); Reverse: TCCAGTTCACAGTCCAGGTC (SEQ ID NO:53), and JAM (F11r) (Forward: TGCCGGGAT-TAAAAGCATGG (SEQ ID NO:54; Reverse: ACAGGGACAGCAGGATTAGG (SEQ ID NO:55)). IP efficiency of all samples was verified by qPCR analysis of the promoter region of Gapdh (Forward: CTGCAGTACTGTGGGGAGGT (SEQ ID NO:56); Reverse: CAAAGGCGGAGTTACCAGAG (SEQ ID NO:57)). Data analysis was determined as percent of input

TABLE 2

| qPCR Probe | Forward | Reverse |
|---|---|---|
| GAPDH | CCACAGTCCATGCCATCACTGC | GCCCAAGATGCCCTTCAGTGGG |
| SLC5A8 | GCTGGATTTGCATCCGTAAT | TGGGACTGGTTGACACCATA |
| GPR43 | CACGGCCTACATCCTCATCT | TTGGTAGGTACCAGCGGAAG |
| p300 | TGCCTCCCATTGTTGATCCT | ACTCGTTGCAGGTGTAGACA |
| TIP60 | TGGACGGAAGCGGAAATCTA | CGGCCAAGCTCAATACACTC |
| BAK | CAGATGGATCGCACAGAGAG | TCTGTGTACCACGAATTGGC |
| BAX | ACTAAAGTGCCCGAGCTGAT | ATGGTCACTGTCTGCCATGT |
| BCL-B (Bcl2110) | TCATAGTGACCCGAGACTGC | TGTTGCAAAGAAGCCTGACA |
| JAM | ACTGCTCAATCTGACGTCCA | ATAGGGAGCTGTGATCTGGC |
| Occludin | CTCTCAGCCAGCGTACTCTT | CTCCATAGCCACCTCCGTAG |
| E-Cadherin | CCTGTCTTCAACCCAAGCAC | CAACAACGAACTGCTGGTCA |
| HDAC1 | TGGGGCTGGCAAAGGCAAGT | GACCACTGCACTAGGCTGGAACA |
| HDAC4 | AGCTCTGGCAACGTCAGCACT | AAGTGGGGCGACTGAGCCTTCT |
| HDAC7 | GCTCAGCATGTGCATGTGGAACAC | TGAGAGCCTGGTGTGTCTGGCT |
| HDAC9 | TGCACCTTTGCCTCAGAGCACG | TGGCTGCCTGGTTGCTTCAGT |
| HDAC10 | TAGCAGCCAAACATGCCAAGCAGA | ATGCTCATAGCGGTGCCAAGAGAAA |

GADPH Forward SEQ ID NO: 18 GADPH Reverse SEQ ID NO: 19 SLC5A8 Forward SEQ ID NO: 20 SLC5A8 Reverse SEQ ID NO: 21 GPR43 Forward SEQ ID NO: 22 GPR43 Reverse SEQ ID NO: 23 p300 Forward SEQ ID NO: 24 p300 Reverse SEQ ID NO: 25 TIP60 Forward SEQ ID NO: 26 TIP60 Reverse SEQ ID NO: 27 BAK Forward SEQ ID NO: 28 BAK Reverse SEQ ID NO: 29 BAX Forward SEQ ID NO: 30 BAX Reverse SEQ ID NO: 31 BCL-B (Bcl2110) Forward SEQ ID NO: 32 BCL-B (Bcl2110) Reverse SEQ ID NO: 33 JAM Forward SEQ ID NO: 34 JAM Reverse SEQ ID NO: 35 Occludin Forward SEQ ID NO: 36 Occludin Reverse SEQ ID NO: 37 E-Cadherin Forward SEQ ID NO: 38 E-Cadherin Reverse SEQ ID NO: 39 HDAC1 Forward SEQ ID NO: 40 HDAC1 Reverse SEQ ID NO: 41 HDAC4 Forward SEQ ID NO: 42 HDAC4 Reverse SEQ ID NO: 43 HDAC7 Forward SEQ ID NO: 44 HDAC7 Reverse SEQ ID NO: 45 HDAC9 Forward SEQ ID NO: 46 HDAC9 Reverse SEQ ID NO: 47 HDAC10 Forward SEQ ID NO: 48 HDAC10 Reverse SEQ ID NO: 49

Chromatin Immunoprecipitation:

Primary CD326+ IECs were seeded on gelatin (Cell Biologics; Chicago, Ill.) coated cell culture dishes (100 mm) overnight followed by treatment with butyrate 1 mM for 24 hours. Cells were harvested and used for ChIP analysis using EZ-Magna ChIP kit from EMD Millipore (Billerica, Mass.) following the manufacturers instructions. Briefly, cells were cross-linked with 1% formaldehyde and extracted chromatin was sonicated using a Bioruptor Pico by Diagenode (Denville, N.J.) to yield DNA fragments predominately in the range of 200-1000 bp. Sonicated lysates were immunoprecipitated (IP) utilizing ChIP grade specific antibodies purchased from EMD Millipore for acetylated histone-H4 and RNA Pol II or IgG control antibody. De-crosslinked DNA was next examined by qPCR using primers targeting the promoter region of the target gene BCL-B (Bcl2110) (For-utilizing the equations: ΔCt[normalized ChIP]=(Ct[ChIP]−(Ct[Input]−Log 2 (6.644))) and % Input=2(−ΔCt [normalized ChIP]).

Flow Cytometry:

To analyze immunophenotype surface markers, lymphocytes contained in the IEC fraction or spleen were harvested, stained using recommended dilutions indicated by manufacturer product sheets and gated on CD4-conjugated PerCP/Cy5.5 (Clone: GK1.5) or CD8-conjugated APC (Clone: 53-6.7) and configurations of the following per mouse in duplicate: CD69-PE (Clone: H1.2F3), CD62L-PE (Clone: MEL-14), CD25-PE (Clone: 3C7), CD44-PerCP/Cy5.5 (Clone: IM7), CD44-APC (Clone: IM7), FoxP3-APC (Clone: FJK-16s). Stained cells were then analyzed with an Accuri C6 Flow Cytometer (BD Biosciences). IECs were stained with CD326-conjugated APC (Clone: G8.8) and DAPI and sorted to >98% purity using a FACSAria III (BD Biosciences) gating on live cells.

All antibodies have been validated for this species and application as found in respective 1 DegreeBio validation profile. CD4, CD8, CD69, CD62L, CD25, CD44, CD326 antibodies were purchased from Biolegend, FoxP3 from eBioscience, and DAPI from Life Technologies.

CTL Assay:

CD8+ T cells were isolated from Balb/c (H-2d) mice using anti-CD8 microbeads and LS columns (Miltenyi Biotec) following the manufacturer's instructions. CD8+ T cells were primed in the presence of irradiated (30 Gy) C57BL/6J (H-2b) splenocytes for 6 days prior to culture with primary IECs for 6 h and 16 h. Primary C57BL/6J IECs were harvested and incubated overnight in the presence or absence of butyrate 1 mM in gelatin coated (Cell Biologics Inc.; Chicago, Ill.) 100 mm-culture dishes (Fisher Scientific)

Reproducibility:

Experiments were repeated at least 2 times with 3 sample replicates, bringing the n to at least 6; sample size is indicated in figure legends. To analyze one variable in one BMT experiment, at least two groups of 3 recipients are required.

Statistics:

Bars and error bars represent the means and standard errors of the mean, respectively. Non-survival analysis was performed using students unpaired t test between two groups. ANOVA was used for comparisons with more than two groups. Survival data analysis was performed using a Mantel-Cox log-rank test.

Results

Targeted Microbial Metabolite Profiling:

It was hypothesized that alterations in the composition of the microbiota in the GI lumen would result in an altered microbial metabolome after GVHD (Jenq, R. R. et al. Regulation of intestinal inflammation by microbiota following allogeneic bone marrow transplantation. *Journal of Experimental Medicine* 209, 903-911 (2012); Hill, G. R. & Ferrara, J. L. The primacy of the gastrointestinal tract as a target organ of acute graft-versus-host disease: rationale for the use of cytokine shields in allogeneic bone marrow transplantation. *Blood* 95, 2754-2759 (2000)). The concentration of microbial FA metabolites, both short-chain FAs and long-chain FAs up to 18 carbons in length, was determined from several sites seven days (day +7) after BMT. The serum, spleen, liver, intestines, and luminal contents (stool) of the intestines were analyzed with gas chromatography mass spectrometry (GC/MS). A well-established, clinically relevant model of MHC-mismatched BMT with C57BL/6J (H-2b) cells transferred to lethally irradiated Balb/c (H-2d) mice was used and results were compared to syngeneic transplant and naive animals. The animal cages were exchanged on day 3 to take any alterations in the microbial environment into account, and analysis following GC/MS was performed in a blinded manner. The concentrations of the FAs were not significantly different in the luminal contents of the intestines between any of the groups (FIG. 1a). They were also not significantly different in the serum or the tissues such as the spleen and liver of allogeneic animals compared with syngeneic animals and naive controls.

However, the greatest and the only statistically significant difference was observed in just one SCFA, butyrate, which was significantly decreased only in the intestinal tissue at day 7 (FIG. 1b). Similar results were observed on day 21 as on day 7. Collectively these data demonstrate that butyrate levels are consistently reduced only in the intestinal tissue after allo-BMT.

Functional Impact of Altered Levels of SCFA in the IECs:

In light of the reduction of butyrate in allogeneic animals only in the intestinal tissue, the functional impact of reduced butyrate in IECs was analyzed. Because butyrate is an HDACi (Ganapathy, V., Thangaraju, M., Prasad, P. D., Martin, P. M. & Singh, N. Transporters and receptors for short-chain fatty acids as the molecular link between colonic bacteria and the host. *Curr Opin Pharmacol* 13, 869-874 (2013); Sealy, L. & Chalkley, R. The effect of sodium butyrate on histone modification. *Cell* 14, 115-121 (1978); Gao, S.-M. et al. Histone deacetylases inhibitor sodium butyrate inhibits JAK2/STAT signaling through upregulation of SOCS1 and SOCS3 mediated by HDAC8 inhibition in myeloproliferative neoplasms. *Exp. Hematol.* 41, 261-70.e4 (2013)), the degree of histone acetylation was analyzed by immunoblotting purified CD326+ IECs after BMT. The degree of acetylation of histone H4 was significantly decreased on day 7 and day 21 (FIG. 2a) following allo-BMT demonstrating that reduced butyrate resulted in decreased histone acetylation. Therefore to confirm if the decreased acetylation is secondary to decreased HDAC inhibition from reduction in butyrate and not due to potential alterations in HDAC and HAT enzyme levels20 following transplant, the expression of HDACs and HATs in IECs after BMT was analyzed. Similar levels of several HDACs (Hdac 1,4,7,9, and 10) (FIG. 2b) and HATs (p300 and TIP60) (FIG. 2c) were observed by qPCR in the IECs (CD326+) of both syngeneic and allogeneic BMT recipients. Furthermore both HDAC (FIG. 2d) and HAT (FIG. 2e) enzyme activity were not different in these animals. These data show that reduction in histone acetylation in the IECs after allo-BMT is from reduced levels of butyrate.

Reduced Uptake of Butyrate by the IECs:

It was next explored whether the diminished concentration of butyrate observed in the intestinal tissue was from impaired uptake of butyrate following allo-BMT. To this end, the expression of the known butyrate monocarboxylate transporter (SLC5A8) and the receptor of butyrate (GPR43) was analyzed in IECs following allo-BMT (Ganapathy, V., Thangaraju, M., Prasad, P. D., Martin, P. M. & Singh, N. Transporters and receptors for short-chain fatty acids as the molecular link between colonic bacteria and the host. *Curr Opin Pharmacol* 13, 869-874 (2013); Furusawa, Y. et al. Commensal microbe-derived butyrate induces the differentiation of colonic regulatory T cells. *Nature* (2013)). Decreased gene expression (FIG. 2f) and protein (FIG. 2g) of both SLC5A8 and GPR43 were observed in IECs from allogeneic animals following transplant on day +21 and also on day +7 showing that reduction in butyrate concentration in the IECs is due to reduced uptake of the microbiota-derived luminal butyrate. Primary IECs were cultured with proinflammatory mediators (IFN-γ and/or TNF) and expression of the butyrate transporter SLC5A8 was analyzed. Exposure of IECs to inflammatory cytokines significantly decreased the expression of Slc5a8. These data indicate that the intense inflammatory milieu following allo-BMT causes reduced expression of butyrate transporters and receptors leading to reduction in butyrate and histone acetylation in IECs.

Rescuing the Cellular Effects of Reduced Butyrate:

It was next determined if the reduced amount of butyrate in IECs could be restored in vivo and further, whether this would have a functional impact on histone acetylation. In addition to utilizing transporters, butyrate can also diffuse across the mucosal barrier into IECs when present in high concentrations (Ganapathy, V., Thangaraju, M., Prasad, P. D., Martin, P. M. & Singh, N. Transporters and receptors for short-chain fatty acids as the molecular link between colonic bacteria and the host. *Curr Opin Pharmacol* 13, 869-874 (2013); Charney, A. N., Micic, L. & Egnor, R. W. Nonionic diffusion of short-chain fatty acids across rat colon. *Am. J Physiol.* 274, G518-24 (1998)). Therefore, it was hypothesized that administration of high amounts of butyrate locally would restore histone acetylation of IECs, in vivo. To test this, C57BL/6J cells were transferred to Balb/c mice and administered vehicle or butyrate via daily intragastric gavage. Daily butyrate administration for 21 days significantly restored acetylation of histone H4 compared with untreated allo-BMT recipients (FIG. 3a).

It was next determined whether there was a difference in the uptake and metabolism of the exogenously administered butyrate between the syngeneic and allogeneic recipients. To this end, metabolic flux analysis (MFA) assessing label incorporation of heavy 13C labeled butyrate into luminal and intestinal tissue butyrate pools was performed by utilizing GC/MS as above. Recipients of syngeneic and allogeneic transplant were treated 7 days after BMT with a bolus of either $^{13}$C-butyrate or regular $^{12}$C-butyrate, which served as the control. The IECs and luminal contents were harvested 6 hours later and analyzed for incorporation of $^{13}$C. Similar amounts of heavy $^{13}$C butyrate was observed in the lumen of the large intestine; however, significantly decreased $^{13}$C heavy butyrate was observed in the intestinal tissue of recipients of allo-BMT, indicating reduced uptake (FIG. 3b). To determine whether there were any differences in the metabolism of butyrate, the presence of $^{13}$C-butyrate in different stages of the tricarboxylic acid (TCA) cycle was analyzed. Specifically, the incorporation of $^{13}$C-butyrate into citrate, succinate and further downstream, into malate was analyzed. There was a significant difference in the amount of heavy carbon in citrate and malate (FIG. 3c) and a trend towards greater incorporation into succinate within the IECs from the large intestine. Similarly, examination of IECs from both small and large intestines combined also revealed an overall increased level of $^{13}$C incorporation in the downstream metabolite of the TCA cycle, malate, in allo-BMT recipients compared with syngeneic animals, showing an increased rate of metabolism in the IECs of these animals. Furthermore, daily intragastric gavage of butyrate resulted in an increase in butyrate transporter SLC5A8 (FIG. 3d), indicating that butyrate has a positive feedback mechanism resulting in an increase of its own transporter. To determine whether butyrate was directly responsible for induction of its own transporter, the degree of histone acetylation at the promoter of SLC5A8 was analyzed with chromatin immunoprecipitation (ChIP). An increased association of acetylated histone H4 in the promoter region of Slc5a8 was found in IECs (CD326+) treated with butyrate (FIG. 3e). These data demonstrate that reduced butyrate following allo-BMT has functional effects on IECs.

Increase in Intestinal Butyrate Mitigated GVHD:

Systemic administration of HDACi decreases acute GVHD (Reddy, P. et al. Histone deacetylase inhibitor suberoylanilide hydroxamic acid reduces acute graft-versus-host disease and preserves graft-versus-leukemia effect. *Proc Natl Acad Sci USA* 101, 3921-3926 (2004); Reddy, P. et al. Histone deacetylase inhibition modulates indoleamine 2,3-dioxygenasedependent DC functions and regulates experimental graft-versus-host disease in mice. *J. Clin. Invest.* 118, 2562-2573 (2008); Sun, Y. et al. Cutting edge: Negative regulation of dendritic cells through acetylation of the nonhistone protein STAT-3. *J Immunol* 182, 5899-5903 (2009)). It was therefore determined if increasing local levels of endogenous HDACi, butyrate, would impact GVHD severity. Again using the C57BL/6J into Balb/c model, vehicle control or butyrate was administered via daily intragastric gavage for one week, followed by administration every other day for the remainder of the experiment. Administration of butyrate resulted in decreased weight loss (FIG. 3b), GVHD clinical scores (FIG. 3c), and increased survival (FIG. 3d). Similar improved survival was found using a second clinical model of BMT, a MHC-matched, minor antigen mismatched model. C3H.SW (H-2b) cells were transferred to C57BL/6J (H-2b) mice, thus demonstrating strain-independent results. Furthermore, histopathological analysis 21 days following BMT exhibited decreased histological scores in the intestines of the major MHC mismatch model (FIG. 3e) and decreased histological scores in both the intestines and liver in the model of minor antigen mismatch. To determine whether irradiation related inflammation was critical for butyrate induced protection, the butyrate induced protective effects were observed in a non-irradiated model of parent (C57BL/6J, H-2b) into F1 (B6D2F1, H-2b/d) BMT. Significantly less weight loss and improved survival was observed in allogeneic recipients that were treated with intragastric butyrate. Next, to further evaluate the magnitude of the butyrate-induced protective effect, GVHD mortality was determined utilizing the MHC disparate B6 into BALB/c model. Intragastric gavage of butyrate induced significant GVHD survival benefit in allogeneic animals that received higher doses of T cells. These data collectively show that butyrate induced GVHD protective effects regardless of strain combinations, conditioning, or higher alloreactive T cell doses.

Figures 4, 4A:
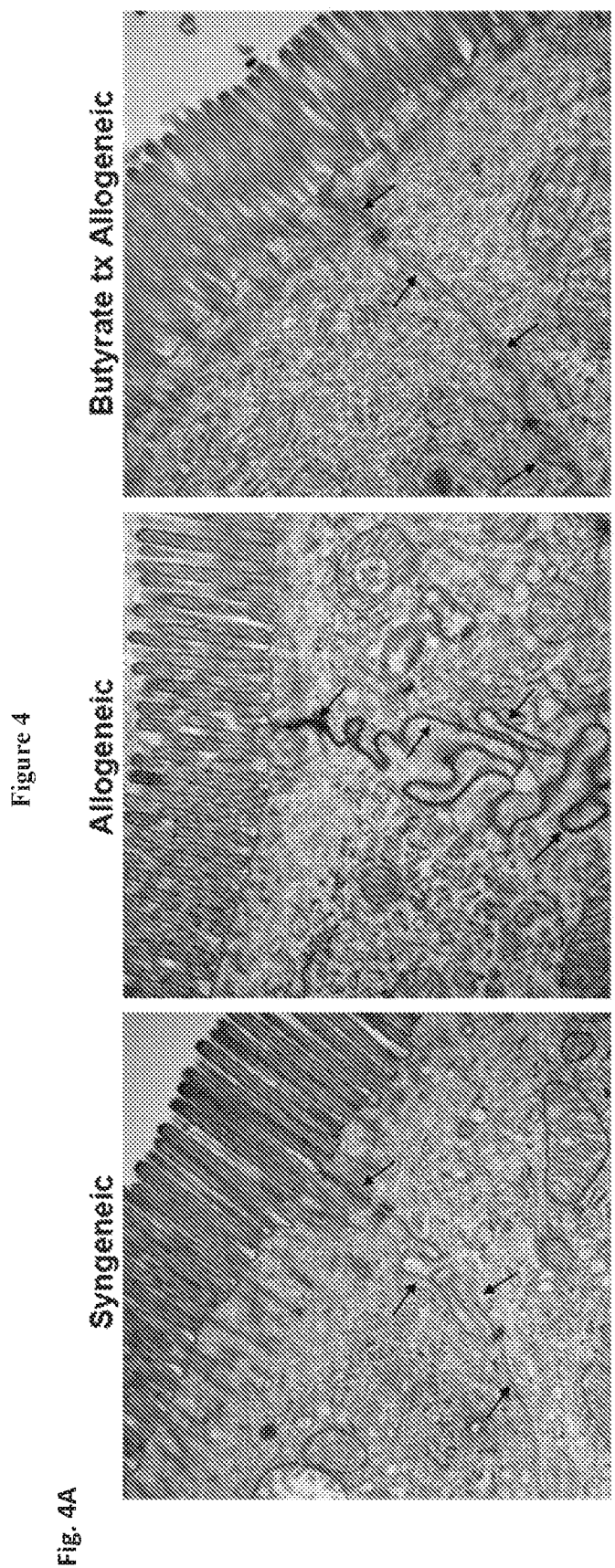
FIG. 4.
(FIG. 4A) Transmission electron microscopy (TEM) of intestines, isolated from recipients of syngeneic or allogeneic transplant with or without intragastric gavage of butyrate; stained with ruthenium red (0.1%). Arrows indicate cell junctions.
Figure 4:
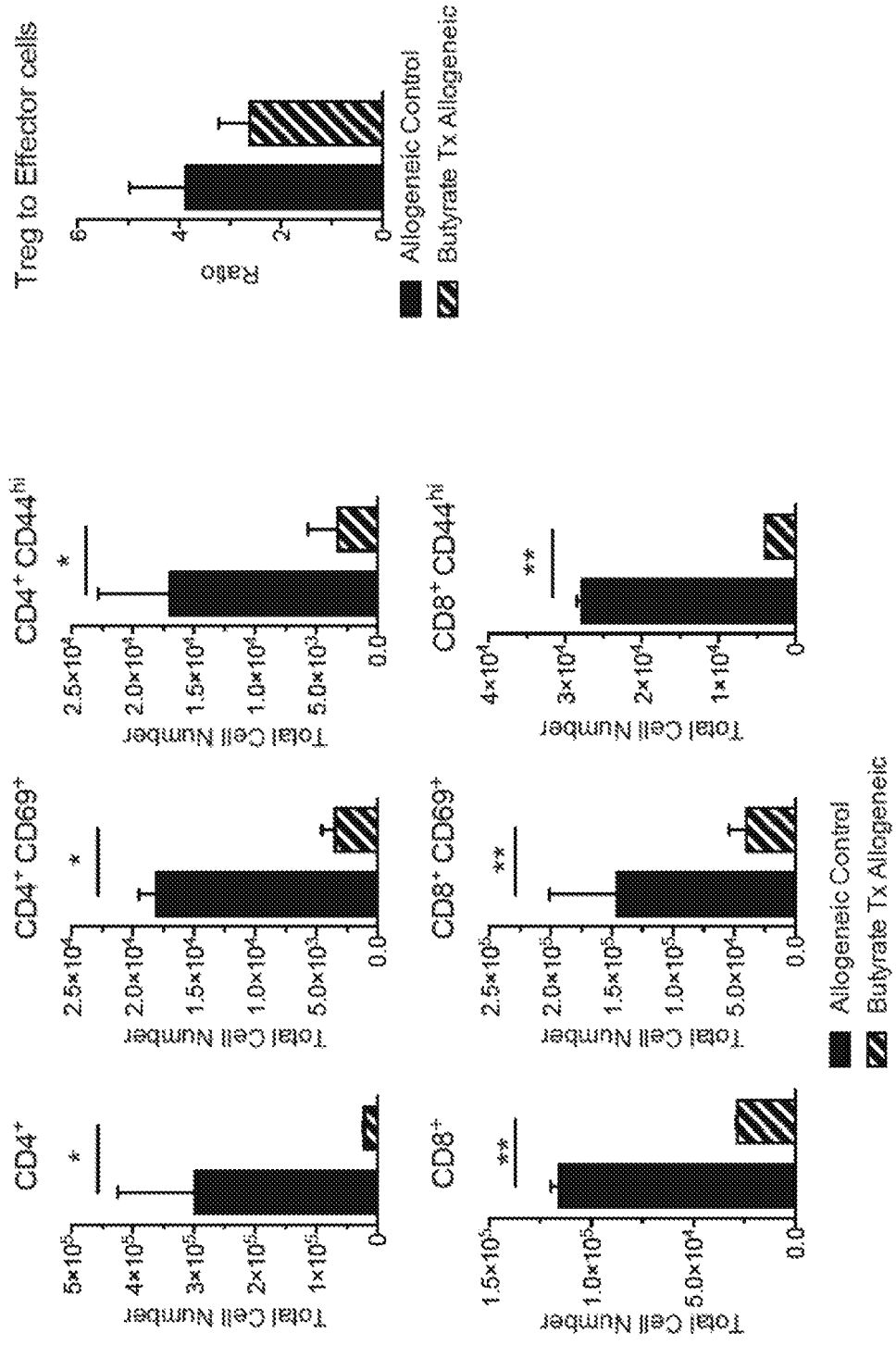

Increase in Intracellular Butyrate Protects GI Epithelium:

It was next determined if the decreased GI GVHD resulted in reduced translocation of luminal contents and improved epithelial integrity (Noth, R. et al. Increased intestinal permeability and tight junction disruption by altered expression and localization of occludin in a murine graft versus host disease model. *BMC Gastroenterol* 11, 109 (2011); Soler, A. P. et al. Increased tight junctional permeability is associated with the development of colon cancer. *Carcinogenesis* 20, 1425-1431 (1999); Suzuki, T. Regulation of intestinal epithelial permeability by tight junctions. *Cell. Mol. Life Sci.* 70, 631-659 (2013)) using transmission electron microscopy (TEM) to examine the ability of butyrate to preserve cellular junctions following allo-BMT. Significantly, intense leakage of the electron dense stain ruthenium red25 was found in allo-BMT recipients treated with vehicle alone (FIG. 4a, middle panel). However, TEM studies demonstrate that the integrity of the IEC junction was preserved at both day 7 (FIG. 4a, right panel) and day 21 in allo-BMT recipients that received local intragastric administration of butyrate. Intestinal permeability after allo-BMT was assessed by intragastric administration of FITC-dextran, a non-metabolized carbohydrate (Hanash, A. M. et al. Interleukin-22 protects intestinal stem cells from immune-mediated tissue damage and regulates sensitivity to graft versus host disease. *Immunity* 37, 339-350 (2012)). Butyrate-treated allo-BMT recipients exhibited significantly less detectable FITC-dextran in the serum at 21 days following transplant (FIG. 4b).

Reduction in GVHD is Independent of Donor Treg Cells:

Treg cells mitigate GVHD and butyrate has been shown to increase intestinal Treg cells (Atarashi, K. et al. Treg induction by a rationally selected mixture of Clostridia strains from the human microbiota. *Nature* (2013); Arpaia, N. et al. Metabolites produced by commensal bacteria promote peripheral regulatory T-cell generation. *Nature* 504, 451-455 (2013)). The cellular contents of the intestine were analyzed 21 days after allo-BMT to determine whether butyrate had an impact on local Treg cells. The total numbers of CD45.1+ cells recovered from the intestinal lamina propria were not different between vehicle- and butyrate-treated allo-BMT recipients. By contrast, intestinal infiltration of donor CD4+ and CD8+ T cells and activated T cells (CD69+ or CD44hi) was decreased in animals that received local intragastric butyrate administration (FIG. 4a). However, the ratio of donor Treg cells to effector T cells was not different in the intestines of these animals (FIG. 4b). Microbiota-derived butyrate has been shown to increase immune-regulatory macrophages in the GI tract which increased Treg cells (Chang, P. V., Hao, L., Offermanns, S. & Medzhitov, R. The microbial metabolite butyrate regulates intestinal macrophage function via histone deacetylase inhibition. *Proc Natl Acad Sci USA* 111, 2247-2252 (2014)). However, no difference in the total number of donor macrophages in the intestine of allogenenic recipients that were treated with either vehicle or butyrate was observed (FIG. 4c).

To further determine whether the salutary effects of local treatment with butyrate on GI GVHD were dependent on donor Treg cells, a BMT was performed utilizing the same HC mismatched BMT model in which C57BL/6J (H-2b) cells are transferred to Balb/c (H-2d) mice. T cell-depleted (TCD) bone marrow was transplanted and purified CD4+ CD25− T cells from donors. Vehicle or butyrate was administered to the recipients daily for 1 week, then every other day thereafter as above. Decreased GVHD was observed (FIG. 4d-e), indicating that donor Treg cells may be dispensable for the reduction of GVHD. To further confirm the donor Treg cell-independent protective effects of butyrate on GVHD, donor C57BL/6J mice with a knock-in of human diphtheria toxin receptor (DTR) expressed only on Treg cells (DREG) was utilized (Lahl, K. et al. Selective depletion of Foxp3+ regulatory T cells induces a scurfy-like disease. *J. Exp. Med.* 204, 57-63 (2007); Lahl, K. & Sparwasser, T. In vivo depletion of FoxP3+ Tregs using the DEREG mouse model. *Methods Mol. Biol.* 707, 157-172 (2011), DREG donor mice were injected with diphtheria toxin (DT) (10 µg/kg) on day −2 and day −1 and loss of Foxp3-Treg expression was confirmed. The Treg depleted T cells were then used as donor cells in the major MHC mismatch model used above. Significantly improved clinical GVHD, less weight loss, and improved survival was observed. To further examine whether the local administration of butyrate impacted donor T cells directly, the HDAC and HAT enzymatic activity was determined in donor T cells harvested from the recipient animals. Both the HDAC activity or HAT activity in the donor T cells harvested from the recipient spleen were similar between butyrate and vehicle treated allogeneic animals. These collectively demonstrate that the reduction in GI GVHD upon intragastric administration of butyrate is independent of its potential effects from donor Treg cells.

Butyrate Protects IECs from Allo-T Cell Mediated Damage:

The potential mechanisms that contribute to butyrate-induced protection from severe GVHD were explored. Because (a) butyrate is decreased in IECs, (b) administration of butyrate mitigated GI GVHD independent of Treg cells, but (c) improved junction integrity, it was explored whether butyrate had direct effects on protecting IECs from allo-T cell mediated damage and conditioning. IECs were treated ex vivo with vehicle or butyrate for 24 hours irradiation (6 Gy) or no-irradition, followed by 24 hours of additional incubation with butyrate was performed. It was observed that butyrate was not toxic to IECs (FIG. 5a, left) and more importantly conferred protection from irradiation-induced apoptosis (FIG. 5a, right). The ability of butyrate-treated IECs to withstand damage mediated by alloreactive T cells was determined by isolating and culturing primary IECs with butyrate or vehicle control, overnight. The pre-treated IECs were next co-cultured with primed allogeneic CD8+ T cells, in the absence of butyrate. Fewer butyrate pre-treated IECs succumbed to CD8+ T cell killing within 6 hours (FIG. 5b, left) and 16 hours (FIG. 5b, right) following co-culture, compared with control. Because butyrate is a primary energy source for IECs 1-13, it was next determined whether butyrate enhances survival and growth of IECs in vitro. To this end, intestinal organoids were cultured in the presence or absence of butyrate. It was observed that culture in the presence of butyrate significantly increased organoid size (FIG. 5c). Next, the impact of butyrate on IEC junctional function in the organoid cultures was confirmed by determining the mRNA expression of claudins (FIG. 5E). It was observed that culture of organoids with butyrate significantly increased the mRNA expression of claudins (Cldn1, Cldn5, Cldn6, Cldn10, Cldn11, Cldn13, Cldn14, Cldn17, and Cldn18).

Molecular Mechanisms of IEC Protection:

It was hypothesized that butyrate would increase anti-apoptotic genes by modulation of histone acetylation. Pro- and anti-apoptotic mRNA expression levels (Topham, C. H. & Taylor, S. S. Mitosis and apoptosis: how is the balance set? *Curr. Opin. Cell Biol.* 25, 780-785 (2013)) were analyzed and it was found that Bakl and Bax were significantly decreased, whereas transcripts of the antiapoptotic protein BCL-B (Bcl2110) were significantly increased (FIG. 5d) in butyrate treated IECs. mRNA expression of junctional proteins such as occludin (Ocln) and JAM (F11r) was examined (FIG. 5e) in IECs following butyrate treatment, which significantly increased their expression. It was also determined if the restored acetylation of histone H4 observed in butyrate-treated allo-BMT recipients was responsible for increased BCL-B (Bcl2110) and JAM (F11r) expression via ChIP. Acetylation of histone H4 was associated with the promoter region of Bcl2110 (FIG. 5f) and F11r (FIG. 5g) in butyrate treated IECs (CD326+).

These data thus collectively indicate butyrate has several salutary effects on IECs that may or may not be mutually exclusive, such as regulating the expression of genes involved in decreased IEC apoptosis and increased junctional proteins in IECs. To determine if these are involved in in vivo protection from GVHD, the expression of pro- and anti-apoptotic proteins as well as junctional proteins in IECs isolated 21 days following allo-BMT was determined. Pro-apoptotic transcripts of Bak1 and Bax were significantly decreased in allo-BMT recipients that received intragastric butyrate treatment (FIG. 5h) while the anti-apoptotic BCL-B (Bcl2110) expression was increased (FIG. 5g). Further, gene expression of junctional proteins were, again, similarly increased in butyrate treated animals (FIG. 5h). To determine if these results have biological consequences on protein expression, the protein amounts of Occludin, JAM, and Claudin 5 were assayed. Indeed, immunoblot analysis revealed increased junctional proteins in recipients of allo-BMT treated with intragastric butyrate. Overall, the results identify several ways in which butyrate can directly enhance epithelial cell function ranging from protection from irradiation and allo-T cell mediated apoptosis to proliferation and junctional protein expression, both in vitro and in vivo.

Figure 6:
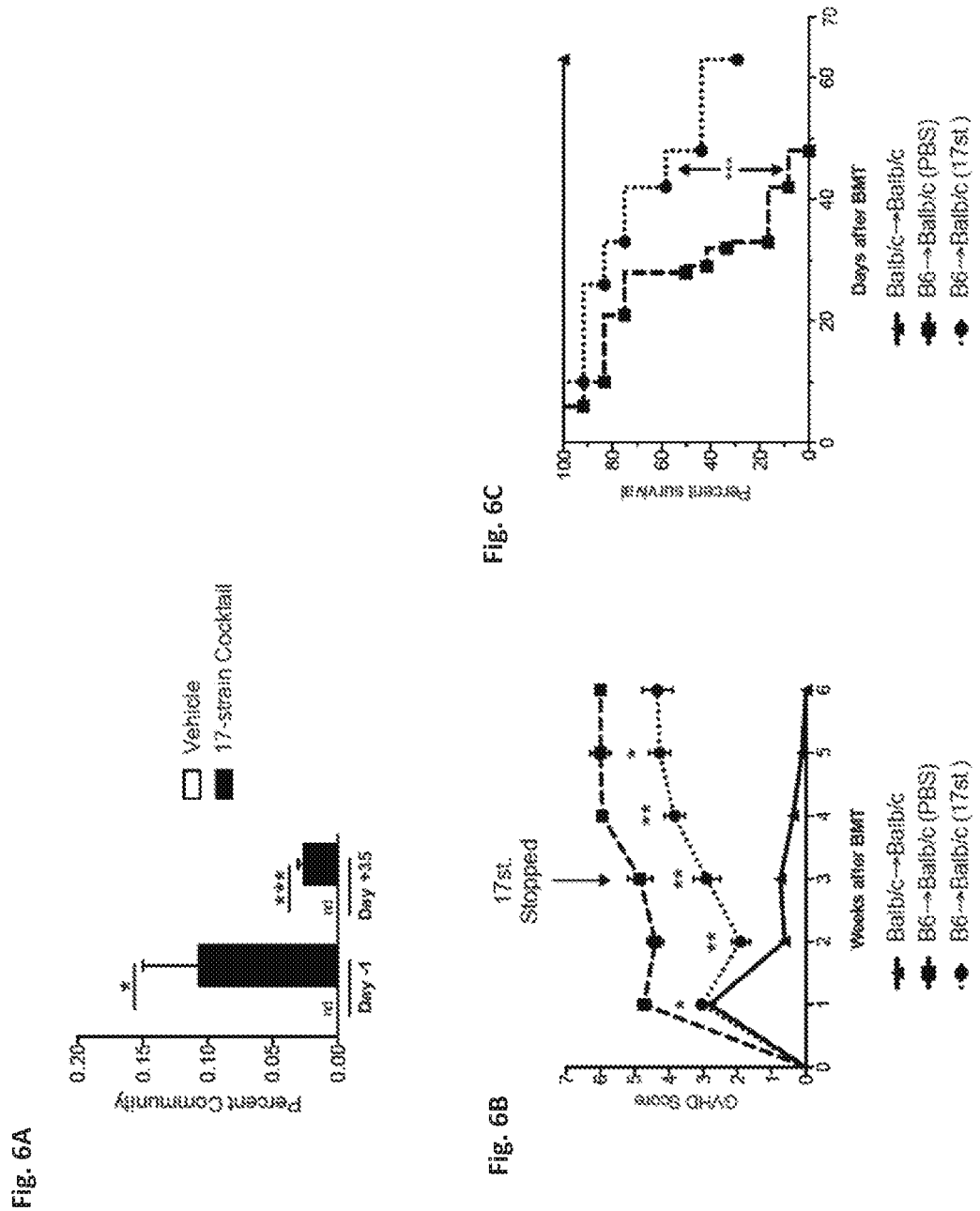
FIG. 6.

High Butyrate Producing Microbiota Mitigate GVHD:

The endogenous HDACi butyrate is a by-product of microbial fermentation (Wong, J. M. W., de Souza, R., Kendall, C. W. C., Emam, A. & Jenkins, D. J. A. Colonic health: fermentation and short chain fatty acids. J. Clin. Gastroenterol. 40, 235-243 (2006). Therefore, the hypothesis that altering the composition of indigenous GI microbiota in hosts to those that can produce high levels of butyrate will mitigate GVHD was tested. Seventeen rationally selected strains of Clostridia that have been shown to increase butyrate both in vitro and in vivo (Atarashi, K. et al. Treg induction by a rationally selected mixture of Clostridia strains from the human microbiota. *Nature* (2013); Narushima, S. et al. Characterization of the 17 strains of regulatory T cell-inducing human-derived Clostridia. *Gut Microbes* 5, 333-339 (2014) were administered these strains via intragastric gavage every other day to naive mice starting 14 days prior to allo-BMT and continued administration of the 17-strain cocktail for 21 days post-BMT. The microbiota in feces collected from animals that received vehicle and 17-strain administration was analyzed by 16S rRNA-encoding gene sequencing. In animals that received the 17 Clostridial strains, 16S analysis (Schloss, P. D. et al. Introducing mothur: open-source, platform-independent, community supported software for describing and comparing microbial communities. *Appl. Environ. Microbiol.* 75, 7537-7541 (2009); Schloss, P. D., Gevers, D. & Westcott, S. L. Reducing the effects of PCR amplification and sequencing artifacts on 16S rRNA-based studies. *PLoS ONE* 6, e27310 (2011); DeSantis, T. Z. et al. Greengenes, a chimera-checked 16S rRNA gene database and workbench compatible with ARB. *Appl. Environ. Microbiol.* 72, 5069-5072 (2006)) revealed an important biologically significant shift in the microbiota indicating that these organisms could be detected (FIG. 6a). Furthermore, GC/MS analysis 21 days following allo-BMT revealed a significant increase of butyrate in the luminal contents (FIG. 6b) and significantly increased butyrate in the intestinal tissues (FIG. 6c) of animals that received intragastric gavage of the 17 Clostridial strains. The recipients of intragastric gavage of the 17 strains and allo-BMT exhibited significantly decreased GVHD (FIG. 6d-e). Detectable levels of the 17 Clostridial strains were diminished within 2 weeks (day +35) of ceasing intragastric administration (FIG. 6a).

Because microbiota variations are known to occur in different colonies of mice, it was also determined whether mice housed at another institution (Memorial Sloan Kettering Cancer Center, USA) and treated with the same 17 Clostridial strains would also mitigate GVHD. Additionally, because clinical BMT patients are often treated with antibiotics and as an alternative approach to colonizing the indigenous microbiota, C57BL/6J mice were treated with an antibiotic cocktail (ampicillin 5 mg, metronidazole 4 mg, clindamycin 5 mg, vancomycin 5 mg) daily by intragastric gavage for 6 days to target obligate anaerobes. The mice were then colonized 4 and 6 days later with either human *Enterococcus faecium* or the same cocktail of 17 strains of human Clostridia17 by intragastric gavage. Once again, the fecal microbiota was characterized by 16S gene sequence analysis on day −1, relative to BMT. Upon analysis, increased presence of Clostridia species in recipients that received the cocktail of 17 Clostridial strains was observed, compared to recipients ofE. *faecium*. The animals were next used as recipients of a MHC-mismatched B10.BR (H-2k) BMT and followed for survival. Animals that were treated with antibiotics, but were not recolonized with bacteria, died significantly faster (P<0.0001) than mice not treated with the antibiotic mixture. These data demonstrate that antibiotic treatment eliminated beneficial microbiota similar to previous Reports (Jenq, R. R. & van den Brink, M. R. M. Allogeneic haematopoietic stem cell transplantation: individualized stem cell and immune therapy of cancer. *Nature Reviews Cancer* 10, 213-221 (2010). Sinificantly increased survival was observed in the animals treated with the cocktail of 17 Clostridial strains (FIG. 6g). These results show that altering the indigenous microbiota with 17 rationally selected strains of Clostridia, known to produce high amounts of butyrate (Atarashi, K. et al. Treg induction by a rationally selected mixture of Clostridia strains from the human microbiota. *Nature* (2013); Narushima, S. et al. Characterization of the 17 strains of regulatory T cell-inducing human-derived Clostridia. *Gut Microbes* 5, 333-339 (2014)), can decrease the severity of GVHD and improve survival across multiple institutions with strain independent results.

In summary, the present example describes unbiased profiling of the microbial metabolome with a specific focus on targeted FAs after experimental allo-BMT. Only one SCFA, namely butyrate was significantly reduced only in the intestinal tissue of allo-BMT recipients resulting in decreased acetylation of histone H4 within IECs. Increasing intestinal butyrate restored acetylation of histone H4, protected IECs, and decreased the severity of GVHD. Furthermore, rationally altering host GI microbiota to high butyrate producers 17 mitigated GVHD.

The community structure of the microbiota is altered following allo-BMT (Jenq, R. R. et al. Regulation of intestinal inflammation by microbiota following allogeneic bone marrow transplantation. *Journal of Experimental Medicine* 209, 903-911 (2012); Eriguchi, Y. et al. Graft-versus-host disease disrupts intestinal microbial ecology by inhibiting Paneth cell production of α-defensins. *Blood* 120, 223-231 (2012)). The results described herein now provide a novel perspective on microbial metabolites and their impact on GVHD. The study revealed that the only significantly decreased SCFA, butyrate, is diminished in the intestinal tissue after allo-BMT. Reduction of butyrate in allo-BMT IECs decreased acetylation of histones while increasing butyrate via intragastric gavage restored acetylation of histone H4 and GVHD.

An important observation was the lack of changes in luminal (stool) butyrate, despite a documented shift in the microbiome species that produce less butyrate after allo-BMT (Jenq, R. R. et al. Regulation of intestinal inflammation by microbiota following allogeneic bone marrow transplantation. *Journal of Experimental Medicine* 209, 903-911 (2012)). It is contemplated that this may be because of reduced uptake into IECs due to decreased butyrate transporter, thus leaving overall butyrate levels not significantly reduced in the lumen because less is being taken into the IECs despite a decreased production by the shift in the microbiota after allo-BMT.

The reasons for decreased transporter proteins after allo-BMT are intriguing. Previous reports observed a decrease in SLC5A8 following alterations in the microbiota (Cresci, G. A., Thangaraju, M., Mellinger, J. D., Liu, K. & Ganapathy, V. Colonic gene expression in conventional and germ-free mice with a focus on the butyrate receptor GPR109A and the butyrate transporter SLC5A8. *J Gastrointest. Surg.* 14, 449-461 (2010).). Thus, the findings that SLC5A8 and GPR43 are decreased in IECs following allo-BMT are consistent with previous Reports (Jenq, R. R. et al. Regulation of intestinal inflammation by microbiota following allogeneic bone marrow transplantation. *Journal of Experimental Medicine* 209, 903-911 (2012); Eriguchi, Y. et al. Graftversus-host disease disrupts intestinal microbial ecology by inhibiting Paneth cell production of α-defensins. *Blood* 120, 223-231 (2012)). Furthermore, it was demonstrated that exposure of IECs to inflammatory cytokines leads to reduction in the expression of butyrate transporters. These data show that the inflammatory milieu early after allo-BMT reduces the butyrate transporter SLC5A8 leading to its reduction in the IECs and further reducing transporter expression and butyrate intake in a feedback mechanism.

Administered butyrate is more rapidly metabolized as shown by the greater incorporation of carbon from butyrate into the TCA cycle. These data point to a novel observation on the role of energy requirements of IECs in the context of inflammation and GVHD. The data collectively provide new insights into the role and interactions of the microbiome-derived metabolite, butyrate after allo-BMT. These data indicate that butyrate has direct salutary effects on IECs. Butyrate altered the ratio of the expression of anti-apoptotic to pro-apoptotic molecules and increased the expression of proteins relevant for junctional integrity.

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the disclosure to enable one skilled in the art to utilize the disclosure in various embodiments and with various modifications as suited to the particular use contemplated. It is intended that the scope of the disclosure be defined by the claims appended hereto and their equivalents.

What is claimed is:

1. A method of treating Graft versus Host Disease (GvHD), the method comprising administering to the digestive tract of a subject in need thereof a therapeutically effective amount of a bacterial composition, the bacterial composition comprising bacterial strains comprising 16S rDNA sequences of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, and SEQ ID NO:17, wherein said bacterial composition is administered prior to and following a bone marrow transplant.

2. The method of claim 1, wherein one or more of the bacterial strains does not have an antibiotic resistance gene.

3. The method of claim 1, wherein one or more of the bacterial strains is not resistant to vancomycin.

4. The method of claim 1, wherein one or more of the bacterial strains produces butyrate.

5. The method of claim 1, wherein the method does not include the administration of an antibiotic.

6. The method of claim 1, wherein the bacterial composition is administered every other day for 14 days prior to bone marrow transplant.

7. The method of claim 1, wherein the bacterial composition is administered every other day for at least 21 days after bone marrow transplant.

8. The method of claim 1, wherein the subject has chronic GvHD.

9. The method of claim 1, wherein the subject has acute GvHD.

10. The method of claim 1, wherein the bacterial composition is a pharmaceutical composition.

11. The method of claim 10, wherein the pharmaceutical composition comprises a pharmaceutical acceptable excipient.

12. The method of claim 10, wherein the pharmaceutical composition is formulated for oral administration.

13. The method of claim 10, wherein the pharmaceutical composition is formulated for delivery to the intestine.

14. The method of claim 10, wherein the pharmaceutical composition is formulated for delivery to the colon.

15. The method of claim 1, wherein one or more of the bacterial strains is lyophilized.

16. The method of claim 10, wherein the pharmaceutical composition is in the form of a capsule.

17. The method of claim 10, wherein the pharmaceutical composition further comprises a pH sensitive composition comprising one or more enteric polymers.

* * * * *